United States Patent
Yamazaki et al.

(10) Patent No.: US 7,176,227 B2
(45) Date of Patent: Feb. 13, 2007

(54) AMINE COMPOUNDS AND USE THEREOF

(75) Inventors: Toru Yamazaki, Tokyo (JP); Shigeyuki Kikumoto, Tokyo (JP); Masahiro Ono, Kanagawa (JP); Atsushi Saitou, Chiba (JP); Haruka Takahashi, Tokyo (JP); Sei Kumakura, Saitama (JP); Kunitaka Hirose, Tokyo (JP); Mikiro Yanaka, Chiba (JP); Yoshiyuki Takemura, Tokyo (JP); Shigeru Suzuki, Tokyo (JP); Ryo Matsui, Tokyo (JP)

(73) Assignee: Kureha Corporation, Tokyo (JP)

( * ) Notice: Subject to any disclaimer, the term of this patent is extended or adjusted under 35 U.S.C. 154(b) by 60 days.

(21) Appl. No.: 10/516,158

(22) PCT Filed: Sep. 5, 2003

(86) PCT No.: PCT/JP03/11381

§ 371 (c)(1),
(2), (4) Date: Feb. 2, 2005

(87) PCT Pub. No.: WO2004/024697

PCT Pub. Date: Mar. 25, 2004

(65) Prior Publication Data

US 2005/0165063 A1    Jul. 28, 2005

(30) Foreign Application Priority Data

Sep. 11, 2002   (JP)   ............... 2002-265247

(51) Int. Cl.
C07D 403/12    (2006.01)
A61K 314/178   (2006.01)

(52) U.S. Cl. .................... 514/397; 548/312.7

(58) Field of Classification Search ............. 548/312.7; 514/397
See application file for complete search history.

(56) References Cited

U.S. PATENT DOCUMENTS

| | | |
|---|---|---|
| 5,086,069 A | 2/1992 | Klein et al. |
| 5,633,231 A | 5/1997 | Habich et al. |
| 5,886,044 A | 3/1999 | Widdowson et al. |
| 6,096,773 A | 8/2000 | Scott et al. |
| 6,750,348 B1 | 6/2004 | Bridger et al. |
| 7,091,217 B2 | 8/2006 | Bridger et al. |
| 2004/0092556 A1 | 5/2004 | Yamazaki et al. |
| 2004/0157818 A1 | 8/2004 | Yanaka et al. |
| 2004/0254221 A1* | 12/2004 | Yamazaki et al. .......... 514/332 |

FOREIGN PATENT DOCUMENTS

| | | |
|---|---|---|
| EP | 0 183 271 A2 | 6/1986 |
| EP | 0 628 551 | 12/1994 |
| EP | 0 646 598 A1 | 4/1995 |
| EP | 1 389 460 A1 | 2/2004 |
| JP | 7-89988 | 4/1995 |
| WO | WO 98/06397 A1 | 2/1998 |
| WO | WO 99/33787 A1 | 7/1999 |
| WO | WO 2000/006086 | 2/2000 |
| WO | WO 2000/056729 A1 | 9/2000 |
| WO | WO 01/10842 A | 2/2001 |
| WO | WO 01/79168 A1 | 10/2001 |
| WO | WO 2002/022600 A1 | 3/2002 |
| WO | WO 02/094261 A1 | 5/2002 |
| WO | WO 03/029218 A1 | 4/2003 |
| WO | WO 2005/085209 A1 | 10/2005 |

OTHER PUBLICATIONS

Molino, M. et al., "CXCR4 on human endothelial cells can serve as both a mediator of biological responses and as a receptor for HIV-2," Biochimica et Biophysica Acta (BBA), Molecular Basis of Disease, vol. 1500, Issue 2, Feb. 21, 2000, p. 227-240.
U.S. Appl. No. 10/591,722, filed Sep. 5, 2006, Atsushi Saitou et al.

* cited by examiner

*Primary Examiner*—Golam M. M. Shameem
*Assistant Examiner*—Andrew B. Freistein
(74) *Attorney, Agent, or Firm*—Hollander Law Firm, P.L.C.

(57) ABSTRACT

Novel amine compounds which are efficacious against diseases such as infection with HIV virus, rheumatism, and cancer metastasis include compounds represented by the following general formula (1), a pharmacologically acceptable salt thereof, or a prodrug thereof:

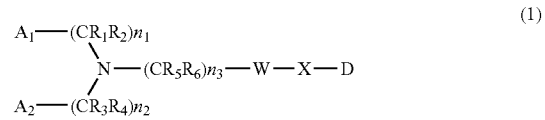

wherein each of $n_1$, $n_2$, and $n_3$ is an integer of 1; each of $R_1$, $R_2$, $R_3$, $R_4$, $R_5$, and $R_6$ is independently a hydrogen atom; $A_1$ is imidazole; $A_2$ is imidazole or imidazole substituted with an alkyl group; W is a phenyl group or naphthyl group; X is $CH_2$; D is a group represented by -Q-Y-B, wherein Q is $NR_{12}$ and $R_{12}$ is a hydrogen atom or an alkyl group; Y is $(CH_2)m_3$ and $m_3$ is an integer of 2 to 4; and B is $N(R_{25}R_{26})$, wherein each of $R_{25}$ and $R_{26}$ are independently a hydrogen atom, a $C_1$–$C_6$ alkyl group or a $C_3$–$C_6$ cycloalkyl group.

9 Claims, 13 Drawing Sheets

AMINE COMPOUNDS AND USE THEREOF

This application is a 371 U.S. national stage application of international application PCT/JP2003/011381 filed Sep. 5, 2003, which claims priority of Japanese patent application 265247/2002 filed Sep. 11, 2002.

TECHNICAL FIELD

The present invention relates to an amine compound or a pharmacologically acceptable salt thereof, or a prodrug thereof, in particular, an amine compound having anti-virus activity based on antagonism to chemokine receptor CXCR4. Furthermore, the present invention relates to a pharmaceutical drug for associated diseases such as rheumatic diseases and cancer metastatic diseases, based on antagonism against a chemokine receptor CXCR4.

BACKGROUND ART

While examples of therapeutic drugs against the acquired immunodeficiency syndrome (AIDS) caused by an infection with the human immunodeficiency virus (HIV) include a reverse transcriptase inhibitor and a protease inhibitor, therapeutic effectiveness of those drugs has been lost due to the emergence of drug resistant HIV mutants (see, for example, Saishin Igaku, Vol. 53, No. 9, p. 2031 (1998)). Also, the polypharmacy using the combination of such drugs has such disadvantages that it requires many conditions to be observed in administration, that it is complex, that it needs many kinds of drugs to be administered, and that it causes various side effects (see, for example, Nikkei Science, October, p. 29 (1998)). Moreover, particularly in case of using the protease inhibitor, it is known that the probability of causing emergence and screening of the resistant strain will increase unless the administration of approximately 100% of the drugs is kept, in spite of the complex administration method and many side effects thereof (see, for example, Molecular Medicine, Vol. 36, No. 9, p. 1012 (1999)).

Alternatively, development of vaccine has been attempted because many viral diseases were destroyed or remarkably weakened by vaccines in the past. However, this is considered to be extremely difficult since mutations are occurred frequently in HIV (see, for example, Nikkei Science, October, p. 42 (1998)).

Although several kinds of compounds having an anti-HIV effect have been reported as described above, it is now strongly desired to develop a novel antiviral drug which has excellent anti-retrovirus effect, is capable of opposing to the expression of the resistance, and which has little toxicity and causes little side effect, thereby allowing long term administration.

Chemokines is one kind of cytokine which renders chemotaxis to leukocytes, and is a secretory protein. Chemokine is classified into CXC-chemokine, CC-chemokine, C-chemokine, CX3C-chemokine according to the cysteine (Cys) sequence at N-terminal, and the total number thereof is said to be about 30. The chemokine receptor includes several sub types. Among them, it is known that the CXCR4 which is a ligand for CXC-chemokine SDF-1 is utilized as a coreceptor on infection to a host cell of T cell-directive HIV (see, for example, Science, 272, 872 (1996) and Nature, 382, 829 (1996). The HIV invades through binding to the CXCR4 on the surface of a host cell of an envelope protein gp120. That is, the drug having antagonism against the CXCR4 is expected as an anti-HIV drug based on a novel mechanism of invasion inhibition, and there have been reported three low molecular compounds as such drugs: AMD3100 (see, for example, J. Exp. Med, 186, 1383 (1997), T22 (see, for example, J. Exp. Med, 186, 1389 (1997)), and ALX40-4C (see, for example, J. Exp. Med, 186, 1395 (1997)).

On the other hand, it has been elucidated that the CXCR4 associates with various diseases besides HIV infection. For example, there has been reported its association with rheumatic disease (see, for example, WO 00/06086), cancer metastatic disease (see, for example, Nature, 410, 50 (2001)), etc.

As a therapeutic drug for such diseases, it is strongly desired to develop a novel low-molecular drug which has CXCR4 antagonism, and which has little toxicity and causes little side effect, thereby allowing long-term administration.

DISCLOSURE OF THE INVENTION

An object of the present invention is to provide a drug and a prodrug thereof having an excellent anti-retrovirus effect, and also a novel chemical structure having an excellent CXCR4 antagonism against SDF-1, and high safety.

As a result of studies to develop a compound having an excellent anti-retrovirus effect, and also having a novel chemical structure useful as an excellent CXCR4 antagonist against SDF-1, the present inventors have found a group of amine compounds which exhibit protection characteristics in a cell vaccinated with HIV-1 and therefore are regarded as having a potentiality for treatments of AIDS, AIDS-associated complication, and the like, and which also exhibit a powerful CXCR4 antagonism and therefore are regarded as having a potentiality for treatments of rheumatic disease, cancer metastatic diseases, and the like. Thus, another object of the present invention is to provide a compound represented by the general formula (1) defined below, which has an anti-virus activity for mainly HIV and a CXCR4 antagonism, and still another object of the invention is to provide a drug comprising the compound represented by the general formula (1), for treating virus-infected patients and patients suffering from rheumatism, cancer, or the like.

That is, the present invention relates to a compound represented by the following general formula (1), a pharmacologically acceptable salt thereof, or a prodrug thereof:

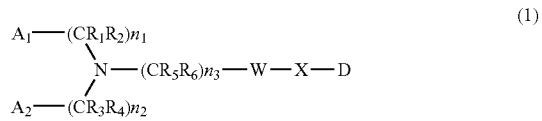

(1)

wherein
each of $n_1$, $n_2$, and $n_3$ is an integer of 0 to 3;

each of $R_1$, $R_2$, $R_3$, $R_4$, $R_5$, and $R_6$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms; and each of $A_1$ and $A_2$ is independently a substitutable monocyclic or polycyclic heteroaromatic ring, a partly saturated substitutable polycyclic heteroaromatic ring, a substitutable monocyclic or polycyclic aromatic ring, a partly saturated substitutable polycyclic aromatic ring, a substitutable heterocycle, or a group represented by the following formula (2):

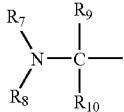
(2)

wherein each of $R_7$, $R_8$, $R_9$, and $R_{10}$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms;

W is a substitutable alkylene group having 1 to 15 carbon atoms, preferably 1 to 10 carbon atoms, and more preferably 1 to 7 carbon atoms, a substitutable alkenylene group having 2 to 15 carbon atoms, preferably 2 to 10 carbon atoms, and more preferably 2 to 7 carbon atoms, a substitutable alkynylene group having 2 to 15 carbon atoms, preferably 2 to 10 carbon atoms, and more preferably 2 to 7 carbon atoms, a substitutable cyclic alkylene group having 3 to 15 carbon atoms, preferably 3 to 10 carbon atoms, and more preferably 3 to 7 carbon atoms, a substitutable monocyclic or polycyclic heteroaromatic ring, a partly saturated substitutable polycyclic heteroaromatic ring, a substitutable monocyclic or polycyclic aromatic ring, a partly saturated substitutable polycyclic aromatic ring, or a substitutable heterocycle;

X is O, $CH_2$, $NR_{11}$, or a group represented by the following formula (3);

$R_{11}$ is a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms;

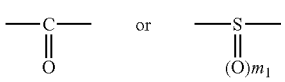
(3)

wherein $m_1$ is an integer of 1 or 2;

D is a group represented by the following formula (4) or (6):

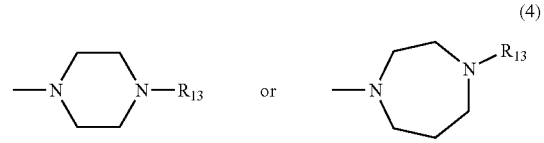
(4)

wherein $R_{13}$ is a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms, or a group represented by the following formula (5):

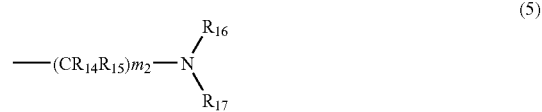
(5)

wherein $m_2$ is an integer of 2 to 4;

each of $R_{14}$, $R_{15}$, $R_{16}$, and $R_{17}$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms;

(6)

wherein

Q is a single bond when X is O, a single bond or a group represented by the formula (3) when X is $NR_{11}$, or a single bond, S, O, or $NR_{12}$ when X is $CH_2$ or represented by the formula (3);

$R_{12}$ is a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms; and Y is a group represented by the following formula (7):

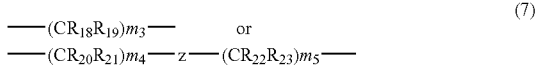
(7)

wherein $m_3$ is an integer of 0 to 6;

each of $R_{18}$ and $R_{19}$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, a substitutable cyclic alkyl group having 3 to 15 carbon atoms, preferably 3 to 10 carbon atoms, and more preferably 3 to 7 carbon atoms, or a substitutable aromatic ring, and $R_{12}$ and $R_{18}$ may form a ring;

each of $m_4$ and $m_5$ is an integer of 0 to 2;

each of $R_{20}$, $R_{21}$, $R_{22}$, and $R_{23}$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, or a substitutable cyclic alkyl group having 3 to 15 carbon atoms, preferably 3 to 10 carbon atoms, and more preferably 3 to 7 carbon atoms;

z is a substitutable cyclic alkylene group having 3 to 15 carbon atoms, preferably 3 to 10 carbon atoms, and more preferably 3 to 7 carbon atoms, a substitutable monocyclic or polycyclic heteroaromatic ring, a partly saturated substitutable polycyclic heteroaromatic ring, a substitutable monocyclic or polycyclic aromatic ring, a partly saturated substitutable polycyclic aromatic ring, or a substitutable heterocycle;

B is a group represented by the following formula (8):

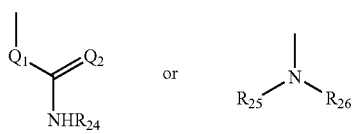
(8)

wherein $Q_1$ is S, O, or NH and $Q_2$ is S, O, or $NR_{27}$;

each of $R_{24}$ and $R_{27}$ is independently a hydrogen atom, a substitutable alkyl group having 1 to 15 carbon atoms, preferably 1 to 10 carbon atoms, and more preferably 1 to 7 carbon atoms, a substitutable alkenyl group having 2 to 15 carbon atoms, preferably 2 to 10 carbon atoms, and more preferably 2 to 7 carbon atoms, a substitutable alkynyl group having 2 to 15 carbon atoms, preferably 2 to 10 carbon atoms, and more preferably 2 to 7 carbon atoms, a substitutable cyclic alkyl group having 3 to 15 carbon atoms, preferably 3 to 10 carbon atoms, and more preferably 3 to 7 carbon atoms, or a substitutable aromatic ring, and $R_{24}$ and $R_{27}$ may form a ring;

each of $R_{25}$ and $R_{26}$ is, when above X is $CH_2$, independently a hydrogen atom, a substitutable alkyl group having 1 to 15 carbon atoms, preferably 1 to 10 carbon atoms, and more preferably 1 to 7 carbon atoms, a substitutable cyclic alkyl group having 3 to 15 carbon atoms, preferably 3 to 10 carbon atoms, and more preferably 3 to 7 carbon atoms, a substitutable alkenyl group having 2 to 15 carbon atoms, preferably 2 to 10 carbon atoms, and more preferably 2 to 7 carbon atoms and 1 to 3 double bonds, or a substitutable alkynyl group having 2 to 15 carbon atoms, preferably 2 to 10 carbon atoms, and more preferably 2 to 7 carbon atoms and having 1 to 3 triple bonds, where $R_{25}$ and $R_{26}$ may form a ring and, depending on circumstances, the ring may be formed by binding through a heteroatom, a cyclic alkyl group, an aromatic ring, a heteroaromatic ring, or a heterocycle;

each of $R_{25}$ and $R_{26}$ is, when above X is not $CH_2$, independently a hydrogen atom, a substituent represented by the following formula (9), a substitutable alkyl group having 1 to 15 carbon atoms, preferably 1 to 10 carbon atoms, and more preferably 1 to 7 carbon atoms, a substitutable cyclic alkyl group having 3 to 15 carbon atoms, preferably 3 to 10 carbon atoms, and more preferably 3 to 7 carbon atoms, a substitutable alkenyl group having 1 to 3 double bonds and 2 to 15 carbon atoms, preferably 2 to 10 carbon atoms, and more preferably 2 to 7 carbon atoms, or a substitutable alkynyl group having 1 to 3 triple bonds and 2 to 15 carbon atoms, preferably 2 to 10 carbon atoms, and more preferably 2 to 7 carbon atoms, and $R_{25}$ and $R_{26}$ may form a ring and, depending on circumstances, the ring may be formed by binding through a heteroatom, a cyclic alkyl group, an aromatic ring, a heteroaromatic ring, or a heterocycle:

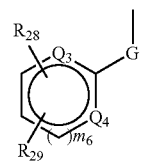
(9)

wherein $m_6$ is 0 or 1, where when $m_6=0$, $Q_3$ is CH or N and $Q_4$ is N, S, or O, and when $m_6=1$, each of $Q_3$ and $Q_4$ is independently CH or N;

G is a substitutable alkylene group having 1 to 15 carbon atoms, preferably 1 to 10 carbon atoms, and more preferably 1 to 7 carbon atoms or a substitutable alkenylene group having 2 to 15 carbon atoms, preferably 2 to 10 carbon atoms, and more preferably 2 to 7 carbon atoms;

$R_{28}$ is an alkyl group having 1 to 15 carbon atoms, preferably 1 to 10 carbon atoms, and more preferably 1 to 7 carbon atoms to be substituted at any position except a nitrogen atom which may be present on the ring, a substitutable alkenyl group having 2 to 15 carbon atoms, preferably 2 to 10 carbon atoms, and more preferably 2 to 7 carbon atoms, a substitutable alkynyl group, alkoxy group, a haloalkyl group, a haloalkoxy group, a hydroxyalkoxy group, a halogen atom, an amino group, an alkylamino group, a carboxyl group, an alkoxycarbonyl group, a carbamoyl group, an alkylcarbamoyl group, a saturated heterocycle, or a heteroaromatic ring having 2 to 15 carbon atoms, preferably 2 to 10 carbon atoms, and more preferably 2 to 7 carbon atoms, or may be a hydrogen atom when $m_6=1$ and $Q_3$ and $Q_4$ are both CH; and $R_{29}$ is a hydrogen atom or the same group as $R_{24}$, which may be coupled with G to form a ring.

one or two or more asymmetric carbon atoms may exist in the compound represented by the general formula (1), where when one asymmetric carbon atom exists, the compound may be in the form of any one of a pure optically active substance represented by the absolute configuration R or S, a mixture thereof in a predetermined ratio, and a racemic mixture thereof or when two or more asymmetric carbon atoms exist, the compound may be in the form of any one of an optically pure diastereomer, a racemic mixture thereof, and a combination thereof in a predetermined ratio.

The terms as used in this specification are defined as described below, and they may be used singly or in combination.

An alkyl group represents a saturated hydrocarbon group with any structure of a linear chain, a branched chain, or a ring. Examples of the alkyl group include a methyl group, an ethyl group, an n-propyl group, an isopropyl group, an n-butyl group, an isobutyl group, a pentyl group, and a neopentyl group.

An alkenyl group represents a hydrocarbon group with any structure of a linear chain, a branched chain, or a ring having a double bond. Examples of the alkenyl group include an allyl group, a 1-butenyl group, a 2-butenyl group, an isobutenyl group, and a cyclohexenyl group.

An alkynyl group represents a hydrocarbon group with any structure of a linear chain, a branched chain, or a ring having a triple bond. Examples of the alkynyl group include a propynyl group and a 1-butynyl group.

A cyclic alkyl group represents a cyclic hydrocarbon group. Examples of the cyclic alkyl group include a cyclopropyl group, a cyclobutyl group, a cyclopentyl group, a cyclohexyl group, and a cycloheptyl group.

An aromatic ring represents an aromatic ring formed of a hydrocarbon. Examples of a monocyclic aromatic ring include a benzene ring; and examples of a polycyclic aromatic ring include a naphthalene ring and an anthracene ring. Examples of a partly saturated polycyclic aromatic ring include a dihydronaphthalene ring, a tetralin ring, an indan ring and the like. A heteroaromatic ring represents an aromatic ring having one or two or more nitrogen atoms, oxygen atoms, or sulfur atoms in the ring. Examples of a monocyclic heteroaromatic ring include a pyrrole ring, a furan ring, a thiophene ring, a pyridine ring, a pyrimidine ring, a pyridazine ring, a pyrazine ring, an imidazole ring, a pyrazole ring, an oxazole ring, a thiazole ring, a thiadiazole ring, an oxadiazole ring, and a triazole ring. Examples of a polycyclic heteroaromatic ring include a quinoline ring, an isoquinoline ring, a benzimidazole ring, an indazole ring, a benzothiazole ring, a benzoxazole ring, an indole ring, a benzofuran ring, and a benzothiophene ring.

Examples of a partly saturated polycyclic aromatic ring include a tetrahydroisoquinoline ring and a tetrahydroquinoline ring. A heterocycle represents a saturated ring that may have one or two or more nitrogen atoms, oxygen atoms, or sulfur atoms in the ring. Examples of the heterocycle include pyrrolidine, piperidine, piperazine, morpholine, and thiomorpholine.

An alkylene group represents a hydrocarbon group that can be bonded two groups at the terminals. Examples of the alkylene group include an ethylene group, a propylene group, an isopropylene group, a butylene group, an isobutylene group, and a 2,2-dimethylethylene group.

An alkenylene group represents an alkylene group having a double bond. Examples of the alkenylene group include a propenylene group, a 2-butenylene group, and a 1,3-butadienylene group.

An alkynylene group represents an alkylene group having a triple bond. Examples of the alkynylene group include a propynylene group and a butynylene group.

The cyclic alkylene group in W represents a cyclic hydrocarbon group that can be bonded two groups at any positions. Examples of the cyclic alkylene group include a cyclopropylene group, a cyclopentylene group, a cyclohexylene group, and a tetralinylene group. An aromatic ring also represents an aromatic ring that can be bonded two groups at any positions. Examples of the aromatic ring group include a phenylene group and a napthalene group.

A heteroaromatic ring also represents a heteroaromatic ring that can be bonded two groups at any positions. Examples of the heteroaromatic ring to be used include a pyrrole ring, a furan ring, a thiophene ring, a pyridine ring, a pyrimidine ring, a pyrazine ring, a pyridazine ring, an imidazole ring, a thiazole ring, an oxazole ring, a triazole ring, a quinoline ring, an isoquinoline ring, a benzimidazole ring, a benzothiazole ring, a benzoxazole ring, an indole ring, a benzofuran ring, and a benzothiophene ring.

B represents $R_{25}(R_{26})N—$, where $R_{25}$ and $R_{26}$ may form a ring. Examples of a ring formed by binding $R_{25}$ and $R_{26}$ directly together with a nitrogen atom to which they are bound include a pyrrolidine ring, a piperidine ring, a hexamethyleneimine ring, and a heptamethyleneimine ring. Examples of a ring formed by binding $R_{25}$ and $R_{26}$ through a heteroatom together with a nitrogen atom to which they are bound include a morpholine ring and a piperazine ring. Examples of a ring formed by binding $R_{25}$ and $R_{26}$ through an aromatic ring together with a nitrogen atom to which they are bound include a tetrahydroisoquinoline ring and a tetrahydroindole ring.

When $R_{25}$ and/or $R_{26}$ is a group represented by the formula (8) and $R_{29}$ and G form a ring, examples of $R_{25}$ and $R_{26}$ include a tetralinyl group, an indanyl group, a tetrahydroquinolyl group, and a tetrahydroisoquinolyl group.

Examples of the "substitutable" groups in the expressions for each substituent include a hydroxyl group, a thiol group, a formyl group, a carboxyl group, a sulfonyl group, an amino group, an amide group, a carbamoyl group, a cyano group, an alkoxy group, an alkoxycarbonyl group, an alkylamino group, an acylamino group, an alkoxycarbonylamino group, alkylthio group, an aminosulfonyl group, a dialkylaminosulfonyl group, a methanesulfonyl group, a p-toluenesulfonyl group, and a phenyl group. The alkoxy group represents a group in which an alkyl group binds through an oxygen atom, and the acylamino group represents a group in which an alkyl group or a phenyl group binds to an amino group through a carbonyl group. Further, examples of the "substitutable" groups in $A_1$ and $A_2$ include an alkyl group, a hydroxyalkyl group, an alkoxyalkyl group, and an aminoalkyl group other than the group described above.

The prodrug is a precursor substance that becomes an effective drug through biochemical metabolism after administration to the living body. Specifically, the prodrug is a compound which is obtained by binding one or more appropriate groups, that is eliminated by metabolism in the living body, such as alkoxycarbonyl group or dialkylaminosulfone group with N in the ring or chain of a heterocycle or the like contained in the compound represented by the general formula (1). Alternatively, the prodrug is a compound coupled with one or more ester groups or the like that utilize alcohol or carboxylic acid, which may be contained in the compound represented by the general formula (1).

In addition, pharmacologically acceptable salts include trifluoroacetates, hydrochlorides, acetates, sulfates, nitrates, lactates, maleates, methane sulfonates, toluene sulfonates, tartrates, citrates, oxalates, malonates, succinates, fumarates, propionates, butyrates, glucuronates, terephthalates, and phosphorates.

BRIEF DESCRIPTION OF THE DRAWINGS

FIGS. 1 to 24 show reaction process steps of Production Method Examples 1–24, respectively.

BEST MODE FOR CARRYING OUT THE INVENTION

Compounds of the present invention can be produced by organic chemical reactions generally employed in the art. Hereinafter, production methods therefor will be exemplified with reference to the accompanying drawings, FIGS. 1–24. However, the synthesis of the compounds of the present invention is not limited to these methods.

PRODUCTION METHOD EXAMPLE 1

Figure 1:
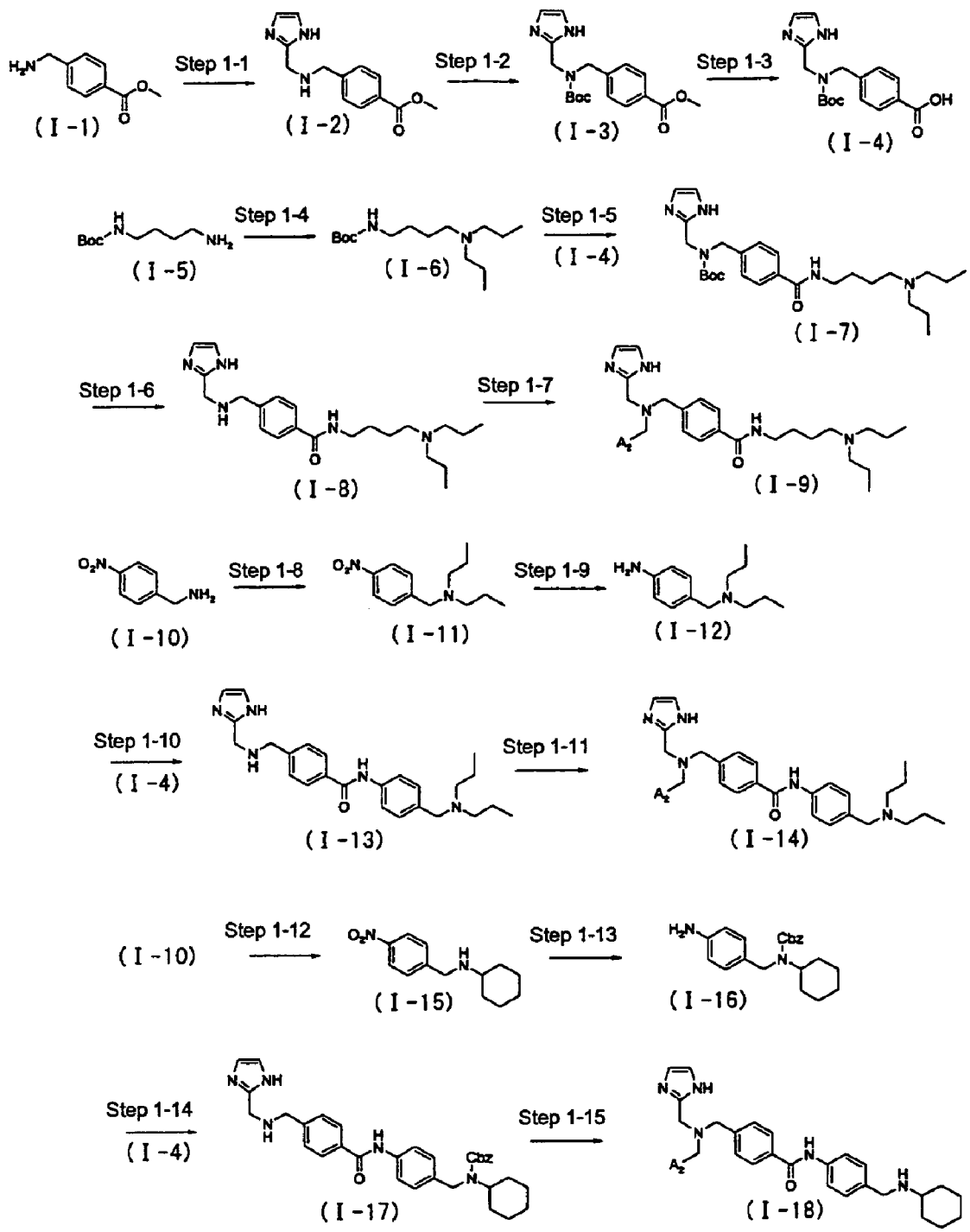
FIGS. 1–24 illustrate process steps of production methods described below for several compounds of the present invention. In other words.

The reaction process steps of Production Method Example 1 are shown in FIG. 1.

Step 1-1

An easily obtainable compound (I-1) is reacted with commercially available 2-imidazole carboxaldehyde and an appropriate reductant such as sodium cyanoborohydride in an appropriate solvent such as methanol to obtain a compound (I-2).

Step 1-2

The compound (I-2) is reacted with commercially available di-t-butyl dicarbonate and an appropriate base such as triethylamine in an appropriate solvent such as chloroform to thereby obtain a compound (I-3).

Step 1-3

The compound (I-3) is reacted with an appropriate base such as a sodium hydroxide aqueous solution in an appropriate solvent such as methanol to thereby obtain a compound (I-4).

Step 1-4

An easily obtainable compound (I-5) is reacted with commercially available propionaldehyde, an appropriate dehydrating agent such as trimethyl orthoformate, and an appropriate reductant such as sodium cyanoborohydride in an appropriate solvent such as methanol to thereby obtain a compound (I-6).

Step 1-5

The compound (I-6) is deprotected by reaction with an appropriate acid such as a hydrogen chloride/dioxane solution in an appropriate solvent such as methanol. Then, the resultant is reacted with the compound (I-4) and an appropriate condensing agent such as commercially available 1-ethyl-3-(3-dimethyl aminopropyl)-carbodiimide (hereinafter, referred to as WSCI)/1-hydroxy benzotriazole (hereinafter, referred to as HOBt) in an appropriate solvent such as chloroform to thereby obtain a compound (I-7).

Step 1-6

The compound (I-7) is deprotected by reaction with an appropriate acid such as a hydrogen chloride/dioxane solution in an appropriate solvent such as methanol to thereby obtain a compound (I-8).

Step 1-7

Easily obtainable aldehyde $A_2$-CHO ($A_2$ is as described above) is reacted with the compound (I-8), an appropriate dehydrating agent such as trimethyl orthoformate, and an appropriate reductant such as sodium cyanoborohydride in an appropriate solvent such as methanol to thereby obtain a compound (I-9) represented by the general formula (1).

Step 1-8

A commercially available compound (I-10) is reacted with commercially available propionaldehyde and an appropriate reductant such as sodium cyanoborohydride in an appropriate solvent such as methanol to thereby obtain the compound (I-11).

Step 1-9

The compound (I-11) is reacted with an appropriate reductant such as hydrazine monohydrate in an appropriate solvent such as methanol/tetrahydrofuran (hereinafter, referred to as THF) to thereby obtain a compound (I-12).

Step 1-10

The compound (I-12) is reacted with the compound (I-4) and an appropriate condensing agent such as commercially available PS-carbodiimide/HOBt in an appropriate solvent such as DMF to thereby obtain a compound (I-13).

Step 1-11

An easily obtainable aldehyde $A_2$-CHO ($A_2$ is as described above) is reacted with the compound (I-13) and an appropriate reductant such as sodium cyanoborohydride in an appropriate solvent such as methanol to thereby obtain a compound (I-14) represented by the general formula (1).

Step 1-12

A commercially available compound (I-10) is reacted with commercially available cyclohexanone, an appropriate dehydrating agent such as trimethyl orthoformate, and an appropriate reductant such as sodium cyanoborohydride in an appropriate solvent such as methanol to thereby obtain a compound (I-15).

Step 1-13

The compound (I-15) is reacted with commercially available benzyloxycarbonyl chloride and an appropriate base such as a sodium hydroxide aqueous solution in an appropriate solvent such as dioxane to obtain a benzyloxycarbonyl (hereinafter, referred to as Cbz) protecting substance, followed by the reaction with an appropriate reductant such as hydrazine monohydrate in an appropriate solvent such as methanol/THF to thereby obtain a compound (I-16).

Step 1-14

The compound (I-16) is reacted with the compound (I-4) and an appropriate condensing agent such as commercially available WSCI/HOBt in an appropriate solvent such as chloroform and then deprotected by reaction with an appropriate acid such as a hydrogen chloride/dioxane solution in an appropriate solvent such as methanol to thereby obtain a compound (I-17).

Step 1-15

An easily obtainable aldehyde $A_2$-CHO ($A_2$ is as described above) is reacted with the compound (I-17) and an appropriate reductant such as sodium cyanoborohydride in an appropriate solvent such as methanol and then deprotected by reaction with an appropriate reductant such as 10% palladium-carbon under hydrogen atmosphere in an appropriate solvent such as ethanol to thereby obtain a compound (I-18), which is a compound represented by the general formula (1).

PRODUCTION METHOD EXAMPLE 2

Figure 2:
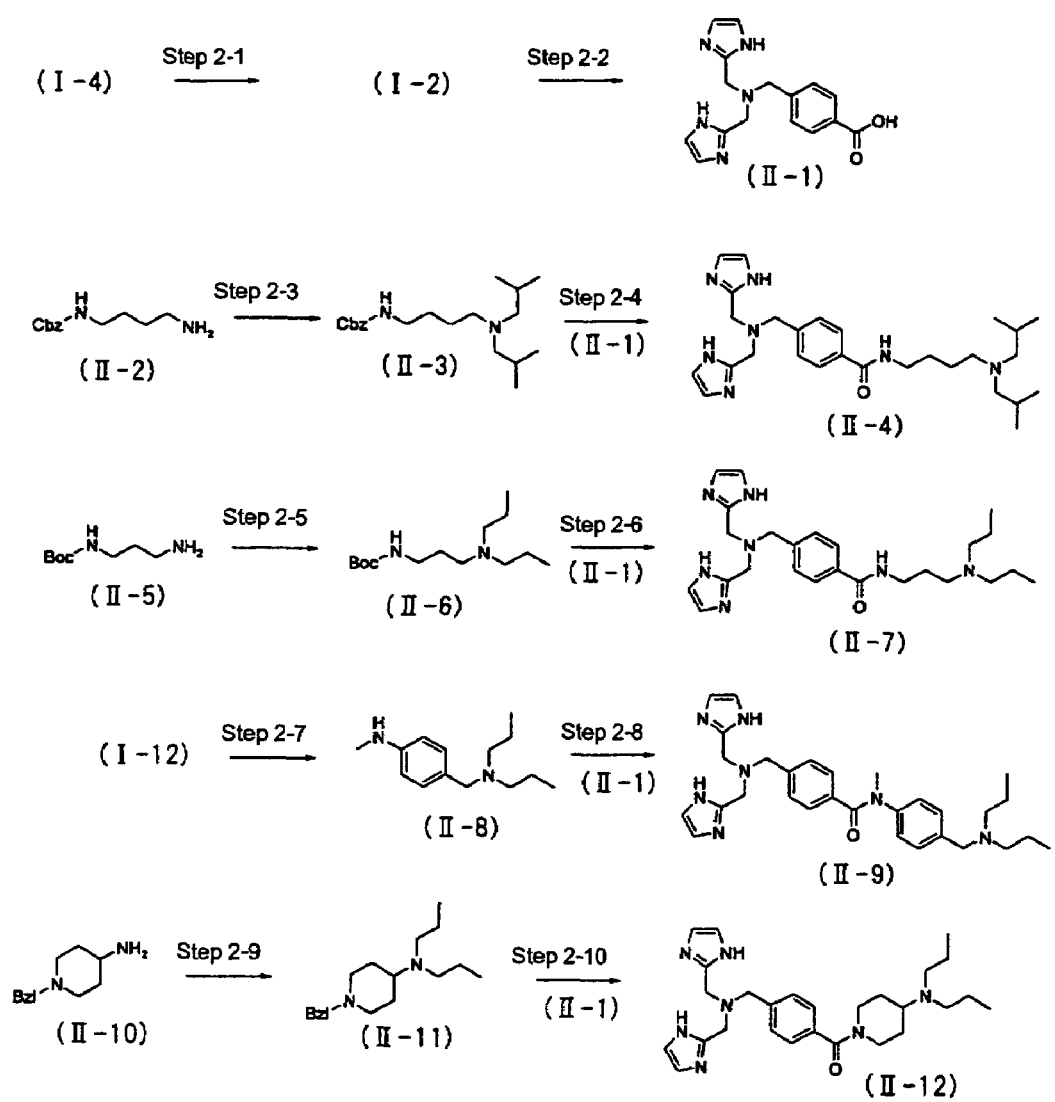

The reaction process steps of Production Method Example 2 are shown in FIG. 2.

Step 2-1

The compound (I-4) is deprotected and esterified by reaction with an appropriate acid such as hydrochloric acid in an appropriate solvent such as methanol to thereby obtain a compound (I-2).

Step 2-2

The compound (I-2) is reacted with 2-imidazole carboxaldehyde and an appropriate reductant such as sodium cyanoborohydride in an appropriate solvent such as methanol and then reacted with an appropriate base such as a sodium hydroxide aqueous solution in an appropriate solvent such as methanol to thereby obtain a compound (II-1).

Step 2-3

An easily obtainable compound (II-2) is reacted with commercially available isobutylaldehyde and an appropriate reductant such as sodium cyanoborohydride in an appropriate solvent such as methanol to thereby obtain a compound (II-3).

Step 2-4

The compound (II-3) is deprotected by reaction with an appropriate reductant such as 10% palladium-carbon under hydrogen atmosphere in an appropriate solvent such as ethanol. Then, the resultant is reacted with the compound (II-1) and an appropriate condensing agent such as commercially available dicyclohexylcarbodiimide (hereinafter, referred to as DCC)/HOBt in an appropriate solvent such as DMF to thereby obtain a compound (II-4) which is a compound represented by the general formula (1).

Step 2-5

An easily obtainable compound (II-5) is reacted with commercially available propionaldehyde and an appropriate reductant such as sodium cyanoborohydride in an appropriate solvent such as methanol to thereby obtain a compound (II-6).

Step 2-6

The compound (II-6) is deprotected by reaction with an appropriate acid such as hydrochloric acid in an appropriate solvent such as methanol and then reacted with the compound (II-1) and an appropriate condensing agent such as DCC/HOBt in an appropriate solvent such as DMF to thereby obtain a compound (II-7) which is a compound represented by the general formulation (1).

Step 2-7

The compound (I-12) is reacted with formic acid in an appropriate solvent such as acetic anhydride/THF and then reacted with an appropriate reductant such as lithium aluminum hydride in an appropriate solvent such as THF to thereby obtain a compound (II-8).

Step 2-8

The compound (II-8) is reacted with the compound (II-1) and an appropriate condensing agent such as DCC/HOBt in an appropriate solvent such as DMF to thereby obtain a compound (II-9) which is a compound represented by the general formula (1).

Step 2-9

A commercially available compound (II-10) is reacted with commercially available propionaldehyde, an appropriate dehydrating agent such as trimethyl orthoformate, and an appropriate reductant such as sodium cyanoborohydride in an appropriate solvent such as methanol to thereby obtain a compound (II-11).

Step 2-10

The compound (II-11) is deprotected by reaction with an appropriate reductant such as 10% palladium-carbon under hydrogen atmosphere in an appropriate solvent such as ethanol. Then, the resultant is reacted with the compound (II-1) and an appropriate condensing agent such as DCC/HOBt in an appropriate solvent such as DMF to thereby obtain a compound (II-12) which is a compound represented by the general formula (1).

PRODUCTION METHOD EXAMPLE 3

Figure 3:
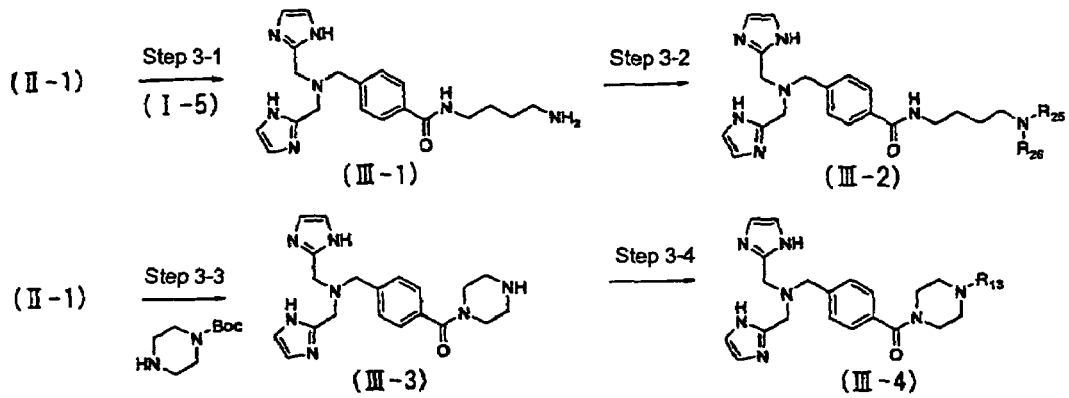

The reaction process steps of Production Method Example 3 are shown in FIG. 3.

Step 3-1

The compound (II-1) is reacted with the compound (I-5) and an appropriate condensing agent such as DCC/HOBt in an appropriate solvent such as DMF and then deprotected by reaction with an appropriate acid such as hydrochloric acid in an appropriate solvent such as methanol to thereby obtain a compound (III-1).

Step 3-2

The compound (III-1) is reacted with easily obtainable aldehyde or ketone corresponding to $R_{25}$ and $R_{26}$ ($R_{25}$ and $R_{26}$ are as described above), an appropriate dehydrating agent such as trimethyl orthoformate, and an appropriate reductant such as sodium cyanoborohydride in an appropriate solvent such as DMF to thereby obtain a compound (III-2) which is a compound represented by the general formula (1).

Step 3-3

The compound (II-1) is reacted with commercially available 1-t-butoxycarbonyl-piperazine and an appropriate condensing agent such as WSCI/HOBt in an appropriate solvent such as DMF, and then deprotected by reaction with an appropriate acid such as hydrochloric acid in an appropriate solvent such as methanol to thereby obtain a compound (III-3).

Step 3-4

The compound (III-3) is reacted with easily obtainable aldehyde or ketone corresponding to $R_{13}$ ($R_{13}$ is as described above), an appropriate dehydrating agent such as trimethyl orthoformate, and an appropriate reductant such as sodium cyanoborohydride in an appropriate solvent such as DMF to thereby obtain a compound (III-4) which is a compound represented by the general formula (1).

PRODUCTION METHOD EXAMPLE 4

Figure 4:
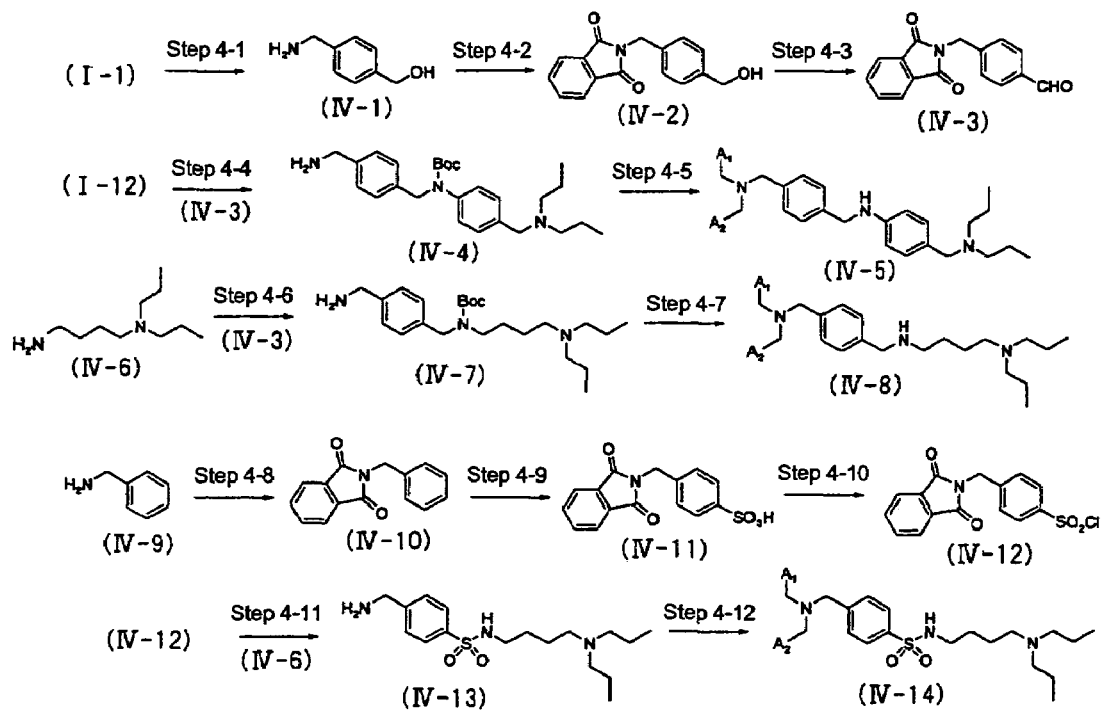

The reaction process steps of Production Method Example 4 are shown in FIG. 4.

Step 4-1

The compound (I-1) is reacted with an appropriate reductant such as lithium aluminum hydride in an appropriate solvent such as THF to thereby obtain a compound (IV-1).

Step 4-2

The compound (IV-1) is reacted with commercially available N-carbethoxyphthalimide and an appropriate base such as sodium carbonate in an appropriate solvent such as THF/water to thereby obtain a compound (IV-2).

Step 4-3

The compound (IV-2) is reacted with an appropriate oxidant such as manganese dioxide in an appropriate solvent such as chloroform to thereby obtain a compound (IV-3).

Step 4-4

The compound (I-12) is reacted with the compound (IV-3) and an appropriate reductant such as sodium cyanoborohydride in an appropriate solvent such as methanol and then t-butoxycarbonylated (hereinafter, butoxycarbonyl is referred to as Boc) by reaction with commercially available di-t-butyl dicarbonate, and an appropriate base such as triethylamine in an appropriate solvent such as DMF, and further reacted with an appropriate base such as an aqueous methylamine solution in an appropriate solvent such as methanol to thereby obtain a compound (IV-4).

Step 4-5

Easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with the compound (IV-4) and an appropriate reductant such as sodium cyanoborohydride in an appropriate solvent such as methanol, and then deprotected by reaction with an appropriate acid such as hydrochloric acid in an appropriate solvent such as methanol to thereby obtain a compound (IV-5) which is a compound represented by the general formula (1).

Step 4-6

A compound (IV-6), which is obtained by deprotecting the compound (I-6) with acid, is reacted with the compound (IV-3) and an appropriate reductant such as sodium cyanoborohydride in an appropriate solvent such as methanol, then t-butoxycarbonylated by reaction with commercially available di-t-butyl dicarbonate and an appropriate base such as triethylamine in an appropriate solvent such as DMF, and further reacted with an appropriate base such as an aqueous methylamine solution in an appropriate solvent such as methanol to thereby obtain a compound (IV-7).

Step 4-7

Easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with the compound (IV-7) and an appropriate reductant such as sodium cyanoborohydride in an appropriate solvent such as methanol, and then deprotected by reaction with an appropriate acid such as hydrochloric acid in an appropriate solvent such as methanol to thereby obtain a compound (IV-8) which is a compound represented by the general formula (1).

Step 4-8

A commercially available compound (IV-9) is reacted with commercially available N-carbethoxyphthalimide and an appropriate base such as sodium carbonate in an appropriate solvent such as water to thereby obtain a compound (IV-10).

Step 4-9

The compound (IV-10) is reacted with chlorosulfonic acid in an appropriate solvent such as chloroform to thereby obtain a compound (IV-11).

Step 4-10

The compound (IV-11) is reacted with phosphorous pentachloride, to thereby obtain a compound (IV-12).

Step 4-11

The compound (IV-12) is reacted with the compound (IV-6) and an appropriate base such as triethylamine in an appropriate solvent such as chloroform, and then reacted with an appropriate reductant such as an aqueous methylamine solution in an appropriate solvent such as methanol to thereby obtain a compound (IV-13).

Step 4-12

Easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with the compound (IV-13) and an appropriate reductant such as sodium cyanoborohydride in an appropriate solvent such as methanol to thereby obtain a compound (IV-14) which is a compound represented by the general formula (1).

PRODUCTION METHOD EXAMPLE 5

Figure 5:
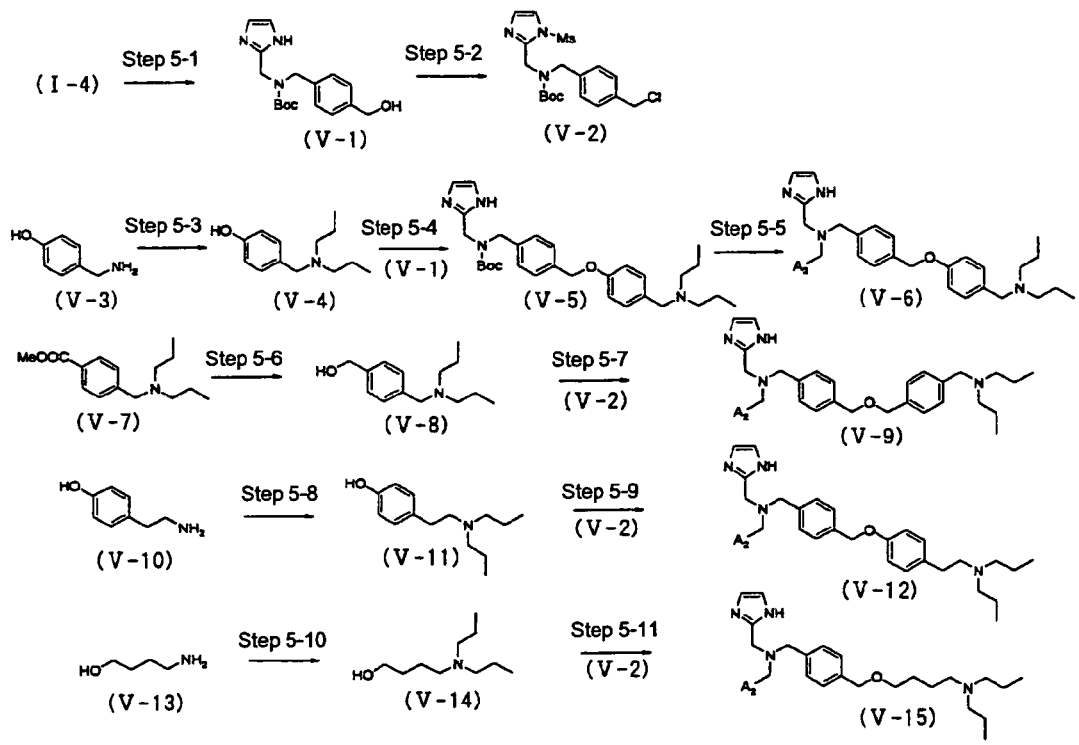

The reaction process steps of Production Method Example 5 are shown in FIG. 5.

Step 5-1

The compound (I-4) is esterified and then reacted with an appropriate reductant such as lithium aluminum hydride in an appropriate solvent such as THF to thereby obtain a compound (V-1).

Step 5-2

The compound (V-1) is reacted with commercially available methanesulfonyl chloride and an appropriate base such as diisopropylethylamine in an appropriate solvent such as dichloromethane to thereby obtain a compound (V-2).

Step 5-3

A commercially available compound (V-3) is reacted with commercially available propionaldehyde and an appropriate reductant such as sodium cyanoborohydride in an appropriate solvent such as methanol to thereby obtain a compound (V-4).

Step 5-4

The compound (V-4) is reacted with the compound (V-1) and an appropriate Mitsunobu reagent such as triphenylphosphine/diethylazodicarboxylate in an appropriate solvent such as THF to thereby obtain a compound (V-5).

Step 5-5

The compound (V-5) is deprotected by reaction with an appropriate acid such as hydrochloric acid in an appropriate solvent such as methanol. Then, the resultant is reacted with an easily obtainable aldehyde $A_2$-CHO ($A_2$ is as described above) and an appropriate reductant such as sodium cyanoborohydride in an appropriate solvent such as methanol to thereby obtain a compound (V-6) which is a compound represented by the general formula (1).

Step 5-6

A compound (V-7), which is obtained such that commercially available 4-aminomethylbenzoic acid is esterified and subjected to reductive condensation reaction with propionaldehyde, is reacted with an appropriate reductant such as lithium aluminum hydride in an appropriate solvent such as THF to thereby obtain a compound (V-8).

Step 5-7

The compound (V-8) is reacted with the compound (V-2) and an appropriate base such as potassium carbonate in an appropriate solvent such as DMF, then deprotected by reaction with an appropriate acid such as hydrochloric acid in an appropriate solvent such as methanol, and further reacted with easily obtainable aldehyde $A_2$-CHO ($A_2$ is as described above) and an appropriate reductant such as sodium cyanoborohydride in an appropriate solvent such as methanol to thereby obtain a compound (V-9) which is a compound represented by the general formula (1).

Step 5-8

A commercially available compound (V-10) is reacted with commercially available propionaldehyde and an appropriate reductant such as sodium cyanoborohydride in an appropriate solvent such as methanol to thereby obtain a compound (V-11).

Step 5-9

The compound (V-11) is reacted with the compound (V-2) and an appropriate base such as potassium carbonate in an appropriate solvent such as DMF, then deprotected by reaction with an appropriate acid such as hydrochloric acid in an appropriate solvent such as methanol, and further reacted with easily obtainable aldehyde $A_2$-CHO ($A_2$ is as described above) and an appropriate reductant such as sodium cyanoborohydride in an appropriate solvent such as methanol to thereby obtain a compound (V-12) which is a compound represented by the general formula (1).

Step 5-10

A commercially available compound (V-13) is reacted with commercially available propionaldehyde and an appropriate reductant such as sodium cyanoborohydride in an appropriate solvent such as methanol to thereby obtain a compound (V-14).

Step 5-11

The compound (V-14) is reacted with the compound (V-2) and an appropriate base such as potassium bicarbonate in an appropriate solvent such as dichloromethane, then deprotected by reaction with an appropriate acid such as hydrochloric acid in an appropriate solvent such as methanol, and further reacted with easily obtainable aldehyde $A_2$-CHO ($A_2$ is as described above) and an appropriate reductant such as sodium cyanoborohydride in an appropriate solvent such as methanol to thereby obtain a compound (V-15) which is a compound represented by the general formula (1).

PRODUCTION METHOD EXAMPLE 6

Figure 6:
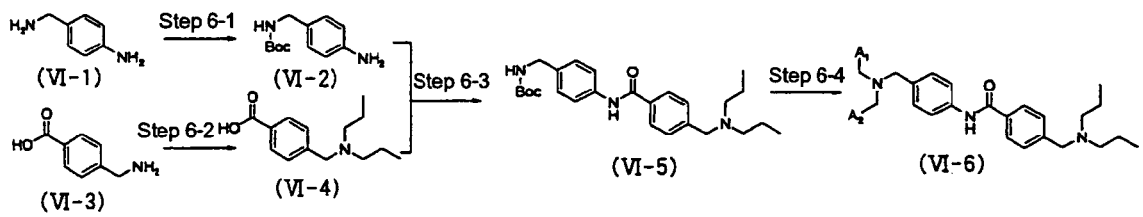

The reaction process steps of Production Method Example 6 are shown in FIG. 6.

Step 6-1

The commercially available compound (VI-1) is reacted with commercially available di-t-butyl dicarbonate and an appropriate base such as triethylamine in an appropriate solvent such as dichloromethane to thereby obtain a compound (VI-2).

Step 6-2

A commercially available compound (VI-3) is reacted with commercially available propionaldehyde, an appropriate dehydrating agent such as trimethyl orthoformate, and an appropriate reductant such as sodium cyanoborohydride in an appropriate solvent such as methanol to thereby obtain a compound (VI-4).

Step 6-3

The compound (VI-2) is reacted with the compound (VI-4) and an appropriate condensing agent such as WSCI/HOBt in an appropriate solvent such as DMF to thereby obtain a compound (VI-5).

Step 6-4

A compound (VI-5) is deprotected by reaction with an appropriate acid such as hydrochloric acid in an appropriate solvent such as methanol, and then easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with an appropriate reductant such as sodium cyanoborohydride in an appropriate solvent such as methanol to thereby obtain a compound (VI-6) which is a compound represented by the general formula (1).

PRODUCTION METHOD EXAMPLE 7

Figure 7:
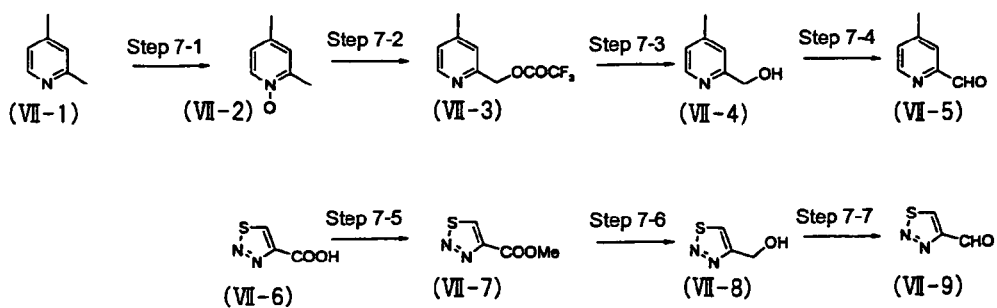

The reaction process steps of Production Method Example 7 are shown in FIG. 7.

Step 7-1

A commercially available compound (VII-1) is reacted with an appropriate oxidant such as m-chloroperbenzoic acid in an appropriate solvent such as dichloromethane to thereby obtain a compound (VII-2).

Step 7-2

The compound (VII-2) is reacted with trifluoroacetic anhydride in an appropriate solvent such as dichloromethane to thereby obtain a compound (VII-3).

Step 7-3

The compound (VII-3) is reacted with an appropriate base such as sodium methoxide in an appropriate solvent such as methanol to thereby obtain a compound (VII-4).

Step 7-4

The compound (VII-4) is reacted with an appropriate oxidant such as manganese dioxide in an appropriate solvent such as chloroform to thereby obtain a compound (VII-5) which is raw material aldehyde $A_2$-CHO ($A_2$ is as described above).

Step 7-5

A commercially available compound (VII-6) is esterified to thereby obtain a compound (VII-7).

Step 7-6

The compound (VII-7) is reacted with an appropriate reductant such as sodium borohydride in an appropriate solvent such as ethanol/THF to thereby obtain a compound (VII-8).

Step 7-7

The compound (VII-8) is reacted with an appropriate oxidant such as manganese dioxide in an appropriate solvent such as chloroform to thereby obtain a compound (VII-9) which is raw material aldehyde $A_1$-CHO ($A_1$ is as described above).

PRODUCTION METHOD EXAMPLE 8

Figure 8:
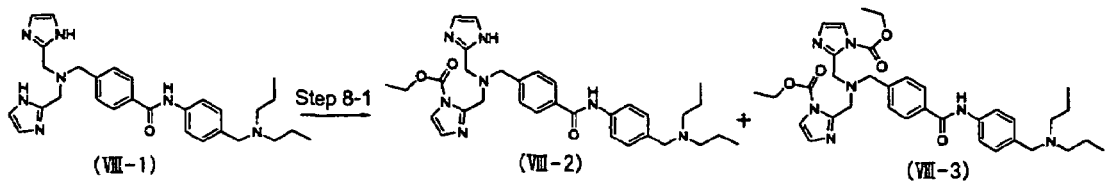

The reaction process steps of Production Method Example 8 are shown in FIG. 8.

Step 8-1

A compound (VIII-1) is reacted with a prodrug reagent such as ethyl chloroformate and an appropriate base such as triethylamine in an appropriate solvent such as chloroform to thereby obtain a compound (VIII-2) and a compound (VIII-3), which are the compounds represented by the general formula (1) and prodrugs.

PRODUCTION METHOD EXAMPLE 9

Figure 9:
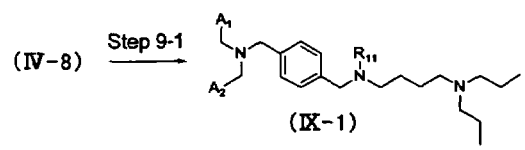

The reaction process steps of Production Method Example 9 are shown in FIG. 9.

Step 9-1

A compound (IV-8) is reacted with easily obtainable aldehyde $R_{11}$—CHO ($R_{11}$ is as described above) and an appropriate reductant such as sodium cyanoborohydride in an appropriate solvent such as methanol to thereby obtain a compound (IX-1) which is a compound represented by the general formula (1).

PRODUCTION METHOD EXAMPLE 10

Figure 10:
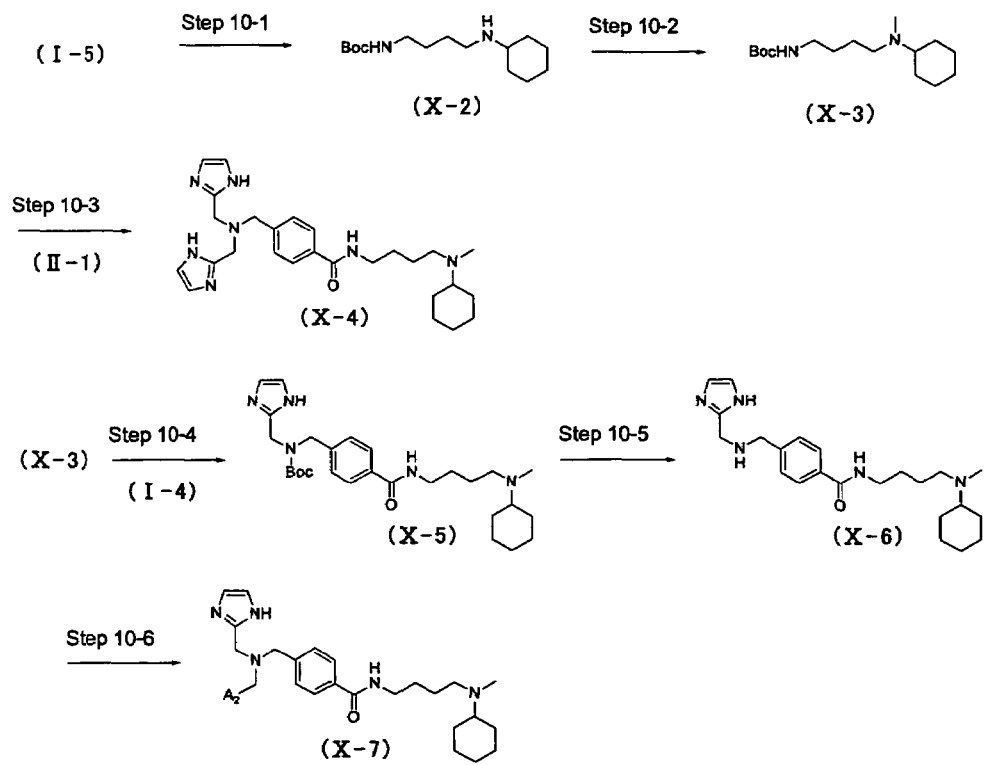

The reaction process steps of Production Method Example 10 are shown in FIG. 10.

Step 10-1

A commercially available compound (I-5) is reacted with commercially available cyclohexane and an appropriate reductant such as sodium cyanoborohydride in an appropriate solvent such as methanol to thereby obtain a compound (X-2).

Step 10-2

The compound (X-2) is reacted with a commercially available aqueous formaldehyde solution and an appropriate reductant such as sodium cyanoborohydride in an appropriate solvent such as methanol to thereby obtain a compound (X-3).

Step 10-3

The compound (X-3) is deprotected by reaction with an appropriate acid such as a hydrogen chloride/dioxane solution in an appropriate solvent such as methanol, and then reacted with the compound (II-1) and an appropriate condensing agent such as WSCI/HOBt in an appropriate solvent such as DMF to thereby obtain a compound (X-4).

Step 10-4

The compound (X-3) is deprotected by reaction with an appropriate acid such as a hydrogen chloride/dioxane solution in an appropriate solvent such as methanol, and then reacted with the compound (I-4) and an appropriate condensing agent such as WSCI/HOBt in an appropriate solvent such as chloroform to thereby obtain a compound (X-5).

Step 10-5

The compound (X-5) is reacted with an appropriate acid such as a hydrogen chloride/dioxane solution in an appropriate solvent such as methanol to thereby obtain a compound (X-6).

Step 10-6

The compound (X-6) is reacted with easily obtainable aldehyde $A_2$-CHO ($A_2$ is as described above) and an appropriate reductant such as sodium cyanoborohydride in an appropriate solvent such as methanol to thereby obtain a compound (X-7) which is a compound represented by the general formula (1).

PRODUCTION METHOD EXAMPLE 11

Figure 11:
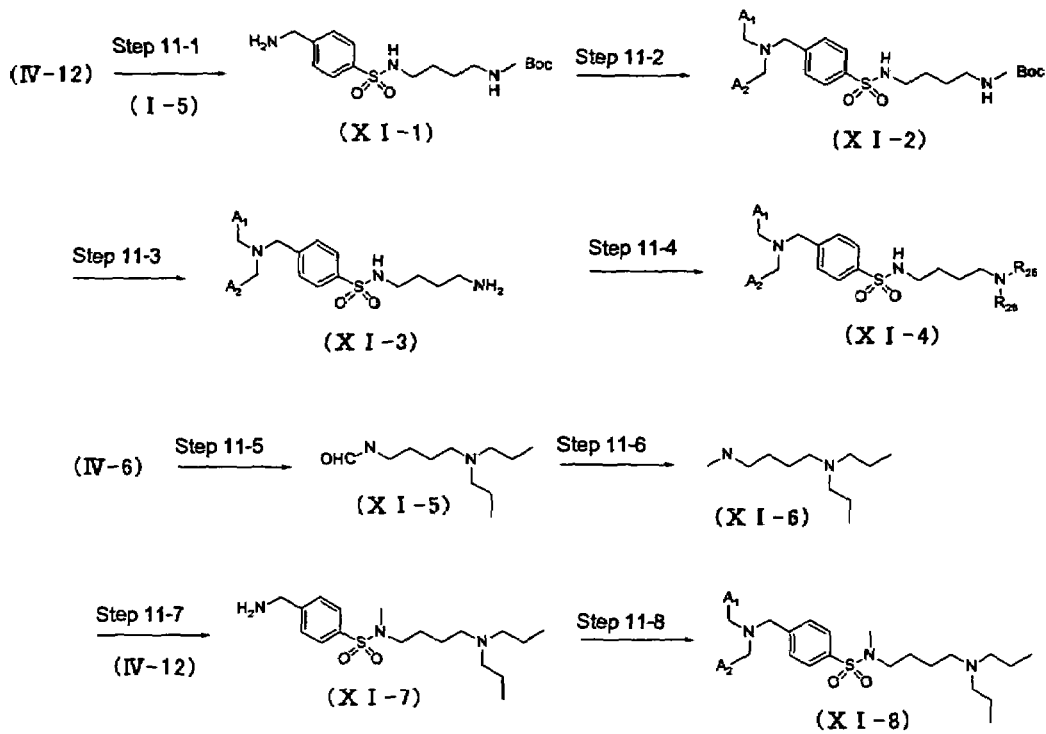

The reaction process steps of Production Method Example 11 are shown in FIG. 11.

Step 11-1

The compound (IV-12) is reacted with the compound (I-5) and an appropriate base such as triethylamine in an appropriate solvent such as chloroform, and then further reacted with an appropriate base such as methylamine in an appropriate solvent such as methanol to thereby obtain a compound (XI-1).

Step 11-2

Easily obtainable aldehyde $A_1$-CHO when $A_1$ and $A_2$ are identical or easily obtainable aldehydes $A_1$-CHO and $A_2$-CHO when $A_1$ and $A_2$ are not identical ($A_1$ and $A_2$ are as described above) is/are separately one after another reacted with the compound (XI-1) and an appropriate reductant such as sodium cyanoborohydride in an appropriate solvent such as methanol to thereby obtain a compound (XI-2) which is a compound represented by the general formula (1).

Step 11-3

The compound (XI-2), which is a compound represented by the general formula (1), is reacted with an appropriate acid such as a hydrogen chloride/dioxane solution in an appropriate solvent such as methanol to thereby obtain a compound (XI-3) which is a compound represented by the general formula (1).

Step 11-4

The compound (XI-3) which is a compound represented by the general formula (1) is reacted with an easily obtainable aldehyde or ketone corresponding to $R_{25}$ and $R_{26}$ ($R_{25}$ and $R_{26}$ are as described above), and an appropriate reductant such as sodium cyanoborohydride in an appropriate solvent such as methanol to thereby obtain a compound (XI-4) which is a compound represented by the general formula (1).

Step 11-5

A compound (IV-6), which is prepared by deprotecting the compound (I-6) with acid, is reacted with a formylating agent such as a mixture of formic acid and acetic anhydride in an appropriate solvent such as THF to thereby obtain a compound (XI-5).

Step 11-6

The compound (XI-5) is reacted with an appropriate reductant such as lithium aluminum hydride in an appropriate solvent such as THF to thereby obtain a compound (XI-6).

Step 11-7

The compound (XI-6) is reacted with the compound (IV-12) and an appropriate base such as triethylamine in an appropriate solvent such as chloroform, and then reacted with an appropriate reductant such as an aqueous methylamine solution in an appropriate solvent such as methanol to thereby obtain a compound (XI-7).

Step 11-8

Easily obtainable aldehyde $A_1$-CHO when $A_1$ and $A_2$ are identical or easily obtainable aldehydes $A_1$-CHO and $A_2$-CHO when $A_1$ and $A_2$ are not identical ($A_1$ and $A_2$ are as described above) is/are separately one after another reacted with the compound (XI-7) and an appropriate reductant such as sodium cyanoborohydride in an appropriate solvent such as methanol to thereby obtain a compound (XI-8) which is a compound represented by the general formula (1).

PRODUCTION METHOD EXAMPLE 12

Figure 12:
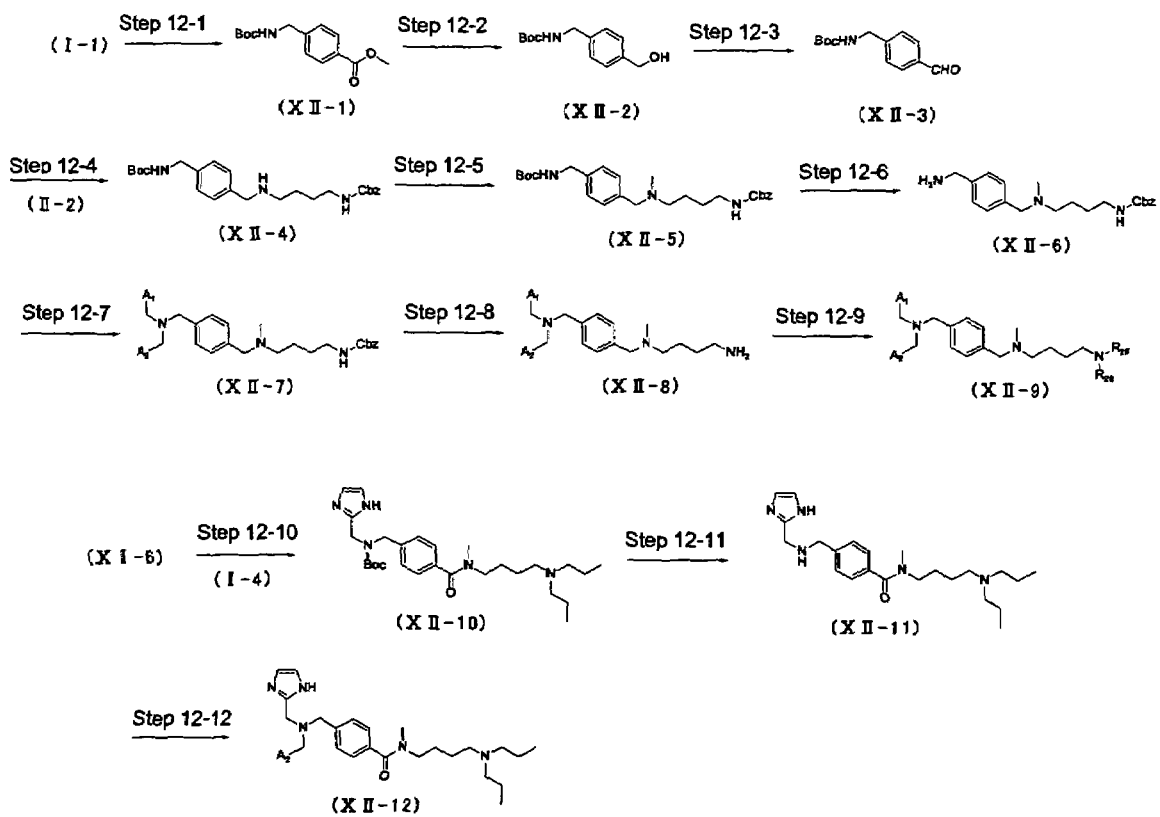

The reaction process steps of Production Method Example 12 are shown in FIG. 12.

Step 12-1

The easily obtainable compound (I-1) is reacted with commercially available di-t-butyl dicarbonate and an appropriate base such as triethylamine in an appropriate solvent such as chloroform to thereby obtain a compound (XII-1).

Step 12-2

The compound (XII-1) is reacted with an appropriate reductant such as lithium aluminum hydride in an appropriate solvent such as THF to thereby obtain a compound (XII-2).

Step 12-3

The compound (XII-2) is reacted with an appropriate oxidant such as manganese dioxide in an appropriate solvent such as chloroform to thereby obtain a compound (XII-3).

Step 12-4

The compound (XII-3) is reacted with the compound (II-2), an appropriate dehydrating agent such as trimethyl orthoformate, and an appropriate reductant such as sodium borohydride in an appropriate solvent such as methanol to thereby obtain a compound (XII-4).

Step 12-5

The compound (XII-4) is reacted with an aqueous formaldehyde solution and an appropriate reductant such as sodium cyanoborohydride in an appropriate solvent such as methanol to thereby obtain a compound (XII-5).

Step 12-6

The compound (XII-5) is reacted with an appropriate acid such as a hydrogen chloride/dioxane solution in an appropriate solvent such as methanol, to thereby obtain a compound (XII-6).

Step 12-7

Easily obtainable aldehyde $A_1$-CHO when $A_1$ and $A_2$ are identical or easily obtainable aldehydes $A_1$-CHO and $A_2$-CHO when $A_1$ and $A_2$ are not identical ($A_1$ and $A_2$ are as described above) is/are separately one after another reacted with the compound (XII-6) and an appropriate reductant such as sodium cyanoborohydride in an appropriate solvent such as methanol to thereby obtain a compound (XII-7) which is a the compound represented by the general formula (1).

Step 12-8

The compound (XII-7) which is a compound represented by the general formula (1) is reacted with an appropriate reductant such as 10% palladium-carbon under a hydrogen atmosphere in an appropriate solvent such as ethanol to thereby obtain a compound (XII-8) which is a compound represented by the general formula (1).

Step 12-9

The compound (XII-8) which is a compound represented by the general formula (1) is reacted with an easily obtainable aldehyde or ketone corresponding to $R_{25}$ and $R_{26}$ ($R_{25}$ and $R_{26}$ are as described above), and an appropriate reductant such as sodium cyanoborohydride in an appropriate solvent such as methanol to thereby obtain a compound (XII-9) which is a compound represented by the general formula (1).

Step 12-10

The compound (XI-6) is reacted with the compound (I-4) and an appropriate condensing agent such as WSCI/HOBt in an appropriate solvent such as chloroform to thereby obtain a compound (XII-10).

Step 12-11

The compound (XII-10) is reacted with an appropriate acid such as a hydrogen chloride/dioxane solution in an appropriate solvent such as methanol to thereby obtain a compound (XII-11).

Step 12-12

The compound (XII-11) is reacted with an easily obtainable aldehyde $A_2$-CHO ($A_2$ is as described above) and an appropriate reductant such as sodium cyanoborohydride in an appropriate solvent such as methanol to thereby obtain a compound (XII-12) which is a compound represented by the general formula (1).

PRODUCTION METHOD EXAMPLE 13

Figure 13:
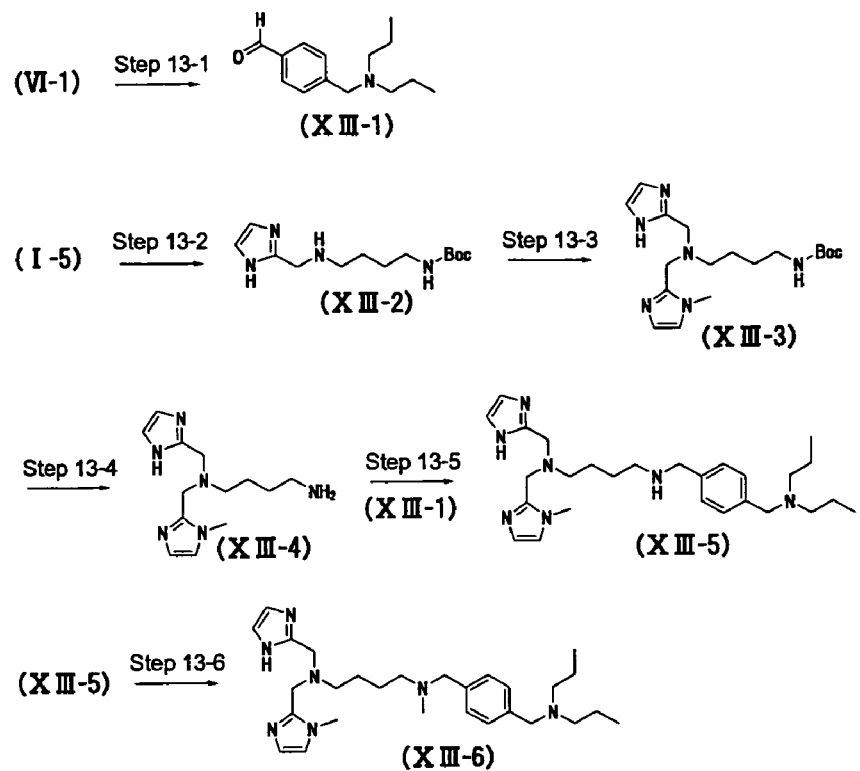

The reaction process steps of Production Method Example 13 are shown in FIG. 13.

Step 13-1

The compound (VI-1) is reacted with an appropriate oxidant such as manganese dioxide in an appropriate solvent such as dichloromethane, to thereby obtain a compound (XIII-1).

Step 13-2

The compound (I-5) is reacted with commercially available 2-imidazole carboxaldehyde, an appropriate dehydrating agent such as trimethyl orthoformate, and an appropriate reductant such as sodium borohydride in an appropriate solvent such as methanol to thereby obtain a compound (XIII-2).

Step 13-3

The compound (XIII-2) is reacted with commercially available 1-methyl-2-imidazole carboxaldehyde, an appropriate acid such as acetic acid, and an appropriate reductant such as sodium cyanoborohydride in an appropriate solvent such as methanol to thereby obtain a compound (XIII-3).

Step 13-4

The compound (XIII-3) is reacted with an appropriate acid such as hydrochloric acid in an appropriate solvent such as methanol to thereby obtain a compound (XIII-4).

Step 13-5

The compound (XIII-4) is reacted with the compound (XIII-1), an appropriate dehydrating agent such as trimethyl orthoformate and an appropriate reductant such as sodium borohydride in an appropriate solvent such as methanol to thereby obtain a compound (XIII-5).

Step 13-6

The compound (XIII-5) is reacted with a commercially available aqueous formaldehyde solution, an appropriate dehydrating agent such as trimethyl orthoformate, and an appropriate reductant such as sodium borohydride in an appropriate solvent such as methanol to thereby obtain a compound (XIII-6) which is a compound represented by the general formula (1).

PRODUCTION METHOD EXAMPLE 14

Figure 14:
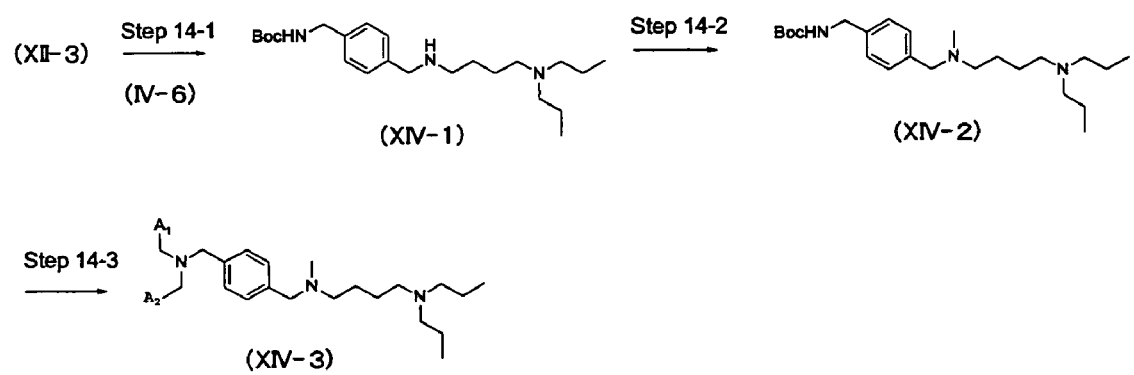

The reaction process steps of Production Method Example 14 are shown in FIG. 14.

Step 14-1

The compound (IV-6), which is prepared by deprotecting the compound (I-6) with acid, is reacted with the compound (XII-3), an appropriate dehydrating agent such as trimethyl orthoformate and an appropriate reductant such as sodium borohydride in an appropriate solvent such as methanol to thereby obtain a compound (XIV-1).

Step 14-2

The compound (XIV-1) is reacted with an aqueous formaldehyde solution and an appropriate reductant such as sodium cyanoborohydride in an appropriate solvent such as methanol to thereby obtain a compound (XIV-2).

Step 14-3

The compound (XIV-2) is deprotected by a reaction with an appropriate acid such as a hydrogen chloride/dioxane solution, and then easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with an appropriate reductant such as sodium cyanoborohydride in an appropriate solvent such as methanol to thereby obtain a compound (XIV-3) which is a compound represented by the general formula (1).

PRODUCTION METHOD EXAMPLE 15

Figure 15:
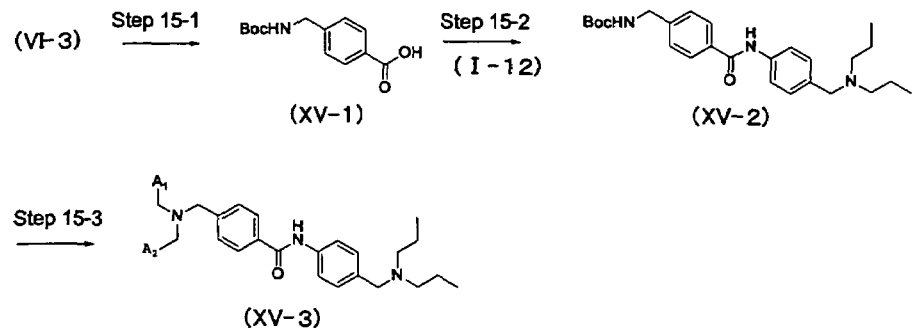

The reaction process steps of Production Method Example 15 are shown in FIG. 15.

Step 15-1

The commercially available compound (VI-3) is reacted with di-t-butyl dicarbonate and an appropriate base such as a sodium hydroxide aqueous solution in an appropriate solvent such as dioxane to thereby obtain a compound (XV-1).

Step 15-2

The compound (XV-1) is reacted with the compound (I-12) and an appropriate condensing agent such as WSCI in an appropriate solvent such as chloroform, to thereby obtain a compound (XV-2).

Step 15-3

The compound (XV-2) is deprotected by a reaction with an appropriate acid such as a hydrogen chloride/dioxane solution, and then easily obtainable aldehyde $A_1$-CHO when $A_1$ and $A_2$ are identical or easily obtainable $A_1$-CHO and $A_2$-CHO when $A_1$ and $A_2$ are not identical ($A_1$ and $A_2$ are as described above) is/are separately one after another reacted with an appropriate reductant such as sodium cyanoborohydride in an appropriate solvent such as methanol to thereby obtain a compound (XV-3) which is a compound represented by the general formula (1).

PRODUCTION METHOD EXAMPLE 16

Figure 16:
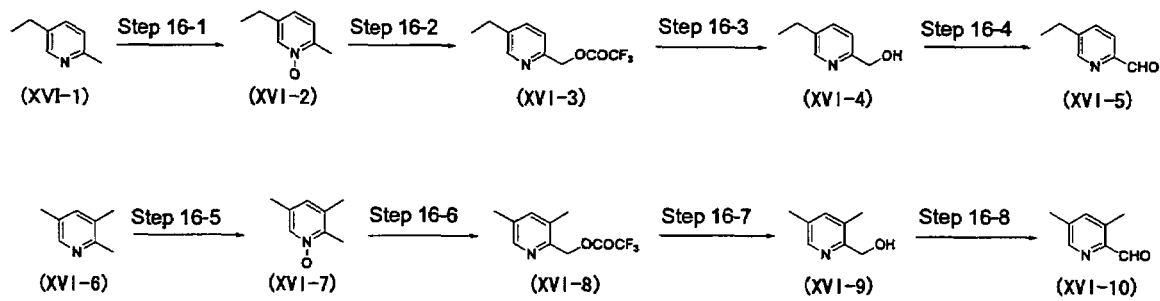

The reaction process steps of Production Method Example 16 are shown in FIG. 16.

Step 16-1

A commercially available compound (XVI-1) is reacted with an appropriate oxidant such as meta-chloroperbenzoic acid in an appropriate solvent such as dichloromethane to thereby obtain a compound (XVI-2).

Step 16-2

The compound (XVI-2) is reacted with trifluoroacetic anhydride in an appropriate solvent such as dichloromethane to thereby obtain a compound (XVI-3).

Step 16-3

The compound (XVI-3) is reacted with an appropriate base such as sodium methoxide in an appropriate solvent such as methanol to thereby obtain a compound (XVI-4).

Step 16-4

The compound (XVI-4) is reacted with an appropriate oxidant such as manganese dioxide in an appropriate solvent such as chloroform to thereby obtain a compound (XVI-5) which is raw material aldehyde $A_2$-CHO ($A_2$ is as described above).

Step 16-5

A commercially available compound (XVI-6) is reacted with an appropriate oxidant such as meta-chloroperbenzoic acid in an appropriate solvent such as dichloromethane to thereby obtain a compound (XVI-7).

Step 16-6

The compound (XVI-7) is reacted with trifluoroacetic anhydride in an appropriate solvent such as dichloromethane to thereby obtain a compound (XVI-8).

Step 16-7

The compound (XVI-8) is reacted with an appropriate base such as sodium methoxide in an appropriate solvent such as methanol to thereby obtain a compound (XVI-9).

Step 16-8

The compound (XVI-9) is reacted with an appropriate oxidant such as manganese dioxide in an appropriate solvent such as chloroform to thereby obtain a compound (XVI-10) which is raw material aldehyde $A_1$-CHO ($A_1$ is as described above).

PRODUCTION METHOD EXAMPLE 17

Figure 17:
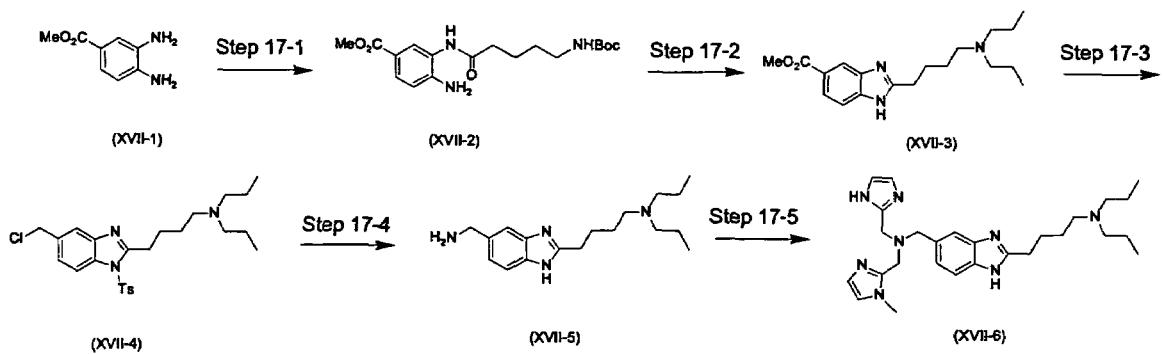

The reaction process steps of Production Method Example 17 are shown in FIG. 17.

Step 17-1

An easily obtainable compound (XVII-1) is reacted with 5-t-butoxycarbonylaminovaleric acid, an appropriate condensing agent and catalyst such as WSCI or HOBt in an appropriate solvent such as DMF to thereby obtain a compound (XVII-2).

Step 17-2

The compound (XVII-2) is reacted in an appropriate solvent such as methanol in the presence of an appropriate acid such as hydrochloric acid. Then, the resultant is reacted with propionaldehyde, an appropriate reductant such as sodium cyanoborohydride, and an appropriate dehydrating agent such as trimethyl orthoformate in an appropriate solvent such as methanol to thereby obtain a compound (XVII-3).

Step 17-3

The compound (XVII-3) is reacted with an appropriate reductant such as lithium aluminum hydride in an appropriate solvent such as THF, and then reacted with p-toluenesulfonyl chloride and an appropriate base such as triethylamine in an appropriate solvent such as dichloromethane to thereby obtain a compound (XVII-4).

Step 17-4

The compound (XVII-4) is reacted with potassium phthalimide in an appropriate solvent such as DMF, and then reacted with an appropriate base such as methylamine in an appropriate solvent such as methanol to thereby obtain a compound (XVII-5).

Step 17-5

The compound (XVII-5) is reacted with commercially available 2-imidazole carboxaldehyde, an appropriate reductant such as sodium borohydride, and an appropriate dehydrating agent such as trimethyl orthoformate in an appropriate solvent such as methanol, and then reacted with commercially available 1-methyl-2-imidazole carboxaldehyde, an appropriate reductant such as sodium borohydride, and an appropriate dehydrating agent such as trimethyl orthoformate or an appropriate acid catalyst such as acetic acid in an appropriate solvent such as methanol to thereby obtain a compound (XVII-6) which is a compound represented by the general formula (1).

PRODUCTION METHOD EXAMPLE 18

Figure 18:
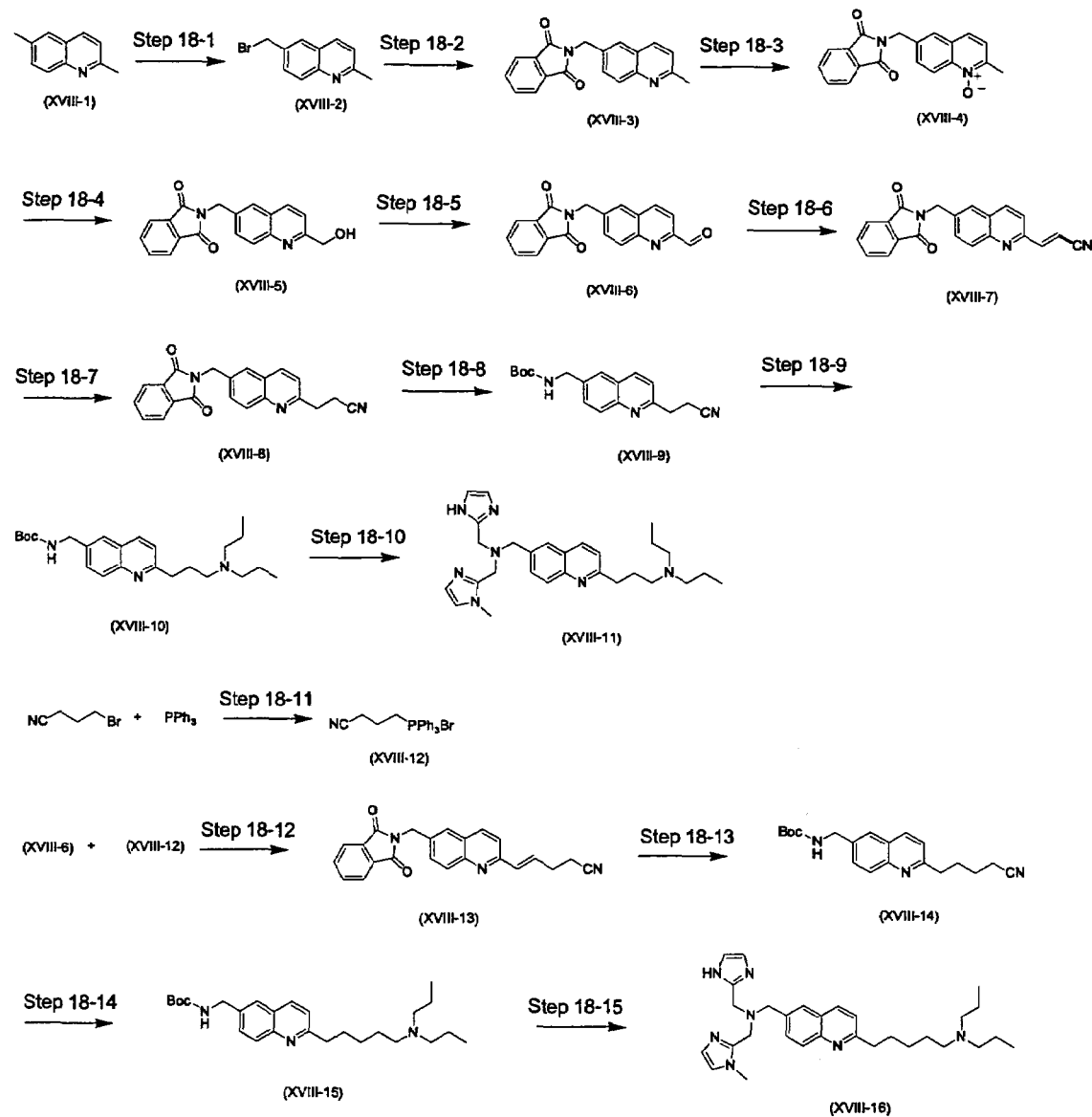

The reaction process steps of Production Method Example 18 are shown in FIG. 18.

Step 18-1

A commercially available compound (XVIII-1) is reacted with N-bromosuccinimide and an appropriate radical generator such as azobisisobutyronitrile in an appropriate solvent such as carbon tetrachloride to thereby obtain a compound (XVIII-2).

Step 18-2

The compound (XVIII-2) is reacted with potassium phthalimide in an appropriate solvent such as DMF to thereby obtain a compound (XVIII-3).

Step 18-3

The compound (XVIII-3) is reacted with an appropriate oxidant such as meta-chloroperbenzoic acid in an appropriate solvent such as chloroform, resulting in a compound (XVIII-4).

Step 18-4

The compound (XVIII-4) is reacted with appropriate acid anhydride such as trifluoroacetic anhydride in an appropriate solvent such as dichloromethane, and then reacted with an appropriate base such as sodium hydrogen carbonate in an appropriate solvent such as methanol to thereby obtain a compound (XVIII-5).

Step 18-5

The compound (XVIII-5) is reacted with an appropriate oxidant such as manganese dioxide in an appropriate solvent such as chloroform to thereby obtain a compound (XVIII-6).

Step 18-6

The compound (XVIII-6) is reacted with triphenyl phosphonylideneacetonitrile in an appropriate solvent such as THF to thereby obtain a compound (XVIII-7).

Step 18-7

The compound (XVIII-7) is reacted, under hydrogen atmosphere, with an appropriate catalyst such as palladium hydroxide-carbon in an appropriate solvent such as ethanol to thereby obtain a compound (XVIII-8).

Step 18-8

The compound (XVIII-8) is reacted with an appropriate base such as methylamine in an appropriate solvent such as methanol, and then reacted with di-t-butyl dicarbonate and an appropriate base such as triethylamine to thereby obtain a compound (XVIII-9).

Step 18-9

The compound (XVIII-9) is reacted with an appropriate reductant such as lithium aluminum hydride in an appropriate solvent such as THF, and then reacted with propionaldehyde, an appropriate reductant such as sodium cyanoborohydride, and an appropriate dehydrating agent such as trimethyl orthoformate in an appropriate solvent such as methanol to thereby obtain a compound (XVIII-10).

Step 18-10

The compound (XVIII-10) is reacted in an appropriate solvent such as methanol in the presence of an appropriate acid such as hydrochloric acid. Then, it is reacted with commercially available 2-imidazole carboxaldehyde, an appropriate reductant such as sodium borohydride, and an appropriate dehydrating agent such as trimethyl orthoformate in an appropriate solvent such as methanol. Subsequently, the resultant was reacted with commercially available 1-methyl-2-imidazole carboxaldehyde, an appropriate reductant such as sodium borohydride, an appropriate dehydrating agent, and appropriate acid catalyst such as acetic acid in an appropriate solvent such as methanol to thereby obtain a compound (XVIII-11) which is a compound represented by the general formula (1).

Step 18-11

A commercially available compound, 4-bromobutyronitrile is reacted with triphenylphosphine in an appropriate solvent such as toluene to thereby obtain a compound (XVIII-12).

Step 18-12

The above compound (XVIII-6) is reacted with the compound (XVIII-12) and an appropriate base such as lithium diisopropylamide in an appropriate solvent such as THF to thereby obtain a compound (XVIII-13).

Step 18-13

The compound (XVIII-13) is reacted with an appropriate base such as methylamine in an appropriate solvent such as methanol, and then reacted with di-t-butyl dicarbonate and an appropriate base such as triethylamine. Subsequently, under hydrogen atmosphere, the resultant is reacted with an appropriate catalyst such as palladium hydroxide in an appropriate solvent such as ethanol to thereby obtain a compound (XVIII-14).

Step 18-14

The compound (XVIII-14) is reacted with an appropriate reductant such as lithium aluminum hydride in an appropriate solvent such as THF, and then reacted with propionaldehyde, an appropriate reductant such as sodium cyanoborohydride, and an appropriate dehydrating agent such as trimethyl orthoformate in an appropriate solvent such as methanol to thereby obtain a compound (XVIII-15).

Step 18-15

The compound (XVIII-15) is reacted in an appropriate solvent such as methanol in the presence of an appropriate acid such as hydrochloric acid.

Then, the resultant is reacted with commercially available 2-imidazole carboxaldehyde, an appropriate reductant such as sodium borohydride, and an appropriate dehydrating agent such as trimethyl orthoformate in an appropriate solvent such as methanol.

Subsequently, the resultant was reacted with commercially available 1-methyl-2-imidazole carboxaldehyde, an appropriate reductant such as sodium borohydride, an appropriate dehydrating agent, and appropriate acid catalyst such as acetic acid in an appropriate solvent such as methanol to thereby obtain a compound (XVIII-16) which is a compound represented by the general formula (1).

PRODUCTION METHOD EXAMPLE 19

Figure 19:
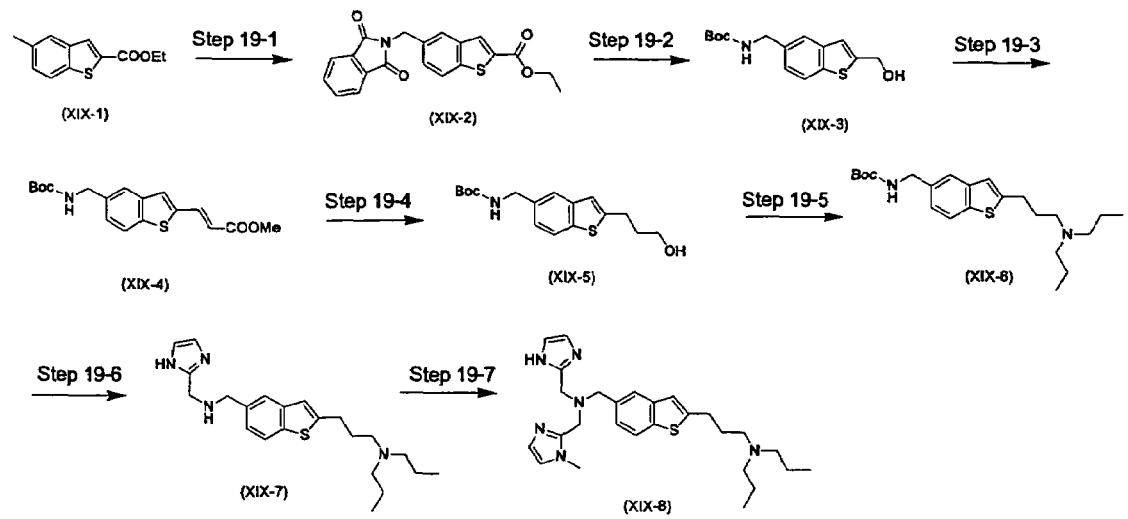

The reaction process steps of Production Method Example 19 are shown in FIG. 19.

Step 19-1

A known compound (XIX-1) is reacted with N-bromo-succinimide, an appropriate radical generator such as azobisisobutyronitrile in an appropriate solvent such as carbon tetrachloride, and then reacted with potassium phthalimide in an appropriate solvent such as DMF to thereby obtain a compound (XIX-2).

Step 19-2

The compound (XIX-2) is reacted with an appropriate base such as methylamine in an appropriate solvent such as methanol, then reacted with di-t-butyl dicarbonate and an appropriate base such as triethylamine. Subsequently, the resultant is reacted with an appropriate reductant such as lithium aluminum hydride in an appropriate solvent such as THF to thereby obtain a compound (XIX-3).

Step 19-3

The compound (XIX-3) is reacted with an appropriate oxidant such as manganese dioxide in an appropriate solvent such as chloroform, and then reacted with methyl triphenylphosphoranylideneacetate in an appropriate solvent such as THF to thereby obtain a compound (XIX-4).

Step 19-4

The compound (XIX-4) is reacted under a hydrogen atmosphere with an appropriate catalyst such as palladium-carbon in an appropriate solvent such as a chloroform-methanol mixture solvent, and then reacted with an appropriate reductant such as lithium aluminum hydride in an appropriate solvent such as THF to thereby obtain a compound (XIX-5).

Step 19-5

The compound (XIX-5) is reacted with an appropriate oxidant such as Dess-Martin periodinane in an appropriate solvent such as dichloromethane. Then, the resultant is reacted with dipropylamine, an appropriate reductant such as sodium cyanoborohydride, and an appropriate dehydrating agent such as trimethyl orthoformate in an appropriate solvent such as methanol to thereby obtain a compound (XIX-6).

Step 19-6

The compound (XIX-6) is reacted with an appropriate acid catalyst such as hydrochloric acid in an appropriate solvent such as dioxane, and then reacted with commercially available 2-imidazole carboxaldehyde, an appropriate reductant such as sodium borohydride, and an appropriate dehydrating agent such as trimethyl orthoformate in an appropriate solvent such as methanol to thereby obtain a compound (XIX-7).

Step 19-7

The compound (XIX-7) is reacted with commercially available 1-methyl-2-imidazole carboxaldehyde, an appropriate reductant such as sodium borohydride, an appropriate dehydrating agent, and an appropriate acid catalyst such as acetic acid in an appropriate solvent such as methanol to thereby obtain a compound (XIX-8) which is a compound represented by the general formula (1).

PRODUCTION METHOD EXAMPLE 20

Figure 20:
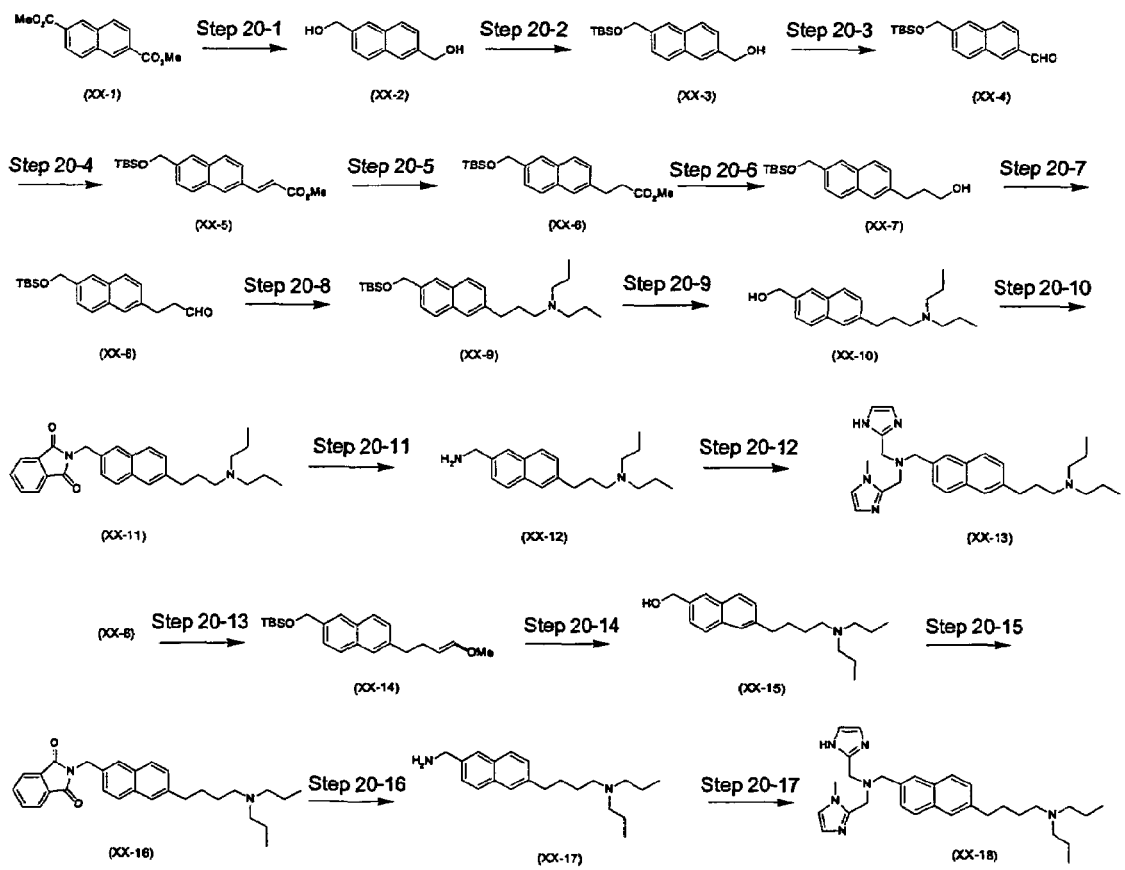

The reaction process steps of Production Method Example 20 are shown in FIG. 20.

Step 20-1

A commercially available compound (XX-1) is reacted with an appropriate reductant such as lithium aluminum hydride in an appropriate solvent such as THF to thereby obtain a compound (XX-2).

Step 20-2

The compound (XX-2) is reacted with t-butyldimethylsilyl chloride and an appropriate base such as imidazole in an appropriate solvent such as DMF to thereby obtain a compound (XX-3).

Step 20-3

The compound (XX-3) is reacted with an appropriate oxidant such as manganese dioxide in an appropriate solvent such as chloroform to thereby obtain a compound (XX-4).

Step 20-4

The compound (XX-4) is reacted with methyl triphenylphosphoranylideneacetate in an appropriate solvent such as THF, to thereby obtain a compound (XX-5).

Step 20-5

The compound (XX-5) is reacted, under hydrogen atmosphere, with an appropriate catalyst such as palladium black in an appropriate solvent such as benzene to thereby obtain a compound (XX-6).

Step 20-6

The compound (XX-6) is reacted with an appropriate reductant such as lithium aluminum hydride in an appropriate solvent such as THF to thereby obtain a compound (XX-7).

Step 20-7

The compound (XX-7) is reacted with an appropriate oxidant such as Dess-Martin periodinane in an appropriate solvent such as dichloromethane, to thereby obtain a compound (XX-8).

Step 20-8

The compound (XX-8) is reacted with dipropylamine, an appropriate reductant such as sodium cyanoborohydride, and an appropriate dehydrating agent such as trimethyl orthoformate in an appropriate solvent such as methanol to thereby obtain a compound (XX-9).

Step 20-9

The compound (XX-9) is reacted with an appropriate deprotecting agent such as tetrabutylammonium fluoride (hereinafter, referred to as TBAF) in an appropriate solvent such as THF to thereby obtain a compound (XX-10).

Step 20-10

The compound (XX-10) is reacted with phthalimide, an appropriate dehydrating agent such as triphenylphosphine and diethyl azodicarboxylate in an appropriate solvent to thereby obtain a compound (XX-11).

Step 20-11

The compound (XX-11) is reacted with an appropriate base such as methylamine in an appropriate solvent such as methanol to thereby obtain a compound (XX-12).

Step 20-12

The compound (XX-12) is reacted with commercially available 2-imidazole carboxaldehyde, an appropriate reductant such as sodium borohydride, and an appropriate dehydrating agent such as trimethyl orthoformate in an appropriate solvent such as methanol. Then, the resultant is reacted with commercially available 1-methyl-2-imidazole carboxaldehyde, an appropriate reductant such as sodium borohydride, and an appropriate acid catalyst such as acetic acid in an appropriate solvent such as methanol to thereby obtain a compound (XX-13) which is a compound represented by the general formula (1).

Step 20-13

Methoxymethyltriphenylphosphonium chloride is reacted with an appropriate base such as lithium diisopropylamide in an appropriate solvent such as THF. Then, the resulting reaction mixture is added and reacted with the above compound (XX-8) to thereby obtain a compound (XX-14).

Step 20-14

The compound (XX-14) is reacted with an appropriate acid catalyst such as acetic acid in an appropriate solvent such as methanol, and then reacted with dipropylamine, an appropriate reductant such as sodium cyanoborohydride, and an appropriate dehydrating agent such as trimethyl orthoformate in an appropriate solvent such as methanol to thereby obtain a compound (XX-15).

Step 20-15

The compound (XX-15) is reacted with phthalimide and an appropriate dehydrating agent such as triphenylphosphine and diethyl azodicarboxylate in an appropriate solvent to thereby obtain a compound (XX-16).

Step 20-16

The compound (XX-16) is reacted with an appropriate base such as methylamine in an appropriate solvent such as methanol to thereby obtain a compound (XX-17).

Step 20-17

The compound (XX-17) is reacted with commercially available 2-imidazole carboxaldehyde, an appropriate reductant such as sodium borohydride, and an appropriate dehydrating agent such as trimethyl orthoformate in an appropriate solvent such as methanol. Then, the resultant is reacted with commercially available 1-methyl-2-imidazole carboxaldehyde and an appropriate reductant such as sodium borohydride, an appropriate dehydrating agent such as trimethyl orthoformate or an appropriate acid catalyst such as acetic acid in an appropriate solvent such as methanol to thereby obtain a compound (XX-18) which is a compound represented by the general formula (1).

PRODUCTION METHOD EXAMPLE 21

Figure 21:
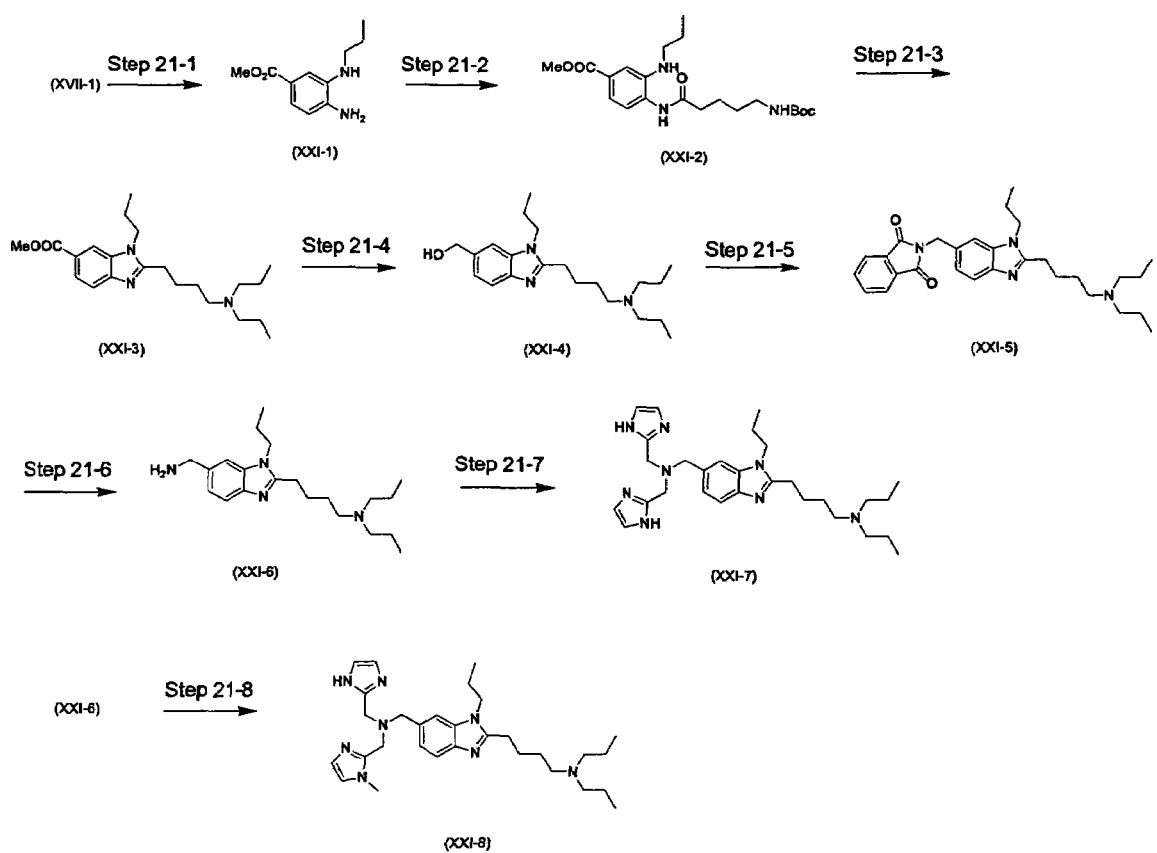

The reaction process steps of Production Method Example 21 are shown in FIG. 21.

Step 21-1

The above compound (XVII-1) is reacted with iodopropane in an appropriate solvent such as DMF in the presence of an appropriate base such as potassium carbonate to thereby obtain a compound (XXI-1).

Step 21-2

The compound (XXI-1) is reacted with 5-t-butoxycarbonylaminovaleric acid, an appropriate condensing agent and catalyst such as WSCI and HOBt in an appropriate solvent such as DMF to thereby obtain a compound (XXI-2).

Step 21-3

The compound (XXI-2) is reacted in an appropriate solvent such as methanol in the presence of an appropriate acid such as hydrochloric acid, and then reacted with propionaldehyde, an appropriate reductant such as sodium cyanoborohydride, and optionally an appropriate dehydrating agent such as trimethyl orthoformate in an appropriate solvent such as methanol to thereby obtain a compound (XXI-3).

Step 21-4

The compound (XXI-3) is reacted with an appropriate reductant such as lithium aluminum hydride in an appropriate solvent such as THF to thereby obtain a compound (XXI-4).

Step 21-5

The compound (XXI-4) is reacted with phthalimide and an appropriate dehydrating agent such as triphenylphosphine and diethyl azodicarboxylate in an appropriate solvent to thereby obtain a compound (XXI-5).

Step 21-6

The compound (XXI-5) is reacted with an appropriate base such as methylamine in an appropriate solvent such as methanol to thereby obtain a compound (XXI-6).

Step 21-7

The compound (XXI-6) is reacted with commercially available 2-imidazole carboxaldehyde, an appropriate reductant such as sodium borohydride, and an appropriate dehydrating agent such as trimethyl orthoformate in an appropriate solvent such as methanol to thereby obtain a compound (XXI-7) which is a compound represented by the general formula (1).

Step 21-8

The compound (XXI-6) is reacted with commercially available 2-imidazole carboxaldehyde, an appropriate reductant such as sodium borohydride, an appropriate dehydrating agent such as trimethyl orthoformate in an appropriate solvent such as methanol. Then, the resultant is reacted with commercially available 1-methyl-2-imidazole carboxaldehyde, an appropriate reductant such as sodium borohydride, and an appropriate dehydrating agent such as trimethyl orthoformate or an appropriate acid catalyst such as acetic acid in an appropriate solvent such as methanol to thereby obtain a compound (XXI-8) which is a compound represented by the general formula (1).

PRODUCTION METHOD EXAMPLE 22

Figure 22:
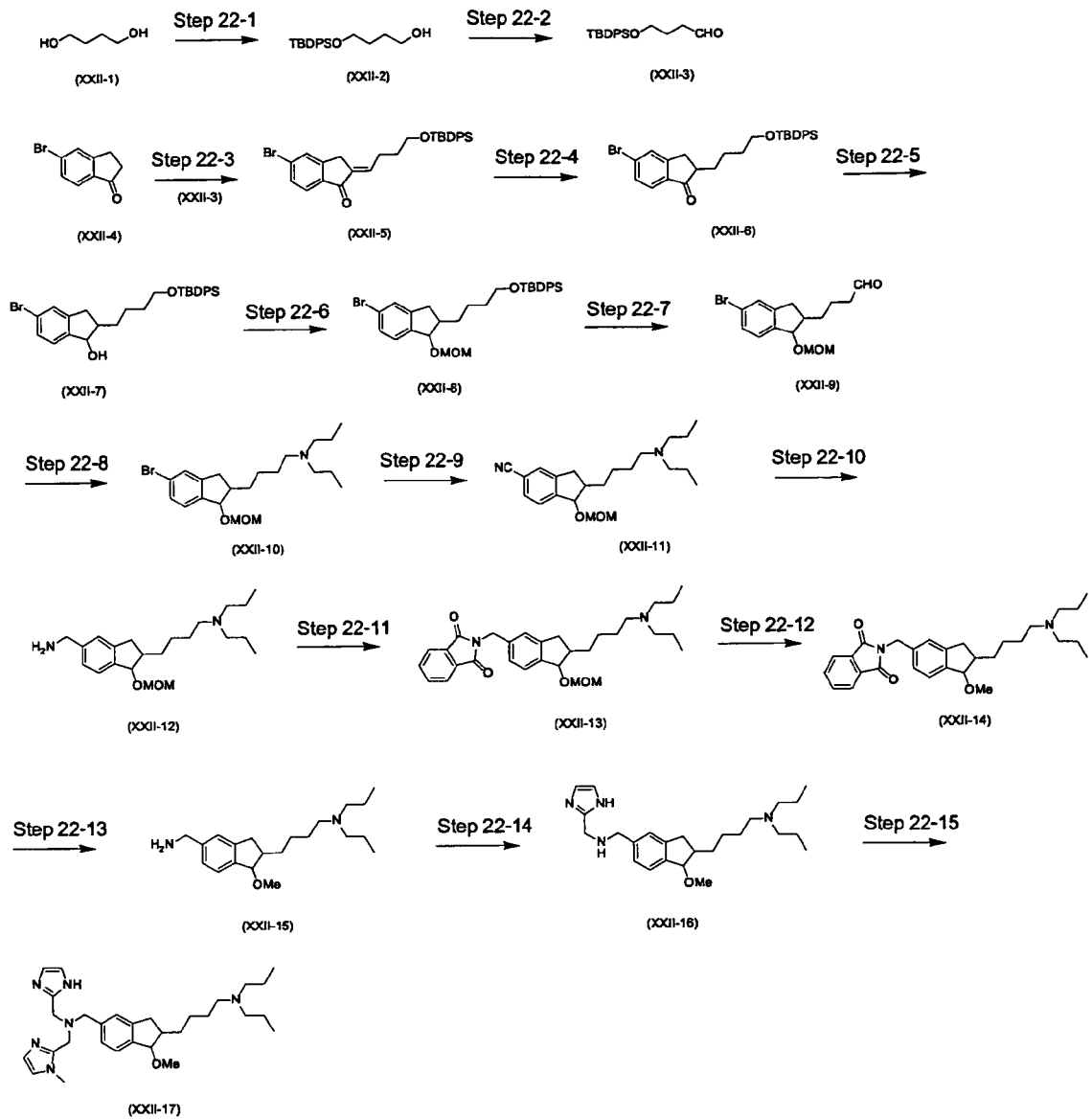

The reaction process steps of Production Method Example 22 are shown in FIG. 22.

Step 22-1

A commercially available compound (XXII-1) is reacted with t-butyldiphenylsilyl chloride and an appropriate base such as imidazole in an appropriate solvent such as DMF to thereby obtain a compound (XXII-2).

Step 22-2

The compound (XXII-2) is reacted with an appropriate oxidant such as N-methyl-morpholine-N-oxide and tetrapropylammonium perruthenate in an appropriate solvent such as dichloromethane to thereby obtain a compound (XXII-3).

Step 22-3

The compound (XXII-3) is reacted with the compound (XXII-4) and an appropriate base such as lithium bistrimethylsilyl amide in an appropriate solvent such as THF. Then, the resultant is reacted with methanesulfonyl chloride and an appropriate base such as triethylamine in an appropriate solvent such as DMF, and further reacted with an appropriate strong base such as DBU to thereby obtain a compound (XXII-5).

Step 22-4

The compound (XXII-5) is reacted with an appropriate reductant such as K-Selectride® in an appropriate solvent such as THF to thereby obtain a compound (XXII-6).

Step 22-5

The compound (XXII-6) is reacted with an appropriate reductant such as sodium borohydride in an appropriate solvent such as methanol to thereby obtain a compound (XXII-7).

Step 22-6

The compound (XXII-7) is reacted with methoxymethyl chloride and an appropriate base such as sodium hydride in an appropriate solvent such as DMF to thereby obtain a compound (XXII-8).

Step 22-7

The compound (XXII-8) is reacted with an appropriate deprotecting agent such as TBAF in an appropriate solvent such as THF. Then, the resultant is reacted with an appropriate oxidant such as N-methyl-morpholine-N-oxide and tetrapropylammonium perruthenate in an appropriate solvent such as dichloromethane to thereby obtain a compound (XXII-9).

Step 22-8

The compound (XXII-9) is reacted with dipropylamine and an appropriate reductant such as sodium triacetoxy borohydride in an appropriate solvent such as dichloroethane to thereby obtain a compound (XXII-10).

Step 22-9

The compound (XXII-10) is reacted with an appropriate cyanide reagent such as zinc cyanide and an appropriate catalyst such as tetrakistriphenylphosphine palladium in an appropriate solvent such as DMF to thereby obtain a compound (XXII-11).

Step 22-10

The compound (XXII-11) is reacted with an appropriate reductant such as lithium aluminum hydride in an appropriate solvent such as THF to thereby obtain a compound (XXII-12).

Step 22-11

The compound (XXII-12) is reacted with carbethoxyphthalimide and an appropriate base such as potassium carbonate in an appropriate solvent such as DMF to thereby obtain a compound (XXII-13).

Step 22-12

The compound (XXII-13) is reacted with an appropriate acid catalyst such as hydrochloric acid in an appropriate solvent such as a methanol/dioxane mixture to thereby obtain a compound (XXII-14).

Step 22-13

The compound (XXII-14) is reacted with an appropriate base such as hydrazine monohydrate in an appropriate solvent such as methanol to thereby obtain a compound (XXII-15).

Step 22-14

The compound (XXII-15) is reacted with commercially available 2-imidazole carboxaldehyde, an appropriate reductant such as sodium borohydride, and an appropriate dehydrating agent such as trimethyl orthoformate in an appropriate solvent such as methanol to thereby obtain a compound (XXII-16).

Step 22-15

The compound (XXII-26) is reacted with commercially available 1-methyl-2-imidazole carboxaldehyde, an appropriate reductant such as sodium borohydride, an appropriate dehydrating agent, and an appropriate acid catalyst such as acetic acid in an appropriate solvent such as methanol to thereby obtain a compound (XXII-17) which is a compound represented by the general formula (1).

PRODUCTION METHOD EXAMPLE 23

Figure 23:
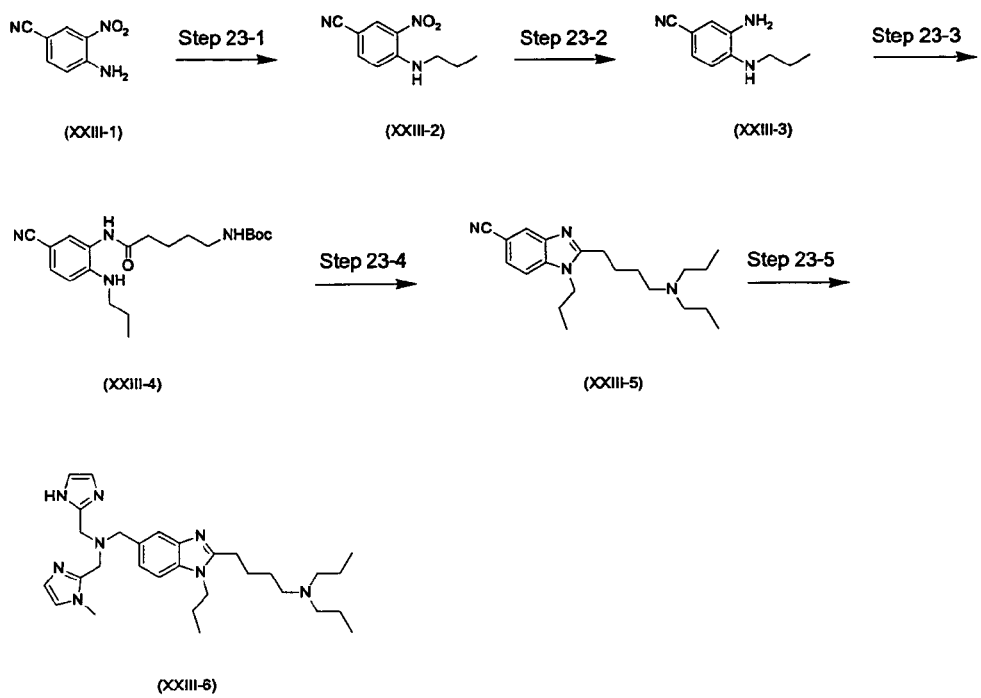

The reaction process steps of Production Method Example 23 are shown in FIG. 23.

Step 23-1

A commercially available compound (XXIII-1) is reacted with 1-iodopropane and an appropriate base such as sodium hydride in an appropriate solvent such as DMF to thereby obtain a compound (XXIII-2).

Step 23-2

The compound (XXIII-2) is reacted with an appropriate reductant such as tin(II) chloride and sodium borohydride in an appropriate solvent such as ethanol to thereby obtain a compound (XXIII-3).

Step 23-3

The compound (XXIII-3) is reacted with 5-t-butoxy carbonylaminovaleric acid and an appropriate condensing agent and catalyst such as WSCI and HOBt in an appropriate solvent such as DMF to thereby obtain a compound (XXIII-4).

Step 23-4

The compound (XXIII-4) is reacted in an appropriate solvent such as methanol in the presence of an appropriate acid such as hydrochloric acid. Then, the resultant is reacted with propionaldehyde, an appropriate reductant such as sodium cyanoborohydride, and an appropriate acid catalyst such as acetic acid in an appropriate solvent such as methanol to thereby obtain a compound (XXIII-5).

Step 23-5

The compound (XXIII-5) is reacted with an appropriate reductant such as lithium aluminum hydride in an appropriate solvent such as THF. Then, the resultant is reacted with commercially available 2-imidazole carboxaldehyde, an appropriate reductant such as sodium borohydride, and an appropriate dehydrating agent such as trimethyl orthoformate in an appropriate solvent such as methanol. Subsequently, the resultant is reacted with commercially available 1-methyl-2-imidazole carboxaldehyde, an appropriate reductant such as sodium borohydride, and an appropriate dehydrating agent such as trimethyl orthoformate or an appropriate acid catalyst such as acetic acid in an appropriate solvent such as methanol to thereby obtain a compound (XXIII-6) which is a compound represented by the general formula (1).

PRODUCTION METHOD EXAMPLE 24

Figure 24:
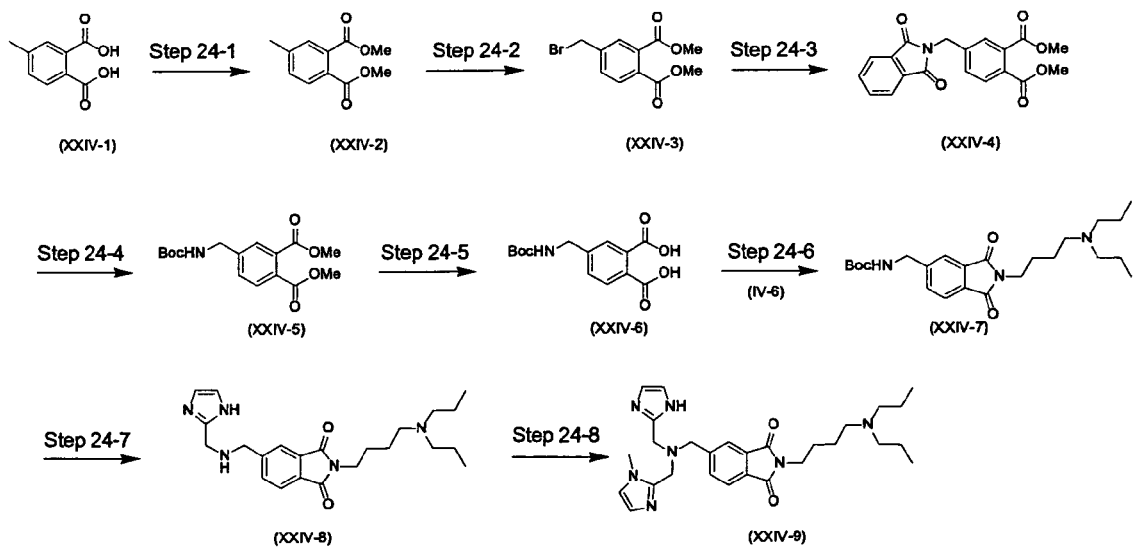

The reaction process steps of Production Method Example 24 are shown in FIG. 24.

Step 24-1

A commercially available compound (XXIV-1) is reacted with an appropriate condensing agent and catalyst such as WSCI and HOBt in methanol to thereby obtain a compound (XXIV-2).

Step 24-2

The compound (XXIV-2) is reacted with N-bromosuccinimide (hereinafter, referred to as NBS) and an appropriate radical generator such as azobisisobutyronitrile in an appropriate solvent such as carbon tetrachloride to thereby obtain a compound (XXIV-3).

Step 24-3

The compound (XXIV-3) is reacted with potassium phthalimide in an appropriate solvent such as DMF to thereby obtain a compound (XXIV-4).

Step 24-4

The compound (XXIV-4) is reacted with an appropriate base such as hydrazine monohydrate in an appropriate solvent such as methanol, and then reacted with di-t-butyl dicarbonate and an appropriate base such as triethylamine to thereby obtain a compound (XXIV-5).

Step 24-5

The compound (XXIV-5) is reacted with an appropriate base such as sodium hydroxide and water in an appropriate solvent such as methanol to thereby obtain a compound (XXIV-6).

Step 24-6

The compound (XXIV-6) is reacted with the above compound (IV-6) in an appropriate solvent such as xylene to thereby obtain a compound (XXIV-7).

Step 24-7

The compound (XXIV-7) is reacted in an appropriate solvent such as methanol in the presence of an appropriate acid such as hydrochloric acid. Then, the resultant is reacted with commercially available 2-imidazole carboxaldehyde, an appropriate reductant such as sodium borohydride, and an appropriate dehydrating agent such as trimethyl orthoformate in an appropriate solvent such as methanol to thereby obtain a compound (XXIV-8).

Step 24-8

The compound (XXIV-8) is reacted with commercially available 1-methyl-2-imidazole carboxaldehyde, an appropriate reductant such as sodium borohydride, an appropriate dehydrating agent, and an appropriate acid catalyst such as acetic acid in an appropriate solvent such as methanol to thereby obtain a compound (XXIV-9) which is a compound represented by the general formula (1).

The following compounds can be exemplified as the amine compounds of the present invention:

4-{[bis(1H-imidazol-2-ylmethyl)-amino]-methyl}-N-(4-dipropylamino-butyl)-benzamide [Compound No. 1], 4-{[bis(1H-imidazol-2-ylmethyl)-amino]-methyl}-N-(4-diisobutylamino-butyl)-benzamide [Compound No. 2], 4-{[bis(1H-imidazol-2-ylmethyl)-amino]-methyl}-N-(4-aminobutyl)-benzamide [Compound No. 3], 4-{[bis(1H-imidazol-2-ylmethyl)-amino]-methyl}-N-(4-cyclohexylamino-butyl)-benzamide [Compound No. 4], 4-{[bis(1H-imidazol-2-ylmethyl)-amino]-methyl}-N-(4-benzyloxycarbonylaminobutyl)-benzamide [Compound No. 5], 4-{[bis(1H-imidazol-2-ylmethyl)-amino]-methyl}-N-[4-(2-methoxy-benzylamino)-butyl]-benzamide [Compound No. 6], 4-{[bis(1H-imidazol-2-ylmethyl)-amino]-methyl}-N-(2-dipropylamino-ethyl)-benzamide [Compound No. 7], 4-{[bis(1H-imidazol-2-ylmethyl)-amino]-methyl}-N-(2-cyclohexylaminoethyl)-benzamide [Compound No. 8], 4-{[bis(1H-imidazol-2-ylmethyl)-amino]-methyl}-N-[4-(cyclohexylmethyl-amino)-butyl]-benzamide [Compound No. 9], 4-{[bis(1H-imidazol-2-ylmethyl)-amino]-methyl}-N-[4-(4-t-butyl-benzylamino)-butyl]-benzamide [Compound No. 10], 4-{[bis(1H-imidazol-2-ylmethyl)-amino]-methyl}-N-[4-(2-trifluoromethyl)-benzylamino-butyl]-benzamide [Compound No. 11], 4-{[bis(1H-imidazol-2-ylmethyl)-amino]-methyl}-N-[4-(2-trifluoromethoxy)-benzylamino-butyl]-benzamide [Compound No. 12], 4-{[bis(1H-imidazol-2-ylmethyl)-amino]-methyl}-N-[4-(4-methylsulfanyl-benzylamino)-butyl]-benzamide [Compound No. 13], 4-{[bis(1H-imidazol-2-ylmethyl)-amino]-methyl}-N-{4-[(3-methyl-pyridin-2-ylmethyl)-amino]-butyl}-benzamide [Compound No. 14], 4-{[bis(1H-imidazol-2-ylmethyl)-amino]-methyl}-N-(4-dipropylaminophenyl)-benzamide [Compound No. 15], 4-{[bis(1H-imidazol-2-ylmethyl)-amino]-methyl}-N-{4-[bis(3-methyl-butyl)-amino]butyl}-benzamide [Compound No. 16], 4-{[bis(1H-imidazol-2-ylmethyl)-amino]-methyl}-N-(4-dimethylamino-butyl)-benzamide [Compound No. 17], 4-{[bis(1H-imidazol-2-ylmethyl)-amino]-methyl}-N-(4-cycloheptylaminobutyl)-benzamide [Compound No. 18], 4-{[bis(1H-imidazol-2-ylmethyl)-amino]-methyl}-N-(4-dipropylaminomethylphenyl)-benzamide [Compound No. 19], N-(4-dipropylaminobutyl)-4-{[(1H-imidazol-2-ylmethyl)-(pyridin-2-ylmethyl)-amino]-methyl}-benzamide [Compound No. 20], N-(4-dipropylaminobutyl)-4-{[(1H-imidazol-2-ylmethyl)-(thiazol-2-ylmethyl)-amino]-methyl}-benzamide [Compound No. 21], 4-{[bis(1H-imidazol-2-ylmethyl)-amino]-methyl}-N-(3-dipropylaminopropyl)-benzamide [Compound No. 22], 4-{[bis(1H-imidazol-2-ylmethyl)-amino]-methyl}-N-(3-dipropylamino-2,2-dimethylpropyl)-benzamide [Compound No. 23], 4-{[bis(1H-imidazol-2-ylmethyl)-amino]-methyl}-N-(4-dipropylaminobutyl)-benzenesulfonamide [Compound No. 24], N-(4-{[bis(1H-imidazol-2-ylmethyl)-amino]-methyl}-benzyl)-N', N'-dipropylbutane-1,4-diamine [Compound No. 25]

N-(4-dipropylaminobutyl)-4-{[(1H-imidazol-2-ylmethyl)-(1-methyl-1H-imidazol-2-ylmethyl)-amino]-methyl}-benzamide [Compound No. 26], N-(4-dipropylaminobutyl)-4-{[(1H-imidazol-2-ylmethyl)-(1H-pyrazol-3-ylmethyl)-amino]-methyl}-benzamide [Compound No. 27], N-(4-dipropylaminobutyl)-4-{[(1H-imidazol-2-ylmethyl)-((2R)-pyrrolidin-2-ylmethyl)-amino]-methyl}-benzamide [Compound No. 28], N-(4-dipropylaminobutyl)-4-{[(1H-imidazol-2-ylmethyl)-((2S)-pyrrolidin-2-ylmethyl)-amino]-methyl}-benzamide [Compound No. 29], N-(4-dipropylaminobutyl)-4-{[(1H-imidazol-2-ylmethyl)-(4-methyl-1H-imidazol-5-ylmethyl)-amino]-methyl}-benzamide [Compound No. 30], (4-{[bis(1H-imidazol-2-ylmethyl)-amino]-methyl}-phenyl)-(4-dipropylaminopiperidin-1-yl)-methanone [Compound No. 31], (4-{[bis(1H-imidazol-2-ylmethyl)-amino]-methyl}-phenyl)-(4-propylpiperazin-1-yl)-methanone [Compound No. 32], 4-{[bis(1H-imidazol-2-ylmethyl)-amino]-methyl}-N-(3-dipropylaminomethylphenyl)-benzamide [Compound No. 33], 4-{[bis(1H-imidazol-2-ylmethyl)-amino]-methyl}-N-(4-{[(1H-imidazol-2-ylmethyl)-amino]-methyl}-phenyl)-benzamide [Compound No. 34],

[4-(4-{[bis(1H-imidazol-2-ylmethyl)-amino]-methyl}-benzyloxy)-benzyl]-dipropylamine [Compound No. 35], 4-{[bis(1H-imidazol-2-ylmethyl)-amino]-methyl}-naphtalene-1-carboxylic acid (4-dipropylaminomethylphenyl)-amide [Compound No. 36], (4-{[bis(1H-imidazol-2-ylmethyl)-amino]-methyl}-phenyl)-[4-(1-propylbutyl)-piperazin-1-yl]-methanone [Compound No. 37], (4-{[bis(1H-imidazol-2-ylmethyl)-amino]-methyl}-phenyl)-(4-cyclohexylpiperazin-1-yl)-methanone [Compound No. 38], (4-{[bis(1-methyl-1H-imidazol-2-ylmethyl)-amino]-methyl}-benzyl)-(4-dipropylaminomethylphenyl)-amine [Compound No. 39], 4-{[bis(1-methyl-1H-imidazol-2-ylmethyl)-amino]-methyl}-N-(4-dipropylaminobutyl)-benzamide [Compound No. 40], 4-{[bis(1-methyl-1H-imidazol-2-ylmethyl)-amino]-methyl}-N-(4-dipropylaminomethylphenyl)-benzamide [Compound No. 41],

[4-(4-{[bis(1H-imidazol-2-ylmethyl)-amino]-methyl}-benzylamino)-butyl]-carbamic acid benzyl ester [Compound No. 42], (4-{[bis(1H-imidazol-2-ylmethyl)-amino]-methyl}-benzyl)-(4-dipropylaminomethylphenyl)-amine [Compound No. 43], (4-dipropylaminomethylphenyl)-(4-{[(1H-imidazol-2-ylmethyl)-(1-methyl-1H-imidazol-2-ylmethyl)-amino]-methyl}-benzyl)-amine [Compound No. 44], (4-dipropylaminomethylphenyl)-(4-{[(1H-imidazol-2-ylmethyl)-(2H-pyrazol-3-ylmethyl)-amino]-methyl}-benzyl)-amine [Compound No. 45], N-(4-dipropylaminobutyl)-4-{[(1H-imidazol-2ylmethyl)-(6-methylpyridin-2-yl-methyl)-amino]-methyl}-benzamide [Compound No. 46], N-(4-dipropylaminomethylphenyl)-4-{[(1H-imidazol-2-ylmethyl)-(isoquinolin-3-ylmethyl)-amino]-methyl}-benzamide [Compound No. 47], N-(4-dipropylaminomethylphenyl)-4-{[(1H-imidazol-2-ylmethyl)-(pyridin-2-ylmethyl)-amino]-methyl}-benzamide [Compound No. 48], N-(4-dipropylaminomethylphenyl)-4-{[(1H-imidazol-2-ylmethyl)-(1-methyl-1H-imidazol-2-ylmethyl)-amino]-methyl}-benzamide [Compound No. 49], N-(4-{[bis(1H-imidazol-2-ylmethyl)-amino]-methyl}-benzyl)-N-methyl-N',N'-dipropylbutane-1,4-diamine [Compound No. 50], N-(4-dipropylaminomethylphenyl)-4-{[(1H-imidazol-2-ylmethyl)-(6-methylpyridin-2-ylmethyl)-amino]-methyl}-benzamide [Compound No. 51], N-(4-dipropylaminomethylphenyl)-4-{[(1H-imidazol-2-ylmethyl)-(6-bromopyridin-2-ylmethyl)-amino]-methyl}-benzamide [Compound No. 52], N-(4-dipropylaminomethylphenyl)-4-{[(1H-imidazol-2-ylmethyl)-(3-methylpyridin-2-ylmethyl)-amino]-methyl}-benzamide [Compound No. 53], N-(4-dipropylaminomethylphenyl)-4-{[(1H-imidazol-2-ylmethyl)-(quinolin-4-ylmethyl)-amino]-methyl}-benzamide [Compound No. 54], N-(4-dipropylaminomethylphenyl)-4-{[(1H-imidazol-2-ylmethyl)-(quinolin-2-ylmethyl)-amino]-methyl}-benzamide [Compound No. 55], N-(4-dipropylaminomethylphenyl)-4-{[(1H-imidazol-2-ylmethyl)-(5-methylpyridin-2-ylmethyl)-amino]-methyl}-benzamide [Compound No. 56], N-(4-dipropylaminomethylphenyl)-4-{[(1H-imidazol-2-ylmethyl)-(pyridin-3-ylmethyl)-amino]-methyl}-benzamide [Compound No. 57], N-(4-dipropylaminomethylphenyl)-4-{[(1H-imidazol-2-ylmethyl)-(pyridin-4-ylmethyl)-amino]-methyl}-benzamide [Compound No. 58], N-(4-dipropylaminomethylphenyl)-4-{[(1H-imidazol-2-ylmethyl)-(3-ethoxypyridin-2-ylmethyl)-amino]-methyl}-benzamide [Compound No. 59],

[4-(4-{[bis(1H-imidazol-2-ylmethyl)-amino]-methyl}-benzyloxy)-butyl]-dipropylamine [Compound No. 60], N-(4-dipropylaminomethylphenyl)-4-{[(1H-imidazol-2-ylmethyl)-(1H-benzimidazol-2-ylmethyl)-amino]-methyl}-benzamide [Compound No. 61], N-(4-dipropylaminomethylphenyl)-4-{[(1H-imidazol-2-ylmethyl)-(2-methylthiazol-4-ylmethyl)-amino]-methyl}-benzamide [Compound No. 62], N-(4-dipropylaminomethylphenyl)-4-{[(1H-imidazol-2-ylmethyl)-(isoquinolin-1-ylmethyl)-amino]-methyl}-benzamide [Compound No. 63], N-(4-dipropylaminomethylphenyl)-4-{[(1H-imidazol-2-ylmethyl)-(4-methoxy-3,5-dimethylpyridin-2-ylmethyl)-amino]-methyl}-benzamide [Compound No. 64], 4-({bis[1-(toluene-4-sulfonyl)-1H-imidazol-2-ylmethyl]-amino}-methyl)-N-(4-dipropylaminomethylphenyl)-benzamide [Compound No. 65], 4-{[bis(1-methanesulfonyl-1H-imidazol-2-ylmethyl)-amino]-methyl}-N-(4-dipropylaminomethylphenyl)-benzamide [Compound No. 66], 2-({[4-(4-dipropylaminomethylphenylcarbamoyl)-benzyl]-(1-methyl-1H-imidazol-2-ylmethyl)-amino}-methyl)-imidazol-1-carboxylic acid ethyl ester [Compound No. 67], 4-{[bis(1H-imidazol-2-ylmethyl)-amino]-methyl}-N-(4-dipropylaminomethylphenyl)-N-methylbenzamide [Compound No. 68], N-(4-dipropylaminomethylphenyl)-{[(1H-imidazol-2-ylmethyl)-(quinolin-3-ylmethyl)-amino]-methyl}-benzamide [Compound No. 70], N-(4-{[bis(1H-imidazol-2-ylmethyl)-amino]-methyl}-phenyl)-4-dipropylaminomethylbenzamide [Compound No. 71], N-(4-dipropylaminomethylphenyl)-4-{[(8-hydroxyquinolin-2-ylmethyl)-(1H-imidazol-2-ylmethyl)-amino]-methyl}-benzamide [Compound No. 72], N-(4-dipropylaminomethylphenyl)-4-{[(1H-imidazol-2-yl-methyl)-(5-methylpyrazine-2-ylmethyl)-amino]-methyl}-benzamide [Compound No. 73], N-(4-dipropylaminomethylphenyl)-4-{[(1H-imidazol-2-yl-methyl)-(pyrazine-2-ylmethyl)-amino]-methyl}-benzamide [Compound No. 85], N-(4-{[(1H-imidazol-2-ylmethyl)-(5-methylpyridine-2-yl-methyl)-amino]-methyl}-benzyl)-N',N'-dipropylbutane-1,4-diamine [Compound No. 75], N-(4-dipropylaminomethylphenyl)-4-{[(1-methyl-1H-imidazol-2-ylmethyl)-(5-methylpyridin-2-ylmethyl)-amino]-methyl}-benzamide [Compound No. 76], 4-{[bis(5-methylpyridin-2-ylmethyl)-amino]-methyl}-N-(4-dipropylaminomethylphenyl)-benzamide [Compound No. 77], N-(4-dipropylaminomethylphenyl)-4-{[N-(1H-imidazol-2-ylmethyl)-(4-methylpyridin-2-ylmethyl)-amino]-methyl}-benzamide [Compound No. 78], {2-[4-(4-{[bis(1H-imidazol-2-ylmethyl)-amino]-methyl}-benzyloxy)-phenyl]-ethyl}-dipropylamine [Compound No. 79],

[4-(4-{[bis(1H-imidazol-2-ylmethyl)-amino]-methyl}-benzyloxymethyl)-benzyl]-dipropylamine [Compound No. 80], N-(4-dipropylaminomethylphenyl)-4-{[(1H-imidazol-2-yl-methyl)-([1,2,3]-thiadiazole-4-ylmethyl)-amino]-methyl}-benzamide [Compound No. 81], 4-{[(1-dimethylsulfamoyl-1H-imidazol-2-ylmethyl)-(1H-imidazol-2-ylmethyl)-amino]-methyl}-N-(4-dipropylaminomethylphenyl)-benzamide [Compound No. 82], 2-({[4-(4-dipropylaminomethylphenylcarbamoyl)-benzyl]-(1-methyl-1H-imidazol-2-ylmethyl)-amino}-methyl)-imidazol-1-carboxylic acid dimethylamide [Compound No. 83], 4-{[bis(1-dimethylsulfamoyl-1H-imidazol-2-ylmethyl)-amino]-methyl}-N-(4-dipropylaminomethylphenyl)-benzamide [Compound No. 84], N-(4-dipropylaminomethylphenyl)-4-{[(1H-imidazol-2-yl-methyl)-pyrazine-2-ylmethylamino]-methyl}-benzamide [Compound No. 85], N-(4-dipropylaminomethylphenyl)-4-{[(1H-imidazol-2-yl-methyl)-(5-methylisoxazol-3-ylmethyl)-amino]-methyl}-benzamide [Compound No. 86], 4-(4-{[bis(1H-imidazol-2-ylmethyl)-amino]-methyl}-benzoyl)-(2-dipropylaminoethyl)-piperazine [Compound No. 87], N-(4-cyclohexylaminomethylphenyl)-4-{[(1H-imidazol-2-ylmethyl)-(1-methyl-1H-imidazol-2-ylmethyl)-amino]-methyl}-benzamide [Compound No. 88], 4-{[bis(1H-imidazol-2-ylmethyl)-amino]-methyl}-N-(4-cyclohexylaminomethylphenyl)-benzamide [Compound No. 89], N-(4-{[(1H-imidazol-2-ylmethyl)-(1-methyl-1H-imidazol-2-ylmethyl)-amino]-methyl}-benzyl)-N',N'-dipropylbutane-1,4-diamine [Compound No. 90], N-(4-dipropylaminomethylphenyl)-4-{[(1-ethyl-1H-imidazol-2-ylmethyl)-(1H-imidazol-2-ylmethyl)-amino]-methyl}-benzamide [Compound No. 91), N-(4-dipropylaminomethylphenyl)-4-{[(1H-imidazol-2-yl-methyl)-(1-propyl-1H-imidazol-2-ylmethyl)-amino]-methyl}-benzamide [Compound No. 92], N-(4-dipropylaminomethylphenyl)-4-({(1H-imidazol-2-yl-methyl)-[1-(2-methoxymethoxyethyl)-1H-imidazol-2-yl-methyl]-amino}-methyl)-benzamide [Compound No. 93], N-(4-dipropylaminomethylphenyl)-4-({[1-(2-hydroxy-ethyl)-1H-imidazol-2-ylmethyl]-(1H-imidazol-2-yl-methyl)-amino}-methyl)-benzamide [Compound No. 94], 4-{[bis(1-hexyloxycarbonyl-1H-imidazol-2-ylmethyl)-amino]-methyl}-N-(4-dipropylaminomethylphenyl)-benzamide [Compound No. 95], 4-{[bis(1-heptyloxycarbonyl-1H-imidazol-2-ylmethyl)-amino]-methyl}-N-(4-dipropylaminomethylphenyl)-benzamide [Compound No. 96], 4-{[bis(1-butoxycarbonyl-1H-imidazol-2-ylmethyl)-amino]-methyl}-N-(4-dipropylaminomethylphenyl)-benzamide [Compound No. 97], N-(4-{[(1H-imidazol-2-ylmethyl)-(1-methyl-1H-imidazol-2-ylmethyl)-amino]-methyl}-benzyl)-N-methyl-N',N'-dipropylbutane-1,4-diamine [Compound No. 98], 4-{[bis-(1H-imidazol-2-ylmethyl)-amino]-methyl}-N-[4-(cyclohexyl-methyl-amino)-butyl]-benzamide [Compound No. 99], N-[4-(cyclohexyl-methyl-amino)-butyl]-4-{[(1H-imidazol-2-ylmethyl)-(1-methyl-1H-imidazol-2-ylmethyl)-amino]-methyl}-benzamide [Compound No. 100], 4-{[(3,5-dimethyl-pyridin-2-ylmethyl)-(1H-imidazol-2-yl-methyl)-amino]-methyl}-N-(4-dipropylaminomethyl-phenyl)-benzamide [Compound No. 101], N-(4-dipropylaminomethyl-phenyl)-4-{[(5-ethyl-pyridin-2-ylmethyl)-(1H-imidazol-2-ylmethyl)-amino]-methyl}-benzamide [Compound No. 102], N-(4-cyclohexylamino-butyl)-4-{[(1H-imidazol-2-ylm-ethyl)-(1-methyl-1H-imidazol-2-ylmethyl)-amino]-methyl}-benzenesulfonamide [Compound No. 103], N-cyclohexyl-N'-(4-{[(1H-imidazol-2-ylmethyl)-(1-me-thyl-1H-imidazol-2-ylmethyl)-amino]-methyl}-benzyl)-N'-methyl-butane-1,4-diamine [Compound No. 104], N-(4-dipropylamino-butyl)-4-{[(1H-imidazol-2-ylmethyl)-(1-methyl-1H-imidazol-2-ylmethyl)-amino]-methyl}-benzenesulfonamide [Compound No. 105], N-(4-diisobutylamino-butyl)-4-{[(1H-imidazol-2-ylm-ethyl)-(1-methyl-1H-imidazol-2-ylmethyl)-amino]-methyl}-benzenesulfonamide [Compound No. 106], 4-{[(1H-imidazol-2-ylmethyl)-(1-methyl-1H-imidazol-2-ylmethyl)-amino]-methyl}-N-(4-isobutylamino-butyl)-benzenesulfonamide [Compound No. 107], 4-{[bis-(1H-imidazol-2-ylmethyl)-amino]-methyl}-N-(4-dipropylamino-butyl)-N-methylbenzamide [Compound No. 108], N-[4-(cyclohexyl-methyl-amino)-butyl]-4-{[(1H-imidazol-2-ylmethyl)-(1-methyl-1H-imidazol-2-ylmethyl)-amino]-methyl}-benzenesulfonamide [Compound No. 109], 2-[(4-dipropylamino-butyl)-(4-{[(1H-imidazol-2-ylm-ethyl)-(1-methyl-1H-imidazol-2-ylmethyl)-amino]-me-thyl}-benzyl)-amino]-ethanol [Compound No. 110], 4-{[(1H-imidazol-2-ylmethyl)-(1-methyl-1H-imidazol-2-ylmethyl)-amino]-methyl}-N-{4-[(3-methyl-pyridin-2-ylmethyl)-amino]-butyl}-benzenesulfonamide [Compound No. 111], N-(4-dipropylamino-butyl)-4-{[(1H-imidazol-2-ylmethyl)-(1-methyl-1H-imidazol-2-ylmethyl)-amino]-methyl}-N-methylbenzamide [Compound No. 112], N-(4-dipropylamino-butyl)-4-{[(1H-imidazol-2-ylmethyl)-(1-methyl-1H-imidazol-2-ylmethyl)-amino]-methyl}-N-methyl-benzenesulfonamide [Compound No. 113], N-(4-di-n-propylaminomethyl-phenyl)-4-{[(1H-imidazol-2-ylmethyl)-(1H-[1,2,4]-triazol-3-ylmethyl)-amino]-methyl}-benzamide [Compound No. 114],

[4-(6-{[(1H-imidazol-2-ylmethyl)-(1-methyl-1H-imidazol-2-ylmethyl)-amino]-methyl}-benzimidazol-2-yl)-butyl]-dipropylamine [Compound No. 115], N-(4-{[(imidazol-2-ylmethyl)-([1,2,4]-triazol-3-ylmethyl)-amino]-methyl}-benzyl)-N-methyl-N',N'-dipropylbu-tane-1,4-diamine [Compound No. 116], N-methyl-N-(4-{[(1-methyl-imidazol-2-ylmethyl)-([1,2,4]-triazol-3-ylmethyl)-amino]-methyl}-benzyl)-N',N'-dipropyl-butane-1,4-diamine [Compound No. 117], N-(4-dipropylaminomethylbenzyl)-N'-(1H-imidazol-2-ylmethyl)-N'-(1-methyl-1H-imidazol-2-ylmethyl)-1,4-butanediamine [Compound No. 118], N-(4-dipropylaminomethylbenzyl)-N'-(1H-imidazol-2-ylmethyl)-N-methyl-N'-(1-methyl-1H-imidazol-2-ylmethyl)-butane-1,4-diamine [Compound No. 119],

[3-(6-{[(1H-imidazol-2-ylmethyl)-(1-methyl-1H-imidazol-2-ylmethyl)-amino]-methyl}-quinolin-2-yl)-propyl]-dipropylamine [Compound No. 120],

[3-(5-{[(1H-imidazol-2-ylmethyl)-(1-methyl-1H-imidazol-2-ylmethyl)-amino]-methyl}-benzo[b]-thiophen-2-yl)-propyl]-dipropyl-amine [Compound No. 121], 2-{[(1H-imidazol-2-ylmethyl)-(1-methyl-1H-imidazol-2-ylmethyl)-amino]-methyl}-6-(3-dipropylaminopropyl)-naphtalene [Compound No. 122], N-(4-di-n-propylaminomethyl-phenyl)-4-{[(1-methyl-imidazol-2-ylmethyl)-(1H-[1,2,4]-triazol-3-ylmethyl)-amino]-methyl}-benzamide [Compound No. 123],

[5-(6-{[(1H-imidazol-2-ylmethyl)-(1-methyl-1H-imidazol-2-ylmethyl)-amino]-methyl}-quinolin-2-yl)-pentyl]-dipropylamine [Compound No. 124], 2-{[(1H-imidazol-2-ylmethyl)-(1-methyl-1H-imidazol-2-ylmethyl)-amino]-methyl}-6-(4-dipropylaminobutyl)-naphtalene [Compound No. 125],

[4-(6-{[bis(1H-imidazol-2-ylmethyl)-amino]-methyl}-1-propyl-1H-benzimidazol-2-yl)-butyl]-dipropylamine [Compound No. 126],

[4-(6-{[(1H-imidazol-2-ylmethyl)-(1-methyl-1H-imidazol-2-ylmethyl)-amino]-methyl}-1-propyl-1H-benzimidazol-2-yl)-butyl]-dipropylamine [Compound No. 127],

[4-(5-{[(imidazol-2-ylmethyl)-(1-methylimidazol-2-ylmethyl)-amino]-methyl}-1-methoxy-indan-2-yl)-butyl]-dipropylamine [Compound No. 128],

[4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropylamine [Compound No. 129], 2-(4-di-n-propylamino-butyl)-5-{[(1H-imidazol-2-ylmethyl)-(1-methyl-1H-imidazol-2-ylmethyl)-amino]-methyl}-isoindole-1,3-dione [Compound No. 130], N-(4-{[(1H-imidazol-2-ylmethyl)-(1-methyl-1H-imidazol-2-ylmethyl)-amino]-methyl}-1H-imidazol-2-ylmethyl)-N-methyl-N',N'-dipropyl-butane-1,4-diamine [Compound No. 131], N-(4-{[(1H-imidazol-2-ylmethyl)-(1-methyl-1H-imidazol-2-ylmethyl)-amino]-methyl}-thiazol-2-ylmethyl)-N-methyl-N',N'-dipropyl-butane-1,4-diamine [Compound No. 132], 5-{[(1H-imidazol-2-ylmethyl)-(1-methyl-1H-imidazol-2-ylmethyl)-amino]-methyl}-pyridin-2-carboxylic acid (4-dipropylamino-butyl)-amide [Compound No. 133], 5-{[(1H-imidazol-2-ylmethyl)-(1-methyl-1H-imidazol-2-ylmethyl)-amino]-methyl}-pyrazine-2-carboxylic acid (4-dipropylamino-butyl)-amide [Compound No. 134],

[3-(5-{[(1H-imidazol-2-ylmethyl)-(1-methyl-1H-imidazol-2-ylmethyl)-amino]-methyl}-1H-indol-2-yl)-propyl]-dipropyl-amine [Compound No. 135]

2-(4-dipropylamino-butyl)-5-{[(1H-imidazol-2-ylmethyl)-(1-methyl-1H-imidazol-2-ylmethyl)-amino]-methyl}-indan-1-one [Compound No. 136], 2-(4-dipropylamino-butyl)-5-{[(1H-imidazol-2-ylmethyl)-(1-methyl-1H-imidazol-2-ylmethyl)-amino]-methyl}-inden-1-one [Compound No. 137], 3-amino-2-(4-dipropylamino-butyl)-5-{[(1H-imidazol-2-ylmethyl)-(1-methyl-1H-imidazol-2-ylmethyl)-amino]-methyl}-inden-1-one [Compound No. 138],

[4-(6-{[(1H-imidazol-2-ylmethyl)-(1-methyl-1H-imidazol-2-ylmethyl)-amino]-methyl}-benzothiazol-2-yl)-butyl]-dipropyl-amine [Compound No. 139],

[3-(6-{[(1H-imidazol-2-ylmethyl)-(1-methyl-1H-imidazol-2-ylmethyl)-amino]-methyl}-1H-benzimidazol-2-ylsulfanyl)-propyl]-dipropyl-amine [Compound No. 140],

[3-(5-{[(1H-imidazol-2-ylmethyl)-(1-methyl-1H-imidazol-2-ylmethyl)-amino]-methyl}-1H-inden-2-yl)-propyl]-dipropyl-amine [Compound No. 141]

[3-(5-{[(1H-imidazol-2-ylmethyl)-(1-methyl-1H-imidazol-2-ylmethyl)-amino]-methyl}-benzofuran-2-yl)-propyl]-dipropyl-amine [Compound No. 142], 2-(4-dipropylamino-butyl)-5-{[(1H-imidazol-2-ylmethyl)-(1-methyl-1H-imidazol-2-ylmethyl)-amino]-methyl}-2,3-dihydro-isoindol-1-one [Compound No. 143], 2-(4-dipropylamino-butyl)-6-{[(1H-imidazol-2-ylmethyl)-(1-methyl-1H-imidazol-2-ylmethyl)-amino]-methyl}-1,1-dioxo-1,2-dihydro-1λ6-benzo[d]-isothiazol-3-one [Compound No. 144],

[4-(6-{[(1H-imidazol-2-ylmethyl)-(1-methyl-1H-imidazol-2-ylmethyl)-amino]-methyl}-1,1-dioxo-1H-1(6-benzo[e]-[1,2]-thiazin-2-yl)-butyl]-dipropyl-amine [Compound No. 145], 2-(4-dipropylamino-butyl)-6-{[(1H-imidazol-2-ylmethyl)-(1-methyl-1H-imidazol-2-ylmethyl)-amino]-methyl}-1,2-dihydro-indazol-3-one [Compound No. 146],

[4-(6-{[(1H-imidazol-2-ylmethyl)-(1-methyl-1H-imidazol-2-ylmethyl)-amino]-methyl}-3,4-dihydro-1H-isoquinolin-2-yl)-butyl]-dipropyl-amine [Compound No. 147],

[4-(6-{[(1H-imidazol-2-ylmethyl)-(1-methyl-1H-imidazol-2-ylmethyl)-amino]-methyl}-quinolin-2-yl)-butyl]-dipropyl-amine [Compound No. 148],

[4-(6-{[(1H-imidazol-2-ylmethyl)-(1-methyl-1H-imidazol-2-ylmethyl)-amino]-methyl}-quinoxalin-2-yl)-butyl]-dipropyl-amine [Compound No. 149], 3-(4-dipropylamino-butyl)-7-{[(1H-imidazol-2-ylmethyl)-(1-methyl-1H-imidazol-2-ylmethyl)-amino]-methyl}-chromen-2-one [Compound No. 150], (3-dipropylaminomethyl-phenyl)-(4-{[(1H-imidazol-2-ylmethyl)-(1-methyl-1H-imidazol-2-ylmethyl)-amino]-methyl}-phenyl)-methanone [Compound No. 151], 3-(4-dipropylamino-butyl)-8-{[(1H-imidazol-2-ylmethyl)-(1-methyl-1H-imidazol-2-ylmethyl)-amino]-methyl}-3,4-dihydro-1H-benzo[e]-[1,4]-diazepin-2,5-dione [Compound No. 152], 3-(4-dipropylamino-butyl)-7-{[(1H-imidazol-2-ylmethyl)-(1-methyl-1H-imidazol-2-ylmethyl)-amino]-methyl}-3,4-dihydro-1H-benzo[e]-[1,4]-diazepin-2,5-dione [Compound No. 153], 2-(4-dipropylamino-butyl)-6-{[(1H-imidazol-2-ylmethyl)-(1-methyl-1H-imidazol-2-ylmethyl)-amino]-methyl}-3,4-dihydro-2H-isoquinolin-1-one [Compound No. 154], N-(4-{[(1H-imidazol-2-ylmethyl)-(1-methyl-1H-imidazol-2-ylmethyl)-amino]-methyl}-thiophen-2-ylmethyl)-N-methyl-N',N'-dipropyl-butane-1,4-diamine [Compound No. 155],

[4-(6-{[(1H-imidazol-2-ylmethyl)-(1-methyl-1H-imidazol-2-ylmethyl)-amino]-methyl}-quinazolin-2-yl)-butyl]-dipropyl-amine [Compound No. 156],

[4-(6-{[(1H-imidazol-2-ylmethyl)-(1-methyl-1H-imidazol-2-ylmethyl)-amino]-methyl}-chroman-2-yl)-butyl]-dipropyl-amine [Compound No. 157],

[4-(7-{[(1H-imidazol-2-ylmethyl)-(1-methyl-1H-imidazol-2-ylmethyl)-amino]-methyl}-chroman-3-yl)-butyl]-dipropyl-amine [Compound No. 158], 3-(4-dipropylamino-butyl)-7-{[(1H-imidazol-2-ylmethyl)-(1-methyl-1H-imidazol-2-ylmethyl)-amino]-methyl}-chromen-4-one [Compound No. 159], 2-(4-dipropylamino-butyl)-7-{[(1H-imidazol-2-ylmethyl)-(1-methyl-1H-imidazol-2-ylmethyl)-amino]-methyl}-2,3-dihydro-1H-isoquinolin-4-one [Compound No. 160], 2-(4-dipropylamino-butyl)-7-{[(1H-imidazol-2-ylmethyl)-(1-methyl-1H-imidazol-2-ylmethyl)-amino]-methyl}-2,3,4,5-tetrahydro-benzo[c]-azepin-1-one [Compound No. 161], 2-(4-dipropylamino-butyl)-7-{[(1H-imidazol-2-ylmethyl)-(1-methyl-1H-imidazol-2-ylmethyl)-amino]-methyl}-2,5-dihydro-benzo[c]-azepin-1-one [Compound No. 162], 6-{[(1H-imidazol-2-ylmethyl)-(1-methyl-1H-imidazol-2-ylmethyl)-amino]-methyl}-4-oxo-3,4-dihydro-quinazolin-2-carboxylic acid (2-dipropylamino-ethyl)-amide [Compound No. 163], 2-dipropylamino-5-[(4-{[(1H-imidazol-2-ylmethyl)-(1-methyl-1H-imidazol-2-ylmethyl)-amino]-methyl}-benzyl)-methyl-amino]-valeric acid [Compound No. 164], 5-dipropylamino-2-[(4-{[(1H-imidazol-2-ylmethyl)-(1-methyl-1H-imidazol-2-ylmethyl)-amino]-methyl}-benzyl)-methyl-amino]-valeric acid [Compound No. 165],

[4-(5-{[(1H-imidazol-2-ylmethyl)-(1-methyl-1H-imidazol-2-ylmethyl)-amino]-methyl}-1H-inden-2-yl)-butyl]-dipropylamine [Compound No. 166],

[4-(5-{[(1H-imidazol-2-ylmethyl)-(1-methyl-1H-imidazol-2-ylmethyl)-amino]-methyl}-1H-indol-2-yl)-butyl]-dipropylamine [Compound No. 167],

[4-(5-{[(1H-imidazol-2-ylmethyl)-(1-methyl-1H-imidazol-2-ylmethyl)-amino]-methyl}-1-methyl-1H-indol-2-yl)-butyl]-dipropylamine [Compound No. 168],

[4-(5-{[(1H-imidazol-2-ylmethyl)-(1-methyl-1H-imidazol-2-ylmethyl)-amino]-methyl}-benzofuran-2-yl)-butyl]-dipropylamine [Compound No. 169],

[4-(5-{[(1H-imidazol-2-ylmethyl)-(1-methyl-1H-imidazol-2-ylmethyl)-amino]-methyl}-benzoxazol-2-yl)-butyl]-dipropylamine [Compound No. 170],

[4-(5-{[(1H-imidazol-2-ylmethyl)-(1-methyl-1H-imidazol-2-ylmethyl)-amino]-methyl}-benzothiazol-2-yl)-butyl]-dipropylamine [Compound No. 171], The present invention relates to a CXCR4 antagonist including the above-described compounds or a pharmacologically acceptable salt thereof as an active ingredient.

The CXCR4 antagonist or salt thereof according to the present invention may be used in treatment or prevention of viral disease such as AIDS, cancer treatment, or treatment or prevention of rheumatism, etc.

The pharmacologically acceptable salt is a salt which may be formed by the amine compound represented by the above described formula (1), and may be any salt that is pharmacologically acceptable. For example, trifluoroacetates, hydrochloric acid saltshydrochlorides, acetates, sulfuric acid salts, nitric acid salts, lactic acid salts, maleic acid salts, methanesulfonic acid salts, toluenesulfonic acid salts, tartaric acid salts, citric acid salts, oxalic acid salts, malonic acid salts, fumaric acid salts, propionic acid salts, butanoic acid saltssulfates, nitrates, lactates, maleates, methane sulfonates, toluene sulfonates, tartrates, citrates, oxalates, malonates, succinates, fumarates, propionates, butyrates, glucuronates, terephthalates, phosphorates, and the like can be given. Those compounds may form a hydrate or a solvate.

One or two or more asymmetric carbon atoms may exist in the compound represented by the general formula (1); when one asymmetric carbon atoms exists, the compound may be in any form of a pure optically-active substance represented as absolute configuration of R or S, a mixture thereof in an arbitrary ratio, and a racemic mixture thereof, and when two or more asymmetric carbon atoms exist in the compound, the compound may be in any form of an optically pure diastereomer, a racemic mixture thereof, and a combination thereof in an arbitrary ratio.

The medical preparation including the compound of the present invention represented by the general formula (1) or pharmacologically acceptable salt thereof as an active ingredient may be administered orally or parenterally in a form of tablet, powder, granule, capsule, pill, suppository, injection, eye-drops, solution, troche, aerosol, suspension, emulsion, syrup, or the like, mixed with a well-known pharmacologically acceptable carrier, excipient, diluent, extender, decaying agent, stabilizer, preservative, buffer, emulsifier, perfuming agent, colorant, sweetener, thickening agent, flavor, solubilizing agent, and other additives, specific examples thereof including: water; vegetable oil; alcohol such as ethanol or benzyl alcohol; carbohydrate such as glycol, glycerol triacetate, gelatin, lactose, or starch; magnesium stearate; potassium stearate; tarc; lanoline; vaseline; macrogol; crystalline cellulose; hydroxypropyl cellulose, and the like. While the dose may vary depending on the kind and degree of disease, the kind of the compound to be administered, the administration path, and the age, sex, and weight of the patient, in general, 0.1 to 5,000 mg), particularly 1 to 3,000 mg) per one adult is preferably administered. In the case of a prodrug, it is preferable to administer 1 to 5,000 mg) per adult.

EXAMPLES

A production method of CXCR4 antagonist of the present invention will now be described in more detail with reference to Examples. Hereinafter, unless particularly described, reagents used are commercially available products (e.g., Tokyo Kasei Kogyo Co. Ltd. (Tokyo), KANTO KAGAKU (Tokyo), etc.) readily available to a person skilled in the art.

EXAMPLES

Production Example 1

Synthesis of 4-{[bis(1H-imidazol-2-ylmethyl)-amino]-methyl}-N-(4-dipropylamino-butyl)-benzamide [Compound No. 1]

Example 1-1

Synthesis of 4-[N-Boc-N-(1H-imidazol-2-ylmethyl)aminomethyl]-benzoic acid

Commercially available methyl bromomethylbenzoate (manufactured by Aldrich Corporation) (10.0 g) was dissolved in DMF (100 ml), and the solution was added with potassium phthalimide potassium salt (manufactured by Tokyo Kasei Kogyo Co., Ltd.) (9.70 g) and stirred at room temperature for 1.5 hours. After completion of the reaction, the solution was concentrated, and water was added to the concentrate. Then, extraction was performed with chloroform. The resultant solution was washed with saturated saline solution and dried with anhydrous sodium sulfate, and the solvent was distilled off, thereby obtaining a white solid (12.9 g). Subsequently, 7.56 g of the solid was dissolved in methanol (100 ml), and the solution was added with hydrazine monohydrate (manufactured by Nacalai Tesque, Inc.) (6.25 ml) and stirred at 60(C for 1.5 hours. After completion of the reaction, the precipitated solid was separated by filtration, and the solvent was distilled off. Water was added to the residue, and extraction was performed with chloroform. The resultant solution was washed with a 0.3 mol/l sodium hydroxide aqueous solution and saturated saline solution and dried with anhydrous sodium sulfate, and the solvent was distilled off. Methanol (120 ml) and 2-imidazole carboxaldehyde (manufactured by Aldrich Corporation) (2.35 g) were added to the residue, followed by stirring at room temperature for 2 days. After completion of the reaction, the precipitated solid was separated by filtration. The liquid layer was evaporated to dryness, and washing was performed by adding anhydrous methanol (30 ml). Then, the solid was separated by filtration. The resultant solid and the solid that had been previously separated by filtration were suspended in methanol (86 ml), and sodium borohydride (1.42 g) was added under ice-cooling. The solution was stirred at room temperature for 1 hour, and the solvent was distilled off. After addition of water, extraction was performed with chloroform, and the organic layer was washed with saturated saline solution and dried with anhydrous sodium sulfate, followed by concentration under reduced pressure and drying, thereby obtaining a colorless viscous liquid (4.32 g). 4.28 g of the liquid was dissolved in DMF (65 ml), and the solution was added with di-t-butyl dicarbonate (8.90 ml) and stirred at room temperature for 1 hour. After completion of the reaction, the solvent was distilled off, and the residue was dissolved in chloroform, followed by washing with saturated saline solution. After drying with anhydrous sodium sulfate, the solvent was distilled off, and THF (43 ml), methanol (43 ml), and a 1 mol/l sodium hydroxide aqueous solution (43 ml) were added to the residue, followed by stirring at room temperature for 14 hours. After completion of the reaction, the solvent was distilled off, and water (5 ml) was added to the residue. Further, a 1 mol/l hydrochloric acid aqueous solution was carefully added to the solution, and the acid-precipitate was separated by filtration and dried, thereby obtaining the subject compound (4.87 g) as a white solid.

MS(FAB, Pos.): m/z=332[M+H]$^+$

Example 1-2

Synthesis of N,N-dipropylbutane-1,4-diamine

N-(4-aminobutyl)carbamic acid t-butyl ester (manufactured by Tokyo Kasei Kogyo Co., Ltd.) (500 ml) was dissolved in methanol (10 ml) and then added with propionaldehyde (manufactured by Tokyo Kasei Kogyo Co., Ltd.) (0.418 ml), sodium cyanoborohydride (404 mg), and trimethyl orthoformate (1.60 g), followed by stirring at room temperature for 12 hours. After completion of the reaction, the solvent was distilled off. Then, the residue was added with chloroform, washed with distilled water and saturated saline solution, and then dried with anhydrous sodium sulfate. After concentration and evaporation to dryness, methanol (4.0 ml) and a 4 mol/l hydrogen chloride/dioxane solution (4.0 ml) were added to the dried product and the whole was stirred at room temperature for 2 hours. After completion of the reaction, the solvent was distilled off and then dioxane was added to wash the residue, thereby obtaining hydrochloride (654 mg) of the subject compound.

MS(FAB, Pos.): m/z=173[M+H]$^+$

Example 1-3

Synthesis of 4-{[N-Boc-N-(1H-imidazol-2-ylmethyl)amino]methyl}-N-(4-dipropylaminobutyl)benzamide The compound (203 mg) obtained in Example 1-2 was dissolved in DMF (5.0 ml) and chloroform (5.0 ml), and then added with triethylamine (0.374 ml), WSCI hydrochloride (382 mg), HOBt (200 mg), and the compound (463 mg) obtained in Example 1-1 and the whole was stirred at room temperature for 23 hours. After completion of the reaction, the solvent was distilled off. Then, the residue was added with chloroform and washed with water and saturated saline solution. The solution was dried with anhydrous sodium sulfate and then the solvent was distilled off. Subsequently, the residue was purified through silica gel column chromatography (chloroform/methanol/water), thereby obtaining the subject compound (168 mg) as colorless foam.

MS(FAB, Pos.): m/z=486[M+H]$^+$

Example 1-4

Synthesis of 4-{[N-(1H-imidazol-2-ylmethyl)amino]methyl-N-(4-dipropylaminobutyl)benzamide The compound (117 mg) obtained in Example 1-3 was dissolved in methanol (1.2 ml) and then added with a 4 mol/l hydrogen chloride/dioxane solution (1.2 ml), followed by stirring at room temperature for 5 hours. After completion of the reaction, the solvent was distilled off. Then, the residue was dissolved in water and then purified through solid-phase extraction column (Sep-Pak®, tC18, manufactured by Waters Corporation), thereby obtaining hydrochloride (118 mg) of the subject compound as a white solid.

MS(FAB, Pos.): m/z=386[M+H]$^+$ $^1$H-NMR(500 MHz, DMSO-d$_6$): δ=0.89(6H, t, J=7.3 Hz), 1.54–1.62(2H, m), 1.61–1.83(6H, m), 2.93–3.01(4H, m), 3.00–3.01(2H, m), 3.30(2H, dd, J=6.1, 12.3 Hz), 4.37(2H, s), 4.52(2H, s), 7.62–7.64(4H, m), 7.92(2H, d, J=8.1 Hz), 8.71(1H, d, J=4.4 Hz).

Example 1-5

Synthesis of 4-{[bis(1H-imidazol-2-ylmethyl)-amino]-methyl}-N-(4-dipropylamino-butyl)-benzamide [Compound No. 1]

The compound (24.0 mg) obtained in Example 1-4 was suspended in chloroform and extracted by the addition of a 1 mol/l sodium hydroxide aqueous solution. The organic layer was dried with anhydrous sodium sulfate. After the solvent had been distilled off, the residue was dissolved in methanol (0.5 ml) and added with 2-imidazole carboxaldehyde (4.60 mg) and sodium cyanoborohydride (4.60 mg). Then, the solution was adjusted to pH 5 with acetic acid and stirred at room temperature for 19 hours. After completion of the reaction, the solvent was distilled off and the residue was then suspended in chloroform, followed by washing with a 1 mol/l sodium hydroxide aqueous solution and saturated saline solution. Subsequently, the residue was dried with anhydrous sodium sulfate and the solvent was then distilled off. The residue was dissolved in chloroform and added with methanesulfonic acid (12.6 μl). The solvent was distilled off and the residue was then purified through silica gel column chromatography (chloroform/methanol/ water), thereby obtaining methanesulfonate (21.9 mg) of the subject compound as a white solid.

MS(FAB, Pos.): m/z=486[M+H]$^+$ $^1$H-NMR(500 MHz, DMSO-d$_6$): δ=0.89(6H, t, J=7.3 Hz), 1.50–1.69(8H, m), 2.94–3.01(4H, m), 3.04–3.13(2H, m), 3.24–3.32(2H, m), 3.75(2H, s), 4.08(4H, s), 7.43(2H, d, J=8.4 Hz), 7.62(4H, s), 7.77(2H, d, J=8.4 Hz), 8.51(1H, t, J=5.8 Hz), 8.99(1H, brs).

Production Example 2

Synthesis of 4-{[bis(1H-imidazol-2-ylmethyl)-amino]-methyl}-N-(4-diisobutylamino-butyl)-benzamide [Compound No. 2]

Example 2-1

Synthesis of 4-(1H-imidazol-2-ylmethylaminomethyl) benzoic acid methyl ester

The compound (2.01 g) obtained in Example 1-1 was dissolved in a solution (20 ml) of 10% hydrogen chloride/methanol and the solution was then stirred at room temperature for 23 hours. After completion of the reaction, the solution was concentrated and suspended in chloroform. Then, the suspension was added with a 1 mol/l sodium hydroxide aqueous solution to separate the solution into layers. The organic layer was dried with anhydrous sodium sulfate and the solvent was then distilled off. The residue was dried under reduced pressure, thereby obtaining the subject compound (0.80 g) as a white solid.

MS(FAB, Pos.): m/z=246[M+H]$^+$

Example 2-2

Synthesis of 4-[N,N-bis-(imidazol-2-ylmethyl)aminomethyl]-benzoic acid

The compound (800 mg) synthesized in Example 2-1 was dissolved in methanol (32 ml) and then the solution was added with 2-imidazole carboxaldehyde (345 mg) and sodium cyanoborohydride (307 mg). Then, the solution was adjusted to approximately pH 5 with acetic acid and stirred at room temperature for 16 hours. After completion of the reaction, the solvent was distilled off and the residue was then suspended in chloroform, followed by washing with a 1 mol/l sodium hydroxide aqueous solution and saturated saline solution. Subsequently, the resultant was dried with anhydrous sodium sulfate and the solvent was then distilled off. The residue was dissolved in methanol (10 ml) and a 1 mol/l sodium hydroxide aqueous solution (10 ml), followed by stirring at room temperature for 2.5 hours. After completion of the reaction, the organic solvent portion was distilled off. Then, the residue was adjusted to pH 6 by the addition of 1 mol/l hydrochloric acid. The aqueous layer was washed with chloroform. The solution was concentrated to remove water and the residue was then added with methanol. After the insoluble matter had been removed through filtration, the methanol was distilled off and the residue was then concentrated under reduced pressure, thereby obtaining the subject compound (1.05 g).

MS(FAB, Pos.): m/z=312[M+H]$^+$ $^1$H-NMR(500 MHz, DMSO-d$_6$): δ=3.70(2H, s), 3.90(4H, s), 7.32(4H, s), 7.52(2H, d, J=8.2 Hz), 7.86(2H, d, J=8.2 Hz).

Example 2-3

Synthesis of N-benzyloxycarbonyl-N',N'-1,4-diaminobutane

N-benzyloxycarbonyl-1,4-diaminobutane (200 mg) synthesized by the method described in Chemical Pharmaceutical Bulletin (Chem. Pharm. Bull) vol. 32, page 3428 (1984) was dissolved in methanol (6.0 ml) and added with di-isobutyl aldehyde (197 μl) and sodium cyanoborohydride (136 mg). Then, the solution was adjusted to approximately pH 5 with acetic acid and stirred at room temperature for 14 hours. After completion of the reaction, the solvent was distilled off and the residue was then suspended in chloroform, followed by washing with a 1 mol/l sodium hydroxide aqueous solution and saturated saline solution. The resultant was dried with anhydrous sodium sulfate and the solvent was then distilled off. Subsequently, the residue was purified through silica gel column chromatography (chloroform/methanol), thereby obtaining the subject compound (125 mg) as a colorless liquid.

MS(FAB, Pos.): m/z=335[M+H]$^+$

Example 2-4

Synthesis of 4-{[bis(1H-imidazol-2-ylmethyl)-amino]-methyl}-N-(4-diisobutylamino-butyl)-benzamide [Compound No. 2]

The compound (125 mg) obtained in Example 2-3 was dissolved in ethanol (7.5 ml). Then, the solution was added with 10% palladium-carbon (63.0 mg), followed by stirring under a hydrogen atmosphere at room temperature for 1 hour. After completion of the reaction, the catalyst was removed by Celite filtration and the solvent was then distilled off, followed by distilling azeotropically with dichloromethane to obtain a deprotected product. Subsequently, the product was dissolved in DMF (3.5 ml) and added with DCC (84.9 mg), HOBt (55.6 mg), and the compound (128 mg) obtained in Example 2-2, followed by stirring at room temperature for 17 hours. After completion of the reaction, insoluble matter was removed by decantation and the solvent was then distilled off. The residue was dissolved in chloroform and washed with a 1 mol/l sodium hydroxide aqueous solution. After the organic layer was added with hydrochloric acid, the solution was separated into layers. Then, the aqueous layer was adjusted to pH 11 by the addition of a sodium hydroxide aqueous solution, followed by extraction with chloroform. Subsequently, the organic layer was dried and concentrated with anhydrous sodium sulfate. The residue was purified through silica gel column chromatography (chloroform/methanol/water) and treated with hydrochloric acid, thereby obtaining hydrochloride (54.5 mg) of the subject compound as a white solid.

MS(FAB, Pos.): m/z=494[M+H]$^+$ $^1$H-NMR(500 MHz, DMSO-d$_6$): δ=0.96(6H, d, J=6.8 Hz), 0.98(6H, d, J=6.8 Hz), 1.51–1.69(2H, m), 1.67–1.75 (2H, m), 2.05(2H, sept., J=6.8 Hz), 2.82–2.96(4H, m), 3.08–3.13(2H, m), 3.25–3.33(2H, m), 3.71(2H, s), 4.13(4H, s), 7.54(2H, d, J=8.1 Hz), 7.61(4H, s), 7.78(2H, d, J=8.1 Hz), 8.59(1H, brs), 8.97(1H, br).

Production Example 3

Synthesis of 4-{[bis(1H-imidazol-2-ylmethyl)-amino]-methyl}-N-(4-aminobutyl)-benzamide [Compound No. 3]

Example 3-1

Synthesis of 4-{N,N-bis-(imidazol-2-ylmethyl)amino]methyl}-N-(Boc-aminobutyl)-benzamide The compound (406 mg) obtained in Example 2-2 and N-(4-aminobutyl)carbamic acid t-butyl ester (Tokyo Kasei Kogyo Co., Ltd.) (206 mg) were dissolved in DMF (12 ml) and added with WSCI hydrochloride (410 mg), followed by stirring for 6.5 hours. After completion of the reaction, the solvent was distilled off and the residue was then dissolved in chloroform. After that, the solution was washed with a 1 mol/l sodium hydroxide aqueous solution and saturated saline solution and then concentrated. The residue was purified through silica gel column chromatography (chloroform/methanol), thereby obtaining the subject compound (23.0 mg) as colorless foam.

MS(FAB, Pos.): m/z=482[M+H]$^+$

Example 3-2

Synthesis of 4-{[bis(1H-imidazol-2-ylmethyl)-amino]-methyl}-N-(4-aminobutyl)-benzamide [Compound No. 3]

The compound (22.0 mg) obtained in Example 3-1 was dissolved in methanol (0.2 ml) and added with a 4 mol/l hydrogen chloride/dioxane solution (0.22 ml), followed by stirring at room temperature for 30 minutes. After completion of the reaction, the solvent was distilled off. The residue was dried under reduced pressure and then suspended in chloroform. The suspension was washed with a 1 mol/l sodium hydroxide aqueous solution and saturated saline solution and dried with anhydrous sodium sulfate. Subsequently, the solvent was distilled off and the residue was then dried under reduced pressure, thereby obtaining the subject compound (32.5 mg).

MS(FAB, Pos.): m/z=382[M+H]$^+$
$^1$H-NMR(500 MHz, DMSO-$d_6$): δ=2.73–2.81(2H, m), 3.24–3.30(2H, m), 3.71(2H, s), 4.14(4H, s), 7.53(2H, d, J=8.2 Hz), 7.60(4H, s), 7.67(2H, d, J=8.2 Hz), 7.93(3H, brs), 8.59(1H, t, J=5.6 Hz), 14.8(3H, brs).

Production Example 4

4-{[bis(1H-imidazol-2-ylmethyl)-amino]-methyl}-N-(4-cyclohexylamino-butyl)-benzamide [Compound No. 4]

Example 4-1

Synthesis of 4-{[bis(1H-imidazol-2-ylmethyl)-amino]-methyl}-N-(4-cyclohexylamino-butyl)-benzamide [Compound No. 4]

The compound (28.8 mg) obtained in Example 3-2 was dissolved in methanol (0.5 ml). The solution was added with cyclohexanone (8.80 μl) and sodium cyanoborohydride (4.40 mg) and then adjusted to approximately pH 5 with acetic acid, followed by stirring at room temperature for 16 hours. After completion of the reaction, the solvent was distilled off. Then, the residue was dissolved in chloroform and washed with a 1 mol/l sodium hydroxide aqueous solution and saturated saline solution, followed by the addition of 1 mol/l hydrochloric acid to extract the objective substance. Subsequently, the aqueous layer was concentrated under reduced pressure and then the residue was purified through a solid-phase extraction column (Bond Elut® C18 (manufactured by Varian Inc.), 200 mg), thereby obtaining hydrochloride (17.6 mg) of the subject compound as a white solid.

MS(FAB, Pos.): m/z=463[M+H]$^+$
$^1$H-NMR(500 MHz, DMSO-$d_6$): δ=1.03–1.14(1H, m), 1.16–1.33(4H, m), 1.54–1.69(5H, m), 1.70–1.80(2H, m), 1.98–2.06(2H, m), 2.85–2.97(3H, m), 3.23–3.31(2H, m), 3.69(2H, s), 4.11(4H, s), 7.45(2H, d, J=8.4 Hz), 7.58(4H, s), 7.76(2H, d, J=8.4 Hz), 8.48(1H, brs), 8.72(1H, br).

Production Example 5

Synthesis of 4-{[bis(1H-imidazol-2-ylmethyl)-amino]-methyl}-N-(4-benzyloxycarbonylaminobutyl)-benzamide [Compound No. 5]

Example 5-1

Synthesis of 4-{[bis(1H-imidazol-2-ylmethyl)-amino]-methyl}-N-(4-benzyloxycarbonylaminobutyl)-benzamide [Compound No. 5]

The compound (413 mg) obtained in Example 2-2 and N-benzyloxycarbonyl-1,4-diaminobutane (247 mg) were dissolved in anhydrous DMF (8.0 ml) and added with WSCI hydrochloride (234 mg) and HOBt (165 mg), followed by stirring at room temperature for 14 hours. After completion of the reaction, the solvent was distilled off. The residue was dissolved in chloroform, washed with 1 mol/l hydrochloric acid, a 1 mol/l sodium hydroxide aqueous solution, and saturated saline solution, and dried with anhydrous magnesium sulfate, followed by distilling the solvent off. Subsequently, the residue was purified through silica gel column chromatography (chloroform/methanol/water) and treated with hydrochloric acid, thereby obtaining hydrochloride (23.0 mg) of the subject compound as a white solid.

MS(FAB, Pos.): m/z=516[M+H]$^+$
$^1$H-NMR(500 MHz, DMSO-$d_6$): δ=1.40–1.50(4H, m), 2.99(2H, dd, J=6.3, 12.4 Hz), 3.22(2H, dd, J=6.1, 12.6 Hz), 3.71(2H, s), 4.12(4H, s), 4.99(2H, s), 7.27–7.37(6H, m), 7.50(2H, d, J=8.3 Hz), 7.61(4H, s), 7.76(2H, dd, J=8.3 Hz), 8.44(1H, t, J=5.6 Hz).

Production Example 6

Synthesis of 4-{[bis(1H-imidazol-2-ylmethyl)-amino]-methyl}-N-[4-(2-methoxy-benzylamino)-butyl]-benzamide [Compound No. 6]

Example 6-1

Synthesis of 4-{[bis(1H-imidazol-2-ylmethyl)-amino]-methyl}-N-[4-(2-methoxy-benzylamino)-butyl]-benzamide [Compound No. 6]

The compound (63.9 mg) obtained in Example 3-2 was dissolved in anhydrous methanol (1.3 ml) and then added with 2-methoxybenzaldehyde (manufactured by Tokyo Kasei Kogyo Co., Ltd.) (0.0350 ml) and trimethyl orthoformate (manufactured by Tokyo Kasei Kogyo Co., Ltd.)

(0.0560 ml), followed by stirring at room temperature for 30 minutes. The solution was added with sodium borohydride (19.3 mg), followed by stirring at room temperature for 15 minutes. After completion of the reaction, the solvent was distilled off. Then, the residue was added with water and extracted with chloroform, and the extract was washed with saturated saline solution, followed by drying with anhydrous magnesium sulfate. The solvent was distilled off and treated with hydrochloric acid. The residue was purified through a solid-phase extraction column (Sep-Pack®, tC18, manufactured by Waters Corporation), thereby obtaining hydrochloride (6.80 mg) of the subject compound as a white solid.

MS(FAB, Pos.): m/z=502[M+H]$^+$ $^1$H-NMR(500 MHz, DMSO-d$_6$): δ=1.53–1.57(2H, m), 1.64–1.69(2H, m), 2.92(2H, br), 3.25(2H, dd, J=6.7, 12.5 Hz), 3.71(2H, s), 3.83(2H, s), 4.06–4.08(2H, m), 4.10(4H, s), 6.99(1H, dt, J=1.1, 7.5 Hz), 7.09(1H, d, J=7.6 Hz), 7.40–7.46(2H, m), 7.52(2H, d, J=8.4 Hz), 7.60(4H, s), 7.77(2H, d, J=8.4 Hz), 8.53(1H, t, J=5.5 Hz), 8.81(2H, br).

Production Example 7

Synthesis of 4-{[bis(1H-imidazol-2-ylmethyl)-amino]-methyl}-N-(2-dipropylamino-ethyl)-benzamide [Compound No. 7]

Example 7-1

Synthesis of mono-N-Boc-ethylenediamine

Ethylenediamine (manufactured by Kanto Kagaku) (5.01 g) was dissolved in chloroform (100 ml) and added with triethylamine (13.9 ml), followed by dropping a chloroform solution (5.0 ml) of di-t-butyl dicarbonate (2.27 g) therein. After the mixture had been stirred at room temperature for 4 hours, the solvent was distilled off under reduced pressure and the residue was then dissolved in ethyl acetate. Then, the residue was washed with a 1 mol/l sodium hydroxide aqueous solution and water and extracted with ethyl acetate, and the extract was washed with saturated saline solution, followed by drying with anhydrous sodium sulfate. After filtration, the solvent was distilled off under reduced pressure and the residue was then purified through silica gel column chromatography (chloroform/methanol/water), thereby obtaining the subject compound (1.09 g) as a pale-yellow liquid.

MS(FAB, Pos.): m/z=161[M+H]$^+$ $^1$H-NMR(500 MHz, DMSO-d$_6$): δ=1.37(9H, s), 2.49–2.54(2H, m), 2.90(2H, q, J=6.1 Hz), 6.74(1H, brs).

Example 7-2

Synthesis of 4-{[bis-(1H-imidazol-2-ylmethyl) amino]methyl}-N-(2-N-Boc-aminoethyl)-benzamide The compound (342 mg) obtained in Example 2-2, DCC (227 mg), and HOBt (149 mg) were dissolved in DMF (3.0 ml), followed by stirring for 10 minutes. A DMF solution (2.0 ml) of the compound (160 mg) obtained in Example 7-1 was dropped in this solution, and the whole was stirred at room temperature for 14 hours. After completion of the reaction, the solvent was distilled off under reduced pressure. The residue was dissolved in 0.2 mol/l hydrochloric acid and washed with chloroform. The aqueous layer was added with a 1 mol/l sodium hydroxide aqueous solution and extracted with chloroform. The organic layer was washed with saturated saline solution, followed by drying with anhydrous sodium sulfate. After filtration, the solvent was distilled off under reduced pressure and the residue was then purified through silica gel column chromatography (chloroform/methanol), thereby obtaining the subject compound (334 mg) as a pale-yellow solid.

MS(FAB, Pos.): m/z=454[M+H]$^+$ $^1$H-NMR(500 MHz, DMSO-d$_6$): δ=1.37(9H, s), 3.09(2H, q, J=6.3 Hz), 3.28(2H, q, J=6.3 Hz), 3.56(2H, s), 3.58(4H, s), 6.90–6.92(2H, m), 7.06(2H, br), 7.48(2H, d, J=8.2 Hz), 7.78(2H, d, J=8.1 Hz), 8.41(1H, t, J=5.4 Hz).

Example 7-3

Synthesis of 4-{[bis(1H-imidazol-2-ylmethyl)-amino]-methyl}-N-(2-dipropylamino-ethyl)-benzamide [Compound No. 7]

The compound (165 mg) obtained in Example 7-2 was dissolved in methanol (1.7 ml). A 4 mol/l hydrogen chloride/dioxane solution (0.83 ml) was added in this solution, and the whole was stirred at room temperature for 1 hour. After completion of the reaction, the solvent was distilled off under reduced pressure and the residue was dried under vacuum. The dried product was dissolved in methanol (4.0 ml) and then added with trimethyl orthoformate (165 μl), acetic acid (200 μl), propionaldehyde (78.0 μl), and sodium cyanoborohydride (68.6 mg) and stirred at room temperature for 23 hours. The solvent was distilled off under reduced pressure. Then, the residue was dissolved in chloroform and washed with a 1 mol/l sodium hydroxide aqueous solution, and added with 1 mol/l hydrochloric acid to transfer the objective substance to the aqueous layer, followed by washing with chloroform. The 1 mol/l sodium hydroxide aqueous solution was added again to alkalinize the solution. The solution was subjected to extraction with chloroform and the extract was then washed with saturated saline solution and dried with anhydrous sodium sulfate. After filtration, the solvent was distilled off under reduced pressure. Then, the residue was dried under vacuum and treated with hydrochloric acid, thereby obtaining hydrochloride (110 mg) of the subject compound as a white solid.

MS(FAB, Pos.): m/z=438[M+H]$^+$ $^1$H-NMR(500 MHz, DMSO-d$_6$): δ=0.89(6H, t, J=7.3 Hz), 1.69(4H, sext., J=7.3 Hz), 3.04–3.08(4H, m), 3.23(2H, m), 3.49–3.66(2H, m), 3.72(2H, s), 4.14(4H, s), 7.54(2H, d, J=8.4 Hz), 7.60(4H, s), 7.83(2H, d, J=8.2 Hz), 8.97(1H, brs), 10.40(1H, br).

Production Example 8

Synthesis of 4-{[bis(1H-imidazol-2-ylmethyl)-amino]-methyl}-N-(2-cyclohexylaminoethyl)-benzamide [Compound No. 8]

Example 8-1

Synthesis of 4-{[bis(1H-imidazol-2-ylmethyl)-amino]-methyl}-N-(2-cyclohexylaminoethyl)-benzamide [Compound No. 8]

The compound (165 mg) obtained in Example 7-2 was dissolved in methanol (1.7 ml). A 4 mol/l hydrogen chloride/dioxane solution (0.83 ml) was added in this solution, and the whole was stirred at room temperature for 1 hour. After completion of the reaction, the solvent was distilled off under reduced pressure and the residue was dried under vacuum, thereby obtaining a crude product. The product was dissolved in methanol (4.0 ml) and then added with trimethyl orthoformate (165 μl), acetic acid (200 μl), cyclohexanone (75.0 μl), and sodium cyanoborohydride (68.6 mg) and stirred for 23 hours at room temperature. The solvent was distilled off under reduced pressure. Then, the residue was dissolved in chloroform and washed with a 1 mol/l sodium hydroxide aqueous solution, and added with 1 mol/l hydrochloric acid to transfer the objective substance to the aqueous layer, followed by washing with chloroform. The 1 mol/l sodium hydroxide aqueous solution was added again to alkalinize the solution. The solution was subjected to extraction with chloroform and the extract was then washed with saturated saline solution and dried with anhydrous sodium sulfate. After filtration, the solvent was distilled off under reduced pressure. Then, the residue was dried under vacuum and treated with hydrochloric acid, thereby obtaining hydrochloride (116.0 mg) of the subject compound as a white solid.

MS(FAB, Pos.) m/z=436[M+H]$^+$ $^1$H-NMR(500 MHz, DMSO-d$_6$): δ=1.08–1.35(6H, m), 1.59(2H, d, J=12.7 Hz), 1.75(2H, d, J=12.7 Hz), 2.04(2H, d, J=10.2 Hz), 3.00–3.09(3H, m), 3.59(2H, q, J=5.9 Hz), 3.72(2H, s), 4.14(4H, s), 7.53(2H, d, J=8.2 Hz), 7.61(4H, s), 7.86(2H, d, J=8.4 Hz), 8.90(1H, t, J=5.9 Hz), 9.07(1H, brs).

Production Example 9

Synthesis of 4-{[bis(1H-imidazol-2-ylmethyl)-amino]-methyl}-N-[4-(cyclohexylmethyl-amino)-butyl]-benzamide [Compound No. 9]

Example 9-1

Synthesis of 4-{[bis(1H-imidazol-2-ylmethyl)-amino]-methyl}-N-[4-(cyclohexylmethyl-amino)-butyl]-benzamide [Compound No. 9]

The compound (50.6 mg) obtained in Example 3-2 was dissolved in anhydrous methanol (2.0 ml) and added with cyclohexane carboxaldehyde (manufactured by Tokyo Kasei Kogyo Co., Ltd.) (0.0240 ml) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (42.0 mg) of the subject compound as a white solid.

MS(FAB, Pos.): m/z=478[M+H]$^+$ $^1$H-NMR(500 MHz, DMSO-d$_6$): δ=0.88–0.95(2H, m), 1.04–1.23(3H, m), 1.51–1.57(2H, m), 1.60–1.69(6H, m), 1.75(2H, d, J=12.4 Hz), 2.69–2.73(2H, m), 2.88(2H, br), 3.24–3.28(2H, m), 3.71(2H, s), 4.12(4H, s), 7.53(2H, d, J=8.2 Hz), 7.61(4H, s), 7.78(2H, d, J=8.4 Hz), 8.55(2H, t, J=5.5 Hz), 8.59(2H, br).

Production Example 10

Synthesis of 4-{[bis(1H-imidazol-2-ylmethyl)-amino]-methyl}-N-[4-(4-t-butyl-benzylamino)-butyl]-benzamide [Compound No. 10]

Example 10-1

Synthesis of 4-{[bis(1H-imidazol-2-ylmethyl)-amino]-methyl}-N-[4-(4-t-butyl-benzylamino)-butyl]-benzamide [Compound No. 10]

The compound (50.6 mg) obtained in Example 3-2 was dissolved in anhydrous methanol (2.0 ml) and added with 4-t-butyl-benzaldehyde (manufactured by Tokyo Kasei Kogyo Co., Ltd.) (0.0330 ml) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (42.0 mg) of the subject compound as a white solid.

MS(FAB, Pos.): m/z=528[M+H]$^+$ $^1$H-NMR(500 MHz, DMSO-d$_6$): δ=1.28(9H, s), 1.53–1.56(2H, m), 1.67(2H, m), 2.91(2H, br), 3.25(2H, d, J=6.3 Hz), 3.71(2H, s), 4.07(2H, t, J=5.5 Hz), 4.11(4H, s), 7.45(4H, d, J=2.1 Hz), 7.52(8.2 Hz), 7.60(4H, s), 7.77(2H, d, J=8.2 Hz), 8.53(1H, t, J=5.6 Hz), 9.08(1H, br).

Production Example 11

Synthesis of 4-{[bis(1H-imidazol-2-ylmethyl)-amino]-methyl}-N-[4-(2-trifluoromethyl)-benzylamino-butyl]-benzamide [Compound No. 11]

Example 11-1

Synthesis of 4-{[bis(1H-imidazol-2-ylmethyl)-amino]-methyl}-N-[4-(2-trifluoromethyl)-benzylamino-butyl]-benzamide [Compound No. 11]

The compound (50.6 mg) obtained in Example 3-2 was dissolved in anhydrous methanol (2.0 ml) and added with 2-trifluoromethylbenzaldehyde (manufactured by Tokyo Kasei Kogyo Co., Ltd.) (0.0260 ml) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (57.1 mg) of the subject compound as a white solid.

MS(FAB, Pos.): m/z=540[M+H]$^+$

¹H-NMR(500 MHz, DMSO-d₆+D₂O): δ=1.57–1.60 (2H, m), 1.69–1.70(2H, m), 3.07(2H, t, J=7.6 Hz), 3.28(2H, t, J=6.8 Hz), 3.74(2H, s), 4.10(4H, s), 4.30(2H, s), 7.45(2H, d, J=8.3 Hz), 7.57(4H, s), 7.67–7.85(6H, m).

Production Example 12

Synthesis of 4-{[bis(1H-imidazol-2-ylmethyl)-amino]-methyl}-N-[4-(2-trifluoromethoxy)-benzylamino-butyl]-benzamide [Compound No. 12]

Example 12-1

Synthesis of 4-{[bis(1H-imidazol-2-ylmethyl)-amino]-methyl}-N-[4-(2-trifluoromethoxy)-benzylamino-butyl]-benzamide [Compound No. 12]

The compound (50.6 mg) obtained in Example 3-2 was dissolved in anhydrous methanol (2.0 ml) and added with 2-trifluoromethoxybenzaldehyde (manufactured by Avocado Co., Ltd.) (0.0290 ml) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (39.7 mg) of the subject compound as a white solid.

MS(FAB, Pos.): m/z=556[M+H]⁺
¹H-NMR(500 MHz, DMSO-d₆): δ=1.55–1.57(2H, m), 1.68–1.70(2H, m), 2.99(2H, br), 3.26(2H, d, J=6.0 Hz), 3.71(2H, s), 4.10(4H, s), 4.20(2H, s), 7.45–7.53(4H, m), 7.56–7.59(1H, m), 7.77–7.82(3H, m), 8.53(1H, t, J=5.5 Hz), 9.24(2H, br).

Production Example 13

Synthesis of 4-{[bis(1H-imidazol-2-ylmethyl)-amino]-methyl}-N-[4-(4-methylsulfanyl-benzylamino)-butyl]-benzamide [Compound No. 13]

Example 13-1

Synthesis of 4-{[bis(1H-imidazol-2-ylmethyl)-amino]-methyl}-N-[4-(4-methylsulfanyl-benzylamino)-butyl]-benzamide [Compound No. 13]

The compound (50.6 mg) obtained in Example 3-2 was dissolved in anhydrous methanol (2.0 ml) and added with 4-methylthiobenzaldehyde (manufactured by Tokyo Kasei Kogyo Co., Ltd.) (0.0270 ml) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (64.0 mg) of the subject compound as a white solid.

MS(FAB, Pos.): m/z=518[M+H]⁺
¹H-NMR(500 MHz, DMSO-d₆): δ=1.50–1.59(2H, m), 1.61–1.70(2H, m), 2.48(3H, s), 2.88(2H, br), 3.24(2H, d, J=5.8 Hz), 3.71(2H, s), 4.07(2H, m), 4.11(4H, s), 7.29(2H, d, J=8.4 Hz), 7.46(2H, d, J=8.4 Hz), 7.52(2h, d, J=8.2 Hz), 7.60(4H, s), 7.77(2H, d, J=8.4 Hz), 8.52(1H, t, J=5.5 Hz), 9.09(2H, br).

Production Example 14

Synthesis of 4-{[bis(1H-imidazol-2-ylmethyl)-amino]-methyl}-N-{4-[(3-methyl-pyridin-2-ylmethyl)-amino]-butyl}-benzamide [Compound No. 14]

Example 14-1

Synthesis of 4-{[bis(1H-imidazol-2-ylmethyl)-amino]-methyl}-N-{4-[(3-methyl-pyridin-2-ylmethyl)-amino]-butyl}-benzamide [Compound No. 14]

The compound (50.6 mg) obtained in Example 3-2 was dissolved in anhydrous methanol (2.0 ml) and added with 3-methylpyridine-2-carboxaldehyde (24.2 mg) and trimethyl orthoformate (0.0430 ml), followed by stirring at room temperature for 30 minutes. Then, the solution was added with sodium borohydride (14.8 mg), followed by stirring at room temperature for 15 minutes. After completion of the reaction, the solvent was distilled off. The residue was dissolved in chloroform and washed with a 1 mol/l sodium hydroxide aqueous solution and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (59.3 mg) of the subject compound as a white solid.

MS(FAB, Pos.): m/z=487[M+H]⁺
¹H-NMR(500 MHz, DMSO-d₆): δ=1.56–1.61(2H, m), 1.73–1.75(2H, m), 2.29(3H, s), 3.03–3.06(2H, m), 3.27(2H, dd, J=6.3, 12.4 Hz), 3.71(2H, s), 4.12(4H, s), 4.33(2H, t, J=5.8 Hz), 7.34–7.36(1H, m), 7.54(2H, d, J=8.2 Hz), 7.61 (4H, s), 7.70(1H, d, J=7.8 Hz), 7.78(2H, d, J=8.2 Hz), 8.45(1H, d, J=3.7 Hz), 8.55(1H, t, J=5.5 Hz), 9.13(2H, br), 12.68(3H, br).

Production Example 15

Synthesis of 4-{[bis(1H-imidazol-2-ylmethyl)-amino]-methyl}-N-(4-dipropylaminophenyl)-benzamide [Compound No. 15]

Example 15-1

Synthesis of N,N-dipropyl-N'-Boc-1,4-phenylenediamine

N-Boc-1,4-phenylenediamine (manufactured by Furka Co., Ltd.) (589 mg) was dissolved in anhydrous methanol (2.0 ml) and then added with sodium cyanoborohydride (533 mg), trimethyl orthoformate (774 µl), and propionaldehyde (510 µl), followed by stirring overnight under a nitrogen atmosphere at room temperature. After completion of the reaction, the solvent was distilled off. Then, the residue was then dissolved in chloroform and added with a saturated aqueous sodium bicarbonate solution, followed by stirring. This solution was subjected to extraction with chloroform and the extract was then washed with a saturated aqueous sodium bicarbonate solution and saturated saline solution. The organic layer was dried with anhydrous sodium sulfate. The solvent was distilled off and the residue was then purified through silica gel column chromatography (chloroform), thereby obtaining the subject compound (863 mg) as an auburn liquid.

MS(FAB, Pos.): m/z=292[M+H]$^+$
$^1$H-NMR(500 MHz, CDCl$_3$): δ=0.90(6H, t, J=7.6 Hz), 1.50(9H, s), 1.57(4H, sext., J=7.6 Hz), 3.18(4H, t, J=7.6 Hz), 6.22(1H, brs), 6.58(2H, d, J=9.0 Hz), 7.15(2H, br).

Production Example 15-2

Synthesis of 4-{[bis(1H-imidazol-2-ylmethyl)-amino]-methyl}-N-(4-dipropylaminophenyl)-benzamide [Compound No. 15]

The compound (300 mg) obtained in Example 2-2 was dissolved in DMF (10 ml) and added with DCC (298 mg), HOBt (195 mg), and the compound (185 mg) obtained in Example 15-1, followed by stirring overnight at room temperature. After completion of the reaction, the solvent was distilled off and the residue was then dissolved in chloroform, followed by separating the solution into layers by the addition of 1 mol/l hydrochloric acid. The aqueous layer was made basic by the addition of a 1 mol/l sodium hydroxide aqueous solution. Then, the solution was subjected to extraction with chloroform. The extract was washed with saturated saline solution and the organic layer was then dried with anhydrous sodium sulfate. The solvent was distilled off. Subsequently, the residue was treated with hydrochloric acid and then purified through silica gel column chromatography (chloroform/methanol/water), thereby obtaining hydrochloride (96.4 mg) of the subject compound as a white solid.

MS(FAB, Pos.): m/z=486[M+H]$^+$
$^1$H-NMR(500 MHz, DMSO-d$_6$): δ=0.83(6H, t, J=6.9 Hz), 1.12–1.30(2H, m), 1.66(2H, brs), 3.44(4H, m), 3.76(2H, s), 4.16(4H, s), 7.62(6H, brs), 7.79(2H, brs), 7.94(2H, d, J=7.6 Hz), 7.99(2H, brs), 10.6(1H, brs), 12.7(1H, brs), 14.8(1H, brs).

Production Example 16

Synthesis of 4-{[bis(1H-imidazol-2-ylmethyl)-amino]-methyl}-N-{4-[bis(3-methyl-butyl)-amino]butyl}-benzamide [Compound No. 16]

Example 16-1

Synthesis of 4-{[bis(1H-imidazol-2-ylmethyl)-amino]-methyl}-N-{4-[bis(3-methyl-butyl)-amino]butyl}-benzamide [Compound No. 16]

The compound (30.0 mg) obtained in Example 3-2 was dissolved in methanol (0.6 ml). Then, the solution was added with trimethyl orthoformate (30.0 μl), acetic acid (30.0 μl), isovaleraldehyde (manufactured by Tokyo Kasei Kogyo Co., Ltd.) (25.3 μl), and sodium cyanoborohydride (14.9 mg), followed by stirring at room temperature for 3 hours.

After completion of the reaction, the solvent was distilled off under reduced pressure and the residue was then dissolved in chloroform. After the residue had been washed with a 1 mol/l sodium hydroxide aqueous solution, the objective substance was transferred to the aqueous layer by the addition of 1 mol/l hydrochloric acid, followed by washing with chloroform. The 1 mol/l sodium hydroxide aqueous solution was added again to alkalinize the solution, followed by extraction with chloroform. Then, the extract was washed with saturated saline solution and then dried with anhydrous sodium sulfate. After filtration, the solvent was distilled off under reduced pressure and the residue was dried under vacuum. Subsequently, the residue was treated with hydrochloric acid, thereby obtaining hydrochloride (21.8 mg) of the subject compound as a white solid.

MS(FAB, Pos.): m/z=522[M+H]$^+$
$^1$H-NMR(500 MHz, DMSO-d$_6$): δ=0.87(12H, d, J=6.1 Hz), 1.46–1.60(8H, m), 1.67(2H, br), 2.98–3.04(6H, m), 3.28(2H, d, J=5.8 Hz), 3.71(2H, s), 4.13(4H, s), 7.54(2H, d, J=8.1 Hz), 7.61(4H, s), 7.79(2H, d, J=8.2 Hz), 8.57(1H, t, J=5.8 Hz), 10.23(1H, brs).

Production Example 17

Synthesis of 4-{[bis(1H-imidazol-2-ylmethyl)-amino]-methyl}-N-(4-dimethylamino-butyl)-benzamide [Compound No. 17]

Example 17-1

Synthesis of 4-{[bis(1H-imidazol-2-ylmethyl)-amino]-methyl}-N-(4-dimethylamino-butyl)-benzamide [Compound No. 17]

The compound (27.7 mg) obtained in Example 3-2 was dissolved in anhydrous methanol (1.1 ml). Then, the solution was added with a 36% formaldehyde aqueous solution (manufactured by Kanto Kagaku) (0.0160 ml) and sodium cyanoborohydride (13.2 mg) and adjusted to pH 5 with acetic acid, followed by stirring at room temperature for 22 hours. After completion of the reaction, the solvent was distilled off and the residue was then dissolved in chloroform, followed by washing with a 1 mol/l sodium hydroxide aqueous solution and saturated saline solution and drying with anhydrous magnesium sulfate. The solvent was distilled off and the residue was then treated with hydrochloric acid. Subsequently, the residue was purified through a solid-phase extraction column (Sep-Pack®, tC18, manufactured by Waters Corporation), thereby obtaining hydrochloride (16.4 mg) of the subject compound as a white solid.

MS(FAB, Pos.): m/z=410[M+H]$^+$
$^1$H-NMR(500 MHz, DMSO-d$_6$): δ=1.51–1.54(2H, m), 1.65(2H, m), 2.73(6H, d, J=4.9 Hz), 3.03–3.04(2H, m), 3.26(2H, d, J=5.6 Hz), 3.72(2H, s), 4.08(4H, s), 7.51(2H, d, J=8.5 Hz), 7.59(4H, s), 7.77(2H, d, J=8.3 Hz), 8.52(1H, t, J=5.5 Hz).

Production Example 18

Synthesis of 4-{[bis(1H-imidazol-2-ylmethyl)-amino]-methyl}-N-(4-cycloheptylaminobutyl)-benzamide [Compound No. 18]

Example 18-1

Synthesis of 4-{[bis(1H-imidazol-2-ylmethyl)-amino]-methyl}-N-(4-cycloheptylaminobutyl)-benzamide [Compound No. 18]

The compound (30.0 mg) obtained in Example 3-2 was dissolved in methanol (0.6 ml). This solution was added with trimethyl orthoformate (30.0 μl), acetic acid (30.0 μl), cycloheptanone (manufactured by Merck, Inc.) (18.7 μl), and sodium cyanoborohydride (14.9 mg), followed by stirring for 3 hours at room temperature. After completion of the reaction, the solvent was distilled off under reduced pressure. Then, the residue was dissolved in chloroform, washed with a 1 mol/l sodium hydroxide aqueous solution, and added with 1 mol/l hydrochloric acid to transfer the objective substance to the aqueous layer, followed by washing with chloroform. The 1 mol/l sodium hydroxide aqueous solution was added again to alkalinize the solution. The solution was subjected to extraction with chloroform and the extract was then washed with saturated saline solution and dried with anhydrous sodium sulfate. After filtration, the solvent was distilled off under reduced pressure. Then, the residue was dried under vacuum and treated with hydrochloric acid, thereby obtaining hydrochloride (32.2 mg) of the subject compound as a white solid.

MS(FAB, Pos.): m/z=478[M+H]$^+$ $^1$H-NMR(500 MHz, DMSO-d$_6$): δ=1.29–1.66(14H, m), 2.00–2.03(2H, m), 2.88(2H, br), 3.06–3.12(1H, m), 3.26 (2H, d, J=6.1 Hz), 3.71(2H, s), 4.13(4H, s), 7.53(2H, d, J=8.2 Hz), 7.61(4H, s), 7.78(2H, d, J=8.4 Hz), 8.57(1H, t, J=6.1 Hz), 8.69(1H, brs).

Production Example 19

Synthesis of 4-{[bis(1H-imidazol-2-ylmethyl)-amino]-methyl}-N-(4-dipropylaminomethylphenyl)-benzamide [Compound No. 19]

Example 19-1

Synthesis of (4-nitrobenzyl) dipropylamine

Commercially available 4-nitrobenzylamine hydrochloride (manufactured by Tokyo Kasei Kogyo., Ltd.) (1.82 g) was suspended in chloroform (15 ml). Then, a 1 mol/l sodium hydroxide aqueous solution (15 ml) was added to the suspension and the aqueous layer was then extracted with chloroform. The extract was dried with anhydrous magnesium sulfate and the solvent was then distilled off, followed by dissolving the residue in anhydrous methanol (20 ml). Subsequently, the solution was added with propionaldehyde (1.66 ml) and sodium cyanoborohydride (1.81 g) and then adjusted to pH 5 with acetic acid, followed by stirring at room temperature for 21 hours. After completion of the reaction, the solvent was distilled off. The residue was added with 1 mol/l sodium hydroxide and then subjected to chloroform extraction. The extract was dried with anhydrous magnesium sulfate and the solvent was then distilled off. The residue was purified through silica gel column chromatography (hexane/ethyl acetate), thereby obtaining the subject compound (1.67 g) as a yellow oily substance.

$^1$H-NMR(500 MHz, CDCl$_3$): δ=0.87(6H, t, J=7.3 Hz), 1.47(4H, sext., J=7.3 Hz), 2.38(4H, t, J=7.1 Hz), 3.63(2H, s), 7.52(2H, d, J=9.0 Hz), 8.16(2H, d, J=8.8 Hz).

Example 19-2

Synthesis of 4-dipropylaminomethyl phenylamine

The compound (492 mg) obtained in Example 19-1 was dissolved in methanol (5.0 ml) and THF (2.5 ml). Then, the solution was added with activated carbon (49.0 mg) and iron trichloride hexahydrate (manufactured by Kanto Kagaku) (4.90 mg), followed by refluxing under heating for 30 minutes. After the solution was cooled to room temperature, hydrazine monohydrate (0.35 ml) was added to the solution and then the whole was refluxed for 3 hours under heat. After completion of the reaction, the reaction product was filtrated through Celite and the solvent was then distilled off. After the addition of water, chloroform extraction was performed. The extract was dried with anhydrous magnesium sulfate. The solvent was distilled off, thereby obtaining the subject compound (437 mg) as a yellow oily substance.

MS(FAB, Pos.): m/z=207[M+H]$^+$

Example 19-3

Synthesis of 4-{[bis(1H-imidazol-2-ylmethyl)-amino]-methyl}-N-(4-dipropylaminomethylphenyl)-benzamide [Compound No. 19]

The compound (57.2 mg) obtained in Example 19-2, the compound (106 mg) obtained in Example 2-2, and HOBt (162 mg) were dissolved in anhydrous DMF (2.5 ml) and then added with PS-carbodiimide (manufactured by Argonaut Technologies, Inc.) (419 mg), followed by stirring at room temperature for 12 hours. After completion of the reaction, the solution was filtrated and the solvent was then distilled off. The residue was dissolved in chloroform and then washed with 1 mol/l sodium hydroxide and saturated saline solution, followed by drying with anhydrous magnesium sulfate. The solvent was distilled off and the residue was then treated with hydrochloric acid. Subsequently, the residue was purified through silica gel column chromatography (chloroform/methanol/water), thereby obtaining hydrochloride (18.3 mg) of the subject compound as a yellow solid.

MS(FAB, Pos.): m/z=500[M+H]$^+$ $^1$H-NMR(500 MHz, DMSO-d$_6$): δ=0.87(6H, t, J=7.3 Hz), 1.67–1.77(4H, m), 2.88–2.93(4H, m), 3.76(2H, s), 4.14(4H, s), 4.26(2H, d, J=5.2 Hz), 7.56(2H, d, J=8.5 Hz), 7.62(4H, s), 7.88(2H, d, J=8.7 Hz), 7.91(2H, d, J=8.2 Hz), 10.18(1H, br), 10.39(1H, s).

Production Example 20

Synthesis of N-(4-dipropylaminobutyl)-4-{[(1H-imidazol-2-ylmethyl)-(pyridin-2-ylmethyl)-amino]-methyl}-benzamide [Compound No. 20]

Example 20-1

Synthesis of N-(4-dipropylaminobutyl)-4-{[(1H-imidazol-2-ylmethyl)-(pyridin-2-ylmethyl)-amino]-methyl}-benzamide [Compound No. 20]

The compound (39.8 mg) obtained in Example 1-3 and pyridine-2-aldehyde (manufactured by Tokyo Kasei Kogyo Co., Ltd.) (16.1 mg) were dissolved in anhydrous methanol (2.0 ml). The solution was added with sodium cyanoborohydride (18.9 mg) and then adjusted to pH 5 with acetic acid, followed by stirring at room temperature for 39.5 hours. After completion of the reaction, the solvent was distilled off. The residue was dissolved in chloroform and then washed with a 1 mol/l sodium hydroxide and saturated saline solution, followed by drying with anhydrous magnesium sulfate. Subsequently, the residue was distilled off and the residue was then treated with hydrochloric acid. The residue was purified through silica gel column chromatography (chloroform/methanol/water), thereby obtaining hydrochloride (7.00 mg) of the subject compound as a yellow solid.

MS(FAB, Pos.): m/z=478[M+H]$^+$ $^1$H-NMR(500 MHz, DMSO-d$_6$): δ=0.89(6H, t, J=7.3 Hz), 1.53–1.56(2H, m), 1.61–1.69(4H, m), 2.94–3.01(4H, m), 3.04(2H, br), 3.28(2H, d, J=6.0 Hz), 3.76(2H, s), 3.95(2H, br), 4.10(2H, s), 7.50(2H, d, J=8.4 Hz), 7.60(2H, s), 7.79 (2H, d, J=8.2 Hz), 8.54(1H, t, J=5.5 Hz), 8.63–8.67(2H, m), 9.83(1H, br).

Production Example 21

Synthesis of N-(4-dipropylaminobutyl)-4-{[(1H-imidazol-2-ylmethyl)-(thiazol-2-ylmethyl)-amino]-methyl}-benzamide [Compound No. 21]

Example 21-1

Synthesis of N-(4-dipropylaminobutyl)-4-{[(1H-imidazol-2-ylmethyl)-(thiazol-2-ylmethyl)-amino]-methyl}-benzamide [Compound No. 21]

The compound (39.8 mg) obtained in Example 1-3 and 2-formylthiazole (manufactured by Tokyo Kasei Kogyo Co., Ltd.) (16.9 mg) were dissolved in anhydrous methanol (2.0 ml) and then added with sodium cyanoborohydride (18.9 mg). The solution was adjusted to pH 5 with acetic acid and then stirred at room temperature for 39.5 hours. After completion of the reaction, the solvent was distilled off. The residue was dissolved in chloroform and then washed with 1 mol/l sodium hydroxide and saturated saline solution, followed by drying with anhydrous magnesium sulfate. The solvent was distilled off and the residue was then treated with hydrochloric acid. The residue was purified through silica gel column chromatography (chloroform/methanol/water) thereby obtaining hydrochloride (9.20 mg) of the subject compound as a white solid.

MS(FAB, Pos.): m/z=483[M+H]$^+$
$^1$H-NMR(500 MHz, DMSO-d$_6$): δ=0.89(6H, t, J=7.3 Hz), 1.61–1.75(8H, m), 3.00–3.05(6H, m), 3.30–3.37(2H, m), 3.81(2H, s), 4.03(2H, s), 4.12(2H, s), 7.50–7.52(3H, m), 7.59(2H, s), 7.71(1H, d, J=3.4 Hz), 7.77(1H, d, J=3.4 Hz), 7.83(2H, d, J=8.4 Hz), 8.56(1H, t, J=5.6 Hz), 9.74(1H, br).

Production Example 22

Synthesis of 4-{[bis(1H-imidazol-2-ylmethyl)-amino]-methyl}-N-(3-dipropylaminopropyl)-benzamide [Compound No. 22]

Example 22-1

Synthesis of N-Boc-1,3-propanediamine 1,3-propanediamine (manufactured by Kanto Kagaku) (2.57 g) was dissolved in anhydrous dichloromethane (75 ml) and then added with triethylamine (4.80 ml) and di-t-butoxydicarbonate (3.78 g), followed by stirring overnight under a nitrogen atmosphere at room temperature. After completion of the reaction, the solution was added with water and then stirred, followed by extraction with dichloromethane. The organic layer was washed with saturated saline solution and then dried with anhydrous sodium sulfate. The solvent was distilled off, thereby obtaining the subject compound (3.15 g) as a colorless liquid.

MS(FAB, Pos.): m/z=175[M+H]$^+$

Example 22-2

Synthesis of N,N-dipropyl-N'-Boc-1,3-propanediamine

The compound (1.50 g) obtained in Example 22-1 was dissolved in anhydrous methanol (20 ml) and added with sodium cyanoborohydride (1.62 g), trimethyl orthoformate (2.35 ml), and propionaldehyde (1.55 ml), followed by stirring under a nitrogen atmosphere at room temperature for 3 days. After completion of the reaction, the solvent was distilled off. Then, the residue was dissolved in chloroform and added with a saturated aqueous sodium bicarbonate solution, followed by stirring. The solution was subjected to extraction with chloroform and then washed with a saturated aqueous sodium bicarbonate solution and saturated saline solution. Subsequently, the organic layer was dried with anhydrous sodium sulfate. The solvent was distilled off, thereby the subject compound (2.67 g) as a colorless liquid.

MS(FAB, Pos.): m/z=259[M+H]$^+$

Example 22-3

Synthesis of N,N-dipropyl-1,3-propanediamine

The compound (2.67 g) obtained in Example 22-2 was dissolved in anhydrous methanol (2.0 ml) and then added with a 4 mol/l hydrogen chloride/dioxane solution (20.0 ml), followed by stirring at room temperature for 1.5 hours. After completion of the reaction, the solvent was distilled off. Then, the residue was added with a 1 mol/l sodium hydroxide aqueous solution and extracted with dichloromethane. The extract was washed with distilled water and saturated saline solution, and then the organic layer was dried with anhydrous sodium sulfate. Subsequently, the solvent was distilled off, thereby obtaining the subject compound (726 mg) as a pale-yellow liquid.

MS(FAB, Pos.): m/z=159[M+H]$^+$

Example 22-4

Synthesis of 4-{[bis(1H-imidazol-2-ylmethyl)-amino]-methyl}-N-(3-dipropylaminopropyl)-benzamide [Compound No. 22]

The compound (190 mg) obtained in Example 2-2 was dissolved in DMF (3.0 ml) and added with DCC (189 mg), HOBt (124 mg), and the compound (96.9 mg) obtained in Example 22-3, followed by stirring overnight at room temperature. After completion of the reaction, the solvent was distilled off and the residue was then dissolved in chloroform, followed by separating the solution into layers by the addition of 1 mol/l hydrochloric acid. The aqueous layer was made basic with a 1 mol/l sodium hydroxide aqueous solution. Then, the solution was subjected to extraction with chloroform. The extract was washed with saturated saline solution and the organic layer was then dried with anhydrous sodium sulfate. The solvent was distilled off. Subsequently, the residue was treated with hydrochloric acid and then purified through silica gel column chromatography (chloroform/methanol/water), thereby obtaining hydrochloride (84.8 mg) of the subject compound as a white solid.

MS(FAB, Pos.): m/z=452[M+H]$^+$
$^1$H-NMR(500 MHz, DMSO-d$_6$): δ=0.89(6H, t, J=7.3 Hz), 1.65(4H, sext., J=7.3 Hz), 1.86–1.94(2H, m), 2.95–2.99(4H, m), 3.04–3.09(2H, m), 3.32(2H, m), 3.72(2H, s), 4.13(4H, s), 7.54(2H, d, J=8.4 Hz), 7.60(4H, s), 7.78(2H, d, J=8.4 Hz), 8.68(1H, t, J=5.8 Hz), 10.2(1H, brs).

Production Example 23

Synthesis of 4-{[bis(1H-imidazol-2-ylmethyl)-amino]-methyl}-N-(3-dipropylamino-2,2-dimethyl-propyl)-benzamide [Compound No. 23]

Example 23-1

Synthesis of N-Boc-2,2-dimethyl-1,3-propanediamine 2,2-dimethyl-1,3-propanediamine (manufactured by Aldrich Corporation) (2.00 g) was dissolved in anhydrous dichloromethane (100 ml) and then added with triethylamine (2.70 ml) and di-t-butoxydicarbonate (2.14 g), followed by stirring overnight under a nitrogen atmosphere at room temperature. After completion of the reaction, the solution was added with water and stirred, followed by extraction with dichloromethane. The organic layer was washed with saturated saline solution and then dried with anhydrous sodium sulfate. The solvent was distilled off, thereby obtaining the subject compound (1.76 g) as a white solid.

MS(FAB, Pos.): m/z=203[M+H]$^+$

Example 23-2

Synthesis of (N,N-dipropyl-N'-Boc)-2,2-dimethyl-1,3-propanediamine

The compound (501 mg) obtained in Example 23-1 was dissolved in anhydrous methanol (5.0 ml) and then added with sodium cyanoborohydride (467 mg), trimethyl orthoformate (677 µl), and propionaldehyde (447 µl), followed by stirring at room temperature under a nitrogen atmosphere for 3 days. After completion of the reaction, the solvent was distilled off. Then, the residue was dissolved in chloroform and added with a saturated aqueous sodium bicarbonate solution, followed by stirring. The solution was extracted with chloroform and the extract was washed with a saturated aqueous sodium bicarbonate solution and saturated saline solution. The organic layer was dried with anhydrous sodium sulfate. The solvent was distilled off, thereby obtaining the subject compound (740 mg) as a pale-yellow liquid.

MS(FAB, Pos.): m/z=287[M+H]$^+$

Example 23-3

Synthesis of N,N-dipropyl-2,2-dimethyl-1,3-propanediamine

The compound (740 mg) obtained in Example 23-2 was dissolved in anhydrous methanol (3.0 ml) and then added with a 4 mol/l hydrogen chloride/dioxane solution (15.0 ml), followed by stirring at room temperature for 1 hour. After completion of the reaction, the solvent was distilled off and the residue was then added with a 1 mol/l sodium hydroxide aqueous solution, followed by extraction with dichloromethane. After the extract had been washed with distilled water and saturated saline solution, the organic layer was dried with anhydrous sodium sulfate. The solvent was then distilled off, thereby obtaining the subject compound (351 mg) as a colorless liquid.

MS(FAB, Pos.): m/z=187[M+H]$^+$

Example 23-4

Synthesis of 4-{[bis(1H-imidazol-2-ylmethyl)-amino]-methyl}-N-(3-dipropylamino-2,2-dimethyl-propyl)-benzamide [Compound No. 23]

The compound (100 mg) obtained in Example 2-2 was dissolved in DMF (2.0 ml) and then added with DCC (55.4 mg), HOBt (36.3 mg), and the compound (50.0 mg) obtained in Example 23-3, followed by stirring overnight at room temperature. After completion of the reaction, the solvent was distilled off and the residue was then dissolved in chloroform. Then, the solution was added with 1 mol/l hydrochloric acid to separate the solution into layers. After the aqueous layer was added with a 1 mol/l sodium hydroxide aqueous solution to make the solution basic, the solution was subjected to extraction with chloroform and the extract was then washed with saturated saline solution. Subsequently, the organic layer was dried with anhydrous sodium sulfate. The solvent was distilled off and the residue was subjected to purification through silica gel column chromatography (chloroform/methanol/water), thereby obtaining hydrochloride (17.5 mg) of the subject compound as a white solid.

MS(FAB, Pos.): m/z=480[M+H]$^+$ $^1$H-NMR(500 MHz, DMSO-d$_6$): δ=0.89(6H, t, J=7.3 Hz), 1.09(6H, s), 1.61–1.78(4H, m), 3.02–3.03(6H, m), 3.26–3.27(2H, m), 3.72(2H, s), 4.12(4H, s), 7.58(2H, d, J=8.2 Hz), 7.61(4H, s), 7.82(2H, d, J=8.2 Hz), 8.61–8.63(1H, m), 9.18(1H, brs).

Production Example 24

Synthesis of 4-{[bis(1H-imidazol-2-ylmethyl)-amino]-methyl}-N-(4-dipropylaminobutyl)-benzenesulfonamide [Compound No. 24]

Example 24-1

Synthesis of 2-benzylisoindole-1,3-dione

Benzylamine (manufactured by Tokyo Kasei Kogyo Co., Ltd.) (1.00 g) was dissolved in purified water (20 ml) and then added with N-carbethoxyphthalimide (manufactured by Tokyo Kasei Kogyo Co., Ltd.) (3.06 g) and sodium carbonate (2.47 g), followed by stirring at room temperature for 3 hours. After completion of the reaction, the solution was filtered and the residue was washed with purified water and then dried under vacuum at 60° C., thereby obtaining the subject compound (1.82 g) as a white solid.

MS(FAB, Pos.): m/z=238[M+H]$^+$

Example 24-2

Synthesis of 4-(1,3-dioxo-1,3-dihydroisoindol-2-ylmethyl)benzenesulfonylchloride The compound (330 mg) obtained in Example 24-1 was dissolved in chloroform and then added with chlorosulfuric acid (manufactured by Kishida Chemical Co., Ltd.) (0.177 ml) under ice-cooling. The solution was stirred at room temperature for 2 days, and then concentrated and dried. The resultant was gradually added with phosphorus pentachloride (300 mg) and then heated to 80° C., followed by stirring for 4 hours.

After completion of the reaction, the reacted solution was stood to cool and then dropped into ice cold water. The product was extracted with chloroform and then washed with a 5% aqueous sodium bicarbonate solution and saturated saline solution. Subsequently, the product was dried with anhydrous sodium sulfate and then concentrated, thereby obtaining the subject compound (440 mg) as a yellowish white solid.

MS(FAB, Pos.): m/z=336[M+H]$^+$ $^1$H-NMR(500 MHz, DMSO-d$_6$): δ=4.95(2H, s), 7.66–7.68(2H, m), 7.74–7.77(2H, m), 7.87–7.90(2H, m), 7.99–8.01(2H, m).

Example 24-3

Synthesis of 4-(1,3-dioxo-1,3-dihydroisoindol-2-ylmethyl)-N-(4-dipropylaminobutyl)benzenesulfonamide The compound (150 mg) obtained in Example 24-2 was dissolved in chloroform (10 ml) and then added with the compound (131 mg) obtained in Example 1-2 and triethylamine (0.224 ml), followed by stirring at room temperature for 15 minutes. The solution was added with water and subjected to extraction. The organic layer was washed with saturated saline solution and then dried and concentrated with anhydrous sodium sulfate, thereby obtaining the subject compound (160 mg) as a colorless viscous liquid.

MS(FAB, Pos.): m/z=472[M+H]$^+$

Example 24-4

Synthesis of 4-aminomethyl-N-(4-dipropylaminobutyl)benzenesulfonamide

The compound (160 mg) obtained in Example 24-3 was added with 2.0 ml of a 40% methylamine/methanol solution (manufactured by Tokyo Kasei Kogyo Co., Ltd.), followed by stirring at room temperature for 40 hours. After completion of the reaction, the solvent was distilled off and the residue was subjected to extraction by the addition of a 1 mol/l sodium hydroxide aqueous solution and chloroform. The organic layer was dried with anhydrous sodium sulfate and the solvent was distilled off, thereby obtaining the subject compound (114 mg) as a colorless viscous liquid.

MS(FAB, Pos.): m/z=342[M+H]$^+$

Example 24-5

Synthesis of 4-{[bis(1H-imidazol-2-ylmethyl)-amino]-methyl}-N-(4-dipropylaminobutyl)-benzenesulfonamide [Compound No. 24]

The compound (114 mg) obtained in Example 24-4 was dissolved in anhydrous methanol (7.0 ml), and then the solution was added with 2-imidazole carboxaldehyde (73.0 mg), sodium cyanoborohydride (42.0 mg), and acetic acid (0.1 ml) in that order, followed by stirring at room temperature for 2 days. The methanol was distilled off and a 1 mol/l sodium hydroxide aqueous solution (1.8 ml) was then added to the residue. The solution was extracted with chloroform and the extract was then dried with anhydrous sodium sulfate, followed by distilling the solvent off. Subsequently, the residue was purified through silica gel column chromatography (chloroform/methanol/water) and then treated with hydrochloric acid, thereby obtaining hydrochloride (160 mg) of the subject compound as a white solid.

MS(FAB, Pos.): m/z=502[M+H]$^+$ $^1$H-NMR(500 MHz, DMSO-d$_6$): δ=0.89(6H, t, J=7.4 Hz), 1.40–1.44(2H, m), 1.60–1.70(6H, m), 2.67–2.72(2H, m), 2.93–3.01(6H, m), 3.76–3.80(2H, m), 4.14–4.16(4H, m), 7.48–7.84(8H, m), 9.94(1H, brs).

Production Example 25

Synthesis of N-(4-{[bis(1H-imidazol-2-ylmethyl)-amino]-methyl}-benzyl)-N',N'-dipropylbutane-1,4-diamine [Compound No. 25]

Example 25-1

Synthesis of 4-(1,3-dioxo-1,3-dihydroisoindol-2-ylmethyl)benzaldehyde

Methyl 4-(aminomethyl)-benzoate hydrochloride (manufactured by Aldrich Corporation) (773 mg) was dissolved in THF (50 ml) and then gradually added with lithium aluminum hydride (300 mg) under ice-cooling. The solution was stirred at room temperature for 3 hours and then cooled with ice, followed by gradual addition of a concentrated sodium hydroxide aqueous solution until foam was not observed. Celite filtration was carried out on the solution using chloroform as a solvent and then the filtrate was concentrated and dried. The dried product was dissolved in purified water (10 ml) and THF (10 ml). After having been cooled with ice, the solution was added with N-carbethoxyphthalimide (1.26 g) and sodium carbonate (900 mg). After the mixture had been stirred at room temperature for 4 hours, THF was distilled off and chloroform was then added to the residue to carry out extraction. The organic layer was dried with anhydrous sodium sulfate and the solvent was then distilled off. Subsequently, the residue was further dried under vacuum. Next, this compound was dissolved in chloroform (20 ml) and then added with manganese dioxide (5.0 g), followed by stirring at room temperature for 3 hours. After the solution had been subjected to Celite filtration, the filtrate was concentrated and then purified through silica gel column chromatography (chloroform/methanol), thereby obtaining the subject compound (259 mg) as a white solid.

MS(FAB, Pos.): m/z=266[M+H]$^+$ $^1$H-NMR(500 MHz, CDCl$_3$): δ=4.92(2H, s), 7.58(2H, d, J=8.3 Hz), 7.72–7.76(2H, m), 7.83–7.89(4H, m) 9.98(1H, s).

Example 25-2

Synthesis of 2-{4-[(4-dipropylaminobutyl amino)-methyl]benzyl}isoindole-1,3-dione The compound (103 mg) obtained in Example 25-1 was dissolved in anhydrous methanol (10 ml) and then added with the hydrochloride (114 mg) of the compound obtained in Example 1-2. Then, the solution was added with triethylamine (0.108 ml) and anhydrous magnesium sulfate (3 g), followed by stirring at room temperature for 1 hour. Anhydrous magnesium sulfate was removed from the solution by Celite filtration. Then, methanol was distilled off and the residue was dried using a vacuum pump. The residue was dissolved in anhydrous methanol (10 ml) and sodium borohydride (22.0 mg) was then gradually added under ice-cooling. The solution was warmed to room temperature and then stirred for 1 hour. After completion of the reaction, methanol was distilled off and the residue was then added with water and chloroform to extract the organic layer. After the organic layer had been dried with anhydrous sodium sulfate, the solvent was distilled off and the residue was then purified through silica gel column chromatography (chloroform/methanol/water), thereby obtaining the subject compound (60.3 mg) as a pale-yellow viscous liquid.

MS(FAB, Pos.): m/z=420[M+H]$^+$

Example 25-3

Synthesis of [4-(1,3-dioxo-1,3-dihydroisoindol-2-ylmethyl)benzyl]-(4-dipropylaminobutyl)carbamic acid t-butyl ester The compound (60.3 mg) obtained in Example 25-2 was dissolved in chloroform and then added with di-t-butoxydicarbonate (47.0 mg). After having been stirred at room temperature for 30 minutes, the solution was subjected to concentration and then purification through silica gel column chromatography (chloroform/methanol), thereby obtaining the subject compound (70.0 mg) as a colorless viscous liquid.

MS(FAB, Pos.): m/z=522[M+H]$^+$

Example 25-4

Synthesis of (4-aminomethylbenzyl)-(4-dipropylaminobutyl)carbamic acid t-butyl ester The compound (70.0 mg) obtained in Example 25-3 was added with a 40% methylamine/methanol solution (3.0 ml) and then stirred at room temperature for 14 hours. After completion of the reaction, the solvent was distilled off. Then, the residue was then added with a 1 mol/l sodium hydroxide aqueous solution and chloroform to extract the aqueous layer therefrom with chloroform. The extract was dried with anhydrous sodium sulfate, and the solvent was distilled off, thereby obtaining the subject compound (65.5 mg) as a colorless viscous liquid.

Example 25-5

Synthesis of N-(4-{[bis(1H-imidazol-2-ylmethyl)-amino]-methyl}-benzyl)-N',N'-dipropylbutane-1,4-diamine [Compound No. 25]

The compound (45.5 mg) obtained in Example 25-4 was dissolved in anhydrous methanol (3.0 ml), and then the solution was added with 2-imidazole carboxaldehyde (25.0 mg), sodium cyanoborohydride (15.0 mg), and acetic acid (0.1 ml) in that order, followed by stirring at room temperature for 15 hours. The methanol was distilled off and a 1 mol/l sodium hydroxide aqueous solution (1.0 ml) was then added to the residue. The solution was extracted with chloroform and the extract was then dried with anhydrous sodium sulfate, followed by distilling the solvent off. Subsequently, the residue was purified through silica gel column chromatography (chloroform/methanol/water) and then treated with hydrochloric acid, thereby obtaining hydrochloride (28.0 mg) of the subject compound as a white solid.

MS(FAB, Pos.): m/z=452[M+H]$^+$ $^1$H-NMR(500 MHz, DMSO-$d_6$): δ=0.90(6H, t, J=7.3 Hz), 1.62–1.78(8H, m), 2.83(2H, brs), 2.93–3.04(8H, m), 3.67(2H, s), 4.05–4.10(2H, m), 4.11(4H, s), 7.46–7.50(4H, m), 7.60–7.64(4H, m), 9.40(2H, brs), 10.24(1H, brs), 14.68(1H, brs).

Production Example 26

Synthesis of N-(4-dipropylaminobutyl)-4-{[(1H-imidazol-2-ylmethyl)-(1-methyl-1H-imidazol-2-ylmethyl)-amino]-methyl}-benzamide [Compound No. 26]

Example 26-1

Synthesis of N-(4-dipropylaminobutyl)-4-{[(1H-imidazol-2-ylmethyl)-(1-methyl-1H-imidazol-2-ylmethyl)-amino]-methyl}-benzamide [Compound No. 26]

The compound (53.8 mg) obtained in Example 1-4 was dissolved in methanol (0.8 ml) and then added with trimethyl orthoformate (50 µl), acetic acid (50 µl), and 1-methyl-2-imidazolecarboxylaldehyde (manufactured by Aldrich Corporation) (28.5 mg). After the solution had been stirred at room temperature for 10 minutes, sodium cyanoborohydride (24.4 mg) was added and then the whole was stirred overnight at room temperature. The solvent was distilled off under reduced pressure and the residue was then dissolved in chloroform, followed by washing with 1 mol/l sodium hydroxide and saturated saline solution and drying with anhydrous sodium sulfate. After filtration, the solvent was distilled off under reduced pressure. The residue was purified through silica gel column chromatography (chloroform/methanol) and then treated with hydrochloric acid, thereby obtaining hydrochloride (10.0 mg) of the subject compound as a pale-yellow solid.

MS(FAB, Pos.) m/z=480[M+H]$^+$ $^1$H-NMR(500 MHz, DMSO-$d_6$): δ=0.89(6H, t, J=7.3 Hz), 1.50–1.56(2H, m), 1.62–1.74(6H, m), 2.94(4H, dt, J=4.6, 2.6 Hz), 3.02–3.06(2H, m), 3.27(2H, q, J=6.4 Hz), 3.71(3H, s), 3.75(2H, s), 4.09(2H, s), 4.17(2H, s), 7.50(2H, d, J=8.2 Hz), 7.54(2H, d, J=8.2 Hz), 7.64(2H, s), 7.79(1H, d, J=8.4 Hz), 8.59(1H, t, J=5.5 Hz), 10.32(1H, brs).

Production Example 27

Synthesis of N-(4-dipropylaminobutyl)-4-{[(1H-imidazol-2-ylmethyl)-(1H-pyrazol-3-ylmethyl)-amino]-methyl}-benzamide [Compound No. 27]

Example 27-1

Synthesis of N-(4-dipropylaminobutyl)-4-{[(1H-imidazol-2-ylmethyl)-(1H-pyrazol-3-ylmethyl)-amino]-methyl}-benzamide [Compound No. 27]

The compound (53.8 mg) obtained in Example 1-4 was dissolved in methanol (0.8 ml). Then, the solution was added with trimethyl orthoformate (50 µl), acetic acid (50 µl), and pyrazol-3-carboxaldehyde (manufactured by Merck, Inc.) (24.9 mg) and stirred at room temperature for 10 minutes. Subsequently, sodium cyanoborohydride (24.4 mg) was added, followed by stirring overnight at room temperature. The solvent was distilled off under reduced pressure and then the residue was dissolved in chloroform, followed by washing with 1 mol/l sodium hydroxide and saturated saline solution and drying with anhydrous sodium sulfate. After filtration, the solvent was distilled off under reduced pressure. Then, the residue was then purified through silica gel column chromatography (chloroform/methanol) and treated with hydrochloric acid, thereby obtaining hydrochloride (26.1 mg) of the subject compound as a white solid.

MS(FAB, Pos.): m/z=466[M+H]$^+$ $^1$H-NMR(500 MHz, DMSO-$d_6$): δ=0.88(6H, t, J=7.3 Hz), 1.53–1.69(8H, m), 2.95(4H, brs), 3.05(2H, brs), 3.25–3.40(2H, m), 3.55(2H, s), 3.58(2H, s), 3.62(2H, s), 6.27(1H, s), 7.04(2H, s), 7.50(2H, d, J=8.2 Hz), 7.81(2H, d, J=8.2 Hz), 8.51(1H, t, J=5.5 Hz).

Production Example 28

Synthesis of N-(4-dipropylaminobutyl)-4-{[(1H-imidazol-2-ylmethyl)-((2R)-pyrrolidin-2-ylmethyl)-amino]-methyl}-benzamide [Compound No. 28]

Example 28-1

Synthesis of N-(4-dipropylaminobutyl)-4-{[(1H-imidazol-2-ylmethyl)-((2R)-pyrrolidin-2-ylmethyl)-amino]-methyl}-benzamide [Compound No. 28]

The compound (53.8 mg) obtained in Example 1-4 was dissolved in methanol (0.8 ml). Then, the solution was added with trimethyl orthoformate (50 µl), acetic acid (50 µl), N-Boc-D-prolinal (manufactured by Aldrich Corporation) (25.7 mg) and stirred at room temperature for 10 minutes.

Subsequently, sodium cyanoborohydride (24.4 mg) was added, followed by stirring overnight at room temperature. The solvent was distilled off under reduced pressure and the residue was then dissolved in chloroform, followed by washing with 1 mol/l sodium hydroxide and saturated saline solution and drying with anhydrous sodium sulfate. After filtration, the solvent was distilled off under reduced pressure and the residue was then purified through silica gel column chromatography (chloroform/methanol). Then, the purified product was dissolved in methanol (500 μl) and added with a 4 mol/l hydrogen chloride/dioxane solution (500 μl), followed by stirring at room temperature for 2 hours. After completion of the reaction, the solvent was distilled off under reduced pressure and the residue was then purified through silica gel column chromatography (chloroform/methanol), thereby obtaining hydrochloride (33.9 mg) of the subject compound as a white solid.

MS(FAB, Pos.) m/z=469[M+H]$^+$ $^1$H-NMR(500 MHz, DMSO-$d_6$): δ=0.89(6H, t, J=7.3 Hz), 1.45–1.58(3H, m), 1.63–1.73(6H, m), 1.83–1.94(2H, m), 2.00–2.05(1H, m), 2.77(1H, dd, J=3.8, 9.9 Hz), 2.90–2.98 (5H, m), 3.03–3.07(2H, m), 3.09–3.23(1H, m), 3.28(2H, m), 3.60–3.86(4H, m), 3.95(1H, d, J=15.6 Hz), 4.15(1H, d, J=15.6 Hz), 7.45(2H, d, J=8.2 Hz), 7.49(2H, s), 7.78(2H, d, J=8.2 Hz), 8.58(1H, t, J=5.6 Hz), 8.94(1H, brs), 9.82(1H, brs), 10.21(1H, brs).

Production Example 29

Synthesis of N-(4-dipropylaminobutyl)-4-{[(1H-imidazol-2-ylmethyl)-((2S)-pyrrolidin-2-ylmethyl)-amino]-methyl}-benzamide [Compound No. 29]

Example 29-1

Synthesis of N-(4-dipropylaminobutyl)-4-{[(1H-imidazol-2-ylmethyl)-((2S)-pyrrolidin-2-ylmethyl)-amino]-methyl}-benzamide [Compound No. 29]

The compound (53.8 mg) obtained in Example 1-4 was dissolved in methanol (0.8 ml). Then, the solution was added with trimethyl orthoformate (50 μl), acetic acid (50 μl), N-Boc-L-prolinal (manufactured by Aldrich Corporation) (25.7 mg) and stirred at room temperature for 10 minutes. Subsequently, sodium cyanoborohydride (24.4 mg) was added, followed by stirring overnight at room temperature. The solvent was distilled off under reduced pressure and the residue was then dissolved in chloroform, followed by washing with 1 mol/l sodium hydroxide and saturated saline solution and drying with anhydrous sodium sulfate. After filtration, the solvent was distilled off under reduced pressure and the residue was then purified through silica gel column chromatography (chloroform/methanol). Then, the purified product was dissolved in methanol (500 μl) and added with a 4 mol/l hydrogen chloride/dioxane solution, followed by stirring at room temperature for 2 hours. After completion of the reaction, the solvent was distilled off under reduced pressure and the residue was then purified through silica gel column chromatography (chloroform/methanol), thereby obtaining hydrochloride (20.5 mg) of the subject compound as a pale brown solid.

MS(FAB, Pos.) m/z=469[M+H]$^+$ $^1$H-NMR(500 MHz, DMSO-$d_6$): δ=0.89(6H, t, J=7.3 Hz), 1.47–1.58(3H, m), 1.63–1.73(6H, m), 1.83–1.91(2H, m), 2.02–2.05(1H, m), 2.78(1H, dd, J=3.8, 9.9 Hz), 2.91–2.98 (5H, m), 3.03–3.07(2H, m), 3.09–3.23(1H, m), 3.26–3.30 (2H, m), 3.57–3.71(2H, m), 3.81(2H, d, J=14.0 Hz), 3.96 (1H, d, J=15.6 Hz), 4.15(1H, d, J=15.6 Hz), 7.45(2H, d, J=8.2 Hz), 7.49(2H, s), 7.78(2H, d, J=8.2 Hz), 8.59(1H, t, J=5.6 Hz), 8.97(1H, brs), 9.85(1H, brs), 10.25(1H, brs).

Production Example 30

Synthesis of N-(4-dipropylaminobutyl)-4-{[(1H-imidazol-2-ylmethyl)-(4-methyl-1H-imidazol-5-ylmethyl)-amino]-methyl}-benzamide [Compound No. 30]

Example 30-1

Synthesis of N-(4-dipropylaminobutyl)-4-{[(1H-imidazol-2-ylmethyl)-(4-methyl-1H-imidazol-5-ylmethyl)-amino]-methyl}-benzamide [Compound No. 30]

The compound (53.8 mg) obtained in Example 1-4 was dissolved in methanol (0.8 ml). Then, the solution was added with trimethyl orthoformate (50 μl), acetic acid (50 μl), and 4-methyl-5-imidazole carboxaldehyde (manufactured by Aldrich Corporation) (28.5 mg) and stirred at room temperature for 10 minutes. Subsequently, sodium cyanoborohydride (24.4 mg) was added, followed by stirring overnight at room temperature. The solvent was distilled off under reduced pressure and then the residue was dissolved in chloroform, followed by washing with 1 mol/l sodium hydroxide and saturated saline solution and drying with anhydrous sodium sulfate. After filtration, the solvent was distilled off under reduced pressure and the residue was then purified through silica gel column chromatography (chloroform/methanol) and then treated with hydrochloric acid, thereby obtaining hydrochloride (33.5 mg) of the subject compound as a white solid.

MS(FAB, Pos.) m/z=480[M+H]$^+$ $^1$H-NMR(500 MHz, DMSO-$d_6$): δ=0.81(6H, t, J=7.3 Hz), 1.32–1.43(6H, m), 1.51(2H, quint., J=7.1 Hz), 2.04(3H, br), 2.28(4H, t, J=7.1 Hz), 2.35(2H, t, J=7.1 Hz), 3.24(2H, dd, J=6.8, 5.9 Hz), 3.31–3.47(2H, m), 3.56(4H, br), 6.85(1H, br), 7.10(1H, br), 7.47(2H, d, J=7.8 Hz), 7.51(1H, s), 7.78 (2H, d, J=8.3 Hz), 8.40(1H, t, J=5.9 Hz).

Production Example 31

Synthesis of (4-{[bis(1H-imidazol-2-ylmethyl)-amino]-methyl}-phenyl)-(4-dipropylaminopiperidin-1-yl)-methanone [Compound No. 31]

Example 31-1

Synthesis of 4-N,N-dipropylaminopiperidine

In methanol (9.0 ml), 4-amino-1-benzylpiperidine (manufactured by Across Co., Ltd.) (571 mg) was dissolved. Then, the solution was added with trimethyl orthoformate (570 μl) and propionaldehyde (645 μl) and stirred at room temperature for 14 hours. After completion of the reaction, the solvent was distilled off under reduced pressure and the residue was then dissolved in chloroform. After having been washed with 1 mol/l sodium hydroxide, the solution was extracted with chloroform. The resulting organic layer was washed with saturated saline solution, followed by drying with anhydrous sodium sulfate. After filtration, the solvent was distilled off under reduced pressure and the residue was then purified through silica gel column chromatography (chloroform/methanol). The purified product was dissolved in ethanol (50 ml) and then added with 10% palladium-carbon (50.0 mg). Subsequently, 3 cycles of deaeration and replacement with nitrogen and then 3 cycles of deaeration and replacement with hydrogen were carried out, followed by stirring overnight at room temperature. Once the palladium catalyst was removed through Celite filtration, 10% palladium-carbon (50.0 mg) was added again. Then, the mixture was subjected to 3 cycles of deaeration and replacement with nitrogen and 3 cycles of deaeration and replacement with hydrogen, followed by stirring overnight at room temperature. After completion of the reaction, the reaction mixture was filtrated through Celite filtration and the filtrate was then subjected to solvent distillation under reduced pressure. Subsequently, the residue was dried under vacuum, thereby obtaining the subject compound (145.9 mg) as a yellow liquid.

MS(FAB, Pos.) m/z=185[M+H]$^+$

Example 31-2

Synthesis of (4-{[bis(1H-imidazol-2-ylmethyl)-amino]-methyl}-phenyl)-(4-dipropylaminopiperidin-1-yl)-methanone [Compound No. 31]

The compound (31.2 mg) obtained in Example 2-2, DCC (30.0 mg), and HOBt (20.5 mg) were dissolved in DMF (0.5 ml) and stirred for 15 minutes. Then, the compound (25.6 mg) obtained in Example 31-1 was added, followed by stirring at room temperature for 5 hours. After completion of the reaction, the solvent was distilled off under reduced pressure and the residue was then dissolved in 1 mol/l hydrochloric acid, followed by removing impurities with chloroform. The resulting aqueous layer was added with chloroform and then added with 1 mol/l sodium hydroxide to make the layer alkaline, followed by extraction with chloroform. The extract was washed with saturated saline solution and then dried with anhydrous sodium sulfate. After filtration, the solvent was distilled off under reduced pressure and the residue was then purified through silica gel column chromatography (chloroform/methanol). Subsequently, the purified product was treated with hydrochloric acid, thereby obtaining hydrochloride (9.9 mg) of the subject compound as a white solid.

MS(FAB, Pos.) m/z=478[M+H]$^+$
$^1$H-NMR(500 MHz, DMSO-d$_6$+D$_2$O): δ=0.93(6H, t, J=7.3 Hz), 1.63–1.74(6H, m), 1.94–2.14(2H, br), 2.74–2.86 (1H, br), 2.91–3.00(2H, br), 3.09–3.17(3H, m), 3.49–3.60 (2H, m), 3.73(2H, s), 4.18(4H, s), 4.54–4.63(1H, br), 7.28 (2H, d, J=8.2 Hz), 7.40(2H, d, J=8.2 Hz), 7.56(2H, s).

Production Example 32

Synthesis of (4-{[bis(1H-imidazol-2-ylmethyl)-amino]-methyl}-phenyl)-(4-propylpiperazin-1-yl)-methanone [Compound No. 32]

Example 32-1

Synthesis of 4-(4-{[bis-(1H-imidazol-2-ylmethyl)-amino]-methyl}-benzoyl)-piperazin-1-carboxylic acid t-butyl ester The compound (500 mg) obtained in Example 2-2 was dissolved in DMF (10 ml) and added with WSCI hydrochloride (257 mg), HOBt (181 mg), and 1-Boc piperazine (manufactured by Aldrich Corporation) (249 mg), followed by stirring at room temperature for 3 days. After completion of the reaction, the solvent was distilled off and the residue was then dissolved in chloroform for extraction, followed by washing with distilled water, a 1 mol/l sodium hydroxide aqueous solution, and saturated saline solution. The resulting organic layer was dried with anhydrous sodium sulfate.

The solvent was distilled off and the residue was then purified through silica gel column chromatography (chloroform/methanol/water), thereby obtaining the subject compound (111 mg) as a yellow oily substance.

MS(FAB, Pos.): m/z=480[M+H]$^+$
$^1$H-NMR(500 MHz, DMSO-d$_6$+D$_2$O): δ=1.40(9H, s), 3.25–3.44(8H, m), 3.54(2H, s), 3.63(4H, s), 7.02(4H, s), 7.34(2H, d, J=8.2 Hz), 7.47(2H, d, J=8.2 Hz).

Example 32-2

Synthesis of (4-{[bis-(1H-imidazol-2-ylmethyl)-amino]-methyl}-phenyl)-piperazin-1-yl-methanone The compound (111 mg) obtained in Example 32-1 was dissolved in anhydrous methanol (1.0 ml) and then added with a 4 mol/l hydrogen chloride/dioxane solution (3.0 ml) and stirred at room temperature for 1 hour. After completion of the reaction, the solvent was distilled off and the residue was added with a 1 mol/l sodium hydroxide aqueous solution, followed by washing with dichloromethane. The aqueous layer was evaporated to dryness, followed by distilling azeotropically with chloroform. Consequently, the subject compound (48.5 mg) was obtained as a yellow oily substance.

MS(FAB, Pos.): m/z=380[M+H]$^+$

Example 32-3

Synthesis of (4-{[bis(1H-imidazol-2-ylmethyl)-amino]-methyl}-phenyl)-(4-propylpiperazin-1-yl)-methanone [Compound No. 32]

The compound (48.8 mg) obtained in Example 32-2 was dissolved in anhydrous methanol (1.0 ml) and then added with sodium cyanoborohydride (16.2 mg), trimethyl orthoformate (21.1 μl), propionaldehyde (13.9 μl), followed by stirring overnight at room temperature under a nitrogen atmosphere. After completion of the reaction, the solvent was distilled off and the residue was then dissolved in chloroform. A saturated aqueous sodium bicarbonate solution was added to the solution, followed by stirring. The resultant solution was subjected to extraction with chloroform and washed with a saturated aqueous sodium bicarbonate solution and saturated saline solution, and then the organic layer was dried with anhydrous sodium sulfate. The solvent was distilled off and the residue was then treated with hydrochloric acid. Subsequently, the treated product was purified through silica gel column chromatography (chloroform/methanol/water), thereby obtaining hydrochloride (33.2 mg) of the subject compound as a white solid.

MS(FAB, Pos.): m/z=422[M+H]$^+$
$^1$H-NMR(500 MHz, DMSO-d$_6$+D$_2$O): δ=0.93(3H, s), 1.68–1.74(2H, m), 3.03–3.08(4H, m), 3.39–3.62(6H, m), 3.74(2H, s), 4.17(4H, s), 7.32(2H, d, J=8.2 Hz), 7.42(2H, d, J=8.2 Hz), 7.56(4H, s).

Production Example 33

Synthesis of 4-{[bis(1H-imidazol-2-ylmethyl)-amino]-methyl}-N-(3-dipropylaminomethylphenyl)-benzamide [Compound No. 33)

Example 33-1

Synthesis of (3-nitro-benzyl)dipropylamine

Commercially available 3-nitrobenzylamine hydrochloride (manufactured by Tokyo Kasei Kogyo Co., Ltd.) (1.62 g) was suspended in chloroform (15 ml) and then added with a 1 mol/l sodium hydroxide aqueous solution (15 ml). The aqueous layer was extracted with chloroform and the extract was then dried with anhydrous magnesium sulfate, followed by distilling the solvent off. Subsequently, the residue was dissolved in anhydrous methanol (25 ml) and then added with propionaldehyde (1.49 ml), trimethyl orthoformate (2.82 ml), and sodium cyanoborohydride (1.62 g), followed by stirring at room temperature for 2 hours. After completion of the reaction, the solvent was distilled off. Then, the residue was added with water and extracted with chloroform. The extract was dried with anhydrous magnesium sulfate and the solvent was then distilled off. The residue was purified through silica gel column chromatography (hexane/ethyl acetate), thereby obtaining the subject compound (608.1 mg) as a yellow oily substance.

MS(FAB, Pos.): m/z=237[M+H]$^+$ $^1$H-NMR(500 MHz, DMSO-d$_6$): δ=0.87(6H, t, J=7.3 Hz), 1.48(4H, sext., J=7.3 Hz), 2.39(4H, t, J=7.1 Hz), 3.63(2H, s), 7.46(1H, t, J=8.1 Hz), 7.69(1H, d, J=7.6 Hz), 8.08(1H, d, J=5.9 Hz), 8.22(1H, s).

Example 33-2

Synthesis of 3-dipropylaminomethylaniline

The compound (595 mg) obtained in Example 33-1 was dissolved in methanol (6.0 ml) and THF (3.0 ml). The solution was added with activated carbon (59.0 mg) and iron trichloride hexahydrate (manufactured by Kanto Kagaku) (5.90 mg), followed by thermal reflux for 30 minutes. After having been cooled to room temperature, the mixture was added with hydrazine monohydrate (0.43 ml) and then subjected to thermal reflux for 24 hours. After completion of the reaction, the mixture was subjected to Celite filtration and the solvent was then distilled off. The residue was added with water and then extracted with chloroform. The extract was dried with anhydrous magnesium sulfate and then solvent was distilled off. Subsequently, the residue was purified through silica gel column chromatography (chloroform/methanol), thereby obtaining the subject compound (343.9 mg) as a yellow oily substance.

MS(FAB, Pos.): m/z=207[M+H]$^+$ $^1$H-NMR(500 MHz, DMSO-d$_6$): δ=0.90(6H, t, J=7.3 Hz), 1.92–1.94(4H, m), 2.89(4H, t, J=8.2 Hz), 3.72(2H, br), 3.78(2H, br), 6.63(1H, dd, J=1.7, 8.0 Hz), 6.72(1H, d, J=7.3 Hz), 6.90(1H, brs), 7.11(1H, t, J=7.8 Hz).

Example 33-3

Synthesis of 4-{[bis(1H-imidazol-2-ylmethyl)-amino]-methyl}-N-(3-dipropylaminomethylphenyl)-benzamide [Compound No. 33]

The compound (51.6 mg) obtained in Example 33-2, the compound (117 mg) obtained in Example 2-2, and HOBt (50.0 mg) were dissolved in anhydrous DMF (2.5 ml). Then, the solution was added with PS-carbodiimide (manufactured by Argonaut Technologies, Inc.) (373.1 mg), followed by stirring at room temperature for 17 hours. After completion of the reaction, the mixture was filtrated and the solvent was then distilled off. The residue was dissolved in chloroform and washed with a 1 mol/l sodium hydroxide aqueous solution and saturated saline solution. The residue was dried with anhydrous magnesium sulfate and the solvent was distilled off, followed by treatment with hydrochloric acid. The residue was purified through silica gel column chromatography (chloroform/methanol/water), thereby obtaining hydrochloride (18.5 mg) of the subject compound as a white solid.

MS(FAB, Pos.): m/z=500[M+H]$^+$ $^1$H-NMR(500 MHz, DMSO-d$_6$): δ=0.88(6H, t, J=7.3 Hz), 1.73(4H, sept., J=7.2 Hz), 2.94–2.96(4H, br), 3.76(2H, s), 4.14(4H, s), 4.30(2H, brs), 7.36(1H, d, J=7.8 Hz), 7.45(1H, t, J=7.9 Hz), 7.60(2H, d, J=2.7 Hz), 7.62(4H, s), 7.75(1H, d, J=9.0 Hz), 7.92(2H, d, J=8.4 Hz), 8.05(1H, s), 10.16(1H, br), 10.40(1H, s).

Production Example 34

Synthesis of 4-{[bis(1H-imidazol-2-ylmethyl)-amino]-methyl}-N-(4-{[(1H-imidazol-2-ylmethyl)-amino]-methyl}-phenyl)-benzamide [Compound No. 34]

Example 34-1

Synthesis of (1H-imidazol-2-ylmethyl)-(4-nitrobenzyl)amine

Commercially available 4-nitrobenzylamine hydrochloride (manufactured by Tokyo Kasei Kogyo Co., Ltd.) (647 mg) was suspended in chloroform (15 ml). Then, the suspension was added with a 1 mol/l sodium hydroxide aqueous solution (10 ml). The aqueous layer was extracted with chloroform and the extract was then dried with anhydrous magnesium sulfate, followed by distilling the solvent off. Subsequently, the residue was dissolved in anhydrous methanol (20 ml). The solution was added with 2-imidazole carboxaldehyde (495 mg) and trimethyl orthoformate (1.13 ml), followed by stirring at room temperature for 15 hours. After that, the solution was cooled with ice and added with sodium borohydride (389 mg), followed by stirring for 1 hour under ice-cooling. The solvent was distilled off under reduced pressure and the residue was added with water, followed by extraction with chloroform. The extract was dried with anhydrous magnesium sulfate and the solvent was then distilled off, thereby obtaining the subject compound (733 mg) as a yellow oily substance.

MS(FAB, Pos.): m/z=233[M+H]$^+$

Example 34-2

Synthesis of (1H-imidazol-2-ylmethyl)-(4-nitrobenzyl)carbamic acid t-butyl ester The compound (733 mg) obtained in Example 34-1 was dissolved in chloroform (15 ml) and then added with di-t-butyl dicarbonate (1.51 g). After having been stirred at room temperature for 1 hour, the solution was concentrated and purified through silica gel column chromatography (chloroform/methanol), thereby obtaining the subject compound (993 mg) as a pale-yellow viscous liquid.

MS(FAB, Pos.): m/z=333[M+H]$^+$

Example 34-3

Synthesis of (4-aminobenzyl)-(1H-imidazol-2-ylmethyl)carbamic acid t-butyl ester The compound (325 mg) obtained in Example 34-2 was dissolved in ethanol (15 ml) and then cooled with ice. The solution was carefully added with 10% palladium-carbon (Mitsuwa Chemicals Co., Ltd.) (300 mg), followed by stirring under a hydrogen atmosphere for 30 minutes. The solution was subjected to Celite filtration and the filtrate was then concentrated, thereby obtaining the subject compound (233 mg) as a pale-red white solid.

MS(FAB, Pos.): m/z=303[M+H]$^+$

Example 34-4

Synthesis of [4-(4-{[bis(1H-imidazol-2-ylmethyl) amino]methyl}benzoylamino)benzyl]-(1H-imidazol-2-ylmethyl)carbamic acid t-butyl ester The compound (150 mg) obtained in Example 34-3 was dissolved in DMF (3.0 ml) and then added with the compound (140 mg) synthesized in Example 2-2. To the mixture solution, HOBt (79.0 mg) and PS-carbodiimide (manufactured by Argonaut Technologies, Inc.) (681 mg) were added, followed by stirring at room temperature for 18 hours. After completion of the reaction, PS-carbodiimide was filtrated and DMF in the filtrate was then distilled off. The residue was added with chloroform and washed with a 1 mol/l sodium hydroxide aqueous solution and saturated saline solution. The residue was brought into an anhydrous state using anhydrous sodium sulfate and then concentrated. Subsequently, the concentrated product was purified through column chromatography (chloroform/methanol), thereby obtaining the subject compound (105 mg) as a white solid.

MS(FAB, Pos.): m/z=596[M+H]$^+$

Example 34-5

Synthesis of 4-{[bis(1H-imidazol-2-ylmethyl)-amino]-methyl}-N-(4-{[(1H-imidazol-2-ylmethyl)-amino]-methyl}-phenyl)-benzamide [Compound No. 34]

The compound (105 mg) obtained in Example 34-4 was dissolved in methanol (10 ml) and then added with 1 mol/l hydrochloric acid (2.0 ml), followed by stirring at room temperature for 5 minutes. The solution was concentrated and dried, and then purified through column chromatography (chloroform/methanol), thereby obtaining hydrochloride (64 mg) of the subject compound as a white solid.

MS(FAB, Pos.): m/z=496[M+H]$^+$
$^1$H-NMR(500 MHz, DMSO-d$_6$): δ=3.78(2H, s), 4.15(4H, s), 4.29(2H, s), 4.53(2H, s), 7.56(2H, d, J=8.7 Hz), 7.62(2H, d, J=8.2 Hz), 7.62(4H, s), 7.73(2H, s), 7.85(2H, d, J=8.7 Hz), 7.92(2H, d, J=8.2 Hz), 10.3(3H, s), 14.6–14.9(4H, brs).

Production Example 35

Synthesis of [4-(4-{[bis(1H-imidazol-2-ylmethyl)-amino]-methyl}-benzyloxy)-benzyl]-dipropylamine [Compound No. 35]

Example 35-1

Synthesis of 4-{[N-Boc(N-1H-imidazol-2-ylmethyl) amino]methyl}benzoic acid methyl ester The compound (2.00 g) obtained in Example 1-1 was dissolved in methanol (40 ml) and then added with WSCI hydrochloride (1.74 g) and HOBt (1.22 g), followed by stirring overnight at room temperature. After completion of the reaction, the solvent was distilled off and the residue was then dissolved in chloroform. The solution was added with a saturated aqueous sodium bicarbonate solution and stirred, followed by extraction with chloroform. The extract was washed with a saturated aqueous sodium bicarbonate solution, a saturated aqueous ammonium chloride solution, and saturated saline solution. The organic layer was dried with anhydrous sodium sulfate. The solvent was distilled off, thereby obtaining the subject compound (2.42 g) as a colorless solid.

MS(FAB, Pos.): m/z=346[M+H]$^+$

Example 35-2

Synthesis of 4-{[N-Boc(N-1H-imidazol-2-ylmethyl) amino]methyl}benzyl alcohol

The compound (2.42 g) obtained in Example 35-1 was dissolved in anhydrous THF (5.0 ml) and then added with lithium aluminum hydride (799 mg) in an ice bath, followed by stirring at room temperature for 2 hours. After completion of the reaction, the solution was added with methanol and then with an aqueous potassium sodium tartrate solution, followed by stirring. The solution was extracted with chloroform, followed by washing with saturated saline solution. Subsequently, the organic layer was dried with anhydrous sodium sulfate. The solvent was distilled off and the residue was then purified through silica gel column chromatography (chloroform/methanol), thereby obtaining the subject compound (1.76 g) as a colorless solid.

MS(FAB, Pos.): m/z=318[M+H]$^+$

Example 35-3

Synthesis of 4-(N,N-dipropylamino)methylphenol

In methanol, 4-hydroxybenzaldehyde (manufactured by Tokyo Kasei Kogyo Co., Ltd.) (1.00 g) was dissolved. Then, the solution was added with dipropylamine (1.24 ml), trimethyl orthoformate (1.0 ml), and acetic acid (500 μl) and stirred at room temperature for 15 minutes. The solution was cooled to 0° C. and added with sodium cyanoborohydride (773 mg), followed by stirring for 6 hours at room temperature. After completion of the reaction, the solvent was distilled off under reduced pressure and the residue was then dissolved in chloroform, followed by the addition of water. The solution was adjusted to about pH 7 with a 1 mol/l sodium hydroxide aqueous solution and then subjected to extraction with chloroform. The resulting organic layer was washed with saturated saline solution and then dried with anhydrous sodium sulfate. After filtration, the solvent was distilled off under reduced pressure and the residue was then purified through silica gel column chromatography (chloroform/methanol), thereby obtaining the subject compound (76.8 mg) as a pale-yellow solid.

MS(FAB, Pos.): m/z=208[M+l]$^+$

Example 35-4

Synthesis of [4-(4-{[N-Boc(N-1H-imidazol-2-ylmethyl)amino]methyl}benzyloxy)benzyl]dipropylamine The compound (107 mg) obtained in Example 35-2 was dissolved in THF (2.0 ml) and then added with the compound (76.8 mg) obtained in Example 35-3, triphenylphosphine (177 mg) and diethylazodicarboxylate (manufactured by Tokyo Kasei Kogyo Co., Ltd.) (305 μl), followed by stirring overnight at room temperature. After completion of the reaction, the solvent was distilled off and the residue was then dissolved in chloroform to extract. The extract was washed with saturated saline solution and the organic layer was then dried with anhydrous sodium sulfate. The solvent was distilled off and the residue was then purified through silica gel column chromatography (chloroform/methanol), thereby obtaining the subject compound (28.4 mg) as a yellow oily substance.

MS(FAB, Pos.): m/z=507[M+H]$^+$

Example 35-5

Synthesis of [4-(4-{[N-(1H-imidazol-2-ylmethyl) amino]methyl}benzyloxy)benzyl]dipropylamine The compound (28.4 mg) obtained in Example 35-4 was dissolved in anhydrous methanol (1.0 ml) and then added with a 4 mol/l hydrogen chloride/dioxane solution (1.00 ml), followed by stirring at room temperature for 2 hours. After completion of the reaction, the solvent was distilled off. Then, the residue was added with a 1 mol/l sodium hydroxide aqueous solution and subjected to extraction with chloroform. The extract was washed with distilled water and saturated saline solution and the organic layer was then dried with anhydrous sodium sulfate. Subsequently, the solvent was distilled off, thereby obtaining the subjected compound (20.4 mg) as a yellow oily substance.

MS(FAB, Pos.): m/z=407[M+H]$^+$

Example 35-6

Synthesis of [4-(4-{[bis(1H-imidazol-2-ylmethyl)-amino]-methyl}-benzyloxy)-benzyl]-dipropylamine [Compound No. 35]

The compound (20.4 mg) obtained in Example 35-5 was dissolved in anhydrous methanol (2.0 ml) and added with sodium cyanoborohydride (9.50 mg), acetic acid (2.0 ml), and 2-imidazole carboxaldehyde (9.60 mg), followed by stirring at room temperature under a nitrogen atmosphere for 6.5 hours and a half. After completion of the reaction, the solvent was distilled off. The residue was dissolved in chloroform and added with a saturated aqueous sodium bicarbonate solution, followed by stirring. The solution was subjected to extraction with chloroform and the extract was then washed with a saturated aqueous sodium bicarbonate solution and saturated saline solution. Subsequently, the organic layer was dried with anhydrous sodium sulfate. The solvent was distilled off, and the residue was treated with hydrochloric acid and then purified through silica gel column chromatography (chloroform/methanol/water), thereby obtaining hydrochloride (4.50 mg) of the subject compound as a white solid.

MS(FAB, Pos.): m/z=487[M+H]$^+$

Production Example 36

Synthesis of 4-{[bis(1H-imidazol-2-ylmethyl)-amino]-methyl}-naphtalene-1-carboxylic acid (4-dipropylaminomethylphenyl)-amide [Compound No. 36]

Example 36-1

Synthesis of methyl 4-bromomethyl-1-naphthalene carboxylic acid

Commercially available 4-methyl-1-naphthalene carboxylic acid (manufactured by Tokyo Kasei Kogyo Co., Ltd.) (251 mg) was dissolved in methanol (7.5 ml) and then aerated under ice-cooling with hydrogen chloride gas for 5 minutes. After that, the solution was stirred at room temperature for 19 hours and the solvent was then distilled off. The residue was dissolved in chloroform and then washed with a 1 mol/l sodium hydroxide aqueous solution. After the solution had been dried with anhydrous sodium sulfate, the solvent was then distilled off. The residue was dissolved in carbon tetrachloride (8.0 ml) and then added with N-bromo succinimide (253 mg) and azobisisobutyronitrile (22.1 mg), followed by stirring at 70° C. for 6 hours. After completion of the reaction, the solid was removed through glass filter, followed by concentration. The residue was dissolved in chloroform and then washed with a 1 mol/l sodium hydroxide aqueous solution and saturated saline solution. The solution was dried with anhydrous sodium sulfate and the solvent was then distilled off. The residue was dried under reduced pressure, thereby obtaining the subject compound (364 mg) as a pale-yellow oily substance.

MS(FAB, Pos.): m/z=279, 281[M+H]$^+$
$^1$H-NMR(60 MHz, CDCl$_3$): δ=3.94(3H, s), 4.86(3H, s), 7.35–7.68(3H, m), 7.88–8.21(2H, m), 8.66–8.89(1H, m).

Example 36-2

Synthesis of methyl-4-aminomethyl-1-naphthalene carboxylic acid

The compound (328 mg) obtained in Example 36-1 was dissolved in DMF (7.2 ml), added with potassium phthalimide (359 mg), and stirred at room temperature for 12 hours. After completion of the reaction, the solvent was distilled off and the residue was then dissolved in chloroform, followed by washing with distilled water, a 1 mol/l sodium hydroxide aqueous solution, and saturated saline solution. The solution was dried with anhydrous sodium sulfate, and the solvent was distilled off, and the residue was then purified through silica gel column chromatography (hexane/ethyl acetate), thereby obtaining a white solid (281 mg). Subsequently, the solid (1.50 g) was dissolved in methanol (30 ml) and then added with hydrazine monohydrate (7.5 ml), followed by heating up to 60° C. Methanol (30 ml) was added further to the solution and the whole was stirred continuously for one hour at 60° C. After completion of the reaction, the solvent was distilled off and the residue was dissolved in chloroform. The solution was washed with distilled water and saturated saline solution and dried with anhydrous sodium sulfate. The solvent was distilled off and the residue was then dried under vacuum, thereby obtaining the subject compound (789 mg) as a pale-yellow solid.

MS(FAB, Pos.): m/z=216[M+H]$^+$
$^1$H-NMR(500 MHz, CDCl$_3$): δ=4.00(3H, s), 4.39(2H, s), 7.55(1H, d, J=7.6 Hz), 7.57–7.65(2H, m), 8.11(1H, d, J=8.3 Hz), 8.15(1H, d, J=7.3 Hz), 8.97(1H, d, J=8.5 Hz).

Example 36-3

Synthesis of 4-{[bis(1H-imidazol-2-ylmethyl) amino]methyl}naphthalene-1-carboxylic acid methyl ester The compound (390 mg) obtained in Example 36-2 was dissolved by the addition of anhydrous methanol (20 ml), and the solution was added with imidazole-2-carboxaldehyde (453 mg) and sodium cyanoborohydride (341 mg), and adjusted to pH 5 by the addition of acetic acid (0.5 ml), followed by stirring for 18 hours. After completion of the reaction, the methanol was distilled off and the residue was then added with 1 mol/l sodium hydroxide (20 ml), followed by extraction with chloroform. The organic layer was washed with saturated saline solution and then dried with anhydrous magnesium sulfate. After that, the solvent was distilled off and the residue was then dried, thereby obtaining the subject compound (680 mg) as a white solid.

MS(FAB, Pos.): m/z=376[M+H]$^+$ $^1$H-NMR(500 MHz, CDCl$_3$): δ=3.49(4H, s), 4.00(3H, s), 4.14(2H, s), 7.06(4H, s), 7.51–7.64(3H, m), 8.06(1H, d, J=7.6 Hz), 8.30(1H, d, J=7.8 Hz), 8.90(1H, d, J=7.8 Hz).

Example 36-4

Synthesis of 4-{[bis(1H-imidazol-2-ylmethyl) amino]methyl}naphthalene-1-carboxylic acid The compound (675 mg) obtained in Example 36-3 was added with methanol (7.0 ml) and a 1 mol/l sodium hydroxide (7.0 ml), followed by stirring for 1 hour. After completion of the reaction, 1 mol/l hydrochloric acid (8.0 ml) was added to adjust the solution to pH 4. Then, the solvent was distilled off and the residue was washed with methanol, followed by drying. Consequently, the subject compound (677 mg) was obtained as a white solid.

MS(FAB, Pos.): m/z=362[M+H]$^+$ $^1$H-NMR(500 MHz, DMSO-d$_6$): δ=4.12(4H, s), 4.17(2H, s), 7.30(4H, s), 7.58–7.66(3H, m), 8.02(1H, d, J=7.5 Hz), 8.07(1H, d, J=7.3 Hz), 8.78(1H, d, J=8.1 Hz).

Example 36-5

Synthesis of 4-{[bis(1H-imidazol-2-ylmethyl)-amino]-methyl}-naphtalene-1-carboxylic acid (4-dipropylaminomethylphenyl)-amide [Compound No. 36]

The compound (130 mg) obtained in Example 36-4 was dissolved in DMF (3.0 ml) and then added with DCC (60.0 mg) and HOBt (40.0 mg), followed by stirring at room temperature for 2 hours. The compound (50.0 mg) obtained in Example 19-2 was added to the solution at room temperature, and the whole was stirred overnight. After completion of the reaction, insoluble matter was removed from the solution through a G4 glass filter and the solvent was distilled off. The residue was dissolved in chloroform and then washed with 1 mol/l hydrochloric acid. The organic layer was added with hydrochloric acid to separate the solution into layers. Then, the aqueous layer was added with a sodium hydroxide aqueous solution to adjust it to pH 12. The aqueous layer was subjected to extraction with chloroform, and the organic layer was dried with anhydrous sodium sulfate. Then, the solvent was distilled off. Subsequently, the residue was treated with hydrochloric acid and then purified through silica gel column chromatography (chloroform/methanol/water) thereby obtaining hydrochloride (17.4 mg) of the subject compound as a white foamed compound.

MS(FAB, Pos.): m/z=550[M+H]$^+$ $^1$H-NMR(500 MHz, DMSO-d$_6$): δ=0.88(6H, t, J=7.3 Hz), 1.73(4H, br), 2.92(4H, br), 4.20(4H, br), 4.27(2H, br), 7.47(4H, s), 7.59(4H, m) 7.67(1H, d, J=7.2 Hz), 7.80(1H, d, J=7.3 Hz), 7.89(2H, d, J=8.5 Hz), 8.13(2H, m), 10.44(1H, br), 10.74(1H, br).

Production Example 37

Synthesis of (4-{[bis(1H-imidazol-2-ylmethyl)-amino]-methyl}-phenyl)-[4-(1-propylbutyl)-piperazin-1-yl]-methanone [Compound No. 37]

Example 37-1

Synthesis of (4-{[bis(1H-imidazol-2-ylmethyl)-amino]-methyl}-phenyl)-[4-(1-propylbutyl)-piperazin-1-yl]-methanone [Compound No. 37]

The compound (57.7 mg) obtained in Example 32-2 was dissolved in methanol (1.73 ml) and then added with 4-heptanone (manufactured by Tokyo Kasei Kogyo Co., Ltd.) (30.7 μl), sodium cyanoborohydride (13.8 mg), and triethylamine (76.5 μl). The solution was adjusted to pH 5 with acetic acid and stirred at room temperature for 7 days. The reaction solution was added with a 1 mol/l sodium hydroxide aqueous solution and then the whole was separated and extracted with chloroform. The organic layer was dried with anhydrous sodium sulfate. The solvent was distilled off and the residue was then purified through silica gel column chromatography (chloroform/methanol) and treated with hydrochloric acid, thereby obtaining hydrochloride (27.7 mg) of the subject compound as a pale-yellow solid.

MS(FAB, Pos.): m/z=478[M+H]$^+$ $^1$H-NMR(500 MHz, DMSO-d$_6$): δ=0.86(6H, t, J=7.1 Hz), 1.21–1.82(12H, m), 3.04–3.55(5H, m), 3.74(2H, s), 4.16 (4H, s), 7.35(2H, d, J=8.3 Hz), 7.41(2H, d, J=8.3 Hz), 7.57(4H, s).

Production Example 38

Synthesis of (4-{[bis(1H-imidazol-2-ylmethyl)-amino]-methyl}-phenyl)-(4-cyclohexylpiperazin-1-yl)-methanone [Compound No. 38]

Example 38-1

Synthesis of (4-{[bis(1H-imidazol-2-ylmethyl)-amino]-methyl}-phenyl)-(4-cyclohexylpiperazin-1-yl)-methanone [Compound No. 38]

The compound (57.7 mg) obtained in Example 32-3 was dissolved in methanol (1.73 ml) and then added with cyclohexanone (21.6 mg), sodium cyanoborohydride (13.8 mg), and triethylamine (76.5 μl). The solution was adjusted to pH 5 with acetic acid and stirred at room temperature for 7 days. The reaction solution was added with a 1 mol/l sodium hydroxide aqueous solution and then the whole was separated and extracted with chloroform. The organic layer was dried with anhydrous sodium sulfate. The solvent was distilled off and the residue was then purified through silica gel column chromatography (chloroform/methanol) and treated with hydrochloric acid, thereby obtaining hydrochloride (7.9 mg) of the subject compound as a pale-yellow solid.

MS(FAB, Pos.): m/z=462[M+H]$^+$ $^1$H-NMR(500 MHz, DMSO-d$_6$): δ=1.00–2.18(15H, m), 3.02–3.16(4H, m), 3.71(2H, s), 4.13(4H, s), 7.33(2H, d, J=8.1 Hz), 7.45(2H, d, J=8.1 Hz), 7.56(4H, s).

Production Example 39

Synthesis of (4-{[bis(1-methyl-1H-imidazol-2-ylmethyl)-amino]-methyl}-benzyl)-(4-dipropylaminomethylphenyl)-amine [Compound No. 39]

Example 39-1

Synthesis of 2-{4-[(4-dipropylaminomethylphenylamino)methyl]benzyl}isoindole-1,3-dione The compound (17.6 mg) obtained in Example 25-1, the compound (13.2 mg) obtained in Example 19-2, and sodium cyanoborohydride (8.7 mg) were dissolved in anhydrous methanol (1.0 ml). The solution was then adjusted to pH 5 with the addition of acetic acid, followed by stirring at room temperature for 4 hours. The reaction solution was added with distilled water and then subjected to extraction with chloroform. After that, the organic layer was washed with saturated saline solution and dried with anhydrous sodium sulfate. The solvent was distilled off and the residue was then purified through silica gel preparative thin-layer chromatography (chloroform/methanol), thereby obtaining the subject compound (72.9 mg) as a yellow solid.

MS(FAB, Pos.): m/z=456[M+H]$^+$
$^1$H-NMR(500 MHz, CDCl$_3$): 2.35(4H, t, J=7.1 Hz), 3.46 (2H, brs), 4.27(2H, s), 4.84(2H, s), 6.56(2H, d, J=8.5 Hz), 7.09(2H, d, J=8.3 Hz), 7.32(2H, d, J=8.1 Hz), 7.41(2H, d, J=8.1 Hz), 7.69–7.73(2H, m), 7.83–7.86(2H, m).

Example 39-2

Synthesis of (4-aminomethylbenzyl)-(4-dipropylaminomethylphenyl)-amine

The compound (521.6 mg) obtained in Example 39-1 was dissolved in methanol (15 ml) and added with hydrazine monohydrate (0.11 ml), followed by stirring at 60° C. for 1.5 hours. The reaction solution was added with a 1 mol/l sodium hydroxide aqueous solution and then subjected to extraction with chloroform. Subsequently, the organic layer was washed with saturated saline solution and then dried with anhydrous sodium sulfate. After the solvent had been distilled off, the subject compound (372 mg) was obtained as a yellow solid.

MS(FAB, Pos.): m/z=326[M+H]$^+$

Example 39-3

Synthesis of (4-{[bis(1-methyl-1H-imidazol-2-ylmethyl)-amino]-methyl}-benzyl)-(4-dipropylaminomethylphenyl)-amine [Compound No. 39]

The compound (57.3 mg) obtained in Example 39-2 was dissolved in methanol (2.5 ml). The solution was added with 1-methyl-2-imidazole carboxaldehyde (158 mg) and then added with sodium cyanoborohydride (68.4 mg). The reaction solution was adjusted to pH 5 by the addition of acetic acid, followed by stirring for 17 hours at room temperature. Then, the reaction solution was added with a 1 mol/l sodium hydroxide aqueous solution and then subjected to extraction with chloroform. After that, the organic layer was washed with saturated saline solution and then dried with anhydrous sodium sulfate. After the solvent had been distilled off, a 10% hydrogen chloride/methanol solution was added to the residue, and the solvent was then distilled off. The residue obtained was purified through silica gel column chromatography (chloroform/methanol/water), thereby obtaining the subject compound (55.2 mg) as a yellow solid.

MS(FAB, Pos.): m/z=514[M+H]$^+$
$^1$H-NMR(500 MHz, DMSO-d$_6$): δ=0.85(6H, t, J=7.3 Hz), 1.65(4H, m), 2.87(4H, m), 3.68(2H, brs), 3.70(6H, s), 4.09 (2H, brs), 4.10(4H, brs), 4.22(2H, brs), 6.58(2H, d, J=8.7 Hz), 7.21(2H, d, J=8.7 Hz), 7.24(4H, s), 7.47–7.51(4H, m).

Production Example 40

Synthesis of 4-{[bis(1-methyl-1H-imidazol-2-ylmethyl)-amino]-methyl}-N-(4-dipropylaminobutyl)-benzamide [Compound No. 40]

Example 40-1

Synthesis of 4-{[bis(1-methyl-1H-imidazol-2-ylmethyl)amino]methyl}-benzoic acid

Commercially available amino methylbenzoic acid methyl ester (manufactured by Tokyo Kasei Kogyo Co., Ltd.) (278 mg) was dissolved in methanol (9 ml). Then, the solution was added with 1-methyl-2-imidazole carboxaldehyde (manufactured by Aldrich Corporation) (407 mg) and sodium cyanoborohydride (317 mg), and then adjusted to about pH 5 with acetic acid, followed by stirring at room temperature for 3 days. After completion of the reaction, the solvent was distilled off and the residue was then dissolved in chloroform, followed by washing with a 1 mol/l sodium hydroxide solution. The solution was dried with anhydrous sodium sulfate, and the solvent was distilled off. Subsequently, the residue was dissolved in methanol (6.0 ml) and then added with 1 mol/l sodium hydroxide, followed by stirring at room temperature for 6 hours. After completion of the reaction, 1 mol/l hydrochloric acid (6.0 ml) was added and the solvent was distilled off. After that, ethanol was added to remove insoluble matter, the solvent was distilled off, and the residue was then dried, thereby obtaining the subject compound (519 mg) as a pale-yellow foamy substance.

MS(FAB, Pos.): m/z=340[M+H]$^+$

Example 40-2

Synthesis of 4-{[bis(1-methyl-1H-imidazol-2-ylmethyl)-amino]-methyl}-N-(4-dipropylaminobutyl)-benzamide [Compound No. 40]

The compound (75.0 mg) obtained in Example 40-1 was dissolved in DMF (2.0 ml) and then added with DCC (46.0 mg) and HOBt (36.0 mg), followed by stirring for 6 hours. A solution of the compound (76.0 mg) obtained in Example 1-2 in DMF was added to the reaction system and then the whole was stirred for 15 hours. After completion of the reaction, DMF was distilled off and the residue was then dissolved in chloroform, followed by extraction with 1 mol/l hydrochloric acid. The aqueous layer was added with a 1 mol/l sodium hydroxide aqueous solution and then extracted with chloroform. The extract was dried with anhydrous magnesium sulfate and the solvent was then distilled off, followed by treating with hydrochloric acid. Subsequently, the treated product was purified through silica gel column chromatography (chloroform/methanol/water), thereby obtaining hydrochloride (23.9 mg) of the subject compound as a white solid.

MS(FAB, Pos.): m/z=494[M+H]$^+$
$^1$H-NMR(500 MHz, DMSO-d$_6$+D$_2$O): δ=0.89(6H, t, J=7.4 Hz), 1.22–1.70(8H, m), 2.99(4H, t, J=8.2 Hz), 3.07 (2H, t, J=7.0 Hz), 3.72(6H, s), 3.78(2H, s), 4.09(4H, s), 7.39(2H, d, J=8.4 Hz), 7.49(4H, d, J=8.1 Hz), 7.76(2H, d, J=8.4 Hz).

Production Example 41

Synthesis of 4-{[bis(1-methyl-1H-imidazol-2-ylm-ethyl)-amino]-methyl}-N-(4-dipropylaminometh-ylphenyl)-benzamide [Compound No. 41]

Example 41-1

Synthesis of 4-{[bis(1-methyl-1H-imidazol-2-ylm-ethyl)-amino]-methyl}-N-(4-dipropylaminometh-ylphenyl)-benzamide [Compound No. 41]

The compound (100 mg) obtained in Example 2-2 was dissolved in DMF (2.0 ml) and then added with DCC (73.0 mg) and HOBt (36.0 mg), followed by stirring for 15 hours. A solution (2.0 ml) of the compound (73.0 mg) obtained in Example 19-2 in DMF was added to the reaction system and then the whole was stirred for 24 hours. After completion of the reaction, DMF was distilled off and the residue was then dissolved in chloroform, followed by extraction with 1 mol/l hydrochloric acid. The aqueous layer was added with a 1 mol/l sodium hydroxide aqueous solution and then extracted with chloroform. The extract was dried with anhydrous magnesium sulfate and the solvent was then distilled off, followed by treating with hydrochloric acid. Subsequently, the treated product was purified through silica gel column chromatography (chloroform/methanol/water), thereby obtaining hydrochloride (14.2 mg) of the subject compound as a white solid.

MS(FAB, Pos.): m/z=528[M+H]$^+$ $^1$H-NMR(500 MHz, DMSO-d$_6$+D$_2$O): δ=0.88(6H, t, J=7.3 Hz), 1.63–1.75(4H, m), 2.96(4H, t, J=7.5 Hz), 3.72 (6H, s), 3.82(2H, s), 4.09(4H, s), 4.29(2H, s), 7.45–7.53(8H, m), 7.85–7.91(4H, m), 10.43(1H, s).

Production Example 42

Synthesis of [4-(4-{[bis(1H-imidazol-2-ylmethyl)-amino]-methyl}-benzylamino)-butyl]-carbamic acid benzyl ester [Compound No. 42]

Example 42-1

Synthesis of {4-[4-(1,3-dioxo-1,3-dihydroisoindol-2-ylmethyl)benzylamino]butyl}carbamic acid benzyl ester In ethanol (40 ml), 1,4-diaminobutane (1.28 g) was dissolved and then the solution was cooled to 0° C., followed by the addition of a 2 mol/l aqueous sodium acetate solution (10 ml) prepared in advance. Benzyloxylcarbonyl chloride (manufactured by Wako Pure Chemical Industries, Ltd.) (1.13 ml) and a 4 mol/l sodium hydroxide aqueous solution (1.2 ml) were added in this order. After having been heated to room temperature, the solution was stirred for 3 hours. Then, the solution was concentrated and ethanol was then distilled off, followed by the addition of chloroform to carry out extraction. The extract was dried with anhydrous sodium sulfate, and the solvent was distilled off. Then, the residue was added with the compound (151 mg) obtained in Example 25-1 and methanol (5.0 ml). Subsequently, the mixture was added with sodium cyanoborohydride (36 mg) and acetic acid (0.1 ml), followed by stirring at room temperature for 18 hours. After completion of the reaction, the solvent was distilled off, a 1 mol/l sodium hydroxide aqueous solution was added to the residue, and then the whole was extracted with chloroform. The extract was dried with anhydrous sodium sulfate and the solvent was then distilled off. After that, the residue was purified through silica gel column chromatography (chloroform/methanol/water), thereby obtaining the subject compound (153 mg) as a colorless viscous liquid.

MS(FAB, Pos.): m/z=472[M+H]$^+$

Example 42-2

Synthesis of (4-benzyloxycarbonylaminobutyl)-[4-(1,3-dioxo-1,3-dihydroisoindol-2-ylmethyl)benzyl]-carbamic acid t-butyl ester The compound (153 mg) obtained in Example 42-1 was dissolved in chloroform (15 ml) and then added with di-t-butyl dicarbonate (106 mg). After having been stirred at room temperature for 1 hour, the solution was concentrated and purified through silica gel column chromatography (chloroform/methanol), thereby obtaining the subject compound (173 mg) as a colorless viscous liquid.

MS(FAB, Pos.): m/z=572[M+H]$^+$

Example 42-3

Synthesis of (4-aminomethylbenzyl)-(4-benzyloxy-carbonylaminobutyl)-carbamic acid t-butyl ester The compound (173 mg) obtained in Example 42-2 was added with a 40% methylamine/methanol solution (3.0 ml), followed by stirring at room temperature for 14 hours. After completion of the reaction, the solvent was distilled off and the residue was then added with a 1 mol/l sodium hydroxide aqueous solution, followed by extraction with chloroform. The extract was dried with anhydrous sodium sulfate. Subsequently, the solvent was distilled off, thereby obtaining the subject compound (98.9 mg) as a colorless viscous liquid.

MS(FAB, Pos.): m/z=442[M+H]$^+$

Example 42-4

Synthesis of [4-(4-{[bis(1H-imidazol-2-ylmethyl)-amino]-methyl}-benzylamino)-butyl]-carbamic acid benzyl ester [Compound No. 42]

The compound (98.9 mg) obtained in Example 42-3 was dissolved in anhydrous methanol (5.0 ml) and then added with 2-imidazole carboxaldehyde (49.0 mg), sodium cyanoborohydride (28.0 mg), and acetic acid (0.1 ml) in this order. The solution was stirred at room temperature for 15 hours and methanol was then distilled off, followed by the addition of a 1 mol/l sodium hydroxide aqueous solution. The solution was subjected to extraction with chloroform and the extract was then dried with anhydrous sodium sulfate, and the solvent was distilled off. The residue was purified through silica gel column chromatography (chloroform/methanol/water) and then treated with hydrochloric acid, thereby obtaining hydrochloride (82.0 mg) of the subject compound as a white solid.

MS(FAB, Pos.): m/z=502[M+H]$^+$ $^1$H-NMR(500 MHz, DMSO-d$_6$): δ=1.41–1.44(2H, m), 1.59–1.64(2H, m), 2.80(2H, brs), 2.97–3.01(2H, m), 3.67 (2H, s), 4.02–4.05(2H, m), 4.11(4H, s), 5.00(2H, s), 7.29–7.38(5H, m), 7.44(2H, d, J=8.2 Hz), 7.49(2H, d, J=8.2 Hz), 7.61(4H, s), 9.18(2H, brs), 14.69(3H, brs).

Production Example 43

Synthesis of (4-{[bis(1H-imidazol-2-ylmethyl)-amino]-methyl}-benzyl)-(4-dipropylaminomethylphenyl)-amine [Compound No. 43]

Example 43-1

Synthesis of (4-dipropylaminomethylphenyl)-(4-{[(1H-imidazol-2-ylmethyl)amino]methyl}benzyl)-amine The compound (63.1 mg) obtained in Example 39-2 was dissolved in methanol (2.0 ml) and then added with 2-imidazole carboxaldehyde (17.9 mg), followed by stirring at room temperature for 17 hours. After the solvent had been distilled off, the residue was dried under vacuum and then dissolved in methanol (2.5 ml). Subsequently, the solution was added with sodium borohydride (14.5 mg) and stirred at room temperature for 1 hour. The reaction solution was added with a saturated aqueous ammonium chloride solution (4.0 ml) and stirred at room temperature for 30 minutes. Then, the reaction solution was added with saturated saline solution and subjected to extraction with chloroform, followed by drying with anhydrous sodium sulfate. After the solvent had been distilled off, the residue obtained was purified through silica gel column chromatography (chloroform/acetone), thereby obtaining the subject compound (45.2 mg) as a yellow solid.

MS(FAB, Pos.): m/z=406[M+H]$^+$ $^1$H-NMR(500 MHz, CDCl$_3$): δ=0.85(6H, t, J=7.3 Hz), 1.46(4H, tq, J=6.9, 7.3 Hz), 2.34(4H, t, J=6.9 Hz), 3.44(2H, s), 3.80(2H, s), 3.93(2H, s), 4.30(2H, brs), 6.58(2H, d, J=8.5 Hz), 6.99(2H, s), 7.11(2H, d, J=8.5 Hz), 7.28 (2H, d, J=8.3 Hz), 7.34(2H, d, J=8.3 Hz).

Example 43-2

Synthesis of (4-{[bis(1H-imidazol-2-ylmethyl)-amino]-methyl}-benzyl)-(4-dipropylaminomethylphenyl)-amine [Compound No. 43]

The compound (199 mg) obtained in Example 43-1 was dissolved in methanol (6 ml) and then added with 2-imidazole carboxaldehyde (57.1 mg) and sodium cyanoborohydride (65.4 mg). The reaction solution was adjusted to pH 5 with the addition of acetic acid, followed by stirring at room temperature for 14 hours. The reaction solution was added with a 1 mol/l sodium hydroxide aqueous solution and then extracted with chloroform. Then, the organic layer was washed with saturated saline solution and dried with anhydrous sodium sulfate. After the solvent had been distilled off, the residue obtained was purified through silica gel column chromatography (chloroform/methanol) and treated with hydrochloric acid, thereby obtaining hydrochloride (231 mg) of the subject compound as a yellow solid.

MS(FAB, Pos.): m/z=486[M+H]$^+$ $^1$H-NMR(500 MHz, DMSO-d$_6$): δ=0.85(6H, t, J=7.3 Hz), 1.65(4H, m), 2.88(4H, m), 3.64(2H, brs), 3.70(2H, brs), 4.09(4H, brs), 4.23(2H, brs), 6.59(2H, d, J=8.5 Hz), 7.19 (2H, d, J=8.5 Hz), 7.24(2H, d, J=8.3 Hz), 7.29(2H, d, J=8.3 Hz), 7.55(4H, s).

Production Example 44

Synthesis of (4-dipropylaminomethylphenyl)-(4-{[(1H-imidazol-2-ylmethyl)-(1-methyl-1H-imidazol-2-ylmethyl)-amino]-methyl}-benzyl)-amine [Compound No. 44]

Example 44-1

Synthesis of (4-dipropylaminomethylphenyl)-(4-{[(1H-imidazol-2-ylmethyl)-(1-methyl-1H-imidazol-2-ylmethyl)-amino]-methyl}-benzyl)-amine [Compound No. 44]

The compound (72.7 mg) obtained in Example 43-1 was dissolved in methanol (3.5 ml) and then added with 1-methyl-2-imidazole carboxaldehyde (28.6 mg) and sodium cyanoborohydride (22.8 mg). The reaction solution was adjusted to pH 5 with the addition of acetic acid, followed by stirring at room temperature for 14 hours. The reaction solution was added with a 1 mol/l sodium hydroxide aqueous solution and then extracted with chloroform. Then, the organic layer was washed with saturated saline solution and dried with anhydrous sodium sulfate. After the solvent had been distilled off, the residue obtained was purified through silica gel column chromatography (chloroform/ethyl acetate) and treated with hydrochloric acid, thereby obtaining hydrochloride (71.3 mg) of the subject compound as a yellow solid.

MS(FAB, Pos.): m/z=500[M+H]$^+$ $^1$H-NMR(500 MHz, DMSO-d$_6$): δ=0.84(6H, t, J=7.4 Hz), 1.69(4H, m), 2.84(4H, m), 3.57(2H, s), 3.65(3H, s), 4.07 (2H, s), 4.08(2H, s), 4.16(2H, s), 6.62(2H, d, J=8.1 Hz), 7.24(2H, d, J=8.1 Hz), 7.28(2H, d, J=8.3 Hz), 7.34(2H, d, J=8.3 Hz), 7.48(1H, d, J=1.9 Hz), 7.49(1H, d, J=1.9 Hz), 7.61(2H, s).

Production Example 45

Synthesis of (4-dipropylaminomethylphenyl)-(4-{[(1H-imidazol-2-ylmethyl)-(2H-pyrazol-3-ylmethyl)-amino]-methyl}-benzyl)-amine [Compound No. 45]

Example 45-1

Synthesis of (4-dipropylaminomethylphenyl)-(4-{[(1H-imidazol-2-ylmethyl)-(2H-pyrazol-3-ylmethyl)-amino]-methyl}-benzyl)-amine [Compound No. 45]

The compound (72.0 mg) obtained in Example 43-1 was dissolved in methanol (3.5 ml) and then added with pyrazole-3-carboxaldehyde (24.5 mg) and sodium cyanoborohydride (35.9 mg). The reaction solution was adjusted to pH 5 with the addition of acetic acid, followed by stirring at room temperature for 14 hours. The reaction solution was added with a 1 mol/l sodium hydroxide aqueous solution and then extracted with chloroform. Then, the organic layer was washed with saturated saline solution and dried with anhydrous sodium sulfate. After the solvent had been distilled off, the residue obtained was purified through silica gel column chromatography (chloroform/ethyl acetate) and treated with hydrochloric acid, thereby obtaining hydrochloride (52.3 mg) of the subject compound as a yellow solid.

MS(FAB, Pos.): m/z=486[M+H]$^+$

¹H-NMR(500 MHz, DMSO-d₆): δ=0.85(6H, t, J=7.5 Hz), 1.65(4H, m), 2.88(4H, m), 3.70(2H, brs), 3.78(2H, brs), 4.00(2H, brs), 4.10(2H, brs), 4.28(2H, brs), 6.34(1H, d, J=2.1 Hz), 6.65(2H, d, J=8.5 Hz), 7.21(2H, d, J=8.5 Hz), 7.32(2H, d, J=8.3 Hz), 7.38(2H, d, J=8.3 Hz), 7.51(2H, s), 7.69(1H, d, J=2.1 Hz).

Production Example 46

Synthesis of N-(4-dipropylaminobutyl)-4-{[(1H-imidazol-2ylmethyl)-(6-methylpyridin-2-yl-methyl)-amino]-methyl}-benzamide [Compound No. 46]

Example 46-1

Synthesis of N-(4-dipropylaminobutyl)-4-{[(1H-imidazol-2ylmethyl)-(6-methylpyridin-2-yl-methyl)-amino]-methyl}-benzamide [Compound No. 46]

The compound (44.3 mg) obtained in Example 1-4 was dissolved in methanol (1.0 ml) and then added with 6-methylpyridine-2-carboxaldehyde (20.7 mg) and sodium cyanoborohydride (10.7 mg). The solution was adjusted to about pH 5 with acetic acid and then stirred at room temperature for 15 hours. After completion of the reaction, the solvent was distilled off and the residue was then dissolved in chloroform, followed by washing with a 1 mol/l sodium hydroxide aqueous solution and saturated saline solution and drying with anhydrous sodium sulfate. The solvent was distilled off and the residue was then purified through silica gel column chromatography (chloroform/methanol/water), thereby obtaining the subject compound (9.9 mg) as a white solid.

MS(FAB, Pos.): m/z=491[M+H]⁺

¹H-NMR(500 MHz, DMSO-d₆+D₂O): δ=0.90(6H, t, J=7.3 Hz), 1.51–1.73(8H, m), 2.66(3H, s), 2.95–3.03(4H, m), 3.03–3.09(2H, m), 3.24–3.32(2H, m), 3.79(2H, s), 4.00 (2H, s), 4.10(2H, s), 7.33(1H, dd, J=7.5, 2.9 Hz), 7.45(2H, d, J=8.3 Hz), 7.59(1H, d, J=7.5 Hz), 7.76(2H, d, J=8.3 Hz), 7.78–7.81(1H, m).

Production Example 47

Synthesis of N-(4-dipropylaminomethylphenyl)-4-{[(1H-imidazol-2-ylmethyl)-(isoquinolin-3-ylmethyl)-amino]-methyl}-benzamide [Compound No. 47]

Example 47-1

Synthesis of isoquinoline-3-aldehyde

Lithium aluminum hydride (229.4 mg) was suspended in anhydrous THF. Then, a solution of isoquinoline-3-carbocylic acid methyl ester (377.1 mg) in THF was gradually added to the suspension, followed by thermal reflux for 4 hours. The reaction solution was cooled down and then added with ethyl acetate and methanol. After that, chloroform was added to the solution and extraction was then carried out with 1 mol/l hydrochloric acid. The aqueous layer was adjusted to pH 12 or more with a 1 mol/l sodium hydroxide aqueous solution, followed by separation/extraction with chloroform. The organic layer was dried with anhydrous sodium sulfate and the solvent was then distilled off to obtain an alcohol product. The alcohol product was redissolved again in chloroform (16.5 ml) and then added with manganese dioxide (chemically processed product: manufactured by Wako Pure Chemical Industries, Ltd., the same shall apply hereinafter) (2.33 g), followed by stirring at room temperature for 0.5 hour. The reaction solution was filtrated through Celite and the solvent was then distilled off. Then the residue was purified through silica gel column chromatography (hexane/ethyl acetate), thereby obtaining the subject compound (20.2 mg) as an orange-color solid.

¹H-NMR(500 MHz, CDCl₃): δ=7.78–7.84(2H, m), 8.04 (1H, d, J=8.1 Hz), 8.09(1H, d, J=7.8 Hz), 8.41(1H, s), 9.39(1H, s), 10.3(1H, s).

Example 47-2

Synthesis of N-(4-dipropylaminomethylphenyl)-4-{[N-Boc-N-(1H-imidazol-2-ylmethyl)amino]methyl}-benzamide The compound (1.34 g) obtained in Example 19-2 was dissolved in DMF (68 ml). The solution was added with WSCI hydrochloride (4.73 g), HOBt (2.45 g), and the compound (5.74 g) obtained in Example 1-1, followed by stirring at room temperature for 24 hours. After completion of the reaction, the solvent was distilled off and the residue was then redissolved in chloroform, followed by washing with distilled water, a 1 mol/l sodium hydroxide aqueous solution, and saturated saline solution. The solution was dried with anhydrous sodium sulfate, and the solvent was distilled off. The residue was recrystallized from ethyl acetate/chloroform, thereby obtaining the subject compound (5.04 g) as a white solid.

MS(FAB, Pos.): m/z=520[M+H]⁺

¹H-NMR(500 MHz, DMSO-d₆): δ=0.82(6H, t, J=7.3 Hz), 1.36(9H, brs), 1.37–1.43(4H, sext., J=7.3 Hz), 2.32(4H, t, J=7.3 Hz), 3.47(2H, s), 4.30–4.55(4H, br), 6.85(1H, s), 7.05(1H, s), 7.26(2H, d, J=8.5 Hz), 7.32(2H, br), 7.70(2H, d, J=8.5 Hz), 7.91(2H, d, J=8.5 Hz), 10.18(1H, s), 11.8–12.0 (1H, br).

Example 47-3

Synthesis of N-(4-dipropylamino-phenyl)-4-{[(1H-imidazol-2-ylmethyl)amino]methyl}-benzamide The compound (2.50 g) obtained in Example 47-2 was dissolved in methanol (25.0 ml) and then added with a 4 mol/l hydrogen chloride/dioxane solution (50.0 ml), followed by stirring at room temperature for 1 hour. The reaction solvent was distilled off and the residue was then added with a 1 mol/l sodium hydroxide aqueous solution, followed by separation/extraction with chloroform. The organic layer was dried with anhydrous sodium sulfate, and the solvent was then distilled off. The residue was dried under vacuum, thereby obtaining the subject compound (1.89 g) as a white solid.

Example 47-4

Synthesis of N-(4-dipropylaminomethylphenyl)-4-{[(1H-imidazol-2-ylmethyl)-(isoquinolin-3-ylmethyl)-amino]-methyl}-benzamide [Compound No. 47]

The compound (53.9 mg) obtained in Example 47-3 was dissolved in methanol (2.0 ml) and then added with the compound (20.2 mg) obtained in Example 47-1 and sodium cyanoborohydride (12.8 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (10.1 mg) of the subject compound as a white solid.

MS(FAB, Pos.): m/z=561[M+H]$^+$ $^1$H-NMR(500 MHz, DMSO-d$_6$): δ=0.88(6H, t, J=7.3 Hz), 1.60–1.80(4H, m), 2.96(4H, t, J=7.3 Hz), 3.86(2H, s), 4.14 (2H, s), 4.17(2H, s), 4.28(2H, s), 7.48–7.60(6H, m), 7.80–7.94(5H, m), 8.04(1H, t, J=8.3 Hz), 8.14(1H, d, J=8.3 Hz), 8.25(1H, s), 8.39(1H, d, J=8.1 Hz), 9.64(1H, s).

Production Example 48

Synthesis of N-(4-dipropylaminomethylphenyl)-4-{[(1H-imidazol-2-ylmethyl)-(pyridin-2-ylmethyl)-amino]-methyl}-benzamide [Compound No. 48]

Example 48-1

Synthesis of N-(4-dipropylaminomethylphenyl)-4-{[(1H-imidazol-2-ylmethyl)-(pyridin-2-ylmethyl)-amino]-methyl}-benzamide [Compound No. 48]

The compound (52.0 mg) obtained in Example 47-3 was dissolved in methanol (1.6 ml) and then added with pyridine-2-aldehyde (15.9 mg) and sodium cyanoborohydride (15.6 mg). The solution was adjusted to pH 5 with acetic acid and stirred at room temperature for 14 hours. After completion of the reaction, the reaction solution was added with a 1 mol/l sodium hydroxide aqueous solution and then separated and extracted with chloroform. The organic layer was dried with anhydrous sodium sulfate. The solvent was distilled off and the residue was then purified through silica gel column chromatography (chloroform/methanol) and treated with hydrochloric acid, thereby obtaining hydrochloride (15.2 mg) of the subject compound as a pale-yellow solid.

MS(FAB, Pos.): m/z=511[M+H]$^+$ $^1$H-NMR(500 MHz, DMSO-d$_6$): δ=0.88(6H, t, J=7.3 Hz), 1.60–1.80(4H, m), 2.96(4H, t, J=7.3 Hz), 3.81(2H, s), 4.04 (2H, s), 4.12(2H, s), 4.28(2H, s), 7.48–7.59(5H, m), 8.18 (1H, t, J=8.3 Hz), 8.69(1H, d, J=4.4 Hz).

Production Example 49

Synthesis of N-(4-dipropylaminomethylphenyl)-4-{[(1H-imidazol-2-ylmethyl)-(1-methyl-1H-imidazol-2-ylmethyl)-amino]-methyl}-benzamide [Compound No. 49]

Example 49-1

Synthesis of N-(4-dipropylaminomethylphenyl)-4-{[(1H-imidazol-2-ylmethyl)-(1-methyl-1H-imidazol-2-ylmethyl)-amino]-methyl}-benzamide [Compound No. 49]

The compound (52.0 mg) obtained in Example 47-3 was dissolved in methanol (1.6 ml) and then added with 1-methylimidazol-2-aldehyde (16.4 mg), and sodium cyanoborohydride (15.6 mg). The solution was adjusted to pH 5 with acetic acid and stirred at room temperature for 14 hours. After completion of the reaction, the reaction solution was added with a 1 mol/l sodium hydroxide aqueous solution and then separated and extracted with chloroform. The organic layer was dried with anhydrous sodium sulfate. The solvent was distilled off and the residue was then purified through silica gel column chromatography (chloroform/methanol) and treated with hydrochloric acid, thereby obtaining hydrochloride (15.2 mg) of the subject compound as a pale-yellow solid.

MS(FAB, Pos.): m/z=514[M+H]$^+$ $^1$H-NMR(500 MHz, DMSO-d$_6$): δ=0.88(6H, t, J=7.3 Hz), 1.60–1.80(4H, m), 2.96(4H, t, J=7.1 Hz), 3.72(3H, s), 3.81 (2H, s), 4.08(2H, s), 4.16(2H, s), 4.28(2H, s), 7.42–7.58(6H, m), 7.60(2H, s), 7.82–7.92(4H, m).

Production Example 50

Synthesis of N-(4-{[bis(1H-imidazol-2-ylmethyl)-amino]-methyl}-benzyl)-N-methyl-N',N'-dipropylbutane-1,4-diamine [Compound No. 50]

Example 50-1

Synthesis of N-(4-{[bis(1H-imidazol-2-ylmethyl)-amino]-methyl}-benzyl)-N-methyl-N',N'-dipropylbutane-1,4-diamine [Compound No. 50]

The compound (150.7 mg) obtained in Example 25-5 was dissolved in methanol (3.0 ml). Then, a 36% formaldehyde aqueous solution (manufactured by Kanto Kagaku) (50 μl) and sodium cyanoborohydride (36.2 mg) were added to the solution in this order. After the reaction solution was adjusted to pH 5 with acetic acid, the solution was stirred at room temperature for 17 hours. The reaction solution was added with a 1 mol/l sodium hydroxide aqueous solution and then extracted with chloroform. Subsequently, the organic layer was washed with saturated saline solution and then dried with anhydrous sodium sulfate. After the solvent had been distilled off, the residue obtained was purified through silica gel column chromatography (chloroform/ethyl acetate) and then treated with hydrochloric acid, thereby obtaining hydrochloride (126.2 mg) of the subjected compound as a white solid.

MS(FAB, Pos.): m/z=466[M+H]$^+$ $^1$H-NMR(500 MHz, DMSO-d$_6$): δ=0.92(6H, t, J=7.6 Hz), 1.63–1.68(6H, m), 1.69–1.93(2H, m), 2.58(3H, brs), 2.98–3.01(6H, m), 3.06(2H, t, J=8.1 Hz), 3.62(2H, s), 3.72 (2H, s), 4.14(4H, s), 7.45(4H, s), 7.58(4H, s).

Example 51-1

Synthesis of N-(4-dipropylaminomethylphenyl)-4-{[(1H-imidazol-2-ylmethyl)-(6-methylpyridin-2-ylmethyl)-amino]-methyl}-benzamide [Compound No. 51]

Example 51-2

Synthesis of N-(4-dipropylaminomethylphenyl)-4-{[(1H-imidazol-2-ylmethyl)-(6-methylpyridin-2-ylmethyl)-amino]-methyl}-benzamide [Compound No. 51]

The compound (104.9 mg) obtained in Example 47-3 was dissolved in methanol (3.2 ml) and then added with 6-methylpyridine-2-carboxaldehyde (36.3 mg) and sodium cyanoborohydride (31.4 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (75.9 mg) of the subject compound as a white solid.

MS(FAB, Pos.): m/z=525[M+H]$^+$ $^1$H-NMR(500 MHz, DMSO-$d_6$): δ=0.88(6H, t, J=7.3 Hz), 1.60–1.80(4H, m), 2.74(3H, s), 2.88–3.00(4H, m), 3.84(2H, s), 4.12(2H, s), 4.17(2H, s), 4.28(2H, s), 7.48–7.60(6H, m), 7.72(1H, d, J=8.1 Hz), 7.82–7.92(4H, m), 7.96(1H, d, J=7.8 Hz), 8.34(1H, t, J=8.1 Hz).

Production Example 52

Synthesis of N-(4-dipropylaminomethylphenyl)-4-{[(1H-imidazol-2-ylmethyl)-(6-bromopyridin-2-ylmethyl)-amino]-methyl}-benzamide [Compound No. 52]

Example 52-1

Synthesis of N-(4-dipropylaminomethylphenyl)-4-{[(1H-imidazol-2-ylmethyl)-(6-bromopyridin-2-ylmethyl)-amino]-methyl}-benzamide [Compound No. 52]

The compound (104.9 mg) obtained in Example 47-3 was dissolved in methanol (3.2 ml) and then added with 6-bromopyridine-2-aldehyde (55.8 mg) and sodium cyanoborohydride (31.4 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (91.9 mg) of the subject compound as a white solid.

MS(FAB, Pos.): m/z=590[M+H]$^+$ $^1$H-NMR(500 MHz, DMSO-$d_6$): δ=0.88(6H, t, J=7.3 Hz), 1.60–1.80(4H, m), 2.88–3.00(4H, m), 3.81(2H, s), 3.81(2H, s), 4.09(2H, s), 4.28(2H, s), 7.50–7.62(8H, m), 7.75(1H, t, J=7.6 Hz), 7.88(2H, d, J=8.5 Hz), 7.95(2H, d, J=8.5 Hz).

Production Example 53

Synthesis of N-(4-dipropylaminomethylphenyl)-4-{[(1H-imidazol-2-ylmethyl)-(3-methylpyridin-2-ylmethyl)-amino]-methyl}-benzamide [Compound No. 53]

Example 53-1

Synthesis of 3-methyl-2-pyridine aldehyde

Commercially available 2,3-lutidine (5.00 g) was dissolved in dichloromethane (50 ml) and the solution was cooled to 0° C. After that, the solution was added with meta-chloroperbenzoic acid (12.1 g) and then stirred at room temperature for 2 hours. After completion of the reaction, the solution was added with dichloromethane and washed with a 1 mol/l sodium hydroxide aqueous solution and saturated saline solution, followed by drying with anhydrous sodium sulfate. Then, the solvent was distilled off, thereby obtaining crude 2,3-lutidin-N-oxide (3.16 g). A 2.00 g part thereof was dissolved in dichloromethane (40 ml) and then the solution was cooled to 0° C. Subsequently, the solution was added with trifluoroacetic anhydride (4.49 ml), followed by stirring at room temperature for 4 hours and then at 45° C. for 3 hours. After completion of the reaction, the solvent was distilled off and the residue was dissolved in methanol (30 ml), followed by the addition of a sodium methoxide/methanol solution until the pH of the solution would reach pH=10. After the solution had been stirred at room temperature for 1 hour, the solvent was distilled off and extraction was then carried out with dichloromethane. The extract was dried with anhydrous sodium sulfate and the solvent was then distilled off, thereby obtaining 3-methyl-2-hydroxymethylpyridine (1.30 g). A 605.3 mg part thereof was dissolved in chloroform (30 ml) and then added with manganese dioxide (chemically processed product) (3.03 g), followed by stirring at 70° C. for 2 hours. After completion of the reaction, the catalyst was removed through Celite filtration and the solvent was then concentrated. Then, the residue was purified through silica gel column chromatography (chloroform/ethyl acetate), thereby obtaining the subject compound (419.8 mg) as a pale-orange colored liquid.

MS(FAB, Pos.): m/z=122[M+H]$^+$ $^1$H-NMR(500 MHz, CDCl$_3$): δ=2.67(3H, s), 7.40(1H, dd, J=7.8, 4.6 Hz), 7.64(1H, d, J=7.8 Hz), 8.67(1H, d, J=4.6 Hz), 10.2(1H, s).

Example 53-2

Synthesis of N-(4-dipropylaminomethylphenyl)-4-{[(1H-imidazol-2-ylmethyl)-(3-methylpyridin-2-ylmethyl)-amino]-methyl}-benzamide [Compound No. 53]

The compound (104.9 mg) obtained in Example 47-3 was dissolved in methanol (3.2 ml) and then added with the compound (36.3 mg) obtained in Example 53-1 and sodium cyanoborohydride (31.4 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (91.5 mg) of the subject compound as a white solid.

MS(FAB, Pos.) m/z=525[M+H]$^+$ $^1$H-NMR(500 MHz, DMSO-$d_6$): δ=0.88(6H, t, J=7.3 Hz), 1.60–1.80(4H, m), 2.37(3H, s), 2.95(4H, t, J=7.1 Hz), 3.84 (2H, s), 4.16(2H, s), 4.25(2H, s), 4.28(2H, s), 7.53(2H, d, J=8.5 Hz), 7.55(2H, d, J=8.3 Hz), 7.62(2H, s), 7.76(1H, dd, J=4.8, 7.6 Hz), 7.83(2H, d, J=8.5 Hz), 7.86(2H, d, J=8.3 Hz), 8.22(1H, d, J=7.6 Hz), 8.65(1H, d, J=4.9 Hz).

Production Example 54

Synthesis of N-(4-dipropylaminomethylphenyl)-4-{[(1H-imidazol-2-ylmethyl)-(quinolin-4-ylmethyl)-amino]-methyl}-benzamide [Compound No. 54]

Example 54-1

Synthesis of N-(4-dipropylaminomethylphenyl)-4-{[(1H-imidazol-2-ylmethyl)-(quinolin-4-ylmethyl)-amino]-methyl}-benzamide [Compound No. 54]

The compound (104.9 mg) obtained in Example 47-3 was dissolved in methanol (3.2 ml) and then added with quinoline-4-aldehyde (47.2 mg) and sodium cyanoborohydride (31.4 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (76.4 mg) of the subject compound as a white solid.

MS(FAB, Pos.): m/z=561[M+H]$^+$ $^1$H-NMR(500 MHz, DMSO-d$_6$): δ=0.88(6H, t, J=7.3 Hz), 1.60–1.80(4H, m), 2.95(4H, br), 3.92(2H, s), 4.17(2H, s), 4.28(2H, s), 4.41 (2H, s), 7.48–7.60(6H, m), 7.82–7.96(5H, m), 8.02–8.28(3H, m), 8.40(1H, d, J=8.3 Hz), 9.16(1H, d, J=5.4 Hz).

Production Example 55

Synthesis of N-(4-dipropylaminomethylphenyl)-4-{[(1H-imidazol-2-ylmethyl)-(quinolin-2-ylmethyl)-amino]-methyl}-benzamide [Compound No. 55]

Example 55-1

Synthesis of N-(4-dipropylaminomethylphenyl)-4-{[(1H-imidazol-2-ylmethyl)-(quinolin-2-ylmethyl)-amino]-methyl}-benzamide [Compound No. 55]

The compound (81.2 mg) obtained in Example 47-3 was dissolved in methanol (3.2 ml) and then added with quinoline-2-aldehyde (36.5 mg) and sodium cyanoborohydride (24.3 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (77.8 mg) of the subject compound as a white solid.

MS(FAB, Pos.): m/z=560[M+H]$^+$ $^1$H-NMR(500 MHz, DMSO-d$_6$): δ=0.88(6H, t, J=7.3 Hz), 1.60–1.80(4H, m), 2.96(4H, br), 3.88(2H, s), 4.03(2H, s), 4.18(2H, s), 4.28 (2H, s), 7.50–7.61(6H, m), 7.70–8.04(7H, m), 8.13(1H, d, J=8.1 Hz), 8.20(1H, d, J=8.8 Hz), 8.70(1H, d, J=8.3 Hz).

Production Example 56

Synthesis of N-(4-dipropylaminomethylphenyl)-4-{[(1H-imidazol-2-ylmethyl)-(5-methylpyridin-2-ylmethyl)-amino]-methyl}-benzamide [Compound No. 56]

Example 56-1

Synthesis of 5-methyl-2-pyridine aldehyde

By the similar procedures as those of Example 53-1, except of using 2,5-lutidine as a raw material, 5-methylpyridine-2-aldehyde (439.9 mg) was obtained.

MS(FAB, Pos.): m/z=122[M+H]$^+$ $^1$H-NMR(500 MHz, CDCl$_3$): δ=2.46(3H, s), 7.67(1H, dd, J=7.9, 1.4 Hz), 7.89(1H, d, J=7.9 Hz), 8.62(1H, d, J=1.4 Hz), 10.05(1H, s).

Example 56-2

Synthesis of N-(4-dipropylaminomethylphenyl)-4-{[(1H-imidazol-2-ylmethyl)-(5-methylpyridin-2-ylmethyl)-amino]-methyl}-benzamide [Compound No. 56]

The compound (79.4 mg) obtained in Example 47-3 was dissolved in methanol (2.4 ml) and then added with the compound (27.5 mg) obtained in Example 56-1 and sodium cyanoborohydride (23.8 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (63.0 mg) of the subject compound as a white solid.

MS(FAB, Pos.): m/z=525[M+H]$^+$ $^1$H-NMR(500 MHz, DMSO-d$_6$): δ=0.88(6H, t, J=7.3 Hz), 1.60–1.80(4H, m), 2.44(3H, s), 2.95(4H, br), 3.80(2H, s), 4.13(2H, s), 4.16 (2H, s), 4.28(2H, s), 7.53(2H, d, J=7.8 Hz), 7.55(2H, d, J=7.8 Hz), 7.58 (2H, s), 7.86(4H, d, J=7.8 Hz), 7.95(1H, d, J=8.3 Hz), 8.30(1H, dd, J=1.5, 8.3 Hz), 8.66(1H, d, J=1.5 Hz).

Production Example 57

Synthesis of N-(4-dipropylaminomethylphenyl)-4-{[(1H-imidazol-2-ylmethyl)-(pyridin-3-ylmethyl)-amino]-methyl}-benzamide [Compound No. 57]

Example 57-1

Synthesis of N-(4-dipropylaminomethylphenyl)-4-{[(1H-imidazol-2-ylmethyl)-(pyridin-3-ylmethyl)-amino]-methyl}-benzamide [Compound No. 57]

The compound (100 mg) obtained in Example 47-3 was dissolved in methanol (5.0 ml) and added with pyridin-3-aldehyde (manufactured by Tokyo Kasei Kogyo Co., Ltd.) (44.8 µl), followed by the addition of sodium cyanoborohydride (44.9 mg). Then, the reaction solution was adjusted to about pH 5 with acetic acid, followed by stirring at room temperature for 65 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and treated with hydrochloric acid, thereby obtaining hydrochloride (95.8 mg) of the subject compound as a white solid.

MS(FAB, Pos.): m/z=511[M+H]$^+$ $^1$H-NMR(500 MHz, DMSO-d$_6$): δ=0.87(6H, t, J=7.2 Hz), 1.68–1.79(4H, m), 2.85–2.96(4H, m), 3.78–4.06(5H, m), 4.25(2H, d, J=5.3 Hz), 7.59–7.63(6H, m), 7.89(2H, d, J=8.7 Hz), 7.95(2H, d, J=8.5 Hz), 7.98–8.00(1H, m), 8.66(1H, d, J=8.1 Hz), 8.79(1H, d, J=5.0 Hz), 9.10(1H, s), 10.48(1H, s), 10.65(1H, brs), 14.78(1H, brs).

Production Example 58

Synthesis of N-(4-dipropylaminomethylphenyl)-4-{[(1H-imidazol-2-ylmethyl)-(pyridin-4-ylmethyl)-amino]-methyl}-benzamide [Compound No. 58]

Example 58-1

Synthesis of N-(4-dipropylaminomethylphenyl)-4-{[(1H-imidazol-2-ylmethyl)-(pyridin-4-ylmethyl)-amino]-methyl}-benzamide [Compound No. 58]

The compound (100 mg) obtained in Example 47-3 was dissolved in methanol (5.0 ml) and added with pyridin-4-aldehyde (manufactured by Tokyo Kasei Kogyo Co., Ltd.) (44.8 µl), followed by the addition of sodium cyanoborohydride (44.9 mg). Then, the reaction solution was adjusted to about pH 5 with acetic acid, followed by stirring at room temperature for 65 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and treated with hydrochloric acid, thereby obtaining hydrochloride (106 mg) of the subject compound as a white solid.

MS(FAB, Pos.): m/z=511[M+H]$^+$ $^1$H-NMR(500 MHz, DMSO-d$_6$): δ=0.87(6H, t, J=7.4 Hz), 1.68–1.78(4H, m), 2.85–2.94(4H, m), 3.81–4.08(5H, m), 4.25(2H, d, J=5.3 Hz), 7.59–7.64(6H, m), 7.89(2H, d, J=8.8 Hz), 7.96(2H, d, J=8.4 Hz), 8.20(2H, d, J=6.6 Hz), 8.86(2H, d, J=6.6 Hz), 10.50(1H, s), 10.73(1H, brs), 14.87(1H, brs).

Production Example 59

Synthesis of N-(4-dipropylaminomethylphenyl)-4-{[(1H-imidazol-2-ylmethyl)-(3-ethoxypyridin-2-ylmethyl)-amino]-methyl}-benzamide [Compound No. 59]

Example 59-1

Synthesis of N-(4-dipropylaminomethylphenyl)-4-{[(1H-imidazol-2-ylmethyl)-(3-ethoxypyridin-2-ylmethyl)-amino]-methyl}-benzamide [Compound No. 59]

The compound (104 mg) obtained in Example 47-3 was dissolved in methanol (5.0 ml) and added with 3-ethoxy-2-pyridine aldehyde (74.7 mg) synthesized by the method described in Marsais, F et al, Synthesis, 235 (1982), followed by the addition of sodium cyanoborohydride (46.6 mg). After that, the reaction solution was adjusted to about pH 5 with acetic acid and then stirred at room temperature for 65 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and then treated with hydrochloric acid, thereby obtaining hydrochloride (132 mg) of the subject compound as a white solid.

MS(FAB, Pos.): m/z=555[M+H]$^+$ $^1$H-NMR(500 MHz, DMSO-d$_6$): δ=0.87(6H, t, J=7.3 Hz), 1.37(3H, t, J=7.0 Hz), 1.67–1.79(4H, m), 2.86–2.96(4H, m), 3.42–3.82(2H, m), 4.12–4.20(4H, m), 4.25–4.30(4H, m), 7.65(2H, s), 7.77(1H, brs), 7.86–7.88(4H, m), 7.98(1H, brs), 8.40(1H, d, J=5.1 Hz), 10.39(1H, brs), 10.57(1H, brs).

Production Example 60

Synthesis of [4-(4-{[bis(1H-imidazol-2-ylmethyl)-amino]-methyl}-benzyloxy)-butyl]-dipropylamine [Compound No. 60]

Example 60-1

Synthesis of 4-{N-Boc(N−1-methanesulfonyl-1H-imidazol-2-ylmethyl)amino]methyl}benzylchloride The compound (257 mg) obtained in Example 35-2 was dissolved in dichloromethane (5.0 ml). The solution was added with diisopropyl ethylamine (423 µl) and then added with methanesulfonylchloride (157 µl) in an ice bath, followed by stirring overnight at room temperature under a nitrogen atmosphere. After completion of the reaction, a saturated aqueous sodium bicarbonate solution was added to the solution, and the whole was stirred. The resultant solution was subjected to extraction with chloroform and washed with a saturated aqueous sodium bicarbonate solution, a saturated aqueous ammonium chloride solution, and saturated saline solution, followed by drying of the organic layer with anhydrous sodium sulfate. The solvent was distilled off and the residue was then purified through silica gel column chromatography (hexane/acetone), thereby obtaining the compound (302 mg) as a yellow oily substance.

MS(FAB, Pos.): m/z=414[M+H]$^+$ $^1$H-NMR(500 MHz, DMSO-d$_6$): δ=1.31(9H, s), 3.59(3H, brs), 4.51(2H, s), 4.63(2H, brs), 4.74(2H, s), 7.05(1H, d, J=1.7 Hz), 7.26(2H, d, J=8.1 Hz), 7.40(2H, d, J=8.1 Hz), 7.52(1H, d, J=1.7 Hz).

Example 60-2

Synthesis of 4-dipropylamino-1-butanol

In anhydrous methanol (20 ml), 4-amino-1-butanol (manufactured by Tokyo Kasei Kogyo Co., Ltd.) (1.03 g) was dissolved. Then, the solution was added with sodium cyanoborohydride (2.18 g), acetic acid (5.00 ml), and propionaldehyde (2.08 ml), followed by stirring under a nitrogen atmosphere at room temperature for 1 week. After completion of the reaction, the solvent was distilled off and the residue was then dissolved in chloroform, followed by stirring after the addition of a saturated aqueous sodium bicarbonate solution. The resultant solution was subjected to extraction with chloroform. The extract was washed with a saturated aqueous sodium bicarbonate solution and saturated saline solution, followed by drying of the organic layer with anhydrous sodium sulfate. The solvent was distilled off, thereby obtaining the subject compound (2.54 g) as a colorless liquid.

MS(FAB, Pos.): m/z=174[M+H]$^+$

Example 60-3

Synthesis of [4-(4-{[N-Boc(N-1-methanesulfonyl-1H-imidazol-2-ylmethyl)amino]methyl}benzyloxyl)butyl]dipropylamine The compound (146 mg) obtained in Example 60-1 was dissolved in dichloromethane (2.0 ml). The solution was added with potassium bicarbonate (53.0 mg) and the compound (61.1 mg) obtained in Example 60-2, followed by stirring at room temperature for 6 days. After completion of the reaction, a saturated aqueous ammonium chloride solution was added to the solution, and the whole stirred. The solution was subjected to extraction with chloroform and the extract was then washed with saturated saline solution. Then, the organic layer was dried with anhydrous sodium sulfate. Subsequently, the solvent was distilled off and the residue was then purified through silica gel column chromatography (chloroform/methanol), thereby obtaining the subject compound (158 mg) as a colorless crystal.

MS(FAB, Pos.): m/z=551[M+H]$^+$
$^1$H-NMR(500 MHz, DMSO-d$_6$): δ=1.04(6H, t, J=7.3 Hz) 1.44(9H, s), 1.63–1.68(2H, m), 1.86–1.95(4H, m), 2.07–2.12(2H, m), 3.09–3.22(4H, m), 3.41(3H, brs), 3.49 (2H, m), 3.75(2H, s), 4.65(2H, s), 4.74(2H, s), 7.04(1H, d, J=1.7 Hz), 7.31(1H, d, J=1.7 Hz), 7.36(2H, d, J=8.1 Hz), 7.45(1H, d, J=8.1 Hz).

Example 60-4

Synthesis of [4-(4-{[N-(1H-imidazol-2-ylmethyl)amino]methyl}benzyloxy)butyl]dipropylamine The compound (158 mg) obtained in Example 60-3 was dissolved in anhydrous methanol (1.0 ml) and then added with a 1 mol/l hydrogen chloride/diethyl ether solution (5.00 ml), followed by stirring at room temperature for 3 hours. After completion of the reaction, the solvent was distilled off. The residue was added with a 1 mol/l sodium hydroxide aqueous solution and washed with chloroform. The aqueous layer was evaporated to dryness and then subjected to extraction with chloroform, thereby obtaining the subject compound (81.2 mg) as a white crystal.

MS(FAB, Pos.): m/z=373[M+H]$^+$

Example 60-5

Synthesis of [4-(4-{[bis(1H-imidazol-2-ylmethyl)-amino]-methyl}-benzyloxy)-butyl]-dipropylamine [Compound No. 60]

The compound (81.2 mg) obtained in Example 60-4 was dissolved in anhydrous methanol (2.0 ml) and then added with sodium cyanoborohydride (27.4 mg), acetic acid (3.00 ml), and 2-imidazole carboxaldehyde (31.4 mg), followed by stirring under a nitrogen atmosphere at 60° C. for 4 days. After completion of the reaction, the solvent was distilled off. Then, the residue was dissolved in chloroform and added with a saturated aqueous sodium bicarbonate solution, followed by stirring. The aqueous layer was washed with chloroform and then evaporated to dryness. The residue was purified through silica gel column chromatography (chloroform/methanol) and treated with hydrochloric acid, thereby obtaining hydrochloride (63.0 mg) of the subject compound as a white solid.

MS(FAB, Pos.): m/z=453[M+H]$^+$
$^1$H-NMR(500 MHz, DMSO-d$_6$+D$_2$O): δ=0.88(6H, t, J=7.2 Hz), 1.42(2H, t, J=6.9 Hz), 1.69–1.79(6H, m), 2.89–2.91(4H, m), 2.92–3.00(2H, m), 3.44(2H, t, J=6.1 Hz), 4.16(4H, s), 4.39(2H, s), 4.72(2H, s), 7.27(2H, d, J=8.2 Hz), 7.43(2H, d, J=8.2 Hz), 7.50(2H, s), 7.52(2H, s).

Production Example 61

Synthesis of N-(4-dipropylaminomethylphenyl)-4-{[(1H-imidazol-2-ylmethyl)-(1H-benzimidazol-2-ylmethyl)-amino]-methyl}-benzamide [Compound No. 61]

Example 61-1

Synthesis of N-(4-dipropylaminomethylphenyl)-4-{[(1H-imidazol-2-ylmethyl)-(1H-benzimidazol-2-ylmethyl)-amino]-methyl}-benzamide [Compound No. 61]

The compound (99.3 mg) obtained in Example 47-3 was dissolved in DMF (3.0 ml) and added with potassium carbonate (81.8 mg) and 2-chloromethylbenzimidazole (manufactured by Aldrich Corporation) (43.4 mg), followed by stirring at 60° C. for 17 hours. After completion of the reaction, the reaction solvent was distilled off and water was then added, followed by separation/extraction with chloroform. The organic layer was dried with anhydrous sodium sulfate. Subsequently, the solvent was distilled off and the residue was then purified through silica gel column chromatography (chloroform/methanol), thereby obtaining the subject compound (70.0 mg) as a white solid.

MS(FAB, Pos.): m/z=550[M+H]$^+$
$^1$H-NMR(500 MHz, DMSO-d$_6$): δ=0.82(6H, t, J=7.1 Hz), 1.42(4H, sext., J=7.1 Hz), 2.31(4H, t, J=7.1 Hz), 3.47(2H, s), 3.71(2H, s), 3.72(2H, s), 3.85(2H, s), 7.26(2H, d, J=8.5 Hz), 7.44–7.62(4H, m), 7.60(2H, d, J=8.3 Hz), 7.68(2H, d, J=8.5 Hz), 7.91(2H, d, J=8.3 Hz).

Production Example 62

Synthesis of N-(4-dipropylaminomethylphenyl)-4-{[(1H-imidazol-2-ylmethyl)-(2-methylthiazol-4-ylmethyl)-amino]-methyl}-benzamide [Compound No. 62]

Example 62-1

Synthesis of N-(4-dipropylaminomethylphenyl)-4-{[(1H-imidazol-2-ylmethyl)-(2-methylthiazol-4-ylmethyl)-amino]-methyl}-benzamide [Compound No. 62]

The compound (99.3 mg) obtained in Example 47-3 was dissolved in DMF (3.0 ml) and then added with potassium carbonate (81.8 mg) and 4-chloromethyl-2-methyl thiazole (manufactured by Lancaster Synthesis Inc.) (47.9 mg), followed by stirring 60° C. for 17 hours. After completion of the reaction, the reaction solvent was distilled off and the residue was then added with water, followed by separation/extraction with chloroform. The organic layer was dried with anhydrous sodium sulfate. Then, the solvent was distilled off and the residue was then purified through silica gel column chromatography (chloroform/ethyl acetate), thereby obtaining hydrochloride (31.2 mg) of the subject compound as a white solid.

MS(FAB, Pos.): m/z=531[M+H]$^+$ $^1$H-NMR(500 MHz, DMSO-d$_6$): δ=0.87(6H, t, J=7.3 Hz), 1.62–1.81(4H, m), 2.68(3H, s), 2.91(4H, br), 3.82(2H, s), 4.10(2H, s), 4.26 (4H, s), 7.52–7.70(7H, m), 7.88(2H, d, J=8.5 Hz), 7.95(2H, d, J=8.1 Hz).

Production Example 63

Synthesis of N-(4-dipropylaminomethylphenyl)-4-{[(1H-imidazol-2-ylmethyl)-(isoquinolin-1-ylmethyl)-amino]-methyl}-benzamide [Compound No. 63]

Example 63-1

Synthesis of isoquinoline-1-aldehyde

Isoquinolin-1-yl-methanol (123.7 mg) was dissolved in chloroform (6.2 ml) and then added with manganese dioxide (chemically processed product) (1.24 g), followed by stirring at room temperature for 30 minutes. The reaction solution was filtrated through Celite and the solvent was then distilled off. The residue was dried under vacuum, thereby obtaining the subject compound (103.9 mg) as a brown solid.

$^1$H-NMR(500 MHz, CDCl$_3$): δ=7.72–7.80(2H, m), 7.88–7.96(2H, m), 8.77(1H, d, J=5.4 Hz), 9.30–9.36(1H, m), 10.3(1H, s).

Example 63-2

Synthesis of N-(4-dipropylaminomethylphenyl)-4-{[(1H-imidazol-2-ylmethyl)-(isoquinolin-1-ylmethyl)-amino]-methyl}-benzamide [Compound No. 63]

The compound (80 mg) obtained in Example 47-3 was dissolved in methanol (5.0 ml) and added with the compound (59.9 mg) obtained in Example 63-1, followed by the addition of sodium cyanoborohydride (35.9 mg). Then, the reaction solution was adjusted to about pH 5 with acetic acid, followed by stirring at room temperature for 14 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and treated with hydrochloric acid, thereby obtaining hydrochloride (97.1 mg) of the subject compound as a white solid.

MS(FAB, Pos.): m/z=561[M+H]$^+$ $^1$H-NMR(500 MHz, DMSO-d$_6$): δ=0.87(6H, t, J=7.4 Hz), 1.67–1.78(4H, m), 2.86–2.93(4H, m), 3.92(2H, s), 4.25–4.26(2H, m), 4.36(2H, s), 4.78(2H, brs), 7.57–7.65 (6H, m), 7.81–7.86(4H, m), 7.95(1H, brs), 8.11(1H, brs), 8.23(1H, brs), 8.48–8.52(1H, m), 8.62(1H, d, J=6.2 Hz), 10.34(1H, s), 10.48(1H, brs).

Production Example 64

Synthesis of N-(4-dipropylaminomethylphenyl)-4-{[(1H-imidazol-2-ylmethyl)-(4-methoxy-3,5-dimethylpyridin-2-ylmethyl)-amino]-methyl}-benzamide [Compound No. 64]

Example 64-1

Synthesis of 4-methoxy-3,5-dimethylpyridine-2-carboxaldehyde (4-methoxy-3,5-dimethyl-pyridin-2-yl)methanol (Tokyo Kasei Kogyo Co., Ltd.) (300 mg) was dissolved in chloroform (15 ml) and added with manganese dioxide (chemically processed product) (3.00 g), followed by stirring for 3 hours. After completion of the reaction, the solution was filtrated through Celite and the solvent was then distilled off, thereby obtaining the subject compound (297 mg) as a white solid.

Example 64-2

Synthesis of N-(4-dipropylaminomethylphenyl)-4-{[(1H-imidazol-2-ylmethyl)-(4-methoxy-3,5-dimethylpyridin-2-ylmethyl)-amino]-methyl}-benzamide [Compound No. 64]

The compound (70.1 mg) obtained in Example 47-3 was dissolved in methanol (5.0 ml) and added with the compound (55.2 mg) obtained in Example 64-1, followed by the addition of sodium cyanoborohydride (31.5 mg). Then, the reaction solution was adjusted to about pH 5 with acetic acid, followed by stirring at room temperature for 21 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and treated with hydrochloric acid, thereby obtaining hydrochloride (36.4 mg) of the subject compound as a white solid.

MS(FAB, Pos.): m/z=569[M+H]$^+$ $^1$H-NMR(500 MHz, DMSO-d$_6$): δ=0.87(6H, t, J=7.3 Hz), 1.69–1.78(4H, m), 2.18(3H, s), 2.31(3H, s), 2.86–2.95(4H, m), 3.79(2H, s), 3.96(3H, s), 4.13(2H, s), 4.25–4.26(4H, m), 7.57–7.61(4H, m), 7.67(2H, s), 7.84–7.87(4H, m), 8.56(1H, s).

Production Example 65

Synthesis of 4-({bis[1-(toluene-4-sulfonyl)-1H-imidazol-2-ylmethyl]-amino}-methyl)-N-(4-dipropylaminomethylphenyl)-benzamide [Compound No. 65]

Example 65-1

Synthesis of 4-({bis[1-(toluene-4-sulfonyl)-1H-imidazol-2-ylmethyl]-amino}-methyl)-N-(4-dipropylaminomethylphenyl)-benzamide [Compound No. 65]

The compound (50.8 mg) obtained in Example 19-3 was dissolved in anhydrous chloroform (2.0 ml). The solution was added with triethylamine (0.049 ml) and then added with p-toluenesulfonyl chloride (manufactured by Kanto Kagaku) (57.2 mg), followed by stirring at room temperature for 16 hours. After completion of the reaction, chloroform (3.0 ml) was added to the solution, and the whole was washed with water. The organic layer was dried with anhydrous magnesium sulfate. Subsequently, the solvent was distilled off and the residue was then purified through silica gel column chromatography (manufactured by Fuji Silysia Chemical Ltd.) (hexane/ethyl acetate), thereby obtaining the subject compound (15.2 mg) as a white solid.

MS(FAB, Pos.): m/z=809[M+H]$^+$ $^1$H-NMR(500 MHz, DMSO-d$_6$): δ=0.82(6H, t, J=7.3 Hz), 1.42(4H, sext., J=7.5 Hz), 2.32(4H, t, J=7.3 Hz), 2.37(6H, s) 3.48(2H, s), 4.00(2H, s), 4.05(4H, s), 7.04(2H, d, J=8.4 Hz), 7.08(2H, d, J=1.8 Hz), 7.27(2H, d, J=8.5 Hz), 7.35(4H, d, J=8.1 Hz), 7.70–7.77(10H, m), 10.14(1H, s).

Production Example 66

Synthesis of 4-{[bis(1-methanesulfonyl-1H-imidazol-2-ylmethyl)-amino]-methyl}-N-(4-dipropylaminomethylphenyl)-benzamide [Compound No. 66]

Example 66-1

Synthesis of 4-{[bis(1-methanesulfonyl-1H-imidazol-2-ylmethyl)-amino]-methyl}-N-(4-dipropylaminomethylphenyl)-benzamide [Compound No. 66]

The compound (52.9 mg) obtained in Example 19-3 was dissolved in anhydrous chloroform (2.0 ml). The solution was added with triethylamine (0.054 ml) and then added with methanesulfonyl chloride (manufactured by Kanto Kagaku) (0.027 ml), followed by stirring at room temperature for 17 hours. After completion of the reaction, chloroform (3.0 ml) was added to the solution, and the whole was washed with water. The organic layer was dried with anhydrous magnesium sulfate. Subsequently, the solvent was distilled off and the residue was then purified through silica gel column chromatography (manufactured by Fuji Silysia Chemical Ltd.) (hexane/ethyl acetate), thereby obtaining the subject compound (31.7 mg) as a white solid.

MS(FAB, Pos.): m/z=656[M+H]$^+$ $^1$H-NMR(500 MHz, DMSO-d$_6$): δ=0.82(6H, t, J=7.3 Hz), 1.42(4H, sext., J=7.2 Hz), 2.32(4H, t, J=7.0 Hz), 3.47(2H, s), 3.66(6H, s), 4.01(2H, s), 4.04(4H, s), 7.03(2H, d, J=1.8 Hz), 7.26(2H, d, J=8.4 Hz), 7.41(2H, d, J=8.2 Hz), 7.52(2H, d, J=1.7 Hz), 7.69(2H, d, J=8.5 Hz), 7.89(2H, d, J=8.3 Hz), 10.17(1H, s).

Production Example 67

Synthesis of 2-({[4-(4-dipropylaminomethylphenyl-carbamoyl)-benzyl]-(1-methyl-1H-imidazol-2-ylmethyl)-amino}-methyl)-imidazol-1-carboxylic acid ethyl ester [Compound No. 67]

Example 67-1

Synthesis of 2-({[4-(4-dipropylaminomethylphenyl-carbamoyl)-benzyl]-(1-methyl-1H-imidazol-2-ylmethyl)-amino}-methyl)-imidazol-1-carboxylic acid ethyl ester [Compound No. 67]

The compound (66.2 mg) obtained in Example 49-1 was dissolved in anhydrous chloroform (2.7 ml). Then, the solution was added with triethylamine (0.028 ml) and then added with methyl chloroformate (manufactured by Kanto Kagaku) (0.015 ml), followed by stirring at room temperature for 6 hours. After completion of the reaction, the solution was added with chloroform (3.0 ml), followed by washing with water and a saturated aqueous sodium bicarbonate solution. The organic layer was dried with anhydrous magnesium sulfate and the solvent was then distilled off, thereby obtaining the subject compound (65.2 mg) as a yellow viscous solid.

MS(FAB, Pos.): m/z=586[M+H]$^+$ $^1$H-NMR(500 MHz, DMSO-d$_6$): δ=0.82(6H, t, J=7.3 Hz), 1.30(3H, t, J=7.2 Hz), 1.42(4H, sext., J=7.5 Hz), 2.32(4H, t, J=7.3 Hz), 3.47(2H, s), 3.54(3H, s), 3.79(4H, d, J=6.7 Hz), 3.99(2H, s), 4.33(2H, q, J=7.2 Hz), 6.76(1H, d, J=1.1 Hz), 6.99(1H, d, J=1.7 Hz), 7.05(1H, d, J=1.1 Hz), 7.25(2H, d, J=8.5 Hz), 7.40(2H, d, J=8.2 Hz), 7.54(1H, d, J=1.7 Hz), 7.69(2H, d, J=8.4 Hz), 7.87(2H, d, J=8.2 Hz), 10.14(1H, s).

Production Example 68

Synthesis of 4-{[bis(1H-imidazol-2-ylmethyl)-amino]-methyl}-N-(4-dipropylaminomethylphenyl)-N-methylbenzamide [Compound No. 68]

Example 68-1

Synthesis of N-(4-dipropylaminomethylphenyl)-methylamine

Acetic anhydride (manufactured by Kanto Kagaku) (1.23 ml) was cooled with ice and then added with formic acid (manufactured by Kanto Kagaku) (0.604 ml), followed by stirring at 50° C. for 2 hours. After the solution had been stood to cool, anhydrous THF (1.0 ml) was added to the solution, and the whole was stirred at 0° C. Then, the solution was added with a THF solution (2.0 ml) in which the compound (1.075 g) obtained in Example 19-2 was dissolved, followed by stirring for 15 minutes. After completion of the reaction, the solvent was distilled off.

Lithium aluminum hydride (manufactured by Wako Pure Chemical Industries, Ltd.) (493 mg) and anhydrous THF (10 ml) were stirred under ice-cooling. Then, the mixture was added with a solution (24 ml) of the previously prepared compound in THF and subjected to thermal reflux for 4 hours. The reaction was terminated with sodium sulfate decahydrate. The resulting solution was added with a 20% sodium hydroxide aqueous solution (2.0 ml) and then filtrated through Celite, followed by distilling the solvent off. The residue was added with chloroform (50 ml) and washed with saturated saline solution, followed by drying with anhydrous magnesium sulfate. The solvent was distilled off and the residue was then purified through silica gel column chromatography (manufactured by Fuji Silysia Chemical Ltd.) (hexane/ethyl acetate), thereby obtaining the subject compound (131.2 mg) as a yellow oily substance.

MS(FAB, Pos.): m/z=221[M+H]$^+$ $^1$H-NMR(500 MHz, DMSO-d$_6$): δ=0.87(6H, t, J=7.3 Hz), 1.45–1.52(4H, m), 2.35–2.38(4H, m), 2.85(3H, s), 3.48(2H, s), 6.59(2H, d, J=8.3 Hz), 7.15(2H, d, J=8.3 Hz).

Example 68-2

Synthesis of 4-{[bis(1H-imidazol-2-ylmethyl)-amino]-methyl}-N-(4-dipropylaminomethylphenyl)-N-methylbenzamide [Compound No. 68]

The compound (278 mg) obtained in Example 2-2, HOBt (95.9 mg), and DCC (147 mg) were dissolved in anhydrous DMF (11.0 ml), followed by stirring at room temperature for 19 hours. Then, the solution was added with a solution (1.2 ml) of the compound (128 mg) obtained in Example 68-1 in DMF and stirred at room temperature for 20 hours. After completion of the reaction, the solvent was distilled off under reduced pressure. The residue was dissolved in chloroform and added with 1 mol/l hydrochloric acid to separate the solution into layers. The aqueous layer was added with a 1 mol/l sodium hydroxide aqueous solution to adjust the solution to pH 11. The aqueous layer was extracted with chloroform and the organic layer was then dried with anhydrous magnesium sulfate. After having been treated with hydrochloric acid, the product was purified through silica gel column chromatography (chloroform/methanol/water), thereby obtaining hydrochloride (10.2 mg) of the subject compound as a white solid.

MS(FAB, Pos.): m/z=514[M+H]$^+$
$^1$H-NMR(500 MHz, DMSO-$d_6$): δ=0.78(6H, t, J=7.3 Hz), 1.63(4H, m), 2.83(4H, m), 3.36(3H, s), 4.06(4H, s), 4.22 (2H, s), 7.14(2H, d, J=8.1 Hz), 7.22(2H, d, J=8.3 Hz), 7.26(2H, d, J=8.3 Hz), 7.51(2H, d, J=8.3 Hz), 7.59(4H, s).

Production Example 69

Synthesis of N,N-bis(1H-imidazol-2-ylmethyl)-N',N'-dipropylnonane-1,9-diamine [Compound No. 69]

Example 69-1

Synthesis of (9-aminononyl)carbamic acid t-butyl ester

Nonan-1,9-diamine (230 mg) was dissolved in chloroform (5.0 ml) and DMF (10 ml) and then added with di-t-butoxydicarbonate (317 mg). After having been stirred at room temperature for 30 minutes, the solution was concentrated and then purified through silica gel column chromatography (chloroform/methanol), thereby obtaining the subject compound (70.0 mg) as a colorless viscous liquid.

MS(FAB, Pos.): m/z=259[M+H]$^+$

Example 69-2

Synthesis of (9-dipropyl)aminononylcarbamic acid t-butyl ester

The compound (299 mg) obtained in Example 69-1 was dissolved in anhydrous methanol (7.0 ml) and then added with trimethyl orthoformate (0.633 ml). Then, the solution was gradually added with sodium borohydride (145 mg) under ice-cooling. Subsequently, the mixture was heated back to room temperature and then stirred for 1 hour. After completion of the reaction, methanol was distilled off and the organic layer was then extracted with the addition of water and chloroform. The extract was dried with anhydrous sodium sulfate. The solvent was distilled off and the residue was then purified through silica gel column chromatography (chloroform/methanol/water), thereby obtaining the subject compound (122 mg) as a pale-yellow viscous liquid.

MS(FAB, Pos.): m/z=343[M+H]$^+$

Example 69-3

Synthesis of N,N-dipropylnonan-1,9-diamine

The compound (122 mg) obtained in Example 69-2 was dissolved in methanol (1.0 ml) and then added with a 1 mol/l hydrogen chloride/diethyl ether solution (2.0 ml), followed by stirring at room temperature for 2 hours. The solution was concentrated and dried and then purified through column chromatography (chloroform/methanol), thereby obtaining hydrochloride (6.0 mg) of the subject compound as a white solid.

MS(FAB, Pos.): m/z=243[M+H]$^+$

Example 69-4

Synthesis of N,N-bis(1H-imidazol-2-ylmethyl)-N',N'-dipropylnonane-1,9-diamine [Compound No. 69]

The compound (6.0 mg) obtained in Example 69-3 was dissolved in anhydrous methanol (2.0 ml) and added with 2-imidazole carboxaldehyde (6.00 mg), followed by gradual addition of sodium borohydride (3.00 mg) under ice-cooling. The solution was heated back to room temperature and then stirred for 1 hour. After completion of the reaction, methanol was distilled off and the organic layer was extracted with the addition of water and chloroform. The extract was dried with anhydrous sodium sulfate. The solvent was distilled off and the residue was then purified through silica gel column chromatography (chloroform/methanol/water), followed by washing with ethyl acetate. Consequently, hydrochloride (5.80 mg) of the subject compound was obtained as a pale-yellow viscous liquid.

MS(FAB, Pos.): m/z=403[M+H]$^+$
$^1$H-NMR(500 MHz, DMSO-$d_6$): δ=0.90(6H, t, J=7.3 Hz), 1.12–1.37(12H, m), 1.60–1.68(6H, m), 2.36–2.40(2H, m), 2.94–3.02(6H, m), 4.12(4H, s), 7.67(4H, s).

Production Example 70

Synthesis of N-(4-dipropylaminomethylphenyl)-{[(1H-imidazol-2-ylmethyl)-(quinolin-3-ylmethyl)-amino]-methyl}-benzamide [Compound No. 70]

Example 70-1

Synthesis of N-(4-dipropylaminomethylphenyl)-{[(1H-imidazol-2-ylmethyl)-(quinolin-3-ylmethyl)-amino]-methyl}-benzamide [Compound No. 70]

Under ice-cooling, the compound (80.0 mg) obtained in Example 47-3 and 3-quinoline carboxaldehyde (Aldrich Corporation) (43.3 mg) were dissolved by the addition of anhydrous methanol (4.0 ml). Subsequently, sodium cyanoborohydride (26.4 mg) and then acetic acid (1.0 ml) were added to adjust the solution to pH 5, followed by stirring for 5 minutes. The solution was taken out of the ice bath and stirred at room temperature for 16 hours. After completion of the reaction, methanol was distilled off and the solution was then adjusted to pH 11 to 12 with the addition of a 1 mol/l sodium hydroxide aqueous solution, followed by extraction with chloroform. The organic layer was washed with saturated saline solution and then dried with anhydrous magnesium sulfate. After that, the solvent was distilled off and the residue was then purified through silica gel column chromatography (manufactured by Fuji Silysia Chemical Ltd.) (chloroform/ethyl acetate). The purified product was treated with hydrochloric acid, thereby obtaining hydrochloride (20.7 mg) of the subject compound as a white crystal.

MS(FAB, Pos.): m/z=561[M+H]$^+$
$^1$H-NMR(500 MHz, DMSO-d$_6$+D$_2$O): δ=0.88(6H, t, J=7.3 Hz), 1.62–1.76(4H, m), 2.92–2.99(4H, m), 3.82(2H, s), 3.95(2H, s), 4.06(2H, s), 4.28(2H, s), 7.52(2H, d, J=8.5 Hz), 7.62(2H, d, J=8.5 Hz), 7.78–8.00(6H, m), 8.15(2H, d, J=8.5 Hz), 8.75(1H, s), 9.17(1H, s).

Production Example 71

Synthesis of N-(4-{[bis(1H-imidazol-2-ylmethyl)-amino]-methyl}-phenyl)-4-dipropylaminomethyl-benzamide [Compound No. 71]

Example 71-1

Synthesis of 4-Boc-aminomethylaniline

In dichloromethane (40 ml), 4-aminobenzylamine (manufactured by Tokyo Kasei Kogyo Co., Ltd.) was dissolved. Then, the solution was added with triethylamine (2.9 ml) and cooled to 0° C. To the solution, a solution of di-t-butyl dicarbonate (3.98 g) in dichloromethane (2.0 ml) was added dropwisely and then the whole was stirred at room temperature for 3 hours. After completion of the reaction, the solvent was distilled off under reduced pressure. The residue was dissolved in chloroform and then washed with a 1 mol/l sodium hydroxide aqueous solution and saturated saline solution, followed by drying with anhydrous sodium sulfate. After filtration, the solvent was distilled off under reduced pressure and the residue was then dried under vacuum, thereby obtaining the subject compound (3.90 g) as a yellow solid.

MS(FAB, Pos.): m/z=223[M+H]$^+$
$^1$H-NMR(500 MHz, CDCl$_3$): δ=1.45(9H, s), 3.65(2H, s), 4.19(2H, d, J=5.6 Hz), 4.74(1H, brs), 6.64(2H, d, J=8.5 Hz), 7.07(2H, d, J=8.1 Hz).

Example 71-2

Synthesis of 4-(N-Boc-aminomethylphenyl)-4-dipropylaminomethylbenzamide

In methanol (4.5 ml), 4-aminomethylbenzoic acid (manufactured by Tokyo Kasei Kogyo Co., Ltd.) (300 mg) was dissolved. Then, trimethyl orthoformate (300 μl) and sodium cyanoborohydride (501 mg) were added to the solution, and then the whole was cooled to 0° C. Subsequently, the solution was added with propionaldehyde (357 ml) and then stirred at room temperature for 6 hours. After completion of the reaction, the solvent was distilled off under reduced pressure. The residue was dissolved in chloroform and then washed with a 1 mol/l sodium hydroxide aqueous solution. After that, chloroform was added. The aqueous layer was neutralized with 1 mol/l hydrochloric acid and extraction with chloroform was then carried out. The solvent was distilled off under reduced pressure and the residue was then dried under vacuum, thereby obtaining a crude product (193.3 mg) as a white viscous solid. Subsequently, the crude product was dissolved in DMF (3.0 ml) and then added with WSCI hydrochloride (236 mg) and HOBt (167 mg), followed by stirring at room temperature for 30 minutes. After that, the solution was added with the compound (183 mg) obtained in Example 71-1 and then stirred overnight at room temperature. After completion of the reaction, the solvent was distilled off under reduced pressure. The residue was dissolved in chloroform and then washed with water, a 1 mol/l sodium hydroxide aqueous solution, and saturated saline solution, followed by drying with anhydrous sodium sulfate. After filtration, the solvent was distilled off under reduced pressure and the residue was then purified through silica gel column chromatography (chloroform/methanol), thereby obtaining the subject compound (213 mg) as a pale-yellow viscous liquid.

MS(FAB, Pos.) m/z=440[M+H]$^+$

Example 71-3

Synthesis of N-(4-{[bis(1H-imidazol-2-ylmethyl)-amino]-methyl}-phenyl)-4-dipropylaminomethyl-benzamide [Compound No. 71]

The compound (213 mg) obtained in Example 71-2 was dissolved in methanol (1.1 ml) and then added with a 4 mol/l hydrogen chloride/dioxane solution (1.1 ml), followed by stirring at room temperature for 1.5 hours. After completion of the reaction, the solvent was distilled off under reduced pressure. Then, the residue was then dissolved in chloroform and then washed with a 1 mol/l sodium hydroxide aqueous solution, followed by extraction with chloroform. After that, the extract was washed with saturated saline solution and then dried with anhydrous sodium sulfate. After filtration, the solvent was distilled off under reduced pressure and the residue was then dried under vacuum, thereby obtaining a crude product (145 mg) as a white solid. The white solid was dissolved in methanol (2.2 ml) and then added with 2-imidazole carboxaldehyde (123 mg) and acetic acid (145 μl), followed by cooling to 0° C. Subsequently, the solution was added with sodium cyanoborohydride (82.5 mg) and stirred overnight at room temperature. After completion of the reaction, the solvent was distilled off under reduced pressure. The residue was dissolved in chloroform and then washed with a 1 mol/l sodium hydroxide aqueous solution and saturated saline solution, followed by drying with anhydrous sodium sulfate. After filtration, the solvent was distilled off under reduced pressure. Then, the residue was purified through silica gel column chromatography (chloroform/ethyl acetate) and treated with hydrochloric acid, thereby obtaining hydrochloride (19.0 mg) of the subject compound as a white solid.

MS(FAB, Pos.) m/z=500[M+H]$^+$
$^1$H-NMR(500 MHz, DMSO-d$_6$): δ=0.87(6H, t, J=7.3 Hz), 1.62–1.78(4H, m), 2.94(4H, br), 3.62(2H, s), 4.12(4H, s), 4.39(2H, d, J=5.2 Hz), 7.49(2H, d, J=8.4 Hz), 7.62(4H, s), 7.72(2H, d, J=8.4 Hz), 7.80(2H, d, J=8.1 Hz), 8.02(2H, d, J=8.1 Hz), 10.38(1H, s), 10.79(1H, br).

Production Example 72

Synthesis of N-(4-dipropylaminomethylphenyl)-4-{[(8-hydroxyquinolin-2-ylmethyl)-(1H-imidazol-2-ylmethyl)-amino]-methyl}-benzamide [Compound No. 72]

Example 72-1

Synthesis of N-(4-dipropylaminomethylphenyl)-4-{[(8-hydroxyquinolin-2-ylmethyl)-(1H-imidazol-2-ylmethyl)-amino]-methyl}-benzamide [Compound No. 72]

The compound (103 mg) obtained in Example 47-3 was dissolved in methanol (5.0 ml). Then, the solution was added with 8-hydroxyquinon-2-aldehyde (85.2 mg) and sodium cyanoborohydride (46.4 mg) in this order, and then adjusted to about pH 5 with acetic acid, followed by stirring at room temperature for 18 hours. The reaction solution was added with a saturated aqueous sodium bicarbonate solution and then subjected to extraction with chloroform. The organic layer was washed with saturated saline solution and dried with anhydrous sodium sulfate. Subsequently, the solvent was distilled off. The resulting crude product was purified through silica gel column chromatography (chloroform/methanol) and treated with hydrochloric acid, thereby obtaining hydrochloride (93.4 mg) of the subject compound as a pale-yellow solid.

MS(FAB, Pos.): m/z=577[M+H]$^+$ $^1$H-NMR(500 MHz, DMSO-d$_6$): δ=0.87(6H, t, J=7.2 Hz), 1.68–1.75(4H, m), 2.84–2.96(4H, m), 3.97–4.29(9H, m), 7.37(1H, d, J=6.4 Hz), 7.54–7.62(8H, m), 7.87(2H, d, J=8.7 Hz), 7.93(2H, d, J=8.5 Hz), 8.01(1H, brs), 8.67(1H, brs), 10.43(1H, s), 10.65(1H, s), 8.56(1H, brs).

Production Example 73

Synthesis of N-(4-dipropylaminomethylphenyl)-4-{[(1H-imidazol-2-ylmethyl)-(5-methylpyrazine-2-ylmethyl)-amino]-methyl}-benzamide [Compound No. 73]

Example 73-1

Synthesis of 5-methylpyrazine-2-aldehyde

In methanol (15 ml), 5-methylpyrazine-2-carboxylic acid (manufactured by Tokyo Kasei Kogyo Co., Ltd.) (1.25 g) was dissolved. Then, the solution was added with WSCI hydrochloride (2.59 g) and N,N-dimethylaminopyridine (1.65 g) in this order, followed by stirring at room temperature for 3 hours. The reaction solution was added with water and then extracted with chloroform. The organic layer was washed with saturated saline solution and then dried with anhydrous sodium sulfate. The solvent was distilled off and the resulting crude product was then purified through silica gel column chromatography (chloroform/methanol). The purified product was dissolved in ethanol (15 ml) and THF (8 ml) and added with calcium chloride (1.11 g). After that, the reaction solution was cooled to 0° C. and then gradually added with sodium borohydride (757 mg), followed by stirring at room temperature for 19 hours. The reaction solution was added with a 1 mol/l citric acid solution (40 ml), followed by extraction with ethyl acetate. The organic layer was washed with saturated saline solution and then dried with anhydrous sodium sulfate, followed by distilling the solvent off. The residue was dissolved in chloroform (10 ml) and then added with manganese dioxide (chemically processed product) (2.2 g), followed by stirring at room temperature for 1 hour. After completion of the reaction, the catalyst was filtrated out through Celite and the solvent was then distilled off. The crude product obtained was purified through silica gel column chromatography (chloroform/methanol), thereby obtaining the subject compound (35.9 mg) as a colorless oily substance.

Example 73-2

Synthesis of N-(4-dipropylaminomethylphenyl)-4-{[(1H-imidazol-2-ylmethyl)-(5-methylpyrazine-2-ylmethyl)-amino]-methyl}-benzamide [Compound No. 73]

The compound (82.2 mg) obtained in Example 47-3 was dissolved in methanol (5.0 ml) and added with the compound (35.9 mg) obtained in Example 73-1, followed by the addition of sodium cyanoborohydride (36.9 mg). Then, the reaction solution was adjusted to about pH 5 with acetic acid, followed by stirring at room temperature for 16 hours. The reaction solution was added with a saturated aqueous sodium bicarbonate solution and then extracted with chloroform. The organic layer was washed with saturated saline solution and then dried with anhydrous sodium sulfate. Subsequently, the solvent was distilled off. The resulting crude product was purified through silica gel column chromatography (chloroform/methanol) and treated with hydrochloric acid, thereby obtaining hydrochloride (84.0 mg) of the subject compound as a pale-yellow solid.

MS(FAB, Pos.): m/z=526[M+H]$^+$ $^1$H-NMR(500 MHz, DMSO-d$_6$): δ=0.87(6H, t, J=7.3 Hz), 1.69–1.78(4H, m), 2.47(3H, s), 2.86–2.95(4H, m), 3.82(2H, s), 3.85(2H, s), 4.11(2H, s), 4.26(2H, d, J=5.2 Hz), 7.58–7.62(6H, m), 7.88–7.89(2H, d, J=8.7 Hz), 7.95–7.96 (2H, d, J=8.4 Hz), 8.47(1H, dd, J=0.6, 1.3 Hz), 8.69(1H, d, J=1.4 Hz), 10.47(1H, s), 10.70(1H, brs), 14.51(1H, brs).

Production Example 74

Synthesis of N-(4-dipropylaminobutyl)-4-{[(1H-imidazol-2-ylmethyl)-(5-methylpyridin-2-ylmethyl)-amino]-methyl}-benzamide [Compound No. 74]

Example 74-1

Synthesis of N-(4-dipropylaminobutyl)-4-{[(1H-imidazol-2-ylmethyl)-(5-methylpyridin-2-ylmethyl)-amino]-methyl}-benzamide [Compound No. 74]

Under ice-cooling, the compound (120 mg) obtained in Example 1-4 and the compound (5.4 mg) obtained in Example 56-1 were dissolved in anhydrous methanol (7.0 ml), and the solution was added with sodium cyanoborohydride (46.9 mg), and then adjusted to pH 5 by the addition of acetic acid (2.0 ml), followed by stirring for 5 minutes. After having been taken out from the ice bath, the solution was stirred at room temperature for 16 hours. After completion of the reaction, methanol was distilled off and then the residue was added with a 1 mol/l sodium hydroxide aqueous solution to adjust the solution to pH 11–12, followed by extraction with chloroform. The organic layer was washed with saturated saline solution and dried with anhydrous magnesium sulfate. After that, the solvent was distilled off and the residue was then purified through silica gel column chromatography (manufactured by Fuji Silysia Chemical Ltd.) (hexane/ethyl acetate). Then, the purified product was added with methanol and 1 mol/l hydrochloric acid and then distillated, thereby obtaining hydrochloride (89.7 mg) of the subject compound as a white crystal.

MS(FAB, Pos.): m/z=491[M+H]$^+$ $^1$H-NMR(500 MHz, DMSO-d$_6$+D$_2$O): δ=0.90(6H, t, J=7.3 Hz), 1.54–1.62(2H, m), 1.63–1.69(6H, m), 2.43(3H, s), 2.97–3.00(4H, m), 3.07(3H, t, J=8.3 Hz), 3.28(2H, t, J=6.8 Hz), 3.75(2H, s), 4.08(2H, s), 4.13(2H, s), 7.45(2H, d, J=8.1 Hz), 7.58(2H, s), 7.73(2H, d, J=8.1 Hz), 7.91(1H, d, J=8.1 Hz), 8.26(1H, d, J=8.5 Hz), 8.65(1H, s).

Production Example 75

Synthesis of N-(4-{[(1H-imidazol-2-ylmethyl)-(5-methylpyridine-2-ylmethyl)-amino]-methyl}-benzyl)-N',N'-dipropylbutane-1,4-diamine [Compound No. 75]

Example 75-1

Synthesis of (4-dipropylaminobutyl)-(4-{[(1H-imidazol-2-ylmethyl)amino]methyl}benzyl)carbamic acid t-butyl ester The compound (0.78 g) obtained in Example 25-4 was dissolved in methanol (20 ml) and added with 2-imidazole carboxaldehyde (214.6 mg), followed by stirring at room temperature for 17 hours. After the solvent had been distilled off, the residue was dried under vacuum and then dissolved in methanol (15 ml) and then added with sodium borohydride (217.8 mg), followed by stirring at room temperature for 45 minutes. The reaction solution was added with a saturated aqueous ammonium chloride solution (10 ml) and stirred at room temperature for 15 minutes. Then, the reaction solution was added with saturated saline solution and extracted with chloroform, followed by drying with anhydrous sodium sulfate. After the solvent had been distilled off, the residue obtained was purified through silica gel column chromatography (chloroform/ethyl acetate), thereby obtaining the subject compound (1.01 g) as a yellow solid.

MS(FAB, Pos.): m/z=472[M+H]$^+$ $^1$H-NMR(500 MHz, CDCl$_3$): δ=0.86(6H, t, J=7.3 Hz), 1.26–1.49(17H, m), 2.32–2.35(6H, m), 3.12(1H, brs), 3.21 (1H, brs), 3.79(2H, brs), 3.92(2H, brs), 4.12(1H, brs), 4.13 (1H, brs), 6.99(2H, s), 7.20(2H, brs), 7.25(2H, d, J=7.5 Hz).

Example 75-2

Synthesis of (4-dipropylaminobutyl)-(4-{[(1H-imidazol-2-ylmethyl)-(5-methylpyridin-2-ylmethyl) amino]methyl}benzyl)carbamic acid t-butyl ester The compound (61.6 mg) obtained in Example 75-1 was dissolved in methanol (2.0 ml) and then added with the compound (23.8 mg) obtained in Example 56-1, followed by the addition of sodium cyanoborohydride (15.8 mg). The reaction solution was added with acetic acid to adjust the solution to pH 5, followed by stirring at room temperature for 17 hours. The reaction solution was added with a 1 mol/l sodium hydroxide aqueous solution and extracted with chloroform. After that, the organic layer was washed with saturated saline solution and dried with anhydrous sodium sulfate. After the solvent had been distilled off, the residue obtained was purified through silica gel column chromatography (chloroform/ethyl acetate), thereby obtaining the subject compound (36.7 mg) as a yellow solid.

MS(FAB, Pos.): m/z=577[M+H]$^+$ $^1$H-NMR(500 MHz, CDCl$_3$): δ=0.85(6H, t, J=7.3 Hz), 1.38–1.45(14H, m), 1.49(3H, brs), 2.31–2.53(9H, m), 3.11 (1H, brs), 3.20(1H, brs), 3.63(2H, s), 3.67(2H, s), 3.75(2H, s), 4.37(1H, brs), 4.41(1H, brs), 7.05(2H, brs), 7.16–7.19 (3H, m), 7.30(2H, d, J=7.8 Hz), 7.49(1H, d, J=7.6 Hz), 8.46(1H, brs).

Example 75-3

Synthesis of N-(4-{[(1H-imidazol-2-ylmethyl)-(5-methylpyridine-2-ylmethyl)-amino]-methyl}-benzyl)-N',N'-dipropylbutane-1,4-diamine [Compound No. 75]

The compound (35.5 mg) obtained in Example 75-2 was dissolved in methanol (1.0 ml) and then added with a 1 mol/l hydrogen chloride/diethyl ether solution (2 ml), followed by stirring at 40° C. for 1 hour. The solvent was distilled off, thereby obtaining hydrochloride (36.9 mg) of the subject compound as a yellow solid.

MS(FAB, Pos.): m/z=477[M+H]$^+$ $^1$H-NMR(500 MHz, DMSO-d$_6$): δ=0.91(6H, t, J=7.3 Hz), 1.60–1.68(8H, m), 2.38(3H, s), 2.92–3.05(8H, m), 3.71(2H, s), 3.91(2H, brs), 4.06(2H, s), 4.09(2H, s), 7.45(4H, s), 7.56(2H, s), 7.70(1H, d, J=7.8 Hz), 8.00(1H, d, J=7.8 Hz), 8.53(1H, brs).

Production Example 76

Synthesis of N-(4-dipropylaminomethylphenyl)-4-{[(1-methyl-1H-imidazol-2-ylmethyl)-(5-methylpyridin-2-ylmethyl)-amino]-methyl}-benzamide [Compound No. 76]

Example 76-1

Synthesis of N-(4-dipropylaminomethylphenyl)-4-{[(5-methylpyridin-2-ylmethyl)amino] methyl}benzamide The compound (98.9 mg) obtained in Example 47-3 was dissolved in methanol (3.0 ml) and then added with the compound (35.3 mg) obtained in Example 56-1, followed by stirring at room temperature for 15 hours. Subsequently, the reaction solvent was distilled off and the residue was then dried under vacuum. The residue was redissolved in methanol (3.0 ml) and then added with sodium borohydride (16.5 mg) while being stirred under ice-cooling, followed by stirring at room temperature for 1.5 hours. After completion of the reaction, the reaction solvent was distilled off and the residue was then added with water, followed by separation/extraction with chloroform. The organic layer was dried with anhydrous sodium sulfate and the solvent was then distilled off. Subsequently, the residue was purified through silica gel column chromatography (chloroform/ethyl acetate), thereby obtaining the subject compound (40.0 mg) as a white solid.

MS(FAB, Pos.): m/z=445[M+H]$^+$

Example 76-2

Synthesis of N-(4-dipropylaminomethylphenyl)-4-{[(1-methyl-1H-imidazol-2-ylmethyl)-(5-methylpyridin-2-ylmethyl)-amino]-methyl}-benzamide [Compound No. 76]

The compound (40.0 mg) obtained in Example 76-1 was dissolved in methanol (1.2 ml) and then added with 1-methylimidazol-2-aldehyde (11.9 mg) and sodium cyanoborohydride (11.3 mg). Then, the solution was adjusted to pH 5 with acetic acid and then stirred at room temperature for 14 hours. After completion of the reaction, a 1 mol/l sodium hydroxide aqueous solution was added to the reaction solution, followed by separation/extraction with chloroform.

The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (42.5 mg) of the subject compound as a white solid.

MS(FAB, Pos.): m/z=539[M+H]$^+$ $^1$H-NMR(500 MHz, DMSO-d$_6$): δ=0.85(6H, t, J=7.3 Hz), 1.59–1.78(4H, m), 2.39(3H, s), 2.94(4H, br), 3.80(2H, s), 4.08(4H, s), 4.25 (2H, s), 7.44(2H, s), 7.43–7.55(4H, m), 7.80–7.88(5H, m), 8.20(1H, d, J=4.9 Hz), 8.60(1H, s).

Production Example 77

Synthesis of 4-{[bis(5-methylpyridin-2-ylmethyl)-amino]-methyl}-N-(4-dipropylaminomethylphenyl)-benzamide [Compound No. 77]

Example 77-1

Synthesis of [4-(4-dipropylaminomethylphenylcarbamoyl)benzyl]carbamic acid t-butyl ester In chloroform (20 ml) and DMF (8.0 ml), 4-(t-butoxycarbonylaminomethyl)benzoic acid (1.95 g) was dissolved. Then, the solution was added with WSCI hydrochloride (1.50 g) and HOBt (1.08 g), followed by stirring at room temperature at 1 hour. The reaction solution was added with the compound (1.23 g) obtained in Example 19-2 and chloroform (10 ml), followed by stirring at room temperature for 15 hours. The solvent was distilled off and the residue obtained was then purified through silica gel column chromatography (chloroform/methanol), thereby obtaining the subject compound (2.86 g) as a yellow oily substance.

MS(FAB, Pos.): m/z=440[M+H]$^+$

Example 77-2

Synthesis of 4-aminomethyl-N-(4-dipropylaminomethylphenyl)benzamide

The compound (1.38 g) obtained in Example 77-1 was dissolved in methanol (10 ml) and then added with a 4 mol/l hydrogen chloride/dioxane solution (15 ml), followed by stirring at room temperature for 30 minutes. The reaction solution was concentrated under reduced pressure and added with anion-exchange resin (Amberlite IRA-410) in methanol to adjust the solution to pH 8. After the resin had been removed through filtration, the solvent was distilled off, thereby obtaining the subject compound (0.79 g) as a yellow solid.

MS(FAB, Pos.): m/z=340[M+H]$^+$

Example 77-3

Synthesis of 4-{[bis(5-methylpyridin-2-ylmethyl)-amino]-methyl}-N-(4-dipropylaminomethylphenyl)-benzamide [Compound No. 77]

The compound (105.7 mg) obtained in Example 77-2 was dissolved in methanol (3.2 ml) and then added with the compound (90.5 mg) obtained in Example 56-1 and sodium cyanoborohydride (58.7 mg). Then, the solution was adjusted to pH 5 with acetic acid and then stirred at room temperature for 16 hours. After completion of the reaction, the reaction solvent was distilled off and a 1 mol/l sodium hydroxide aqueous solution was added to the residue, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (36.0 mg) of the subject compound as a white solid.

MS(FAB, Pos.): m/z=550[M+H]$^+$ $^1$H-NMR(500 MHz, DMSO-d$_6$): δ=0.85(6H, t, J=7.3 Hz), 1.56–1.76(4H, m), 2.37(6H, s), 2.92(4H, br), 4.00(2H, s), 4.18(4H, s), 4.25 (2H, s), 7.49(2H, d, J=8.8 Hz), 7.53(2H, d, J=8.3 Hz), 7.71(2H, d, J=8.1 Hz), 7.81(2H, d, J=8.1 Hz), 7.83(2H, d, J=8.3 Hz), 8.05(2H, d, J=8.1 Hz), 8.57(2H, s).

Production Example 78

Synthesis of N-(4-dipropylaminomethylphenyl)-4-{[N-(1H-imidazol-2-ylmethyl)-(4-methylpyridin-2-ylmethyl)-amino]-methyl}-benzamide [Compound No. 78]

Example 78-1

Synthesis of 4-methylpyridine-2-aldehyde

By the same procedures as those of Example 53-1, except that 2,4-lutidine was used as a raw material, 4-methylpyridine-2-aldehyde (40.5 mg) was obtained.

MS(FAB, Pos.): m/z=122[M+H]$^+$ $^1$H-NMR(500 MHz, CDCl$_3$): δ=2.46(3H, s), 7.35(1H, d, J=4.9 Hz), 7.80(1H, s), 8.65(1H, d, J=4.9 Hz), 10.08(1H, s).

Example 78-2

Synthesis of N-(4-dipropylaminomethylphenyl)-4-{[N-(1H-imidazol-2-ylmethyl)-(4-methylpyridin-2-ylmethyl)-amino]-methyl}-benzamide [Compound No. 78]

The compound (80.2 mg) obtained in Example 47-3 was dissolved in methanol (2.4 ml) and then added with the compound (34.6 mg) obtained in Example 78-1 and sodium cyanoborohydride (18.0 mg). The solution was adjusted to about pH 5 with acetic acid and then stirred at room temperature for 26 hours. After completion of the reaction, the solvent was distilled off and the residue was then dissolved in chloroform, followed by washing with a 1 mol/l sodium hydroxide aqueous solution and saturated saline solution and drying with anhydrous sodium sulfate. The solvent was distilled off and the residue was then purified through silica gel column chromatography (chloroform/methanol), thereby obtaining the subject compound (40.1 mg) as a white solid.

MS(FAB, Pos.): m/z=525[M+H]$^+$ $^1$H-NMR(500 MHz, DMSO-d$_6$): δ=0.82(6H, t, J=7.3 Hz), 1.42(4H, sext., J=7.3 Hz), 2.32(4H, t, J=7.3 Hz), 2.34(3H, s), 3.47(2H, s), 3.64(2H, s), 3.65(2H, s), 3.66(2H, s), 6.86(1H, s), 7.09–7.11(2H, m), 7.25(2H, d, J=8.5 Hz), 7.48(1H, s), 7.57(2H, d, J=8.5 Hz), 7.69(2H, d, J=8.3 Hz), 7.90(2H, d, J=8.3 Hz), 8.35(1H, d, J=4.9 Hz), 10.17(1H, s), 11.96(1H, br).

Production Example 79

Synthesis of {2-[4-(4-{[bis(1H-imidazol-2-ylmethyl)-amino]-methyl}-benzyloxy)-phenyl]-ethyl}-dipropylamine [Compound No. 79]

Example 79-1

Synthesis of 4-(2-dipropylaminoethyl)phenol

Tyramine (manufactured by Tokyo Kasei Kogyo Co., Ltd.) (591 mg) was dissolved in anhydrous methanol (12 ml) and then added with sodium cyanoborohydride (812 mg), acetic acid (5.00 ml), and propionaldehyde (777 µl), followed by stirring at room temperature under a nitrogen atmosphere for 2 days. After completion of the reaction, the solvent was distilled off. Then, the residue was dissolved in diethyl ether and then stirred after the addition of distilled water. The solution was subjected to extraction with diethyl ether and the extract was then washed with distilled water and a saturated aqueous ammonium chloride solution. The organic layer was dried with anhydrous sodium sulfate and the solvent was then distilled off, thereby obtaining the subject compound (412 mg) as a dark brown liquid.

MS(FAB, Pos.): m/z=222[M+H]$^+$

Example 79-2

Synthesis of {2-[4-(4-{[N-Boc(N-1-methane sulfonyl-1H-imidazol-2-ylmethyl)amino]methyl}benzyloxy)phenyl]ethyl}dipropylamine The compound (260 mg) obtained in Example 60-1 was dissolved in DMF (2.0 ml) and then added with potassium carbonate (86.8 mg) and the compound (139 mg) obtained in Example 79-1, followed by stirring under a nitrogen atmosphere at 60° C. for 3 days. After completion of the reaction, the solvent was distilled off. Then, the residue was dissolved in chloroform and added with a saturated aqueous ammonium chloride solution, followed by stirring. The solution was extracted with chloroform and the extract was then washed with a saturated aqueous sodium bicarbonate solution and saturated saline solution. Subsequently, the organic layer was dried with anhydrous sodium sulfate. The solvent was distilled off and the residue was then purified through silica gel column chromatography (chloroform/methanol/water), thereby obtaining the subject compound (149 mg) as a yellow oily substance.

MS(FAB, Pos.): m/z=599[M+H]$^+$

Example 79-3

Synthesis of {2-[4-(4-{[N-(1H-imidazol-2-ylmethyl)amino]methyl}benzyloxy)phenyl]ethyl}dipropylamine The compound (149 mg) obtained in Example 79-2 was dissolved in anhydrous methanol (1.0 ml) and then added with a 4 mol/l hydrogen chloride/dioxane solution (2.00 ml), followed by stirring at room temperature for 6 hours. After completion of the reaction, the solvent was distilled off. Then, the residue was added with a 1 mol/l sodium hydroxide aqueous solution and then washed with chloroform. The aqueous layer was evaporated to dryness and extracted with chloroform, thereby obtaining the subject compound (67.0 mg) as a colorless oily substance.

MS(FAB, Pos.): m/z=421[M+H]$^+$

Example 79-4

Synthesis of {2-[4-(4-{[bis(1H-imidazol-2-ylmethyl)-amino]-methyl}-benzyloxy)-phenyl]-ethyl}-dipropylamine [Compound No. 79]

The compound (67.0 mg) obtained in Example 79-3 was dissolved in anhydrous methanol (1.5 ml) and then added with sodium cyanoborohydride (20.0 mg), acetic acid (1.50 ml), and 2-imidazole carboxaldehyde (23.0 mg), followed by stirring under a nitrogen atmosphere at 60° C. for 2 days. After completion of the reaction, the solvent was distilled off. Subsequently, the residue was purified through silica gel column chromatography (chloroform/methanol) and then treated with hydrochloric acid, thereby obtaining hydrochloride (47.1 mg) of the subject compound as a white solid.

MS(FAB, Pos.): m/z=501[M+H]$^+$

Production Example 80

Synthesis of [4-(4-{[bis(1H-imidazol-2-ylmethyl)-amino]-methyl}-benzyloxymethyl)-benzyl]-dipropylamine [Compound No. 80]

Example 80-1

Synthesis of methyl 4-dipropylaminomethylbenzoate

In anhydrous methanol (30 ml), 4-aminomethylbenzoic acid methyl ester hydrochloride (1.15 g) was dissolved. Then, the solution was added with sodium cyanoborohydride (1.08 g), acetic acid (5.00 ml), and propionaldehyde (1.03 ml), followed by stirring under a nitrogen atmosphere at room temperature for 1 week. After completion of the reaction, the solvent was distilled off and the residue was then dissolved in chloroform, followed by the addition of a 1 mol/l sodium hydroxide aqueous solution to adjust the solution to pH 9. The solution was subjected to extraction with chloroform. Then, the extract was washed with a saturated aqueous sodium bicarbonate solution and saturated saline solution. The organic layer was dried with anhydrous sodium sulfate and the solvent was then distilled off, thereby obtaining the subject compound (1.49 g) as a colorless liquid.

MS(FAB, Pos.): m/z=250[M+H]$^+$

Example 80-2

Synthesis of 4-dipropylaminomethylbenzyl alcohol

The compound (1.47 g) obtained in Example 80-1 was dissolved in anhydrous THF (50 ml). Then, the solution was added with lithium aluminum hydride (671 mg) in an ice bath, followed by stirring at room temperature for 1 hour. After completion of the reaction, the solution was added with methanol and then added with an aqueous potassium sodium tartrate solution, followed by stirring. The solution was extracted with chloroform and the extract was then washed with saturated saline solution. The organic layer was dried with anhydrous sodium sulfate and the solvent was then distilled off, thereby obtaining the subject compound (1.20 g) as a colorless liquid.

MS(FAB, Pos.): m/z=222[M+H]$^+$

Example 80-3

Synthesis of [4-(4-{[N-Boc(N-1-methanesulfonyl-1H-imidazol-2-ylmethyl)amino]methyl}benzyloxymethyl)benzyl]dipropylamine The compound (225 mg) obtained in Example 60-1 was dissolved in DMF (2.0 ml) and then added with potassium carbonate (75.2 mg) and the compound (120 mg) obtained in Example 80-2, followed by stirring under a nitrogen atmosphere at 60° C. for 2 days. In addition, potassium iodide (18.0 mg) was added to the solution, and likewise the whole was stirred overnight at 60° C. under a nitrogen atmosphere. After completion of the reaction, the solvent was distilled off. The residue was dissolved in chloroform and then added with a saturated aqueous ammonium chloride solution, followed by stirring. The solution was extracted with chloroform and washed with a saturated aqueous sodium bicarbonate solution and saturated saline solution. Subsequently, the organic layer was dried with anhydrous sodium sulfate. The solvent was distilled off and the residue was then purified through silica gel column chromatography (chloroform/methanol), thereby obtaining the subject compound (194 mg) as a colorless oily substance.

MS(FAB, Pos.): m/z=599[M+H]$^+$

Example 80-4

Synthesis of [4-(4-{[N-(1H-imidazol-2-ylmethyl)amino]methyl}benzyloxymethyl)benzyl]dipropylamine The compound (193 mg) obtained in Example 80-3 was dissolved in anhydrous methanol (1.0 ml) and then added with a 1 mol/l sodium hydroxide aqueous solution (2.00 ml), followed by stirring for 2 hours at room temperature. Subsequently, a 4 mol/l hydrogen chloride/dioxane solution (3.00 ml) was added to the solution to adjust the solution to pH 2, followed by stirring at room temperature for 1 hour. After completion of the reaction, the solvent was distilled off and the residue was dissolved in methanol. Subsequently, the solution was added with an anion-exchange resin (Amberlite IRA-410) and left to stand. The resultant was filtrated and the solvent was then distilled off, thereby obtaining the subject compound (136 mg) as a colorless oily substance.

MS(FAB, Pos.): m/z=421[M+H]$^+$

Example 80-5

Synthesis of [4-(4-{[bis(1H-imidazol-2-ylmethyl)-amino]-methyl}-benzyloxymethyl)-benzyl]-dipropylamine [Compound No. 80]

The compound (136 mg) obtained in Example 80-4 was dissolved in anhydrous methanol (3.0 ml) and then added with sodium cyanoborohydride (40.6 mg), acetic acid (1.00 ml), and 2-imidazole carboxaldehyde (46.6 mg), followed by stirring under a nitrogen atmosphere at 60° C. overnight. After completion of the reaction, the solvent was distilled off. Subsequently, the residue was purified through silica gel column chromatography (chloroform/methanol) and then treated with hydrochloric acid, thereby obtaining hydrochloride (109 mg) of the subject compound as a white solid.

MS(FAB, Pos.): m/z=501[M+H]$^+$ $^1$H-NMR(500 MHz, DMSO-d$_6$+D$_2$O): δ=0.87 (6H, t, J=7.2 Hz), 1.78–1.90(4H, m), 2.89–3.08(4H, m), 4.11(2H, s), 4.15(2H, s), 4.58(4H, s), 4.76(4H, s), 7.41–7.53(8H, m), 7.55(4H, s).

Production Example 81

Synthesis of N-(4-dipropylaminomethylphenyl)-4-{[(1H-imidazol-2-ylmethyl)-([1,2,3]-thiadiazole-4-ylmethyl)-amino]-methyl}-benzamide [Compound No. 81]

Example 81-1

Synthesis of [1,2,3]thiadiazol-4-aldehyde

[1,2,3]thiazol-4-carboxylic acid (manufactured by Avocado Co., Ltd.) (1.19 g) was dissolved in a 10% hydrogen chloride/methanol solution (35.7 ml), following thermal reflux for 14 hours. The reaction solvent was distilled off and the residue was dried under vacuum. The dried product was dissolved in ethanol (18.0 ml) and THF (9.0 ml) and then added with calcium chloride (1.39 mg) and sodium borohydride (0.945 g), followed by stirring at room temperature for 30 minutes. The reaction solution was added with a 1 mol/l aqueous citric acid solution, followed by separation/extraction with ethyl acetate. The organic layer was washed with a saturated aqueous sodium bicarbonate solution and saturated saline solution in this order, and then dried with anhydrous sodium sulfate, and the solvent was distilled off. The residue was redissolved in chloroform (10.5 ml) and then added with manganese dioxide (chemically processed product) (2.10 g), followed by stirring at room temperature for 1.5 hours. The reaction solution was filtrated using Celite. The solvent was distilled off and the residue was then purified through silica gel column chromatography (chloroform/ethyl acetate), thereby obtaining the subject compound (69.2 mg) as a white solid.

$^1$H-NMR(500 MHz, CDCl$_3$): δ=9.31(1H, s), 10.6(1H, s).

Example 81-2

Synthesis of N-(4-dipropylaminomethylphenyl)-4-{[(1H-imidazol-2-ylmethyl)-([1,2,3]-thiadiazole-4-ylmethyl)-amino]-methyl}-benzamide [Compound No. 81]

The compound (77.8 mg) obtained in Example 47-3 was dissolved in methanol (2.3 ml) and then added with the compound (23.3 mg) obtained in Example 81-1 and sodium cyanoborohydride (23.3 mg). Then, the solution was adjusted to pH 5 with acetic acid and then stirred at room temperature for 19 hours. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/ethyl acetate) and then treated with hydrochloric acid, thereby obtaining hydrochloride (64.9 mg) of the subject compound as a white solid.

MS(FAB, Pos.): m/z=518[M+H]$^+$ $^1$H-NMR(500 MHz, DMSO-d$_6$): δ=0.88(6H, t, J=7.3 Hz), 1.60–1.80(4H, m), 2.96(4H, br), 3.81(2H, s), 4.08(2H, s), 4.26(2H, s), 4.29 (2H, s), 7.53(2H, d, J=8.3 Hz), 7.54(2H, s), 7.59(2H, d, J=8.5 Hz), 7.87 (2H, d, J=8.5 Hz), 7.93(2H, d, J=8.3 Hz), 9.15(1H, s).

Production Example 82

Synthesis of 4-{[(1-dimethylsulfamoyl-1H-imidazol-2-ylmethyl)-(1H-imidazol-2-ylmethyl)-amino]-methyl}-N-(4-dipropylaminomethylphenyl)-benzamide [Compound No. 82] and Synthesis of 4-{[bis(1-dimethylsulfamoyl-1H-imidazol-2-ylmethyl)-amino]-methyl}-N-(4-dipropylaminomethylphenyl)-benzamide [Compound No. 84]

Example 82-1

Synthesis of 4-{[(1-dimethylsulfamoyl-1H-imidazol-2-ylmethyl)-(1H-imidazol-2-ylmethyl)-amino]-methyl}-N-(4-dipropylaminomethylphenyl)-benzamide [Compound No. 82] and Synthesis of 4-{[bis(1-dimethylsulfamoyl-1H-imidazol-2-ylmethyl)-amino]-methyl}-N-(4-dipropylaminomethylphenyl)-benzamide [Compound No. 84]

The compound (55.7 mg) obtained in Example 19-3 was dissolved in anhydrous chloroform (2.2 ml). The solution was added with triethylamine (0.037 ml) and then dimethylsulfamoyl chloride (manufactured by Tokyo Kasei Kogyo Co., Ltd.) (0.026 ml), followed by stirring at room temperature for 42 hours. After the reaction, the solution was added with chloroform (3.0 ml) and then washed with water and a saturated aqueous sodium bicarbonate solution. The organic layer was dried with anhydrous magnesium sulfate. The solvent was distilled off and the residue was then purified through silica gel column chromatography (manufactured by Fuji Silysia Chemical Ltd.) (chloroform/ethyl acetate), thereby obtaining 4-{[(1-dimethylsulfamoyl-1H-imidazol-2-ylmethyl)-(1H-imidazol-2-ylmethyl)-amino]-methyl}-N-(4-dipropylaminomethylphenyl)-benzamide [Compound No. 82] (14.7 mg) as a white solid.

MS(FAB, Pos.): m/z=607[M+H]$^+$ $^1$H-NMR(500 MHz, DMSO-d$_6$): δ=0.82(6H, t, J=7.3 Hz), 1.42(4H, sext., J=7.3 Hz), 2.31(4H, t, J=7.3 Hz), 2.76(6H, s), 3.47(2H, s), 3.85(2H, s), 3.91(2H, s), 3.95(2H, s), 6.85(1H, s), 7.10(2H, d, J=1.7 Hz), 7.25(2H, d, J=8.5 Hz), 7.49(2H, d, J=8.5 Hz), 7.56(1H, d, J=1.7 Hz), 7.69(2H, d, J=8.5 Hz), 7.88(2H, d, J=8.3 Hz), 10.15(1H, s), 11.90(1H, brs).

Furthermore, as a white solid, 4-{[bis(1-dimethylsulfamoyl-1H-imidazol-2-ylmethyl)-amino]-methyl}-N-(4-dipropylaminomethylphenyl)-benzamide [Compound No. 84] (12.7 mg) was obtained from other fraction.

MS(FAB, Pos.): m/z=714[M+H]$^+$ $^1$H-NMR(500 MHz, DMSO-d$_6$): δ=0.82(6H, t, J=7.3 Hz), 1.42(4H, sext., J=7.3 Hz), 2.32(4H, t, J=7.3 Hz), 2.78(12H, s), 3.42(2H, s), 4.14(6H, s), 7.06(2H, d, J=1.7 Hz), 7.26(2H, d, J=8.5 Hz), 7.39(2H, d, J=8.3 Hz), 7.55(2H, d, J=1.7 Hz), 7.69 (2H, d, J=8.5 Hz), 7.86(2H, d, J=8.3 Hz), 10.15(1H, s).

Production Example 83

Synthesis of 2-({[4-(4-dipropylaminomethylphenylcarbamoyl)-benzyl]-(1-methyl-1H-imidazol-2-ylmethyl)-amino}-methyl)-imidazol-1-carboxylic acid dimethylamide [Compound No. 83]

Example 83-1

Synthesis of 2-({[4-(4-dipropylaminomethylphenylcarbamoyl)-benzyl]-(1-methyl-1H-imidazol-2-ylmethyl)-amino}-methyl)-imidazol-1-carboxylic acid dimethylamide [Compound No. 83]

The compound (95.0 mg) obtained in Example 49-1 was dissolved in pyridine (5.0 ml) and added with N,N-dimethylcarbamoyl chloride (20.0 mg). After the solution had been stirred at room temperature for 15 hours, pyridine was distilled off and the residue was then added with a saturated aqueous sodium bicarbonate solution and extracted with chloroform. The extract was concentrated and purified through column chromatography (chloroform/methanol), thereby obtaining the subject compound (45.4 mg) as a white solid.

MS(FAB, Pos.): m/z=585[M+H]$^+$ $^1$H-NMR(500 MHz, DMSO-d$_6$): δ=0.82(6H, t, J=7.3 Hz), 1.38–1.45(4H, m), 2.30–2.38(4H, m), 2.73–2.97(6H, m), 3.33(3H, s), 3.47(4H, m), 3.62(4H, d, J=5.8 Hz), 6.79(1H, d, J=1.2 Hz), 6.97(1H, d, J=1.4 Hz), 7.07(1H, d, J=1.2 Hz), 7.26(2H, d, J=6.8 Hz), 7.41(2H, d, J=8.3 Hz), 7.44(1H, d, J=1.4 Hz), 7.69(2H, d, J=8.5 Hz), 7.90(2H, d, J=8.3 Hz), 10.16(1H, s).

Production Example 84

Synthesis of N-(4-dipropylaminomethylphenyl)-4-{[(1H-imidazol-2-ylmethyl)-(pyrazine-2-ylmethyl)-amino]-methyl}-benzamide [Compound No. 85]

Example 84-1

Synthesis of pyrazine-2-carboxaldehyde

Pyrazine-2-carboxylic acid methyl ester (Lancaster Synthesis Inc.) (400 mg) was dissolved in anhydrous ethanol (8.0 ml) and anhydrous THF (4.0 ml) and then added with sodium borohydride (438 mg) and calcium chloride (646 mg), followed by stirring at room temperature for 68 hours. The solution was added with a 1 mol/l aqueous citric acid solution and extracted with ethyl acetate. The organic layer was washed with a saturated sodium bicarbonate solution and dried with anhydrous magnesium sulfate. Subsequently, the solvent was distilled off and the residue was then purified through silica gel column chromatography (chloroform/ethyl acetate). The purified product was dissolved in chloroform (10 ml) and added with manganese dioxide (chemically processed product) (2.00 g), followed by stirring for 4 hours. The solution was filtrated through Celite and the solvent was then distilled off. The residue was purified through silica gel column chromatography (chloroform/ethyl acetate), thereby obtaining the subject compound (56.0 mg).

MS(EI, Pos.): m/z=108[M]$^+$ $^1$H-NMR(500 MHz, CDCl$_3$): δ=8.78(1H, d, J=2.4 Hz), 8.89(1H, d, J=2.4 Hz), 9.19(1H, s), 10.17(1H, s).

Example 84-2

Synthesis of N-(4-dipropylaminomethylphenyl)-4-{[(1H-imidazol-2-ylmethyl)-(pyrazine-2-ylmethyl)-amino]-methyl}-benzamide [Compound No. 85]

The compound (99 mg) obtained in Example 47-3 and the compound (51.0 mg) obtained in Example 84-1 were dissolved in anhydrous methanol (5.0 ml). The solution was added with sodium cyanoborohydride (35.6 mg) and further added with acetic acid (1.0 ml) to adjust the solution to pH 5, followed by stirring for 5 minutes and then stirring at room temperature for 17 hours. After completion of the reaction, methanol was distilled off and the solution was then added with 1 mol/l sodium hydroxide to adjust the solution to pH 11, followed by extraction with chloroform. The organic layer was washed with saturated saline solution and dried with anhydrous magnesium sulfate. After that, the solvent was distilled off. Then, the residue was purified through silica gel column chromatography (chloroform/methanol) and treated with hydrochloric acid, thereby obtaining hydrochloride (16.8 mg) of the subject compound as a white solid.

MS(FAB, Pos.): m/z=512[M+H]$^+$ $^1$H-NMR(500 MHz, DMSO-d$_6$+D$_2$O): δ=0.82(6H, t, J=7.3 Hz), 1.42(4H, sext., J=7.3 Hz), 2.32(4H, t, J=7.5 Hz), 3.48(2H, s), 3.71(2H, s), 3.73(2H, s), 3.77(2H, s), 6.85(1H, s), 7.11(1H, s), 7.27(2H, d, J=8.5 Hz), 7.56(2H, d, J=8.3 Hz), 7.67(2H, d, J=8.5 Hz), 7.89(2H, d, J=8.3 Hz), 8.51(1H, s), 8.55(1H, s), 8.84(1H, s).

Production Example 85

Synthesis of N-(4-dipropylaminomethylphenyl)-4-{[(1H-imidazol-2-ylmethyl)-(5-methylisoxazol-3-ylmethyl)-amino]-methyl}-benzamide [Compound No. 86]

Example 85-1

Synthesis of 5-methylisoxazole-3-carboxaldehyde

In anhydrous THF (40 ml), 5-methylisoxazole-3-carboxylic acid methyl ester (Avogato Co., Ltd.) (2.00 g) was dissolved. In an ice bath, a solution (20 ml) of lithium aluminum hydride (0.67 g) in anhydrous THF was dropped in the solution over 15 minutes. After 10 minutes, the mixture was taken from the ice bath and then stirred at room temperature for 1 hour. After completion of the reaction, the resultant solution was added with anhydrous sodium sulfate and then added with a 20% sodium hydroxide aqueous solution (15 ml). The solution was filtrated through Celite and the solvent was distilled off. The residue was dissolved in chloroform (85 ml) and added with manganese dioxide (chemically processed product) (17.0 g), followed by stirring for 4.5 hours. After completion of the reaction, the solution was filtrated through Celite and the solvent was then distilled off. The residue was purified through silica gel column chromatography (chloroform/ethyl acetate), thereby obtaining the subject compound (164 mg) as a white solid.

MS(EI, Pos.): m/z=111[M]$^+$ $^1$H-NMR(500 MHz, CDCl$_3$): δ=2.53(3H, s), 6.39(1H, s), 10.12(1H, s).

Example 85-2

Synthesis of N-(4-dipropylaminomethylphenyl)-4-{[(1H-imidazol-2-ylmethyl)-(5-methylisoxazol-3-ylmethyl)-amino]-methyl}-benzamide [Compound No. 86]

The compound (110 mg) obtained in Example 47-3 and the compound (58.0 mg) obtained in Example 85-1 were dissolved in anhydrous methanol (5.0 ml). The solution was added with sodium cyanoborohydride (39.4 mg) and then added with acetic acid (1.0 ml) to adjust the solution to pH 5, followed by stirring for 5 minute and then stirring at room temperature for 17 hours. After completion of the reaction, methanol was distilled off and a 1 mol/l sodium hydroxide aqueous solution was added to adjust the solution to pH 11, followed by extraction with chloroform. The organic layer was washed with saturated saline solution and dried with anhydrous magnesium sulfate, followed by distilling the solvent off. Subsequently, the residue was purified through silica gel column chromatography (chloroform/methanol), added with methanol and 1 mol/l hydrochloric acid, and distilled off, thereby obtaining hydrochloride (21.3 mg) of the subject compound as a white crystal.

MS(FAB, Pos.): m/z=515[M+H]$^+$ $^1$H-NMR(500 MHz, DMSO-d$_6$+D$_2$O): δ=0.82(6H, t, J=7.3 Hz), 1.43(4H, sext., J=7.3 Hz), 2.32(4H, t, J=7.5 Hz), 2.40(3H, s), 3.48(2H, s), 3.59(2H, s), 3.67(2H, s), 3.70(2H, s), 6.34(1H, s), 6.87(1H, s), 7.12(1H, s), 7.27(2H, d, J=8.5 Hz), 7.54(2H, d, J=8.3 Hz), 7.68(2H, d, J=8.5 Hz), 7.89(2H, d, J=8.1 Hz).

Production Example 86

Synthesis of 4-(4-{[bis(1H-imidazol-2-ylmethyl)-amino]-methyl}-benzoyl)-(2-dipropylaminoethyl)-piperazine [Compound No. 87]

Example 86-1

Synthesis of 4-(4-{[bis(1H-imidazol-2-ylmethyl)-amino]-methyl}-benzoyl)-(2-dipropylaminoethyl)-piperazine [Compound No. 87]

The compound (103.8 mg) obtained in Example 2-2 was dissolved in DMF (3.1 ml) and then added with DCC (68.8 mg) and HOBt (45.0 mg), followed by stirring at room temperature for 10 days. The solution was added with 1-(2-dipropylaminoethyl)piperazine (71.1 mg) and further stirred at the same temperature for 4 days. The reaction solvent was distilled off and the residue was then added with 1 mol/l hydrochloric acid, followed by washing with chloroform. The aqueous layer was adjusted to pH 12 with a 1 mol/l sodium hydroxide aqueous solution and then subjected to separation/extraction with chloroform. The organic layer was dried with anhydrous sodium sulfate. The solvent was distilled off and the residue was then purified through silica gel column chromatography (chloroform/methanol) and treated with hydrochloride acid, thereby obtaining hydrochloride (52.5 mg) of the subject compound as a white solid.

MS(FAB, Pos.): m/z=506[M+H]$^+$ $^1$H-NMR(500 MHz, DMSO-d$_6$): δ=0.88(6H, t, J=7.3 Hz), 1.60–1.76(4H, m), 2.78–3.26(12H, m), 3.48–3.58(4H, m), 3.71(2H, m), 4.14(4H, m), 7.24–7.56(8H, m).

Production Example 87

Synthesis of N-(4-cyclohexylaminomethylphenyl)-4-{[(1H-imidazol-2-ylmethyl)-(1-methyl-1H-imidazol-2-ylmethyl)-amino]-methyl}-benzamide [Compound No. 88]

Example 87-1

Synthesis of cyclohexyl(4-nitrobenzyl)carbamic acid benzyl ester

Commercially available 4-nitrobenzylamine hydrochloride (1.88 g) was added with a 1 mol/l sodium hydroxide aqueous solution (12 ml) and then the solution was subjected to extraction with chloroform. The solution was dried with anhydrous magnesium sulfate, and the solvent was distilled off. The residue was dissolved in anhydrous methanol (45 ml) and then added with cyclohexanone (1.55 ml) and trimethyl orthoformate (3.28 ml), followed by stirring at room temperature for 2.5 hours. The solution was cooled with ice and added with sodium borohydride (1.13 g), followed by stirring for 4.5 hours. After completion of the reaction, the solvent was distilled off and the residue was then added with water, followed by extraction with chloroform. The extract was washed with saturated saline solution and dried with anhydrous magnesium sulfate, followed by distilling the solvent off. The residue was dissolved in dioxane (25 ml) and cooled with ice. To this solution, benzyloxycarbonyl chloride (1.57 ml) and a 4 mol/l sodium hydroxide aqueous solution (2.8 ml) were added, and the whole was stirred at room temperature for 4 hours. After completion of the reaction, the solvent was distilled off and the residue was then added with water, followed by extraction with chloroform. The extract was dried with anhydrous magnesium sulfate and the solvent was then distilled off. Subsequently, the residue was purified through silica gel column chromatography (hexane/ethyl acetate), thereby obtaining the subject compound (2.03 g) as a yellow viscous liquid.

MS(FAB, Pos.): m/z=369[M+H]$^+$

Example 87-2

Synthesis of (4-aminobenzyl)cyclohexylcarbamic acid benzyl ester

The compound (1.24 g) obtained in Example 87-1 was dissolved in methanol (12 ml) and THF (6.2 ml) and added with activated carbon (124 mg) and iron trichloride hexahydrate (12.4 mg), followed by thermal reflux for 0.5 hour. After standing to cool, the solution was added with hydrazine monohydrate (0.89 ml) and then subjected to thermal reflux for 3 hours. After completion of the reaction, the resultant was filtrated through Celite and the solvent was then distilled off. The residue was dissolved in chloroform and washed with water. The solution was dried with anhydrous magnesium sulfate. The solvent was distilled off, thereby obtaining the subject compound (1.15 g) as a yellow viscous liquid.

MS(FAB, Pos.): m/z=339[M+H]$^+$

Example 87-3

Synthesis of [4-(4-{[Boc-(1H-imidazol-2-ylmethyl)amino]methyl}benzoylamino)benzyl]cyclohexylcarbamic acid benzyl ester The compound (1.15 g) obtained in Example 87-2 was dissolved in anhydrous chloroform (23 ml) and then added with the compound (1.24 g) obtained in Example 1-1, WSCI hydrochloride (717 mg), and HOBt (505 mg), followed by stirring at room temperature for 4 days. After completion of the reaction, the solution was washed with 1 mol/l hydrochloric acid, a 1 mol/l sodium hydroxide aqueous solution, and saturated saline solution. The solution was dried with anhydrous magnesium sulfate, and the solvent was then distilled off. Then, the residue was purified through silica gel column chromatography (chloroform/methanol), thereby obtaining the subject compound (1.81 g) as a white solid.

MS(FAB, Pos.): m/z=652[M+H]$^+$ $^1$H-NMR(500 MHz, DMSO-d$_6$): δ=1.02(1H, br), 1.21–1.24(2H, m), 1.36(9H, s), 1.41–1.43(2H, m), 1.46–1.58(3H, m), 1.67(2H, br), 3.84(1H, br), 4.35–4.51 (6H, m), 5.08–5.12(2H, br), 6.85(1H, s), 7.05(1H, br), 7.21 (3H, m), 7.32–7.39(4H, br), 7.68(2H, d, J=8.6 Hz), 7.91(2H, d, J=8.1 Hz), 10.18(1H, brs), 11.96(1H, br).

Example 87-4

Synthesis of cyclohexyl-[4-(4-{[(1H-imidazol-2-ylmethyl)amino]methyl}benzoylamino)benzyl]carbamic acid benzyl ester The compound (1.82 g) obtained in Example 87-3 was dissolved in methanol (18 ml) and then added with a 4 mol/l hydrogen chloride/dioxane solution (18 ml), followed by stirring at room temperature for 2 hours. After the reaction, the solvent was distilled off. Then, the residue was adjusted to pH 11 with a 1 mol/l sodium hydroxide aqueous solution and extracted with chloroform, followed by drying with anhydrous magnesium sulfate. Subsequently, the solvent was distilled off, thereby obtaining the subject compound (1.48 g) as a white solid.

MS(FAB, Pos.): m/z=552[M+H]$^+$ $^1$H-NMR(500 MHz, DMSO-d$_6$): δ=1.00–1.05(1H, br), 1.39–1.46(2H, m), 1.52–1.56(3H, br), 1.58–1.67(2H, br), 3.68(2H, s), 3.76(2H, s), 3.84(1H, br), 4.42(2H, s), 5.08–5.17(2H, br), 6.80(1H, br), 7.02(1H, br), 7.19–7.21 (3H, br), 7.31–7.39(4H, m), 7.49(2H, d, J=8.3 Hz), 7.68(2H, d, J=8.5 Hz), 7.90(2H, d, J=8.3 Hz), 10.17(1H, brs).

Example 87-5

Synthesis of cyclohexyl-[4-(4-{[(1H-imidazol-2-ylmethyl)-(1-methyl-1H-imidazol-2-ylmethyl)amino]methyl}benzylamino)benzyl]carbamic acid benzyl ester The compound (236 mg) obtained in Example 87-4 and 1-methyl-2-imidazole carboxaldehyde (46.5 mg) were dissolved in anhydrous methanol (7.1 ml). The solution was added with sodium cyanoborohydride (54.0 mg) and then adjusted to pH 5 with acetic acid, followed by stirring at room temperature for 16 hours. After the reaction, the solvent was distilled off. A 1 mol/l sodium hydroxide aqueous solution was added to the residue, and chloroform extraction was then carried out. The extract was washed with saturated saline solution and then dried with magnesium sulfate, followed by distilling the solvent off. The residue was purified through silica gel column chromatography (chloroform/methanol), thereby obtaining the subject compound (212 mg) as a white solid.

MS(FAB, Pos.): m/z=646[M+H]$^+$

Example 87-6

Synthesis of N-(4-cyclohexylaminomethylphenyl)-4-{[(1H-imidazol-2-ylmethyl)-(1-methyl-1H-imidazol-2-ylmethyl)-amino]-methyl}-benzamide [Compound No. 88]

The compound (212 mg) obtained in Example 87-5 was dissolved in methanol (10 ml). After having been cooled with ice, the solution was added with a suspension of 10% palladium-carbon (105 mg) in ethanol (3.0 ml). After having been subjected to hydrogen displacement, the mixture was stirred under a hydrogen atmosphere at room temperature for 3 hours. After the reaction, the solution was filtrated through Celite and the solvent was then distilled off. Then, the residue was purified through silica gel column chromatography (chloroform/methanol) and treated with hydrochloric acid, thereby obtaining hydrochloride (43.1 mg) of the subject compound as a white solid.

MS(FAB, Pos.): m/z=512[M+H]$^+$

¹H-NMR(500 MHz, DMSO-d₆): δ=1.12(1H, t, J=12.7 Hz), 1.20(2H, q, J=12.7 Hz), 1.35–1.42(2H, m), 1.60(1H, d, J=13.0 Hz), 1.77(2H, d, J=13.1 Hz), 2.11(2H, d, J=10.1 Hz), 2.93(1H, br), 3.73(3H, s), 3.81(2H, s), 4.11(4H, s), 4.18 (2H, s), 7.54–7.56(4H, m), 7.59(2H, d, J=8.2 Hz), 7.66(2H, s), 7.84(2H, d, J=8.7 Hz), 7.93(2H, d, J=8.2 Hz), 9.14(2H, br), 10.38(1H, s), 14.79–14.86(2H, br).

Production Example 88

Synthesis of 4-{[bis(1H-imidazol-2-ylmethyl)-amino]-methyl}-N-(4-cyclohexylaminomethylphenyl)-benzamide [Compound No. 89]

Example 88-1

Synthesis of [4-(4-{[bis(1H-imidazol-2-ylmethyl)amino]methyl}benzoylamino)benzyl]cyclohexyl carbamic acid benzyl ester The compound (242 mg) obtained in Example 87-4 and 2-imidazole carboxaldehyde (63.4 mg) were dissolved in anhydrous methanol (7.2 ml). Then, the solution was added with sodium cyanoborohydride (96.9 mg) and adjusted to pH 5 with acetic acid, followed by stirring at room temperature for 2 days. After the reaction, the solvent was distilled off. The residue was added with a 1 mol/l sodium hydroxide aqueous solution and extracted with chloroform. Subsequently, the extract was washed with saturated saline solution and the residue was then dried with anhydrous magnesium sulfate, followed by distilling the solvent off. The residue was purified through silica gel column chromatography (chloroform/methanol), thereby obtaining the subject compound (282 mg) as a white solid.

MS(FAB, Pos.): m/z=632[M+H]⁺

Example 88-2

Synthesis of 4-{[bis(1H-imidazol-2-ylmethyl)-amino]-methyl}-N-(4-cyclohexylaminomethylphenyl)-benzamide [Compound No. 89]

The compound (282 mg) obtained in Example 88-1 was dissolved in methanol (14 ml). After having been cooled with ice, the solution was added with a suspension of 10% palladium-carbon (140 mg) in ethanol (3.0 ml). After having been subjected to hydrogen displacement, the mixture was stirred under a hydrogen atmosphere at room temperature for 3 hours. After the reaction, the reaction solution was filtrated through Celite and the solvent was then distilled off. Then, the residue was purified through silica gel column chromatography (chloroform/methanol/water) and treated with hydrochloric acid, thereby obtaining hydrochloride (47.1 mg) of the subject compound as a white solid.

MS(FAB, Pos.): m/z=498[M+H]⁺

¹H-NMR(500 MHz, DMSO-d₆): δ=0.12(1H, t, J=12.5 Hz), 1.21(2H, q, J=12.5 Hz), 1.34–1.41(2H, m), 1.60(1H, d, J=12.2 Hz), 1.77(2H, d, J=14.0 Hz), 2.11(2H, d, J=11.0 Hz), 2.94(1H, br), 3.76(2H, s), 4.14(6H, s), 7.54(2H, d, J=8.7 Hz), 7.61(2H, s), 7.63(4H, s), 7.83(2H, d, J=8.5 Hz), 7.92 (2H, d, J=8.4 Hz), 9.06(2H, br), 10.36(1H, brs), 14.70(1H, br).

Production Example 89

Synthesis of N-(4-{[(1H-imidazol-2-ylmethyl)-(1-methyl-1H-imidazol-2-ylmethyl)-amino]-methyl}-benzyl)-N',N'-dipropylbutane-1,4-diamine [Compound No. 90]

Example 89-1

Synthesis of N-Boc(4-{[(1H-imidazol-2-ylmethyl)-(1-methyl-1H-imidazol-2-ylmethyl)amino]methyl}benzyl)-N',N'-dipropylbutan-1,4-diamine The compound (231 mg) obtained in Example 75-1 was dissolved in anhydrous methanol (5.0 ml). The solution was added with sodium cyanoborohydride (61.6 mg), acetic acid (2.00 ml), and 1-methyl-2-imidazole carboxaldehyde (80.9 mg), followed by stirring under a nitrogen atmosphere at room temperature for 6 days. After completion of the reaction, the solvent was distilled off and the residue was then dissolved in chloroform, followed by stirring for a while after the addition of a saturated aqueous sodium bicarbonate solution. The solution was subjected to extract with chloroform and the extract was then washed with a saturated aqueous sodium bicarbonate solution and saturated saline solution. The organic layer was dried with anhydrous sodium sulfate. Subsequently, the solvent was distilled off and the residue was then purified through silica gel column chromatography (chloroform/methanol/water), thereby obtaining the subject compound (197 mg) as a colorless oily substance.

MS(FAB, Pos.): m/z=566[M+H]⁺

Example 89-2

Synthesis of N-(4-{[(1H-imidazol-2-ylmethyl)-(1-methyl-1H-imidazol-2-ylmethyl)-amino]-methyl}-benzyl)-N',N'-dipropylbutane-1,4-diamine [Compound No. 90]

The compound (197 mg) obtained in Example 89-1 was dissolved in methanol (1.0 ml) and added with a 10% hydrogen chloride/methanol solution (3.0 ml), followed by stirring overnight at room temperature. After completion of the reaction, the solvent was distilled off and hydrochloride (159 mg) of the subject compound was obtained as a white solid.

MS(FAB, Pos.): m/z=466[M+H]⁺

¹H-NMR(500 MHz, DMSO-d₆+D₂O): δ=0.87(6H, t, J=7.3 Hz), 1.59–1.67(8H, m), 2.87(2H, brs), 2.94–2.97(4H, m), 3.01(2H, brs), 3.66(3H, s), 3.69(2H, s), 4.03(4H, s), 4.13(2H, s), 7.34(2H, d, J=8.2 Hz), 7.39(2H, d, J=8.2 Hz), 7.40(1H, d, J=2.0 Hz), 7.41(1H, d, J=2.0 Hz), 7.53(2H, s).

Production Example 90

Synthesis of N-(4-dipropylaminomethylphenyl)-4-{[(1-ethyl-1H-imidazol-2-ylmethyl)-(1H-imidazol-2-ylmethyl)-amino]-methyl}-benzamide [Compound No. 91]

Example 90-1

Synthesis of 1-ethyl-1H-imidazole-2-carboxaldehyde

In DMF (15 ml), 2-imidazole carboxaldehyde (500 mg) was dissolved. Then, the solution was added with iodoethane (1.25 ml) and sodium hydride (208 mg), followed by stirring at room temperature for 5 days. After completion of the reaction, the solvent was distilled off and the residue was then added with chloroform, followed by washing with water and saturated saline solution. The resultant was dried with anhydrous sodium sulfate, and the solvent was then distilled off. The residue was purified through silica gel column chromatography (chloroform/methanol), thereby obtaining the subject compound (280 mg) as a yellow oily substance.

$^1$H-NMR(500 MHz, DMSO-$d_6$): δ=1.44(3H, t, J=7.3 Hz), 4.44(2H, q, J=7.3 Hz), 7.18(1H, s), 7.29(1H, s), 9.82(1H, s).

Example 90-2

Synthesis of N-(4-dipropylaminomethylphenyl)-4-{[(1-ethyl-1H-imidazol-2-ylmethyl)-(1H-imidazol-2-ylmethyl)-amino]-methyl}-benzamide [Compound No. 91]

The compound (120 mg) obtained in Example 47-3 was dissolved in methanol (5.0 ml) and then added with the compound (58.0 mg) obtained in Example 90-1 and sodium cyanoborohydride (18.0 mg). Then, the solution was adjusted to pH 5 with acetic acid and then stirred at room temperature for 2 days. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/methanol) and then treated with hydrochloric acid, thereby obtaining hydrochloride (107 mg) of the subject compound as a white solid.

MS(FAB, Pos.): m/z=528[M+H]$^+$ $^1$H-NMR(500 MHz, DMSO-$d_6$): δ=0.86(6H, t, J=7.3 Hz), 1.29(3H, d, J=7.3 Hz), 1.68–1.78(4H, m), 2.86–2.95(4H, m), 3.79(2H, m), 4.10(2H, q, J=7.3 Hz), 4.17(2H, s), 4.19(2H, s), 4.25(2H, d, J=5.1 Hz), 7.57–7.66(8H, m), 7.87–7.94(4H, m), 10.43(1H, s), 10.54(1H, brs),

Production Example 91

Synthesis of N-(4-dipropylaminomethylphenyl)-4-{[(1H-imidazol-2-ylmethyl)-(1-propyl-1H-imidazol-2-ylmethyl)-amino]-methyl}-benzamide [Compound No. 92]

Example 91-1

Synthesis of 1-propyl-1H-imidazole-2-carboxaldehyde

In DMF 15 ml, 2-imidazole carboxaldehyde (500 mg) was dissolved. Then, the solution was added with 1-iodopropane (1.52 ml) and sodium hydride (208 mg), followed by stirring at room temperature for 5 days. After completion of the reaction, the solvent was distilled off and the residue was then added with chloroform, followed by washing with water and saturated saline solution. The resultant was dried with anhydrous sodium sulfate, and the solvent was distilled off. Then, the residue was purified through silica gel column chromatography (chloroform/methanol), thereby obtaining the subject compound (600 mg) as a yellow oily substance.

$^1$H-NMR(500 MHz, DMSO-$d_6$): δ=0.93(3H, t, J=7.3 Hz), 1.78–1.85(2H, tq, J=7.3, 7.3 Hz), 4.36(2H, d, J=7.3 Hz), 7.15(1H, s), 7.28(1H, d, J=0.9 Hz), 9.81(1H, d, J=0.9 Hz).

Example 91-2

Synthesis of N-(4-dipropylaminomethylphenyl)-4-{[(1H-imidazol-2-ylmethyl)-(1-propyl-1H-imidazol-2-ylmethyl)-amino]-methyl}-benzamide [Compound No. 92]

The compound (120 mg) obtained in Example 47-3 was dissolved in methanol (5.0 ml) and then added with the compound (57.0 mg) obtained in Example 91-1 and sodium cyanoborohydride (18.0 mg). Then, the solution was adjusted to pH 5 with acetic acid and then stirred at room temperature for 2 days. After completion of the reaction, a 1 mol/l sodium hydroxide aqueous solution was added to the reaction solution, followed by separation/extraction with chloroform. The organic layer was dried with anhydrous sodium sulfate and the solvent was then distilled off. The residue was purified through silica gel column chromatography (chloroform/methanol) and then treated with hydrochloric acid, thereby obtaining hydrochloride (201 mg) of the subject compound as a white solid.

MS(FAB, Pos.): m/z=542[M+H]$^+$ $^1$H-NMR(500 MHz, DMSO-$d_6$): δ=0.81(3H, t, J=7.3 Hz), 0.87(6H, t, J=7.3 Hz), 1.63–1.77(6H, m), 2.87–2.93(4H, m), 3.78(2H, s), 4.01(2H, d, J=7.3 Hz), 4.15(2H, s), 4.17(2H, s), 4.26(2H, d, J=5.3 Hz), 7.56–7.66(8H, m), 7.88(2H, d, J=8.7 Hz), 7.92(2H, d, J=8.4 Hz), 10.30(1H, brs), 10.41(1H, s).

Production Example 92

Synthesis of N-(4-dipropylaminomethylphenyl)-4-({(1H-imidazol-2-ylmethyl)-[1-(2-methoxymethoxyethyl)-1H-imidazol-2-ylmethyl]-amino}-methyl)-benzamide [Compound No. 93]

Example 92-1

Synthesis of 1-iodo-2-methoxymethoxyethane

A mixture of 2-iodoethanol (2.98 g) and dimethoxymethane (20 ml) was prepared and then added with p-toluenesulfonic acid monohydrate (330 mg) and lithium bromide (150 mg), followed by stirring at room temperature for 16 hours and then stirring at 40° C. for 30 minutes. After completion of the reaction, triethylamine (0.4 ml) was added to the solution, and excess part of dimethoxymethane was distilled off. Then, the residue was added with chloroform and washed with water and saturated saline solution, followed by drying with anhydrous sodium sulfate. The solvent was distilled off and the residue was then dried, thereby obtaining the subject compound (3.68 g) as a yellow transparent liquid.

$^1$H-NMR(500 MHz, DMSO-$d_6$): δ=3.30(2H, t, J=6.6 Hz), 3.40(3H, s), 3.82(2H, t, J=6.6 Hz), 4.68(2H, s).

Example 92-2

Synthesis of 1-(2-methoxymethoxyethyl)-1H-imidazole-2-carboxaldehyde

In DMF (15 ml), 2-imidazole carboxaldehyde (300 mg) was dissolved. Then, the compound (1.01 g) obtained in Example 92-1 and sodium hydride (137 mg) were added to the solution, and the whole was stirred at room temperature for 5 days. After completion of the reaction, the solvent was distilled off and the residue was then added with chloroform, followed by washing with water and saturated saline solution. The resultant was dried with anhydrous sodium sulfate, and the solvent was distilled off. Subsequently, the residue was purified through silica gel column chromatography (chloroform/methanol), thereby obtaining the subject compound (457 mg) as a yellow viscous liquid.

$^1$H-NMR(500 MHz, DMSO-$d_6$): δ=3.21(3H, s), 3.82(2H, t, J=5.1 Hz), 4.55(2H, s), 4.62(2H, t, J=5.1 Hz), 7.28(1H, d, J=0.9 Hz), 7.28(1H, s), 9.82(1H, d, J=0.9 Hz).

Example 92-3

Synthesis of N-(4-dipropylaminomethylphenyl)-4-({(1H-imidazol-2-ylmethyl)-[1-(2-methoxymethoxyethyl)-1H-imidazol-2-ylmethyl]-amino}-methyl)-benzamide [Compound No. 93]

The compound (120 mg) obtained in Example 47-3 was dissolved in methanol (5.0 ml). The solution was added with the compound (73.0 mg) obtained in Example 92-2 and sodium cyanoborohydride (18.0 mg) and then adjusted to pH 5 with acetic acid, followed by stirring at room temperature for 2 days. After completion of the reaction, the reaction solution was added with a 1 mol/l sodium hydroxide aqueous solution, followed by separation/extraction with chloroform. The organic layer was dried with anhydrous sodium sulfate and the solvent was then distilled off. The residue was purified through silica gel column chromatography (chloroform/methanol), thereby obtaining the subject compound (121 mg) as a yellow oily substance.

MS(FAB, Pos.): m/z=588[M+H]$^+$ $^1$H-NMR(500 MHz, DMSO-$d_6$): δ=0.82(6H, t, J=7.3 Hz), 1.38–1.46(4H, m), 2.30–2.36(4H, m), 3.08(3H, s), 3.47(2H, s), 3.53(2H, s), 3.60–3.65(6H, m), 4.12(2H, t, J=5.3 Hz), 4.44(2H, s), 6.76–6.90(2H, m), 7.12(1H, d, J=1.2 Hz), 7.15(2H, d, J=1.2 Hz), 7.26(2H, d, J=8.5 Hz), 7.51(2H, d, J=8.3 Hz), 7.69(2H, d, J=8.5 Hz), 7.90(2H, d, J=8.3 Hz), 10.16(1H, s).

Production Example 93

Synthesis of N-(4-dipropylaminomethylphenyl)-4-({[1-(2-hydroxyethyl)-1H-imidazol-2-ylmethyl]-(1H-imidazol-2-ylmethyl)-amino}-methyl)-benzamide [Compound No. 94]

Example 93-1

Synthesis of N-(4-dipropylaminomethylphenyl)-4-({[1-(2-hydroxyethyl)-1H-imidazol-2-ylmethyl]-(1H-imidazol-2-ylmethyl)-amino}-methyl)-benzamide [Compound No. 94]

The compound (60.0 mg) obtained in Example 92-3 was dissolved in methanol (5.0 ml) and then added with 1 mol/l hydrochloric acid (1.5 ml). The solution was concentrated and dried under reduced pressure, thereby obtaining hydrochloride (80.0 mg) of the subject compound as a white solid.

MS(FAB, Pos.): m/z=544[M+H]$^+$ $^1$H-NMR(500 MHz, DMSO-$d_6$): δ=0.87(6H, t, J=7.3 Hz), 1.65–1.76(4H, m), 2.87–2.95(4H, m), 3.64–3.66(2H, m), 3.70–3.72(2H, m), 4.15–4.26(8H, m), 7.56–7.68(8H, m), 7.88(2H, d, J=8.7 Hz), 7.92(2H, d, J=8.4 Hz), 10.27(1H, brs), 10.41(1H, s).

Production Example 94

Synthesis of 4-{[bis(1-hexyloxycarbonyl-1H-imidazol-2-ylmethyl)-amino]-methyl}-N-(4-dipropylaminomethylphenyl)-benzamide [Compound No. 95]

Example 94-1

Synthesis of 4-{[bis(1-hexyloxycarbonyl-1H-imidazol-2-ylmethyl)-amino]-methyl}-N-(4-dipropylaminomethylphenyl)-benzamide [Compound No. 951

The compound obtained in Example 19-3 was treated with an anion-exchange resin. The treated product was dissolved in chloroform (4.0 ml) and added with n-hexyl chloroformate (manufactured by Tokyo Kasei Kogyo Co., Ltd.) (0.054 ml) and triethylamine (0.060 ml), followed by stirring at room temperature for 16 hours. After completion of the reaction, the solvent was distilled off. The residue was added with chloroform, washed with water and saturated saline solution, and dried with anhydrous sodium sulfate, followed by distilling the solvent off. Subsequently, the residue was purified through silica gel column chromatography (chloroform/methanol), thereby obtaining the subject compound (66.6 mg) as a white solid.

MS(FAB, Pos.): m/z=756[M+H]$^+$ $^1$H-NMR(500 MHz, DMSO-$d_6$): δ=0.85(6H, t, J=7.3 Hz), 0.88–0.91(6H, m), 1.30–1.50(16H, m), 1.71–1.76(4H, m), 2.34–2.38(4H, m), 3.53(2H, s), 4.10(2H, s), 4.29–4.31(8H, m), 6.91(2H, d, J=1.6 Hz), 7.32(2H, d, J=8.5 Hz), 7.34(2H, d, J=1.6 Hz), 7.38(2H, d, J=8.2 Hz), 7.55(2H, d, J=8.3 Hz), 7.73(2H, d, J=8.2 Hz).

Production Example 95

Synthesis of 4-{[bis(1-heptyloxycarbonyl-1H-imidazol-2-ylmethyl)-amino]-methyl}-N-(4-dipropylaminomethylphenyl)-benzamide [Compound No. 96]

Example 95-1

Synthesis of 4-{[bis(1-heptyloxycarbonyl-1H-imidazol-2-ylmethyl)-amino]-methyl}-N-(4-dipropylaminomethylphenyl)-benzamide [Compound No. 96]

The compound (83.8 mg) obtained in Example 19-3 was dissolved in anhydrous dichloromethane (1.5 ml). The solution was added with triethylamine (70.1 μl) and then added with n-heptyl chloroformate (74.9 μl) in an ice bath, followed by stirring overnight under a nitrogen atmosphere at room temperature. After completion of the reaction, the solution was added with a saturated aqueous sodium bicarbonate solution and stirred for a while. Then, the solution was extracted with chloroform and washed with a saturated aqueous sodium bicarbonate solution and saturated saline solution. The organic layer was dried with anhydrous sodium sulfate. Subsequently, the solvent was distilled off and the residue was then purified through silica gel column chromatography (chloroform/methanol), thereby obtaining the subject compound (111 mg) as a brown solid.

MS(FAB, Pos.): m/z=785[M+H]$^+$ $^1$H-NMR(500 MHz, DMSO-$d_6$): δ=0.82(6H, t, J=7.3 Hz), 0.83(6H, t, J=7.0 Hz), 1.22–1.34(16H, m), 1.42(4H, sext., J=7.3 Hz), 1.66(4H, quint., J=7.0 Hz), 2.32(4H, t, J=7.2 Hz), 3.47(2H, s), 3.98(2H, s), 4.17(4H, s), 4.27(4H, t, J=6.6 Hz), 6.95(2H, d, J=1.7 Hz), 7.25(2H, d, J=8.4 Hz), 7.30(2H, d, J=8.2 Hz), 7.51(2H, d, J=1.7 Hz), 7.68(2H, d, J=8.4 Hz), 7.84(2H, d, J=8.2 Hz), 10.12(1H, s).

Production Example 96

Synthesis of 4-{[bis(1-butoxycarbonyl-1H-imidazol-2-ylmethyl)-amino]-methyl}-N-(4-dipropylaminomethylphenyl)-benzamide (Compound No. 97]

Example 96-1

Synthesis of 4-{[bis(1-butoxycarbonyl-1H-imidazol-2-ylmethyl)-amino]-methyl}-N-(4-dipropylaminomethylphenyl)-benzamide [Compound No. 97]

The compound obtained in Example 19-3 was treated with an anion-exchange resin and then dissolved in anhydrous chloroform (2.8 ml). Subsequently, the solution was added with triethylamine (0.059 ml) and n-butyl chloroformate (manufactured by Tokyo Kasei Kogyo Co., Ltd.) (0.044 ml), followed by stirring at room temperature for 17.5 hours. After completion of the reaction, the solution was added with chloroform (3.0 ml), washed with water, and dried with anhydrous magnesium sulfate, followed by distilling the solvent off. The residue was purified through silica gel column chromatography (chloroform/methanol), thereby obtaining the subject compound (66.9 mg) as a brown viscous substance.

MS(FAB, Pos.): m/z=700[M+H]$^+$
$^1$H-NMR(500 MHz, DMSO-d$_6$): δ=0.82(6H, t, J=7.3 Hz), 0.90(6H, t, J=7.3 Hz), 1.33–1.45(8H, m), 1.63–1.69(4H, m), 2.32(4H, br), 3.47(2H, br), 4.00(2H, s), 4.18(4H, s), 4.29 (4H, t, J=6.6 Hz), 6.94(2H, d, J=1.7 Hz), 7.25(2H, d, J=7.9 Hz), 7.31(2H, d, J=8.2 Hz), 7.52(2H, d, J=1.8 Hz), 7.68(2H, d, J=8.1 Hz), 7.84(2H, d, J=8.4 Hz) 10.12(1H, brs).

Production Example 97

Synthesis of N-(4-{[(1H-imidazol-2-ylmethyl)-(1-methyl-1H-imidazol-2-ylmethyl)-amino]-methyl}-benzyl)-N-methyl-N',N'-dipropylbutane-1,4-diamine [Compound No. 98)

Example 97-1

Synthesis of N-(4-{[(1H-imidazol-2-ylmethyl)-(1-methyl-1H-imidazol-2-ylmethyl)-amino]-methyl}-benzyl)-N-methyl-N',N'-dipropylbutane-1,4-diamine [Compound No. 98]

The hydrochloride of the compound obtained in Example 89-2 was treated with an anion-exchange resin. Then, the treated product was dissolved in anhydrous methanol (1.0 ml) and then added with sodium cyanoborohydride (21.9 mg), acetic acid (1.00 ml), and a 36% formaldehyde aqueous solution (19.6 µl), followed by stirring overnight under a nitrogen atmosphere at room temperature. After completion of the reaction, the solvent was distilled off. The residue was then dissolved in chloroform and added with a 1 mol/l sodium hydroxide aqueous solution, followed by stirring for a while. The solution was extracted with chloroform and then the extract was washed with saturated saline solution. Subsequently, the organic layer was dried with anhydrous sodium sulfate. The solvent was distilled off and the residue was then purified through silica gel column chromatography (chloroform/ethyl acetate) and treated with hydrochloric acid, thereby obtaining hydrochloride (89.9 mg) of the subject compound as a white solid.

MS(FAB, Pos.): m/z=480[M+H]$^+$
$^1$H-NMR(500 MHz, DMSO-d$_6$): δ=0.92(6H, t, J=7.3 Hz), 1.62–1.72(6H, m), 1.79(2H, brs), 2.98–3.02(6H, m), 3.08 (2H, t, J=7.9 Hz), 3.75(3H, s), 3.79(3H, s), 3.91–4.34(8H, m), 7.40(2H, d, J=8.1 Hz), 7.45(2H, d, J=8.1 Hz), 7.46(1H, d, J=2.0 Hz), 7.47(1H, d, J=2.0 Hz), 7.59(2H, s).

Production Example 98

Synthesis of 4-{[bis-(1H-imidazol-2-ylmethyl)-amino]-methyl}-N-[4-(cyclohexyl-methyl-amino)-butyl]-benzamide [Compound No. 99]

Example 98-1

Synthesis of 4-(cyclohexylamino-butyl)-carbamic acid t-butyl ester

N-(4-aminobutyl)carbamic acid t-butyl ester (manufactured by Tokyo Kasei Kogyo Co., Ltd.) (500 mg) was dissolved in anhydrous methanol (10 ml). The solution was added with cyclohexanone (312.8 mg) and sodium cyanoborohydride (217 mg) and then adjusted to pH 5 with acetic acid, followed by stirring at room temperature for 3 hours. After the reaction, the solvent was distilled off and the residue was added with a 1 mol/l sodium hydroxide aqueous solution, followed by extraction with chloroform. The extract was washed with saturated saline solution. The extract was dried with magnesium sulfate, and the solvent was distilled off. Consequently, the subject compound (720.3 mg) was obtained as a colorless oily substance.

MS(FAB, Pos.): m/z=271[M+H]$^+$

Example 98-2

Synthesis of N$^1$-cyclohexyl-N$^1$-methyl-1,4-butanediamine

Under ice-cooling, the compound (718 mg) obtained in Example 98-1 was dissolved in anhydrous methanol (15 ml) and a 36% formaldehyde aqueous solution (0.37 ml) was then added to the solution. Next, the solution was added with sodium cyanoborohydride (314 mg). Furthermore, acetic acid was added to the solution to adjust the solution to pH 5, followed by stirring for 5 minutes. After the solution had been stirred at room temperature for 16 hours, the solvent was distilled off and the residue was then added with a 1 mol/l sodium hydroxide aqueous solution, followed by extraction with chloroform. The extract was washed with saturated saline solution and dried with magnesium sulfate, followed by distilling the solvent off.

The residue was dissolved in methanol (15 ml) and added with a 4 mol/hydrogen chloride/dioxane solution (10 ml), followed by stirring under ice-cooling for 30 minutes. After the reaction, the solvent was distilled off and the residue was added with a 1 mol/l sodium hydroxide aqueous solution, followed by extraction with chloroform. The extract was washed with saturated saline solution and dried with magnesium sulfate, followed by distilling the solvent off. Consequently, the subject compound (475 mg) was obtained as a colorless oily substance.

MS(FAB, Pos.): m/z=185[M+H]$^+$
$^1$H-NMR(500 MHz, CDCl$_3$): δ=1.04–1.12(1H, m), 1.16–1.27(4H, m), 1.41–1.54(4H, m), 1.63–1.84(5H, m), 2.25(3H, s), 2.33–2.39(1H, m), 2.44(2H, t, J=7.3 Hz), 2.71 (2H, t, J=6.7 Hz).

Example 98-3

Synthesis of 4-{[bis-(1H-imidazol-2-ylmethyl)-amino]-methyl}-N-[4-(cyclohexyl-methyl-amino)-butyl]-benzamide [Compound No. 99]

The compound (120 mg) obtained in Example 2-2 was dissolved in anhydrous DMF (3.0 ml) and added with WSCI hydrochloride (103.3 mg) and HOBt (72.8 mg). Then, the solution was added with a solution of the compound (76.0 mg) obtained in Example 98-2 in DMF and stirred for 18 hours. After the reaction, the solvent was distilled off and the residue was then added with a 1 mol/l sodium hydroxide aqueous solution, followed by extraction with chloroform. The extract was washed with saturated saline solution and dried with magnesium sulfate, followed by distilling the solvent off. Subsequently, the residue was purified through silica gel column chromatography (chloroform/methanol) and then treated with hydrochloric acid, thereby obtaining hydrochloride (20.4 mg) of the subject compound as a white solid.

MS(FAB, Pos.): m/z=478[M+H]$^+$ $^1$H-NMR(500 MHz, DMSO-d$_6$+D$_2$O): δ=1.03–1.10(1H, m), 1.42(2H, q, J=7.5 Hz), 1.47–1.55(3H, m), 1.68(4H, s), 2.12(3H, s), 2.28(1H, s), 2.37(2H, t, J=7.0 Hz), 3.25(2H, t, J=7.0 Hz), 3.54(2H, s), 3.59(4H, s), 6.87(2H, s), 7.15(2H, s), 7.48–7.50(2H, m), 7.76–7.78(2H, m).

Production Example 99

Synthesis of N-[4-(cyclohexyl-methyl-amino)-butyl]-4-{[(1H-imidazol-2-ylmethyl)-(1-methyl-1H-imidazol-2-ylmethyl)-amino]-methyl}-benzamide [Compound No. 100]

Example 99-1

Synthesis of {4-[4-(cyclohexyl-methylamino)-butyl-carbamoyl]-benzyl}-(1H-imidazol-2-ylmethyl)-carbamic acid t-butyl ester The compound (401.1 mg) obtained in Example 98-2 was dissolved in anhydrous chloroform (12 ml). Then, the solution was added with the compound (795.3 mg) obtained in Example 1-1, HOBt (324.3 mg), and WSCI hydrochloride (460.1 mg) and stirred at room temperature for 16 hours. After the reaction, the solution was added with water and then subjected to extraction with chloroform. The extract was washed with a 1 mol/l sodium hydroxide aqueous solution and saturated saline solution and dried with anhydrous magnesium sulfate. The solvent was distilled off and the residue was then purified through silica gel column chromatography (chloroform/methanol), thereby obtaining the subject compound (778.9 mg) as a white solid.

MS(FAB, Pos.): m/z=497[M+H]$^+$ $^1$H-NMR(500 MHz, DMSO-d$_6$): δ=1.02–1.04(1H, m), 1.06–1.16(4H, m), 1.34(9H, s), 1.37–1.42(2H, m), 1.48–1.54(3H, m), 1.67–1.70(4H, m), 2.12(3H, s), 2.24–2.27(1H, m), 2.37(2H, t, J=6.9 Hz), 3.22–3.26(2H, m), 4.32(1H, br), 4.41(2H, br), 4.47(1H, br), 6.84(1H, s), 7.04 (1H, s), 7.24(2H, br), 7.78(2H, d, J=8.2 Hz), 8.42(1H, t, J=5.5 Hz), 11.95(1H, br).

Example 99-2

Synthesis of N-[4-(cyclohexyl-methyl-amino)-butyl]-4-{[(1H-imidazol-2-ylmethyl)-(1-methyl-1H-imidazol-2-ylmethyl)-amino]-methyl}-benzamide [Compound No. 100]

The compound (778.9 mg) obtained in Example 99-1 was dissolved in methanol (7.8 ml) and added with a 4 mol/l hydrogen chloride/dioxane solution (7.8 ml), followed by stirring at room temperature for 4 hours. After the reaction, the solvent was distilled off. The residue was added with a 1 mol/l sodium hydroxide aqueous solution, followed by extraction with chloroform. The extract was dried with anhydrous magnesium sulfate and the solvent was then distilled off.

The residue was dissolved in anhydrous methanol (28 ml) and added with 1-methyl-2-imidazole carboxaldehyde (259.9 mg) and sodium cyanoborohydride (197.3 mg), followed by adjusting the solution to pH 5 with acetic acid and stirring at room temperature for 3 days. After the reaction, the solvent was distilled off. Then, the residue was added with a 1 mol/l sodium hydroxide aqueous solution, followed by extraction with chloroform. The extract was dried with anhydrous magnesium sulfate. The solvent was distilled off. Then, the residue was then purified through silica gel column chromatography (chloroform/methanol) and treated with hydrochloric acid, thereby obtaining hydrochloride (802.0 mg) of the subject compound as a white solid.

MS(FAB, Pos.): m/z=492[M+H]$^+$ $^1$H-NMR(500 MHz, DMSO-d$_6$): δ=1.08–1.10(1H, m), 1.22–1.29(2H, m), 1.37–1.42(2H, m), 1.51–1.60(3H, m), 1.68–1.79(4H, m), 2.00(1H, d, J=11.4 Hz), 2.09(1H, d, J=11.9 Hz), 2.62(3H, d, J=4.9 Hz), 2.96(1H, m), 3.08–3.17 (2H, m), 3.27(2H, q, J=6.3 Hz), 3.71(3H, s), 3.76(2H, s), 4.20(2H, s), 7.49–7.55(4H, m), 7.64(2H, s), 7.79(2H, d, J=8.2 Hz), 8.63(1H, t, J=5.3 Hz), 10.52(1H, br), 15.04(2H, br).

Production Example 100

Synthesis of 4-{[(3,5-dimethyl-pyridin-2-ylmethyl)-(1H-imidazol-2-ylmethyl)-amino]-methyl}-N-(4-dipropylaminomethyl-phenyl)-benzamide [Compound No. 101]

Example 100-1

Synthesis of 3,5-dimethyl-pyridine-2-carboxaldehyde

In dichloromethane (15.0 ml), 2,3,5-trimethyl-pyridine (1.29 g) was dissolved. The reaction solution was cooled to 0° C. and added with meta-chloroperbenzoic acid (2.53 g), followed by stirring at room temperature for 1.5 hours. The reaction solution was added with a 1 mol/l sodium hydroxide aqueous solution and then subjected to extraction with chloroform. Subsequently, the organic layer was washed with saturated saline solution and dried with anhydrous sodium sulfate. The drying agent was filtrated out and the solvent was then distilled off, followed by dissolving the resulting residue in dichloromethane (25.0 ml). The reaction solution was added with trifluoroacetic anhydride (2.8 ml) and subjected to thermal reflux for 3.5 hours. After the reaction solution had been cooled to room temperature, the solvent was distilled off. The residue obtained was dissolved in methanol (60.0 ml). After having been cooled to 0° C., the reaction solution was added with a 12.5% sodium methoxide/methanol solution to adjust to pH 10, followed by stirring at room temperature for 16.5 hours. After the solvent had been distilled off, the residue was added with distilled water and extracted with chloroform. The organic layer was washed with saturated saline solution and dried with anhydrous sodium sulfate. The drying agent was filtrated out and the solvent was then distilled off, followed by dissolving the resulting residue in chloroform (30.0 ml). The reaction solution was added with manganese dioxide (chemically processed product) (6.10 g) and then stirred at room temperature for 18 hours. The reaction solution was filtrated through Celite. The solvent in the filtrate was distilled off and the residue obtained was then purified through silica gel column chromatography (chloroform/ethyl acetate), thereby obtaining the subject compound (1.14 g) as a yellow oily substance.

MS(FAB, Pos.): m/z=136[M+H]$^+$
$^1$H-NMR(500 MHz, CDCl$_3$): δ=2.40(3H, s), 2.63(3H, s), 7.43(1H, brs), 8.48(1H, brs), 10.16(1H, s).

Example 100-2

Synthesis of 4-{[(3,5-dimethyl-pyridin-2-ylmethyl)-(1H-imidazol-2-ylmethyl)-amino]-methyl}-N-(4-dipropylaminomethyl-phenyl)-benzamide [Compound No. 101]

The compound (146.2 mg) obtained in Example 47-3 was dissolved in anhydrous methanol (5.8 ml) and added with the compound (71.6 mg) obtained in Example 100-1 and sodium cyanoborohydride (66.0 mg), followed by adjusting the solution to pH 5 with acetic acid and stirring at room temperature for 16.5 hours. After the reaction, the solution was added with chloroform and washed with a 1 mol/l sodium hydroxide aqueous solution. Then, the solution was dried with anhydrous magnesium sulfate. The solvent was distilled off. The residue was purified through silica gel column chromatography (chloroform/methanol) and treated with hydrochloric acid, thereby obtaining hydrochloride (110.7 mg) of the subject compound as a white solid.

MS(FAB, Pos.): m/z=539[M+H]$^+$
$^1$H-NMR(500 MHz, DMSO-d$_6$+D$_2$O): δ=0.89(6H, t, J=7.3 Hz), 1.64–1.75(4H, m), 2.32(3H, s), 2.37(3H, s), 2.92–2.99(4H, m), 3.81(2H, s), 4.07(2H, s), 4.20(2H, s), 4.28(2H, s), 7.51–7.54(4H, m), 7.63(2H, s), 7.85(4H, t, J=8.5 Hz), 8.04(1H, br), 8.47(1H, s).

Production Example 101

Synthesis of N-(4-dipropylaminomethyl-phenyl)-4-{[(5-ethyl-pyridin-2-ylmethyl)-(1H-imidazol-2-ylmethyl)-amino]-methyl}-benzamide [Compound No. 102]

Example 101-1

Synthesis of 5-ethyl-pyridine-2-carboxaldehyde

In dichloromethane (25.0 ml), 5-ethyl-2-methyl-pyridine (2.31 g) was dissolved. The reaction solution was cooled to 0° C. and added with meta-chloroperbenzoic acid (4.43 g), followed by stirring at room temperature for 2.5 hours. The reaction solution was added with a 1 mol/l sodium hydroxide aqueous solution and then subjected to extraction with chloroform. Subsequently, the organic layer was washed with saturated saline solution and dried with anhydrous sodium sulfate. The drying agent was filtrated out and the solvent was then distilled off, followed by dissolving the resulting residue in dichloromethane (40.0 ml). The reaction solution was added with trifluoroacetic anhydride (5.6 ml) and subjected to thermal reflux for 3.5 hours. After the reaction solution had been cooled to room temperature, the solvent was distilled off. The residue obtained was dissolved in methanol (80.0 ml). After having been cooled to 0° C., the reaction solution was added with a 12.5% sodium methoxide/methanol solution and adjusted to pH 10, followed by stirring at room temperature for 16.5 hours. After the solvent had been distilled off, the residue was added with distilled water and extracted with chloroform. The organic layer was washed with saturated saline solution and dried with anhydrous sodium sulfate. The drying agent was filtrated out and the solvent was then distilled off, followed by dissolving the resulting residue in chloroform (50.0 ml). The reaction solution was added with manganese dioxide (chemically processed product) (7.44 g) and then stirred at room temperature for 18 hours. The reaction solution was filtrated through Celite. The solvent in the filtrate was distilled off and the residue obtained was then purified through silica gel column chromatography (chloroform/ethyl acetate), thereby obtaining the subject compound (515.6 mg) as a yellow oily substance.

MS(FAB, Pos.): m/z=136[M+H]$^+$
$^1$H-NMR(500 MHz, CDCl$_3$): δ=1.31(3H, t, J=7.6 Hz), 2.77(2H, q, J=7.6 Hz), 7.70(1H, d, J=7.8 Hz), 7.91(1H, d, J=7.8 Hz), 10.06(1H, s).

Example 101-2

Synthesis of N-(4-dipropylaminomethyl-phenyl)-4-{[(5-ethyl-pyridin-2-ylmethyl)-(1H-imidazol-2-ylmethyl)-amino]-methyl}-benzamide [Compound No. 102]

The compound (147.4 mg) obtained in Example 47-3 was dissolved in anhydrous methanol (5.8 ml) and added with the compound (71.6 mg) obtained in Example 101-1 and sodium cyanoborohydride (66.0 mg), followed by adjusting the solution to pH 5 with acetic acid and stirring at room temperature for 16.5 hours. After the reaction, the solution was added with chloroform and washed with a 1 mol/l sodium hydroxide aqueous solution. Then, the solution was dried with anhydrous magnesium sulfate. The solvent was distilled off. The residue was purified through silica gel column chromatography (chloroform/methanol) and treated with hydrochloric acid, thereby obtaining hydrochloride (65.1 mg) of the subject compound as a white solid.

MS(FAB, Pos.): m/z=539[M+H]$^+$
$^1$H-NMR(500 MHz, DMSO-d$_6$+D$_2$O): δ=0.88(6H, t, J=7.5 Hz), 1.19(3H, t, J=7.5 Hz), 1.64–1.75(4H, m), 2.71(2H, q, J=7.5 Hz), 2.92–2.98(4H, m), 3.80(2H, s), 4.02(2H, s), 4.14(2H, s), 4.28(2H, s), 7.53(4H, d, J=7.0 Hz), 7.60(2H, s), 7.78(1H, d, J=8.6 Hz), 7.85–7.88(4H, m), 8.11(1H, br), 8.57(1H, br).

Production Example 102

Synthesis of N-(4-cyclohexylamino-butyl)-4-{[(1H-imidazol-2-ylmethyl)-(1-methyl-1H-imidazol-2-ylmethyl)-amino]-methyl}-benzenesulfonamide [Compound No. 103]

Example 102-1

Synthesis of {4-[4-(1,3-dioxo-1,3-dihydro-isoindol-2-ylmethyl)-benzenesulfonylamino]-butyl}-carbamic acid t-butyl ester The compound (1.4396 g) obtained in Example 24-2 was dissolved in anhydrous chloroform (28 ml) and then added with triethylamine (0.689 ml), followed by ice-cooling. Then, the solution was added with (4-aminobutyl)-carbamic acid t-butyl ester (852.9 mg) and stirred at room temperature for 2.5 hours. After the reaction, the solution was washed with water and dried with anhydrous magnesium sulfate. The solvent was distilled off and the residue was then purified through silica gel column chromatography (chloroform/methanol), thereby obtaining the subject compound (1.4440 g) as a white solid.

MS(FAB, Pos.): m/z=488[M+H]$^+$ $^1$H-NMR(500 MHz, DMSO-d$_6$): δ=1.29–1.36(4H, m), 1.35(9H, s), 2.67(2H, d, J=4.9 Hz), 2.82(2H, d, J=6.1 Hz), 4.86(2H, s), 6.58(1H, t, J=5.7 Hz), 7.51(2H, d, J=8.5 Hz), 7.57(1H, t, J=6.0 Hz), 7.73(2H, d, J=8.4 Hz), 7.86–7.93(4H, m).

Example 102-2

Synthesis of [4-(4-{[(1H-imidazol-2-ylmethyl)-amino]-methyl}-benzenesulfonylamino)-butyl]-carbamic acid t-butyl ester The compound (1.444 g) obtained in Example 102-1 was dissolved in a 40% methylamine/methanol solution (21.6 ml) and stirred at room temperature for 16 hours. After the reaction, the solvent was distilled off and the residue was then added with chloroform. The solution was added with a 1 mol/l sodium hydroxide aqueous solution and subjected to extraction with chloroform. The extract was washed with saturated saline solution and dried with anhydrous magnesium sulfate. The solvent was distilled off. The residue was dissolved in anhydrous methanol (35.5 ml) and then added with 2-imidazole carboxaldehyde (357.5 mg) and trimethyl orthoformate (0.814 ml), followed by stirring at room temperature for 2 hours. The solution was cooled with ice and then added with sodium borohydride (281.5 mg), followed by stirring at room temperature for 3 hours. After the reaction, the solvent was distilled off and the residue was then added with water, followed by extraction with chloroform. The extract was washed with saturated saline solution and dried with anhydrous magnesium sulfate. The solvent was distilled off and the residue was then purified through silica gel column chromatography (chloroform/methanol), thereby obtaining the subject compound (819.2 mg) as a white solid.

MS(FAB, Pos.): m/z=438[M+H]$^+$

Example 102-3

Synthesis of [4-(4-{[(1H-imidazol-2-ylmethyl)-(1-methyl-1H-imidazol-2-ylmethyl)-amino]-methyl}-benzenesulfonylamino)-butyl]-carbamic acid t-butyl ester The compound (817.3 mg) obtained in Example 102-2 was dissolved in anhydrous methanol (24.5 ml) and added with 1-methyl-2-imidazolealdehyde (309.4 mg) and sodium cyanoborohydride (235.0 mg). Then, the solution was adjusted to pH 5 with acetic acid and stirred at room temperature for 24 hours. After the reaction, the solvent was distilled off. The residue was added with a 1 mol/l sodium hydroxide aqueous solution and then subjected to extraction with chloroform. The extract was dried with anhydrous magnesium sulfate and the solvent was distilled off. Subsequently, the residue was purified through silica gel column chromatography (chloroform/methanol), thereby obtaining the subject compound (910.0 mg) as a white solid.

MS(FAB, Pos.): m/z=532[M+H]$^+$

Example 102-4

Synthesis of N-(4-amino-butyl)-4-{[(1H-imidazol-2-ylmethyl)-(1-methyl-1H-imidazol-2-ylmethyl)-amino]-methyl}-benzenesulfonamide The compound (902.3 mg) obtained in Example 102-3 was dissolved in methanol (4.0 ml) and added with a 4 mol/l hydrogen chloride/dioxane solution (4.0 ml), followed by stirring at room temperature for 8.5 hours. After the reaction, the solvent was dissolved off. The residue was added with a 1 mol/l sodium hydroxide aqueous solution (7 ml) and subjected to extraction with chloroform. Then, the extract was dried with magnesium sulfate and the solvent was dissolved off. The residue was then purified through a solid-phase extraction column (ODS type), thereby obtaining the subject compound (844.3 mg) as a brown viscous solid.

MS(FAB, Pos.): m/z=432[M+H]$^+$

Example 102-5

Synthesis of N-(4-cyclohexylamino-butyl)-4-{[(1H-imidazol-2-ylmethyl)-(1-methyl-1H-imidazol-2-ylmethyl)-amino]-methyl}-benzenesulfonamide [Compound No. 103]

The compound (173.5 mg) obtained in Example 102-4 was dissolved in anhydrous methanol (7.0 ml). Then, the solution was added with cyclohexanone (0.083 ml) and sodium cyanoborohydride (75.4 mg) and adjusted to pH 5 with acetic acid, followed by stirring at room temperature for 16.5 hours. After the reaction, the solvent was distilled off. Subsequently, the residue was added with a 1 mol/l sodium hydroxide aqueous solution (7.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (161.6 mg) of the subject compound as a white solid.

MS(FAB, Pos.): m/z=514[M+H]$^+$ $^1$H-NMR(500 MHz, DMSO-d$_6$+D$_2$O): δ=1.09–1.11(1H, m), 1.19–1.30(4H, m), 1.44–1.47(2H, m), 1.60(3H, d, J=7.9 Hz), 1.76(2H, brs), 1.99(2H, brs), 2.69 (t, J=6.4 Hz), 2.86 (2H, t, J=7.6 Hz), 2.94(1H, br), 3.73(3H, s), 3.81(2H, s), 4.10(2H, s), 4.17(2H, s), 7.46–7.60(4H, m), 7.61(2H, d, J=5.0 Hz), 7.66(2H, d, J=8.4 Hz).

Production Example 103

Synthesis of N-cyclohexyl-N'-(4-{[(1H-imidazol-2-ylmethyl)-(1-methyl-1H-imidazol-2-ylmethyl)-amino]-methyl}-benzyl)-N'-methyl-butane-1,4-diamine [Compound No. 104]

Example 103-1

Synthesis of 4-(t-butoxycarbonylaminomethyl)benzoic acid methyl ester

Commercially available 4-aminomethylbenzoic acid methyl ester (16.3 g) was dissolved in chloroform (489 ml) and added with triethylamine (14.6 ml) and di-t-butyl dicarbonate (10.6 g), followed by stirring at room temperature for 2 hours. The reaction solution was added with water and subjected to separation/extraction with chloroform. The resulting organic layer was dried with anhydrous sodium sulfate and then concentrated under reduced pressure, thereby obtaining the subject compound (24.85 g).

Example 103-2

Synthesis of (4-hydroxymethyl-benzyl)-carbamic acid t-butyl ester

Lithium aluminum hydride (5.21 g) was suspended in THF (243 ml). Then, a solution of the compound (24.3 g) obtained in Example 103-1 in THF (243 ml) was gradually added to the suspension over 50 minutes while stirring under ice-cooling, followed by stirring at room temperature for 1 hour. The reaction solution was added with sodium sulfate decahydrate and a 20% sodium hydroxide aqueous solution and then filtrated through Celite. The filtrate was concentrated under reduced pressure and dried under vacuum, thereby obtaining the subject compound (18.5 g).

Example 103-3

Synthesis of (4-formyl-benzyl)-carbamic acid t-butyl ester

The compound (18.0 g) obtained in Example 103-2 was dissolved in chloroform (540 ml) and then added with manganese dioxide (chemically processed product) (118 g), followed by stirring at room temperature for 15 hours. The reaction solution was filtrated through Celite and the filtrate was then concentrated under reduced pressure. The residue was purified through silica gel column chromatography (chloroform/ethyl acetate), thereby obtaining the subject compound (17.1 g) as a white solid.

Example 103-4

Synthesis of 14-[4-(t-butoxycarbonylamino-methyl)-benzylamino]-butyl}-carbamic acid benzyl ester The compound (951.6 mg) obtained in Example 103-3 was dissolved in anhydrous methanol (38 ml) and added with (4-amino-butyl)-carbamic acid benzyl ester (898.0 mg) and trimethyl orthoformate (1.33 ml), followed by stirring at room temperature for 15.5 hours. After that, the solution was cooled with ice and added with sodium borohydride (458.5 mg), followed by stirring at room temperature for 1.5 hours. After the reaction, the solvent was distilled off and the residue was then added with water, followed by extraction with chloroform. The extract was washed with saturated saline solution and dried with anhydrous magnesium sulfate. The solvent was distilled off and the residue was then purified through silica gel column chromatography (chloroform/ethyl acetate), thereby obtaining the subject compound (1.1479 g) as a colorless oily substance.

MS(FAB, Pos.): m/z=442[M+H]$^+$

Example 103-5

Synthesis of {4-[(4-{[(1H-imidazol-2-ylmethyl)-amino]-methyl}-benzyl)-methyl-amino]-butyl}-carbamic acid benzyl ester The compound (1.1479 g) obtained in Example 103-4 was dissolved in anhydrous methanol (33 ml) and added with a 36% formaldehyde aqueous solution (0.602 ml) and sodium cyanoborohydride (490.1 mg). Then, the solution was adjusted to pH 5 with acetic acid and stirred at room temperature for 20 hours. After the reaction, the solution was added with chloroform and washed with a 1 mol/l sodium hydroxide aqueous solution, followed by drying with anhydrous magnesium sulfate. Then, the solvent was distilled off.

The residue was dissolved in methanol (12 ml) and then added with a 4 mol/l hydrogen chloride/dioxane solution (12 ml), followed by stirring at room temperature for 4 hours. After the reaction, the solvent was distilled off. The residue was added with a 1 mol/l sodium hydroxide aqueous solution and extracted with chloroform. The extract was dried with anhydrous magnesium sulfate and the solvent was then distilled off.

The residue was dissolved in anhydrous methanol (33 ml) and added with 2-imidazole carboxaldehyde (339.2 mg) and trimethyl orthoformate (0.771 ml), followed by stirring at room temperature for 14 hours. Subsequently, the solution was cooled with ice and then added with sodium borohydride (266.7 mg), followed by stirring at room temperature for 8 hours. After the reaction, the solvent was distilled off. The residue was added with water and subjected to extraction with chloroform. The extract was washed with saturated saline solution and dried with anhydrous magnesium sulfate. The solvent was distilled off and the residue was then purified through silica gel column chromatography (chloroform/methanol), thereby obtaining the subject compound (608.7 mg) in a colorless oily substance.

MS(FAB, Pos.): m/z=435[M+H]$^+$

Example 103-6

Synthesis of {4-[(4-{[(1H-imidazol-2-ylmethyl)-(1-methyl-1H-imidazol-2-ylmethyl)-amino]-methyl}-benzyl)-methyl-amino]-butyl}-carbamic acid benzyl ester The compound (608.7 mg) obtained in Example 103-5 was dissolved in anhydrous methanol (24 ml) and added with 1-methyl-2-imidazole carboxaldehyde (231.3 mg) and sodium cyanoborohydride (176.0 mg). The solution was adjusted to pH 5 with acetic acid, followed by stirring at room temperature for 3 days. After the reaction, the solvent was distilled off. The residue was added with a 1 mol/l sodium hydroxide aqueous solution and subjected to extraction with chloroform. The extract was dried with anhydrous magnesium sulfate. The solvent was distilled off and the residue was then purified through silica gel column chromatography (chloroform/methanol), thereby obtaining the subject compound (502.6 mg) as a colorless oily substance.

MS(FAB, Pos.): m/z=530[M+H]$^+$

Example 103-7

Synthesis of N$^1$-(4-{[(1H-imidazol-2-ylmethyl)-(1-methyl-1H-imidazol-2-ylmethyl)-amino]-methyl}-benzyl)-N$^1$-methyl-butan-1,4-diamine The compound (502.6 mg) obtained in Example 103-6 was dissolved in methanol (2.5 ml) and cooled with ice. Then, the solution was added with a suspension of 10% palladium-carbon (251.3 mg) in ethanol (2 ml), followed by stirring at room temperature for 2 hours under a hydrogen atmosphere. After the reaction, the solution was filtrated through Celite and the solvent was then distilled off, thereby obtaining the subject compound (382.4 mg) as a white solid.

MS(FAB, Pos.): m/z=396[M+H]$^+$

Example 103-8

Synthesis of N-cyclohexyl-N'-(4-{[(1H-imidazol-2-ylmethyl)-(1-methyl-1H-imidazol-2-ylmethyl)-amino]-methyl}-benzyl)-N'-methyl-butane-1,4-diamine [Compound No. 104]

The compound (110.0 mg) obtained in Example 103-7 was dissolved in anhydrous methanol (4.4 ml). Then, the solution was added with cyclohexanone (0.058 ml) and sodium cyanoborohydride (52.8 mg) and adjusted to pH 5 with acetic acid, followed by stirring at room temperature for 16.5 hours. After the reaction, the solvent was distilled off. Subsequently, the residue was added with a 1 mol/l sodium hydroxide aqueous solution (3.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (96.7 mg) of the subject compound as a white solid.

MS(FAB, Pos.): m/z=478[M+H]$^+$ $^1$H-NMR(500 MHz, DMSO-d$_6$+D$_2$O): δ=1.10–1.12(1H, m), 1.21–1.34(4H, m), 1.60–1.67(3H, m), 1.76–1.83(4H, m), 2.02–2.04(2H, m), 2.58(3H, s), 2.92–3.01(4H, m), 3.06–3.10(1H, m), 3.72(4H, s), 3.74(2H, s), 4.10(3H, s), 4.18(2H, s), 7.41(2H, d, J=8.2 Hz), 7.46(2H, d, J=8.2 Hz), 7.49(2H, s), 7.61(2H, s).

Production Example 104

Synthesis of N-(4-dipropylamino-butyl)-4-{[(1H-imidazol-2-ylmethyl)-(1-methyl-1H-imidazol-2-ylmethyl)-amino]-methyl}-benzenesulfonamide [Compound No. 105]

Example 104-1

Synthesis of N-(4-dipropylamino-butyl)-4-{[(1H-imidazol-2-ylmethyl)-(1-methyl-1H-imidazol-2-ylmethyl)-amino]-methyl}-benzenesulfonamide [Compound No. 105]

The compound (76.9 mg) obtained in Example 102-4 was dissolved in anhydrous methanol (3.0 ml). Then, the solution was added with propionaldehyde (0.039 ml) and sodium cyanoborohydride (45.2 mg) and adjusted to pH 5 with acetic acid, followed by stirring at room temperature for 16.5 hours. After the reaction, the solvent was distilled off. Subsequently, the residue was added with a 1 mol/l sodium hydroxide aqueous solution (2.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (36.9 mg) of the subject compound as a white solid.

MS(FAB, Pos.): m/z=516[M+H]$^+$ $^1$H-NMR(500 MHz, DMSO-d$_6$+D$_2$O): δ=0.90(6H, t, J=7.3 Hz), 1.44(2H, t, J=7.2 Hz), 1.61–1.68(6H, m), 2.69–2.72(2H, m), 2.95–3.03(6H, m), 3.73(3H, s), 3.82(2H, s), 4.12(2H, s), 4.19(2H, s), 7.46–7.55(2H, m), 7.57(2H, d, J=8.5 Hz), 7.61(2H, s), 7.67(2H, d, J=8.4 Hz).

Production Example 105

Synthesis of N-(4-diisobutylamino-butyl)-4-{[(1H-imidazol-2-ylmethyl)-(1-methyl-1H-imidazol-2-ylmethyl)-amino]-methyl}-benzenesulfonamide [Compound No. 106]

Example 105-1

Synthesis of N-(4-diisobutylamino-butyl)-4-{[(1H-imidazol-2-ylmethyl)-(1-methyl-1H-imidazol-2-ylmethyl)-amino]-methyl}-benzenesulfonamide [Compound No. 106]

The compound (86.1 mg) obtained in Example 102-4 was dissolved in anhydrous methanol (3.4 ml). Then, the solution was added with isobutylaldehyde (0.055 ml) and sodium cyanoborohydride (50.3 mg) and adjusted to pH 5 with acetic acid, followed by stirring at room temperature for 16.5 hours. After the reaction, the solvent was distilled off. Subsequently, the residue was added with a 1 mol/l sodium hydroxide aqueous solution (2.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (10.1 mg) of the subject compound as a white solid.

MS(FAB, Pos.): m/z=544[M+H]$^+$ $^1$H-NMR(500 MHz, DMSO-d$_6$+D$_2$O): δ=0.97(12H, t, J=6.4 Hz), 1.44(2H, t, J=7.2 Hz), 1.65–1.66(2H, m), 2.04(2H, t, J=6.9 Hz), 2.71(2H, t, J=6.7 Hz), 2.87–2.94(4H, m), 3.02–3.06(2H, m), 3.72(3H, s), 3.80(2H, s), 4.08(2H, s), 4.15(2H, s), 7.46–7.57(4H, m), 7.61(2H, s), 7.67(2H, d, J=8.5 Hz).

Production Example 106

Synthesis of 4-{[(1H-imidazol-2-ylmethyl)-(1-methyl-1H-imidazol-2-ylmethyl)-amino]-methyl}-N-(4-isobutylamino-butyl)-benzenesulfonamide [Compound No. 107]

Example 106-1

Synthesis of 4-{[(1H-imidazol-2-ylmethyl)-(1-methyl-1H-imidazol-2-ylmethyl)-amino]-methyl}-N-(4-isobutylamino-butyl)-benzenesulfonamide [Compound No. 107]

The compound (86.1 mg) obtained in Example 102-4 was dissolved in anhydrous methanol (3.4 ml). Then, the solution was added with isobutylaldehyde (0.055 ml) and sodium cyanoborohydride (50.3 mg) and adjusted to pH 5 with acetic acid, followed by stirring at room temperature for 16.5 hours. After the reaction, the solvent was distilled off. Subsequently, the residue was added with a 1 mol/l sodium hydroxide aqueous solution (2.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (3.8 mg) of the subject compound as a white solid.

MS(FAB, Pos.): m/z=488[M+H]$^+$
$^1$H-NMR(500 MHz, DMSO-d$_6$+D$_2$O): δ=0.94(6H, d, J=6.7 Hz), 1.43–1.46(2H, m), 1.63(2H, m), 1.91–1.94(1H, m), 2.67–2.73(4H, m), 2.84–2.87(2H, m), 3.71(3H, s), 3.80 (2H, s), 4.06(2H, s), 4.12(2H, s), 7.47(2H, d, J=9.6 Hz), 7.54(2H, d, J=8.2 Hz), 7.68(2H, d, J=8.4 Hz).

Production Example 107

Synthesis of 4-{[bis-(1H-imidazol-2-ylmethyl)-amino]-methyl}-N-(4-dipropylamino-butyl)-N-methylbenzamide [Compound No. 108]

Example 107-1

Synthesis of N-methyl-N,N-dipropyl-butan-1,4-diamine

Formic acid (0.29 ml) was added to acetic anhydride (0.60 ml) and the whole was subjected to thermal reflux for 1.5 hours. After the reaction, the solution was cooled to room temperature. Then, the solution was added with THF (2.0 ml) and a solution (8.0 ml) of the compound (400 mg) obtained in Example 1-2 in THF, followed by stirring at room temperature for about 4 hours. After the reaction, the solvent was distilled off.

Lithium aluminum hydride (429 mg) was suspended in anhydrous THF (10 ml) and then dropwisely added with a solution (8.0 ml) of the previously-obtained compound in anhydrous THF, followed by stirring at room temperature for 4 hours. Then, the solution was added with sodium sulfate decahydrate and then added with a 20% sodium hydroxide aqueous solution. The suspension was filtrated through Celite and the solvent was then distilled off. The residue was purified through silica gel column chromatography (chloroform/ethyl acetate), thereby obtaining the subject compound (61.8 mg) as a colorless oily substance.

MS(FAB, Pos.): m/z=187[M+H]$^+$
$^1$H-NMR(500 MHz, CDCl$_3$): δ=0.87(6H, t, J=7.3 Hz), 1.41–1.50(8H, m), 2.35–2.42(6H, m), 2.43(3H, s), 2.58(2H, t, J=6.8 Hz).

Example 107-2

Synthesis of 4-{[bis-(1H-imidazol-2-ylmethyl)-amino]-methyl}-N-(4-dipropylamino-butyl)-N-methylbenzamide [Compound No. 108]

The compound (120 mg) obtained in Example 2-2 was dissolved in DMF (3.5 ml). The solution was added with DCC (79.4 mg) and HOBt (62.4 mg), followed by stirring at room temperature for 4 hours. The compound (60.0 mg) obtained in Example 107-1 was stirred at room temperature for 86 hours. After the reaction, the solvent was distilled off and then the residue was added with chloroform, followed by extraction with 1 mol/l hydrochloric acid. The extract was made basic with a 1 mol/l sodium hydroxide aqueous solution, followed by extraction with chloroform.

Subsequently, the extract was dried with magnesium sulfate and the solvent was then dissolved. The residue was purified through silica gel column chromatography (chloroform/ethyl acetate) and treated with hydrochloric acid, thereby obtaining hydrochloride (10.8 mg) of the subject compound as a white solid.

MS(FAB, Pos.): m/z=480[M+H]$^+$
$^1$H-NMR(500 MHz, DMSO-d$_6$+H$_2$O): δ=0.91(6H, t, J=7.0 Hz), 1.45–1.53(2H, m), 1.64–1.67(6H, m), 2.80–3.15 (11H, m), 3.72(2H, s), 4.14(2H, s), 7.26(2H, d, J=8.0 Hz), 7.42(2H, 8.0 Hz), 7.57(4H, s).

Production Example 108

Synthesis of N-[4-(cyclohexyl-methyl-amino)-butyl]-4-{[(1H-imidazol-2-ylmethyl)-(1-methyl-1H-imidazol-2-ylmethyl)-amino]-methyl}-benzenesulfonamide [Compound No. 109]

Example 108-1

Synthesis of N-[4-(cyclohexyl-methyl-amino)-butyl]-4-{[(1H-imidazol-2-ylmethyl)-(1-methyl-1H-imidazol-2-ylmethyl)-amino]-methyl}-benzenesulfonamide [Compound No. 109]

The compound (69.5 mg) obtained in Example 102-5 was treated with an anion-exchange resin (Amberlite IRA-410), and the treated product was dissolved in anhydrous methanol (2.7 ml). The solution was added with a 36% formaldehyde aqueous solution (0.025 ml). Subsequently, the solution was added with sodium cyanoborohydride (20.7 mg) and adjusted to pH 5 with acetic acid, followed by stirring at room temperature for 20 hours. After the reaction, the solution was added with a 1 mol/l sodium hydroxide aqueous solution (1.0 ml), followed by extraction with chloroform. The extract was dried with magnesium sulfate. The solvent was distilled off. Then, the residue was purified through silica gel column chromatography (chloroform/methanol) and treated with hydrochloric acid, thereby obtaining hydrochloride (34.8 mg) of the subject compound as a white solid.

MS(FAB, Pos.): m/z=528[M+H]$^+$
$^1$H-NMR(500 MHz, DMSO-d$_6$+D$_2$O): δ=1.09–1.14(1H, m), 1.23–1.46(6H, m), 1.59–1.65(3H, m), 1.79–1.82(2H, m), 1.93–1.97(2H, m), 2.65(3H, s), 2.70(2H, t, J=6.6 Hz), 2.89–2.95(1H, m), 3.03–3.12(2H, m), 3.72(3H, s), 3.81(2H, s), 4.09(2H, s), 4.16(2H, s), 7.46–7.57(4H, m), 7.60(2H, s), 7.67(2H, d, J=8.5 Hz).

Production Example 109

Synthesis of 2-[(4-dipropylamino-butyl)-(4-{[(1H-imidazol-2-ylmethyl)-(1-methyl-1H-imidazol-2-ylmethyl)-amino]-methyl}-benzyl)-amino]-ethanol [Compound No. 110]

Example 109-1

Synthesis of 2-[(4-dipropylamino-butyl)-(4-{[(1H-imidazol-2-ylmethyl)-(1-methyl-1H-imidazol-2-ylmethyl)-amino]-methyl}-benzyl)-amino]-ethanol [Compound No. 110]

The compound (209.3 mg) obtained in Example 89-2 was dissolved in anhydrous methanol (8.4 ml). Then, the solution was added with [1,4]dioxan-2,5-diol (54.0 mg) and sodium cyanoborohydride (56.6 mg) and adjusted to pH 5 with acetic acid, followed by stirring at room temperature for 19.5 hours. After the reaction, the solvent was distilled off. Subsequently, the residue was added with a 1 mol/l sodium hydroxide aqueous solution (1.0 ml), followed by extraction with chloroform. The extract was dried with magnesium sulfate and the solvent was then distilled off. The residue was purified through silica gel column chromatography (chloroform/methanol) and then treated with hydrochloric acid, thereby obtaining hydrochloride (175.8 mg) of the subject compound as a white solid.

MS(FAB, Pos.): m/z=510[M+H]$^+$ $^1$H-NMR(500 MHz, DMSO-d$_6$+D$_2$O): δ=0.92(6H, t, J=7.1 Hz), 1.64–1.68(6H, m), 1.78–1.82(2H, m), 3.00–3.08 (10H, m), 3.71(3H, s), 3.74(4H, s), 4.09(2H, s), 4.17(2H, s), 4.30 (2H, q, J=13.9 Hz), 7.41(2H, d, J=7.8 Hz), 7.48(4H, d, J=5.6 Hz), 7.61(2H, s).

Production Example 110

Synthesis of 4-{[(1H-imidazol-2-ylmethyl)-(1-methyl-1H-imidazol-2-ylmethyl)-amino]-methyl}-N-{4-[(3-methyl-pyridin-2-ylmethyl)-amino]-butyl}-benzenesulfonamide [Compound No. 111]

Example 110-1

Synthesis of 4-{[(1H-imidazol-2-ylmethyl)-(1-methyl-1H-imidazol-2-ylmethyl)-amino]-methyl}-N-{4-[(3-methyl-pyridin-2-ylmethyl)-amino]-butyl}-benzenesulfonamide [Compound No. 111]

The compound (102.2 mg) obtained in Example 102-4 was dissolved in anhydrous methanol (4.8 ml) and was then added with the compound (43.6 mg) obtained in Example 53-1 and trimethyl orthoformate (0.079 ml), followed by stirring at room temperature for 16 hours. After that, the solution was cooled with ice and added with sodium borohydride (27.2 mg), followed by stirring at room temperature for 2 hours. After the reaction, the solvent was distilled off. The residue was added with a 1 mol/l sodium hydroxide aqueous solution (1.0 ml) and then subjected to extraction with chloroform. The extract was dried with magnesium sulfate. The solvent was distilled off. Then, the residue was purified through silica gel column chromatography (chloroform/methanol) and treated with hydrochloric acid, thereby obtaining the hydrochloride (45.9 mg) of the subject compound as a white solid.

MS(FAB, Pos.): m/z=537[M+H]$^+$ $^1$H-NMR(500 MHz, DMSO-d$_6$+D$_2$O): δ=1.48(2H, t, J=8.1 Hz), 1.71–1.73(2H, m), 2.29(3H, s), 2.70(2H, t, J=6.8 Hz), 3.01(2H, t, J=8.1 Hz), 3.72(2H, s), 3.81(2H, s), 4.09 (2H, s), 4.16(2H, s), 4.32(2H, s), 7.35–7.38(1H, m), 7.46–7.56(4H, m), 7.61(2H, d, J=4.6 Hz), 7.68(2H, d, J=8.3 Hz), 7.71(1H. d. J=7.8 Hz), 8.46(1H, d, J=4.2 Hz).

Production Example 111

Synthesis of N-(4-dipropylamino-butyl)-4-{[(1H-imidazol-2-ylmethyl)-(1-methyl-1H-imidazol-2-ylmethyl)-amino]-methyl}-N-methylbenzamide [Compound No. 112]

Example 111-1

Synthesis of N-(4-dipropylaminobutyl)-4-{[(1H-imidazol-2-ylmethyl)-amino]-methyl}-N-methylbenzamide The compound (954.3 mg) obtained in Example 1-1, HOBt (552.1 mg), and DCC (389.2 mg) were dissolved in anhydrous chloroform, followed by stirring at room temperature for 30 minutes. Then, the solution was added with the compound (487.8 mg) obtained in Example 107-1, followed by stirring at room temperature for 16 hours. After the reaction, the solution was washed with water, 1 mol/l hydrochloric acid, and a 1 mol/l sodium hydroxide aqueous solution. The resultant was dried with magnesium sulfate and the solvent was then distilled off. The residue was purified through silica gel column chromatography (chloroform/ethyl acetate).

The purified product was dissolved in methanol (7.4 ml). A 4 mol/l hydrogen chloride/dioxane solution (7.4 ml) was added to the solution, and the whole was stirred at room temperature for 1.5 hours. After the reaction, the solvent was distilled off. The residue was added with a 1 mol/l sodium hydroxide aqueous solution and extracted with chloroform. The extract was dried with magnesium sulfate and the solvent was then distilled off, thereby obtaining the subject compound (533.8 mg) as a white solid.

Example 111-2

Synthesis of N-(4-dipropylamino-butyl)-4-{[(1H-imidazol-2-ylmethyl)-(1-methyl-1H-imidazol-2-ylmethyl)-amino]-methyl}-N-methylbenzamide [Compound No. 112]

The compound (266.9 mg) obtained in Example 111-1 was dissolved in anhydrous methanol (11 ml) and then added with 1-methyl-2-imidazole carboxaldehyde (110.1 mg) and sodium cyanoborohydride (84.2 mg). Then, the solution was adjusted to pH 5 with acetic acid, followed by stirring at room temperature for 3 days. After the reaction, the solvent was distilled off. The residue was added with a 1 mol/l sodium hydroxide aqueous solution (1.0 ml) and extracted with chloroform. The extract was dried with magnesium sulfate. The solvent was distilled off. Then, the residue was purified through silica gel column chromatography (chloroform/methanol) and treated with hydrochloric acid, thereby obtaining hydrochloride (234.9 mg) of the subject compound as a white solid.

MS(FAB, Pos.): m/z=494[M+H]$^+$ $^1$H-NMR(500 MHz, DMSO-d$_6$+D$_2$O): δ=0.91(6H, t, J=7.2 Hz), 1.64(8H, m), 2.83(2H, s), 2.94–3.02(6H, m), 3.10(2H, m), 3.71(3H, s), 3.74(2H, s), 4.08(2H, s), 4.16(2H, s), 7.27(2H, d, J=7.3 Hz), 7.37(2H, d, J=8.1 Hz), 7.50(2H, s), 7.61(2H, s).

Production Example 112

Synthesis of N-(4-dipropylamino-butyl)-4-{[(1H-imidazol-2-ylmethyl)-(1-methyl-1H-imidazol-2-ylmethyl)-amino]-methyl}-N-methyl-benzenesulfonamide [Compound No. 113]

Example 112-1

Synthesis of 4-(1,3-dioxo-1,3-dihydro-isoindol-2-ylmethyl)-N-(4-dipropylamino-butyl)-N-methyl-benzenesulfonamide The compound (318.3 mg) obtained in Example 24-2 was dissolved in anhydrous dichloromethane (6.4 ml) and added with triethylamine (0.159 ml). Then, the mixture was added with the compound (266.5 mg) obtained in Example 107-1, followed by stirring at room temperature for 2 hours. After the reaction, the solution was washed with water and dried with magnesium sulfate. The solvent was distilled off and the residue was then purified through silica gel column chromatography (chloroform/methanol), thereby obtaining the subject compound (354.4 mg).

MS(FAB, Pos.): m/z=486[M+H]$^+$

Example 112-2

Synthesis of N-(4-dipropylamino-butyl)-4-{[(1H-imidazol-2-ylmethyl)-amino]-methyl}-N-methyl-benzenesulfonamide The compound (354.4 mg) obtained in Example 112-1 was dissolved in a 40% methylamine/methanol solution (3.5 ml), followed by stirring at room temperature for 3 days. After the reaction, the solvent was distilled off and the residue was then dissolved in chloroform, followed by washing with a 1 mol/l sodium hydroxide aqueous solution. The resultant was dried with magnesium sulfate, and the solvent was distilled off.

The residue was dissolved in anhydrous methanol (7 ml). Then, 2-imidazole carboxaldehyde (105.7 mg) and trimethyl orthoformate (0.24 ml) were added to the solution, followed by stirring at room temperature for 2 days. After the reaction, the solution was added with sodium borohydride (82.8 mg) and stirred at room temperature for 24 hours. After the reaction, the solvent was distilled off. The residue was added with water and extracted with chloroform. The extract was dried with magnesium sulfate and the solvent was then distilled off. The residue was purified through silica gel column chromatography (chloroform/methanol), thereby obtaining the subject compound (171.8 mg).

MS(FAB, Pos.): m/z=436[M+H]$^+$

Example 112-3

Synthesis of N-(4-dipropylamino-butyl)-4-{[(1H-imidazol-2-ylmethyl)-(1-methyl-1H-imidazol-2-ylmethyl)-amino]-methyl}-N-methyl-benzene-sulfonamide [Compound No. 113]

The compound (171.8 mg) obtained in Example 112-2 was dissolved in anhydrous methanol (7.0 ml). The solution was added with 1-methyl-2-imidazole carboxaldehyde (65.0 mg) and sodium cyanoborohydride (49.0 mg). Then, the solution was adjusted to pH 5 with acetic acid and then stirred at room temperature for 2 days. After the reaction, the solvent was distilled off. The residue was added with a 1 mol/l sodium hydroxide aqueous solution and extracted with chloroform. The extract was dried with magnesium sulfate, and the solvent was distilled off. Then, the residue was purified through silica gel column chromatography (chloroform/methanol) and treated with hydrochloric acid, thereby obtaining hydrochloride (184.8 mg) of the subject compound as a white solid.

MS(FAB, Pos.): m/z=530[M+H]$^+$ $^1$H-NMR(500 MHz, DMSO-d$_6$+D$_2$O): δ=0.92(6H, t, J=7.3 Hz), 1.55(2H, t, J=7.0 Hz), 1.64–1.69(6H, m), 2.61 (3H, s), 2.92(2H, t, J=6.7 Hz), 3.00–3.01(4H, m), 3.06–3.09 (2H, m), 3.73(3H, s), 3.83(2H, s), 4.12(2H, s), 4.19(2H, s), 7.48–7.51(2H, m), 7.57–7.65(6H, m).

Production Example 113

Synthesis of N-(4-di-n-propylaminomethyl-phenyl)-4-{[(1H-imidazol-2-ylmethyl)-(1H-[1,2,4]-triazol-3-ylmethyl)-amino]-methyl}-benzamide [Compound No. 114]

Example 113-1

Synthesis of N-(4-di-n-propylaminomethyl-phenyl)-4-{[(1H-imidazol-2-ylmethyl)-(1H-[1,2,4]-triazol-3-ylmethyl)-amino]-methyl}-benzamide [Compound No. 114]

The compound (100.0 mg) obtained in Example 47-3 was dissolved in methanol (3.0 ml). Then, the solution was added with 1H-[1,2,4]-triazol-3-carboxaldehyde (51.0 mg) synthesized by the method described in Heterocycles (vol. 15, No. 1, page 1981) and sodium cyanoborohydride (30.0 mg). Subsequently, the solution was adjusted to pH 5 with acetic acid and stirred at room temperature for 17 hours. After completion of the reaction, the reaction solution was added with a 1 mol/l sodium hydroxide aqueous solution and then subjected to separation/extraction with a mixture solution of chloroform/methanol. The organic layer was dried with anhydrous sodium sulfate and the solvent was then distilled off. The residue was purified through silica gel column chromatography (chloroform/methanol) and treated with hydrochloric acid, thereby obtaining hydrochloride (37.4 mg) of the subject compound as a white solid.

MS(FAB, Pos.): m/z=501[M+H]$^+$ $^1$H-NMR(500 Mz, DMSO-d$_6$+D$_2$O): δ=0.88(6H, t, J=7.3 Hz), 1.60–1.78(4H, m), 2.92–3.00(4H, m), 3.78(2H, s), 3.87(2H, s), 4.11(2H, s), 4.28(2H, s), 7.53(2H, d, J=8.7 Hz), 7.56(2H, s), 7.57(2H, d, J=8.2 Hz), 7.87(2H, d, J=8.7 Hz), 7.92(2H, d, J=8.2 Hz), 8.49(1H, brs).

Production Example 114

Synthesis of [4-(6-{[(1H-imidazol-2-ylmethyl)-(1-methyl-1H-imidazol-2-ylmethyl)-amino]-methyl}-benzimidazol-2-yl)-butyl]-dipropylamine [Compound No. 115]

Example 114-1

Synthesis of 4-amino-3-{(5-t-butoxycarbonylamino) pentanoyl}aminobenzoic acid methyl ester In DMF 20 ml, 5-t-butoxycarbonyl aminovaleric acid (1.45 g), WSCI hydrochloride (1.74 g), and HOBt (1.25 g) were dissolved, followed by stirring for 15 minutes. Then, the solution was added with methyl 3,4-diaminobenzoate (1.00 g) and stirred at room temperature for 4 hours. After completion of the reaction, the solvent was distilled off under reduced pressure. The residue was dissolved in chloroform and then washed with a saturated aqueous ammonium chloride solution and a 1 mol/l sodium hydroxide aqueous solution. Subsequently, the resultant was subjected to extraction with chloroform and the extract was then washed with saturated saline solution, followed by drying with anhydrous sodium sulfate. After filtration, the solvent was distilled off under reduced pressure. The residue was purified through silica gel column chromatography (chloroform/ethyl acetate), thereby obtaining the subject compound (1.46 g).

MS(FAB, Pos.): m/z=365[M+H]

Example 114-2

Synthesis of 2-(4-dipropylaminobutyl)-3H-benzimidazole-5-carboxylic acid methyl ester 4-amino-3-{(5-t-butoxycarbonylamino)pentanoyl}aminobenzoic acid methyl ester (1.46 g) was dissolved in methanol (7.3 ml) and then added with a 4 mol/l hydrogen chloride/dioxane solution (7.3 ml), followed by stirring overnight at 40° C. After completion of the reaction, the solvent was distilled off under reduced pressure and the residue was dried under vacuum. The dried product was dissolved in methanol (15 ml) and added with triethylamine (0.597 ml), trimethyl orthoformate (1 ml), and propionaldehyde (0.309 ml), followed by stirring at room temperature for 30 minutes. The solution was added with sodium cyanoborohydride (272 mg) and stirred at room temperature for 30 minutes. Furthermore, the solution was added with propionaldehyde (0.310 ml) and sodium cyanoborohydride (270 mg), followed by stirring at room temperature for 4 hours. After completion of the reaction, the solvent was distilled off under reduced pressure. The residue was dissolved in chloroform and then washed with a 1 mol/l sodium hydroxide aqueous solution, followed by extraction with chloroform. The organic layer was washed with saturated saline solution and then dried with anhydrous sodium sulfate. After filtration, the solvent was distilled off under reduced pressure and the residue was then purified through silica gel column chromatography (chloroform/ethyl acetate), thereby obtaining the subject compound (315 mg) as a brown viscous substance.

MS(FAB, Pos.): m/z=332[M+H]$^+$

Example 114-3

Synthesis of {4-[6-chloromethyl-1-(toluene-4-sulfonyl)-1H-benzimidazol-2-yl]butyl}dipropylamine Lithium aluminum hydride (108 mg) was suspended in THF (60 ml) and dropwisely added with a solution (60 ml) of the compound (315 mg) obtained in Example 114-2 in THF, followed by stirring at room temperature for 1 hour. After completion of the reaction, sodium sulfate decahydrate was added to the solution until bubbling was not observed, and a 1 mol/l sodium hydroxide aqueous solution was then gradually added to the mixture until a white precipitate was generated. After filtration, the solvent was distilled off under reduced pressure. The residue was dried under vacuum, and the dried product was dissolved in dichloromethane (10 ml) and then added with triethylamine (263 μl) and p-toluenesulfonyl chloride (364 mg), followed by stirring at room temperature for 2.5 hours. After completion of the reaction, the solution was washed with water and extracted with chloroform. The organic layer was washed with saturated saline solution and then dried with anhydrous sodium sulfate. After filtration, the solvent was distilled off under reduced pressure and the residue was then purified through silica gel column chromatography (chloroform/methanol), thereby obtaining the subject compound (113 mg) as a brown solid.

MS(FAB, Pos.): m/z=476[M+H]$^+$

Example 114-4

Synthesis of [4-(6-aminomethyl-1H-benzimidazol-2-yl)butyl]dipropylamine

The compound (113 mg) obtained in Example 114-3 was dissolved in DMF (2 ml) and added with potassium phthalimide (69.0 mg), followed by stirring at room temperature for 2 days. After completion of the reaction, the solvent was distilled off under reduced pressure and the residue was then dissolved in chloroform, followed by washing with water. After extraction with chloroform, the organic layer was washed with saturated saline solution and dried with anhydrous sodium sulfate. After filtration, the solvent was distilled off under reduced pressure. The residue was dried under vacuum, and the dried product was dissolved in a 40% methylamine/methanol solution (1.5 ml), followed by stirring overnight at room temperature. After completion of the reaction, the solvent was distilled off under reduced pressure and the residue was then dissolved in chloroform, followed by washing with water and a 1 mol/l sodium hydroxide aqueous solution. After extraction with chloroform, the extract was washed with saturated saline solution and dried with anhydrous sodium sulfate. After filtration, the solvent was distilled off under reduced pressure and the residue was then purified through silica gel column chromatography (chloroform/methanol), thereby obtaining the subject compound (39.8 mg) as a brown solid.

MS(FAB, Pos.): m/z=303[M+H]$^+$

Example 114-5

Synthesis of [4-(6-{[(1H-imidazol-2-ylmethyl)-(1-methyl-1H-imidazol-2-ylmethyl)-amino]-methyl}-benzimidazol-2-yl)-butyl]-dipropylamine [Compound No. 115]

The compound (39.8 mg) obtained in Example 114-4 was dissolved in methanol (1.0 ml) and then added with 2-imidazole carboxaldehyde (13.3 mg) and trimethyl orthoformate (0.030 ml), followed by stirring at room temperature for 30 minutes. The solution was gradually added with sodium borohydride (10.5 mg), followed by stirring at room temperature for 1 hour. After completion of the reaction, the solvent was distilled off under reduced pressure and the residue was then dissolved in chloroform. After having been washed with water, the solution was extracted with chloroform. The organic layer was washed with saturated saline solution and then dried with anhydrous sodium sulfate. After filtration, the solvent was distilled off under reduced pressure. Subsequently, the residue was dissolved in methanol (1.0 ml) and added with 1-methyl-2-imidazole carboxaldehyde (63.2 mg), acetic acid (0.023 ml), trimethyl orthoformate (0.030 ml), and sodium cyanoborohydride (23.2 mg), followed by stirring at room temperature for 30 minutes. The solution was added with acetic acid (0.045 ml) and stirred at room temperature for 4 hours. After completion of the reaction, the solvent was distilled off under reduced pressure and the residue was then dissolved in chloroform. After having been washed with a 1 mol/l sodium hydroxide aqueous solution, the solution was extracted with chloroform. The organic layer was washed with saturated saline solution and then dried with anhydrous sodium sulfate. After filtration, the solvent was distilled off under reduced pressure. Subsequently, the residue was purified through silica gel column chromatography (chloroform/methanol) and treated with hydrochloric acid, thereby obtaining hydrochloride (27.6 mg) of the subject compound as a white solid.

MS(FAB, Pos.): m/z=477[M+H]$^+$ $^1$H-NMR(500 MHz, DMSO-d$_6$): δ=0.89(3H, t, J=7.3 Hz), 1.63–1.69(4H, m), 1.70–1.81(2H, m), 1.94–2.01(2H, m), 2.84–3.00(4H, m), 3.03–3.09(2H, m), 3.19–3.23(2H, m), 3.72(3H, s), 3.90(2H, s), 4.13(2H, s), 4.21(2H, s), 4.41(2H, t, J=7.3 Hz), 7.49(1H, s), 7.53(1H, s), 7.59(1H, d, J=8.4 Hz), 7.64–7.66(3H, m), 7.81(1H, s), 10.50(1H, s).

Production Example 115

Synthesis of N-(4-{[(imidazol-2-ylmethyl)-([1,2,4]-triazol-3-ylmethyl)-amino]-methyl}-benzyl)-N-methyl-N',N'-dipropylbutane-1,4-diamine [Compound No. 116]

Example 115-1

Synthesis of {4-[(4-dipropylamino-butylamino)-methyl]-benzyl}-carbamic acid t-butyl ester The compound (225.3 mg) obtained in Example 103-3 was dissolved in methanol (6.76 ml). Then, the solution was added with the compound (165.0 mg) obtained in Example 1-2 and trimethyl orthoformate (304.8 mg), followed by stirring at room temperature for 18 hours. Sodium borohydride (108.7 mg) was added to the solution under ice-cooling, followed by stirring at room temperature for 0.5 hours. The reaction solution was added with water and subjected to separation/extraction with chloroform. Then, the extract was washed with saturated saline solution and dried with anhydrous sodium sulfate, followed by concentration under reduced pressure. The residue was purified through silica gel column chromatography (chloroform/methanol), thereby obtaining the subject compound (297.6 mg) as a colorless oily substance.

Example 115-2

Synthesis of (4-{[(4-dipropylamino-butyl)-methyl-amino]-methyl}-benzyl)-carbamic acid t-butyl ester The compound (625.7 mg) obtained in Example 115-1 was dissolved in methanol (25.0 ml) and added with a 36% formaldehyde aqueous solution (0.246 ml) and sodium cyanoborohydride (220.9 mg). The solution was adjusted to pH 5 with acetic acid and stirred at room temperature for 27 hours. The reaction solution was concentrated under reduced pressure and the residue was added with a 1 mol/l sodium hydroxide aqueous solution, followed by separation/extraction with chloroform. After having been washed with saturated saline solution, the extract was dried with anhydrous sodium sulfate and concentrated under reduced pressure. The residue was purified through silica gel column chromatography (chloroform/ethyl acetate), thereby obtaining the subject compound (648.1 mg) as a colorless oily substance.

Example 115-3

Synthesis of N-(4-aminomethyl-benzyl)-N-methyl-N,N'-dipropyl-butan-1,4-diamine

The compound (0.956 g) obtained in Example 115-2 was dissolved in methanol (9.56 ml) and added with a 4 mol/l hydrogen chloride/dioxane solution (19.1 ml) and stirred at room temperature for 1 hour. After the reaction solution had been concentrated under reduced pressure, the residue was added with a 1 mol/l sodium hydroxide aqueous solution and subjected to separation/extraction with chloroform. Then, the organic layer was washed with saturated saline solution and dried with anhydrous sodium sulfate. Then, the dried product was concentrated under reduced pressure and dried under vacuum, thereby obtaining the subject compound (0.720 g) as a colorless oily substance.

Example 115-4

Synthesis of N-(4-{[(imidazol-2-ylmethyl)-amino]-methyl}-benzyl)-N-methyl-N,N'-dipropyl-butan-1,4-diamine The compound (336.5 mg) obtained in Example 115-3 was dissolved in methanol and added with 2-imidazole carboxaldehyde (158.8 mg) and trimethyl orthoformate (350.7 mg), followed by stirring at room temperature for 17 hours. Sodium borohydride (125.0 mg) was added to the solution under ice-cooling, and the whole was stirred at room temperature for 1.5 hours. The reaction solution was concentrated under reduced pressure. The residue was added with water and then subjected to separation/extraction with chloroform. The organic layer obtained was dried with anhydrous sodium sulfate and concentrated under reduced pressure. The residue was purified through silica gel column chromatography (chloroform/methanol), thereby obtaining the subject compound (409.7 mg) as a colorless oily substance.

Example 115-5

Synthesis of N-(4-{[(imidazol-2-ylmethyl)-([1,2,4]-triazol-3-ylmethyl)-amino]-methyl}-benzyl)-N-methyl-N',N'-dipropylbutane-1,4-diamine [Compound No. 116]

The compound (409.7 mg) obtained in Example 115-4 was dissolved in methanol (12.3 ml) and added with 1H-[1,2,4]-triazol-3-carboxaldehyde (206.3 mg) and sodium cyanoborohydride (133.5 mg). Then, the solution was adjusted to pH 5 with acetic acid and stirred at room temperature for 38 hours. The reaction solution was concentrated under reduced pressure. Subsequently, the residue was then purified through silica gel column chromatography (chloroform/methanol) and treated with hydrochloric acid, thereby obtaining hydrochloride (105.6 mg) of the subject compound as a white solid.

MS(FAB, Pos.): m/z=467[M+H]$^+$

Production Example 116

Synthesis of N-methyl-N-(4-{[(1-methyl-imidazol-2-ylmethyl)-([1,2,4]-triazol-3-ylmethyl)-amino]-methyl}-benzyl)-N',N'-dipropyl-butane-1,4-diamine [Compound No. 117]

Example 116-1

Synthesis of N-methyl-N-(4-{[(1-methyl-1H-imidazol-2-ylmethyl)-amino]-methyl}-benzyl)-N,N'-diamine The compound (336.5 mg) obtained in Example 115-3 was dissolved in methanol (10.1 ml) and added with 1-methyl-2-imidazole carboxaldehyde (181.9 mg) and trimethyl orthoformate (350.7 mg), followed by stirring at room temperature for 17 hours. Sodium borohydride (125.0 mg) was added to the solution under ice-cooling, and then the whole was stirred at room temperature for 1.5 hours. The reaction solution was concentrated under reduced pressure and the residue was then added with water, followed by separation/extraction with chloroform. The organic solvent obtained was dried with anhydrous sodium sulfate and concentrated under reduced pressure. The residue was purified through silica gel column chromatography (chloroform/methanol), thereby obtaining the subject compound (440.2 mg) as a colorless oily substance.

Example 116-2

Synthesis of N-methyl-N-(4-{[(1-methyl-imidazol-2-ylmethyl)-([1,2,4]-triazol-3-ylmethyl)-amino]-methyl}-benzyl)-N',N'-dipropyl-butane-1,4-diamine [Compound No. 117]

The compound (440.2 mg) obtained in Example 116-1 was dissolved in methanol (13.2 ml) and added with 1H-[1,2,4]-triazol-3-carboxaldehyde (213.9 mg) and sodium cyanoborohydride (138.4 mg). Then, the solution was adjusted to pH 5 with acetic acid and stirred at room temperature for 38 hours. The reaction solution was concentrated under reduced pressure. Subsequently, the residue was then purified through silica gel column chromatography (chloroform/methanol) and treated with hydrochloric acid, thereby obtaining hydrochloride (197.0 mg) of the subject compound as a white solid.
MS(FAB, Pos.): m/z=481[M+H]$^+$ Production Example 117

Synthesis of N-(4-dipropylaminomethylbenzyl)-N'-(1H-imidazol-2-ylmethyl)-N'-(1-methyl-1H-imidazol-2-ylmethyl)-1,4-butanediamine [Compound No. 118]

Example 117-1

Synthesis of 4-dipropylaminomethyl benzaldehyde

The compound (443 mg) obtained in Example 80-2 was dissolved in dichloromethane (9.0 ml) and added with manganese (IV) oxide (chemically treated product, manufactured by Wako Pure Chemical Industries, Ltd.) (873 mg), followed by stirring at room temperature for 5 hours. After completion of the reaction, the solution was filtrated through Celite and the filtrate was then concentrated under reduced pressure. The residue was purified through silica gel column chromatography (chloroform/ethyl acetate), thereby obtaining the subject compound (397 mg) as a brown solid.
MS(FAB, Pos.): m/z=220[M+H]$^+$
$^1$H-NMR(500 MHz, CDCl$_3$): δ=0.86(6H, t, J=7.3 Hz), 1.47(4H, sext., J=7.3 Hz), 2.36(4H, t, J=7.3 Hz), 3.54(2H, s), 3.91(3H, s), 7.30(2H, d, J=8.3 Hz), 7.33(2H, d, J=8.3 Hz).

Example 117-2

Synthesis of 4-(1H-imidazol-2-ylmethyl)aminobutyl carbamic acid t-butyl

In methanol (3 ml), 4-aminobutyl carbamic acid t-butyl (202 mg), 2-imidazole carboxaldehyde (152 mg) was dissolved, and trimethyl orthoformate (0.20 ml) were added to the solution. Then, the mixture was stirred at room temperature for 1.5 hours. After having been cooled to 0° C., the solution was added with sodium borohydride (81.1 mg) and stirred at 0° C. for 2 hours, followed by stirring at room temperature for an additional one hour. After completion of the reaction, the solvent was distilled off under reduced pressure. The residue was dissolved in chloroform and washed with a 1 mol/l sodium hydroxide aqueous solution. After extraction with chloroform, the organic layer was washed with saturated saline solution and dried with anhydrous sodium sulfate. Subsequently, the solvent was distilled off and the residue was then dried under vacuum, thereby obtaining the subject compound (334 mg) as a white solid.
MS(FAB, Pos.): m/z=269[M+H]$^+$ Example 117-3

Synthesis of 4-[(1H-imidazol-2-ylmethyl)-(1-methyl-1H-imidazol-2-ylmethyl)]aminobutyl carbamic acid t-butyl The compound (334 mg) obtained in Example 117-2 was dissolved in methanol (4 ml) and added with 1-methyl-2-imidazole carboxaldehyde (175 mg) and acetic acid (0.2 ml), followed by cooling to 0° C. Sodium cyanoborohydride (133 mg) was added to the solution, and the whole was stirred overnight at room temperature. After completion of the reaction, the solvent was distilled off under reduced pressure. The residue was dissolved in chloroform and then washed with a 1 mol/l sodium hydroxide aqueous solution. After extraction with chloroform, the organic layer was washed with saturated saline solution and dried with anhydrous sodium sulfate. After filtration, the solvent was distilled off under reduced pressure and the residue was then dried under vacuum, thereby obtaining the subject compound (429 mg) as a white solid.
MS(FAB, Pos.): m/z=363[M+H]$^+$ Example 117-4

Synthesis of N-(1H-imidazol-2-ylmethyl)-N-(1-methyl-1H-imidazol-2-ylmethyl)butane-1,4-diamine The compound (429 mg) obtained in Example 117-3 was dissolved in methanol (4.0 ml) and added with a 4 mol/l hydrogen chloride/dioxane solution (4.0 ml), followed by stirring at room temperature for 2 hours. After completion of the reaction, the solvent was distilled off under reduced pressure. The residue was dissolved in methanol and neutralized with an anion-exchange resin (Amberlite IRA-410). Subsequently, the solvent was distilled off and the residue was then dried under vacuum, thereby obtaining the subject compound (349 mg) as a pale-yellow solid.
MS(FAB, Pos.): m/z=263[M+H]$^+$ Example 117-5

Synthesis of N-(4-dipropylaminomethylbenzyl)-N'-(1H-imidazol-2-ylmethyl)-N'-(1-methyl-1H-imidazol-2-ylmethyl)-1,4-butanediamine [Compound No. 118]

The compound (349 mg) obtained in Example 117-4 was dissolved in methanol (7.0 ml). Then, the solution was added with the compound (323 mg) obtained in Example 117-1 and trimethyl orthoformate (0.340 ml) and stirred at room temperature for 2 hours, followed by cooling to 0° C. The solution was added with sodium borohydride (75.5 mg) and stirred at room temperature for 30 minutes. After completion of the reaction, the solvent was distilled off under reduced pressure. The residue was dissolved in chloroform and washed with an aqueous sodium bicarbonate solution, followed by extraction with chloroform. The organic layer was washed with saturated saline solution and then dried with anhydrous sodium sulfate. After filtration, the solvent was distilled off under reduced pressure. The residue was purified through silica gel column chromatography (chloroform) and treated with hydrochloric acid, thereby obtaining hydrochloride (89.8 mg) of the subject compound as a white solid.

MS(FAB, Pos.): m/z=466[M+H]$^+$ $^1$H-NMR(500 MHz, DMSO-d$_6$): δ=0.85(6H, t, J=7.3 Hz), 1.51–1.55(2H, m), 1.61–1.64(2H, m), 1.67–1.79(4H, m), 2.47(2H, t, J=7.3 Hz), 2.80(2H, br), 2.84–2.92(4H, m), 3.81(3H, s), 4.12(4H, s), 4.17(2H, s), 4.31(2H, d, J=5.5 Hz), 7.61(1H, s), 7.62–7.73(7H, m), 9.57(2H, brs), 11.08(1H, brs).

Production Example 118

Synthesis of N-(4-dipropylaminomethylbenzyl)-N'-(1H-imidazol-2-ylmethyl)-N-methyl-N'-(1-methyl-1H-imidazol-2-ylmethyl)-butane-1,4-diamine [Compound No. 119]

Example 118-1

Synthesis of N-(4-dipropylaminomethylbenzyl)-N'-(1H-imidazol-2-ylmethyl)-N-methyl-N'-(1-methyl-1H-imidazol-2-ylmethyl)-butane-1,4-diamine [Compound No. 119]

The hydrochloride (39.4 mg) of the compound obtained in Example 117-5 was dissolved in methanol (1.0 ml) and added with triethylamine (0.050 ml), trimethyl orthoformate (0.040 ml), and a 36% formaldehyde solution (0.020 ml), followed by stirring at room temperature for 2 hours. The solution was gradually added with sodium borohydride (15.0 mg) after having been cooled to 0° C., and then warmed to room temperature, followed by stirring for 1 hour. After completion of the reaction, the solvent was distilled off under reduced pressure. The residue was dissolved in chloroform and washed with a 1 mol/l sodium hydroxide aqueous solution, followed by extraction with chloroform. The organic layer was washed with saturated saline solution and dried with anhydrous sodium sulfate. After filtration, the solvent was distilled off under reduced pressure. Then, the residue was purified through silica gel column chromatography (chloroform/methanol) and treated with hydrochloric acid, thereby obtaining hydrochloride (28.2 mg) of the subject compound as a white solid.

MS(FAB, Pos.) m/z=480[M+H]$^+$ $^1$H-NMR(500 MHz, DMSO-d$_6$): δ=0.85(6H, t, J=7.3 Hz), 1.40–1.52(2H, br), 1.66–1.76(6H, m), 2.44–2.52(2H, m), 2.60(3H, s), 2.84–3.04(6H, br), 3.81(3H, s), 4.11(2H, s), 4.15(2H, s), 4.20–4.44(4H, m), 7.63(1H, s), 7.67–7.75(7H, m), 10.95(2H, br).

Production Example 119

Synthesis of [3-(6-{[(1H-imidazol-2-ylmethyl)-(1-methyl-1H-imidazol-2-ylmethyl)-amino]-methyl}-quinolin-2-yl)-propyl]-dipropylamine [Compound No. 120]

Example 119-1

Synthesis of 6-bromomethyl-2-methyl quinoline

In carbon tetrachloride (26 ml), 2,6-dimethylquinoline (manufactured by Tokyo Kasei Kogyo Co., Ltd.) (1.0398 g), N-bromosuccinimide (1.2353 g), and azobisisobutyronitrile (98.5 mg) were dissolved and then the whole was subjected to thermal reflux for 2 hours under an argon atmosphere. After the reaction, a precipitate was removed through filtration and then washed with water, followed by drying with magnesium sulfate. The solvent was distilled off and the residue was then purified through silica gel column chromatography (hexane/ethyl acetate), thereby obtaining the subject compound (427.3 mg) as a white solid.

MS(FAB, Pos.): m/z=236, 238[M+H]$^+$ $^1$H-NMR(500 MHz, DMSO-d$_6$): δ=2.66(3H, s), 4.90(2H, s), 7.44(1H, d, J=8.4 Hz), 7.75(1H, dd, J=2.1, 8.7 Hz), 7.91(1H, d, J=8.5 Hz), 7.99(1H, d, J=2.0 Hz), 8.24(1H, d, J=8.4 Hz).

Example 119-2

Synthesis of 2-(2-methylquinolin-6-ylmethyl)-isoindole-1,3-dione

The compound (421.7 mg) obtained in Example 119-1 was dissolved in anhydrous DMF (12.6 ml) and added with potassium phthalimide (663.1 mg), followed by stirring at room temperature for 2 hours. After the reaction, the solvent was distilled off and the residue was then added with water. The mixture was extracted with chloroform and the extract was dried with magnesium sulfate. The solvent was distilled off and the residue was then purified through silica gel column chromatography (chloroform/ethyl acetate), thereby obtaining the subject compound (536.0 mg) as a white solid.

MS(FAB, Pos.): m/z=303[M+H]$^+$ $^1$H-NMR(500 MHz, DMSO-d$_6$): δ=2.63(3H, s), 4.95(2H, s), 7.39(1H, d, J=8.4 Hz), 7.66(1H, dd, J=2.1, 8.7 Hz), 7.81(1H, d, J=10.4 Hz), 7.86–7.89(3H, m), 7.92–7.94(2H, m), 8.22(1H, d, J=8.4 Hz).

Example 119-3

Synthesis of 2-(2-methyl-1-oxy-quinolin-6-ylmethyl)-isoindole-1,3-dione

The compound (534.7 mg) obtained in Example 119-2 was dissolved in chloroform (16 ml) and then added with meta-chloroperbenzoic acid (321.0 mg), followed by stirring at room temperature for 4 hours. Furthermore, meta-chloroperbenzoic acid (153.6 mg) was added to the solution, and the whole was stirred at room temperature for 1 hour. The solution was washed with a saturated sodium bicarbonate solution and dried with magnesium sulfate. The solvent was distilled off and the residue was then purified through silica gel column chromatography (chloroform/methanol), thereby obtaining the subject compound (511.8 mg) as a white solid.

MS(FAB, Pos.): m/z=319[M+H]$^+$ $^1$H-NMR(500 MHz, DMSO-d$_6$): δ=2.54(3H, s), 4.97(2H, s), 7.56(1H, d, J=8.5 Hz), 7.75(1H, dd, J=2.0, 9.0 Hz), 7.82(1H, d, J=8.8 Hz), 7.87–7.90(2H, m), 7.92–7.96(3H, m), 8.51(1H, d, J=8.8 Hz).

Example 119-4

Synthesis of 2-(2-hydroxymethyl-quinolin-6-ylmethyl)-isoindole-1,3-dione

The compound (510.6 mg) obtained in Example 119-3 was dissolved in dichloromethane (5.1 ml). Under ice-cooling, the solution was added with trifluoroacetic anhydride (0.452 ml) and stirred at room temperature for 2 hours.

After the solvent had been distilled off, methanol (10 ml) and a saturated sodium bicarbonate solution (10 ml) were added to the residue, and the whole was stirred at room temperature for 1 hour. After the reaction, the solvent was distilled off. The residue was extracted with chloroform and the extract was dried with magnesium sulfate. After the solvent had been distilled off, the residue was purified through silica gel column chromatography (chloroform/methanol), thereby obtaining the subject compound (458.2 mg) as a white solid.

MS(FAB, Pos.): m/z=319[M+H]$^+$ $^1$H-NMR(500 MHz, DMSO-d$_6$): δ=4.70(2H, d, J=6.0 Hz), 5.00(2H, s), 5.56(1H, t, J=6.0 Hz), 7.63(1H, d, J=8.5 Hz), 7.69(1H, dd, J=2.1, 8.7 Hz), 7.86–7.89(3H, m), 7.91–7.95(3H, m), 8.34(1H, d, J=8.4 Hz).

Example 119-5

Synthesis of 6-(1,3-dioxy-1,3-dihydro-isoindol-2-ylmethyl)-quinoline-2-carboxaldehyde The compound (457.4 mg) obtained in Example 119-4 was dissolved in chloroform (7 ml) and then added with manganese dioxide (chemically processed product) (2.4556 g), followed by stirring at room temperature for 3.5 hours. After the reaction, the solution was filtrated through Celite. The solvent was distilled off and the residue was then purified through silica gel column chromatography (chloroform/ethyl acetate), thereby obtaining the subject compound (366.9 mg) as a white solid.

MS(FAB, Pos.): m/z=317[M+H]$^+$ $^1$H-NMR(500 MHz, DMSO-d$_6$): δ=5.03(2H, s), 7.87–7.90(3H, m), 7.93–7.98(3H, m), 8.04(1H, d, J=1.2 Hz), 8.21(1H, d, J=8.7 Hz), 8.58(1H, d, J=8.7 Hz), 10.11(1H, s).

Example 119-6

Synthesis of 3-[6-(1,3-dioxo-1,3-dihydro-isoindol-2-ylmethyl)-quinolin-2-yl]-acrylonitrile The compound (153.8 mg) obtained in Example 119-5, (triphenylphosphanylidene)-acetonitrile (manufactured by Aldrich Corporation) (183.3 mg), and anhydrous THF (9.2 ml) were admixed together and stirred at room temperature for 2 hours. After the reaction, the solvent was distilled off under reduced pressure. The residue was purified through silica gel column chromatography (hexane/ethyl acetate), thereby obtaining the subject compound (164.2 mg) as a yellow solid.

MS(FAB, Pos.): m/z=340[M+H]$^+$ $^1$H-NMR(500 MHz, DMSO-d$_6$): δ=5.00(2H, d, J=5.4 Hz), 6.18(1H, d, J=12.0 Hz), 6.91(1H, d, J=16.4 Hz), 7.60(1H, d, J=11.7 Hz), 7.79–7.95(6H, m), 8.00(1H, d, J=8.5 Hz), 8.49(1H, d, J=8.3 Hz).

Example 119-7

Synthesis of 3-[6-(1,3-dioxo-1,3-dihydro-isoindol-2-ylmethyl)-quinolin-2-yl]-propionitrile The compound (574.4 mg) obtained in Example 119-6 was dissolved in ethanol (20 ml) and chloroform (10 ml). Then, the solution was added with 20% palladium hydroxide-carbon (172.3 mg) and then stirred at room temperature for 16 hours under a hydrogen atmosphere. After the reaction, the solution was filtrated through Celite and the solvent was then distilled off under reduced pressure. The residue was purified through silica gel column chromatography (hexane/ethyl acetate), thereby obtaining the subject compound (101.9 mg) as a yellow solid.

MS(FAB, Pos.): m/z=342[M+H]$^+$ $^1$H-NMR(500 MHz, DMSO-d$_6$): δ=3.02(2H, t, J=7.3 Hz), 3.26(2H, t, J=7.3 Hz), 4.97(2H, s), 7.49(1H, d, J=8.5 Hz), 7.71(1H, dd, J=2.2, 8.7 Hz), 7.86–7.88(3H, m), 7.92–7.94 (2H, m), 8.31(1H, d, J=8.5 Hz).

Example 119-8

Synthesis of [2-(2-cyano-ethyl)-quinolin-6-ylmethyl]-carbamic acid t-butyl ester The compound (181.2 mg) obtained in Example 119-7 was dissolved in a 40% methylamine/methanol solution (3.6 ml) and stirred at room temperature for 21 hours. After the reaction, the solvent was distilled off under reduced pressure. The residue was dissolved in chloroform and then washed with a 1 mol/l sodium hydroxide aqueous solution, followed by drying with magnesium sulfate. The solvent was distilled off under reduced pressure. Then, the residue was dissolved in chloroform (5.1 ml) and then added with di-t-butyl dicarbonate (174.6 mg) and triethylamine (0.112 ml), followed by stirring overnight at room temperature. After completion of the reaction, the solvent was distilled off under reduced pressure and the residue was then purified through silica gel column chromatography (chloroform/ethyl acetate), thereby obtaining the subject compound (139.9 mg) as a yellow solid.

MS(FAB, Pos.): m/z=312[M+H]$^+$

Example 119-9

Synthesis of [2-(3-dipropylamino-propyl)-quinolin-6-ylmethyl]-carbamic acid t-butyl ester The compound (139.9 mg) obtained in Example 119-8 was dissolved in anhydrous THF (4.2 ml). Then, lithium aluminum hydride (68.3 mg) was added to the solution, followed by stirring at room temperature for 2 hours. The solution was added with an aqueous potassium sodium tartrate solution and stirred at room temperature. After completion of the reaction, extraction with chloroform was carried out. The organic layer was dried with magnesium sulfate and the solvent was then distilled off under reduced pressure. The residue was added with anhydrous methanol (4.1 ml), propionaldehyde (0.095 ml), trimethyl orthoformate (0.144 ml), and sodium cyanoborohydride (110.6 mg) and stirred at room temperature for 2 hours. After completion of the reaction, the solvent was distilled off under reduced pressure. Then, the residue was dissolved in chloroform and washed with water, followed by drying with magnesium sulfate. The solvent was distilled off under reduced pressure. The residue was purified through silica gel column chromatography (toluene/ethyl acetate), thereby obtaining the subject compound (62.6 mg) as a yellow solid.

MS(FAB, Pos.): m/z=400[M+H]$^+$

Example 119-10

Synthesis of [3-(6-{[(1H-imidazol-2-ylmethyl)-(1-methyl-1H-imidazol-2-ylmethyl)-amino]-methyl}-quinolin-2-yl)-propyl]-dipropylamine [Compound No. 120]

The compound (62.6 mg) obtained in Example 119-9 was dissolved in methanol (1.2 ml). Then, a 4 mol/l hydrogen chloride/dioxane solution (1.2 ml) was added to the solution, and the whole was stirred at room temperature for 2 hours. After the solution had been subjected to an anion-exchange resin (Amberlite IRA-410), the solvent was distilled off under reduced pressure. The residue was dissolved in anhydrous methanol (1.0 ml) and added with 2-imidazole carboxaldehyde (25.0 mg) and trimethyl orthoformate (0.056 ml), followed by stirring at room temperature for 16 hours. Then, sodium borohydride (19.3 mg) was added to the solution, and the whole was stirred at room temperature for 6 hours. After the reaction, the solvent was distilled off under reduced pressure and the residue was added with water, followed by extraction with chloroform. Subsequently, the extract was then dried with magnesium sulfate, followed by distilling the solvent off. The residue was dissolved in anhydrous methanol (2.3 ml) and then added with 1-methyl-2-imidazole carboxaldehyde (28.6 mg) and sodium cyanoborohydride (32.0 mg). Then, the solution was adjusted to about pH 5 with acetic acid, followed by stirring at room temperature for 16 hours. After completion of the reaction, the solvent was distilled off under reduced pressure. Then, the residue was dissolved in chloroform and washed with a 1 mol/l sodium hydroxide aqueous solution. The solution was dried with magnesium sulfate and the solvent was then distilled off under reduced pressure. The residue was purified through silica gel column chromatography (chloroform/ethyl acetate) and treated with hydrochloric acid, thereby obtaining hydrochloride (19.6 mg) of the subject compound as a pale-yellow solid.

MS(FAB, Pos.): m/z=474[M+H]$^+$ $^1$H-NMR(500 MHz, DMSO-d$_6$+D$_2$O): δ=0.92(6H, t, J=7.3 Hz), 1.63–1.71(4H, m), 2.19–2.22(2H, m), 3.02–3.06 (4H, m), 3.13–3.19(4H, m), 3.72(3H, s), 3.95(2H, s), 4.13 (2H, s), 4.20(2H, s), 7.46(2H, s), 7.60(2H, s), 7.75(1H, d, J=8.8 Hz), 7.94(1H, d, J=8.1 Hz), 8.04(1H, d, J=9.0 Hz), 8.10(1H, br), 8.62(1H, d, J=8.8 Hz).

Production Example 120

Synthesis of [3-(5-{[(1H-imidazol-2-ylmethyl)-(1-methyl-1H-imidazol-2-ylmethyl)-amino]-methyl}-benzo[b]-thiophen-2-yl)-propyl]-dipropyl-amine [Compound No. 121]

Example 120-1

Synthesis of 5-(1,3-dioxo-1,3-dihydro-isoindol-2-ylmethyl)-benzo[b]thiophene-2-carboxylic acid ethyl ester In carbon tetrachloride (100 ml), 5-methyl-benzo[b] thiophene-2-carboxylic acid ethyl ester (2.36 g) prepared by the method described in PCT Patent WO 0153291 was dissolved. The solution was added with N-bromosuccinimide (2.00 g) and azobisisobutyronitrile (140.7 mg), and the whole was stirred for 17 hours under thermal reflux. After the insoluble matter had been removed through filtration, the residue was recrystallized with methanol. Then, the crystal was dissolved in DMF (20 ml) and then added with potassium phthalimide (1.18 g), followed by stirring overnight at room temperature. After the solvent had been distilled off, the residue was added with water and extracted with chloroform. The organic layer was washed with saturated saline solution and dried with anhydrous sodium sulfate, thereby obtaining the subject compound (1.15 g) as a pale-yellow solid.

Example 120-2

Synthesis of (2-hydroxymethyl-benzo[b]thiophen-5-ylmethyl)-carbamic acid t-butyl ester The compound (1.05 g) obtained in Example 120-1 was dissolved in methanol (20 ml) and added with hydrazine monohydrate (1.0 ml), followed by thermal reflux for 3 hours. The solution was added with water and subjected to extraction with chloroform. The resulting organic layer was washed with saturated saline solution and then dried with anhydrous sodium sulfate. The dried product was dissolved in DMF (30 ml) and then added with triethylamine (0.60 ml) and di-t-butyl dicarbonate (942.8 mg), followed by stirring overnight at room temperature. After the solvent had been distilled off, the residue was added with water and extracted with chloroform. The organic layer was washed with saturated saline solution and then dried with anhydrous sodium sulfate. The dried product was dissolved in anhydrous THF (10 ml). The solution was gradually dropped in a solution cooled at 0° C., which was prepared by suspending lithium aluminum hydride (218.6 mg) in anhydrous THF (20 ml), over 5 minutes, followed by stirring at 0° C. for 1 hour. Ethyl acetate and methanol were added to the solution, and the whole was concentrated. The residue was then purified through silica gel column chromatography (chloroform/methanol), thereby obtaining the subject compound (600.0 mg) as a white solid.

MS(FAB, Pos.): m/z=294[M+H]$^+$ $^1$H-NMR(500 MHz, DMSO-d$_6$+D$_2$O): δ=1.40(9H, s), 4.21(2H, s), 4.73(2H, s), 7.19–7.21(1H, m), 7.24(1H, s), 7.60(1H, s), 7.84(1H, d, J=8.3 Hz).

Example 120-3

Synthesis of 3-[5-(t-butoxycarbonylamino-methyl)-benzo[b]thiophen-2-yl]-acrylic acid methyl ester The compound (596.0 mg) obtained in Example 120-2 was dissolved in anhydrous chloroform (30 ml). Then, the solution was added with manganese dioxide (chemically processed product) (6.0 g), followed by stirring at room temperature for 15.5 hours. Insoluble matter was filtrated and the filtrate was then dissolved in anhydrous THF (20 ml). Subsequently, the solution was added with methyl triphenylphosphoranilideneacetate (814.5 mg), followed by stirring at room temperature for 22 hours. The solvent was distilled off and the residue was then purified through silica gel column chromatography (hexane/ethyl acetate), thereby obtaining the subject compound (560.0 mg) as a white solid.

MS(FAB, Pos.): m/z=348[M+H]$^+$ $^1$H-NMR(500 MHz, DMSO-d$_6$+D$_2$O): δ=1.40(9H, s), 3.74(3H, s), 4.22(2H, s), 6.32(1H, d, J=15.8 Hz), 7.34(1H, dd, J=1.5 Hz,8.3 Hz), 7.71(1H, s), 7.85(1H, s), 7.90–7.93 (1H, m), 7.96(1H, s).

Example 120-4

Synthesis of 3-[5-(t-butoxycarbonylamino-methyl)-benzo[b]thiophen-2-yl]-acrylic acid methyl ester The compound (560.0 mg) obtained in Example 120-3 was dissolved in methanol (50 ml) and chloroform (30 ml) and then added with 10% palladium-carbon (56 mg), followed by stirring for 2.5 hours under a hydrogen atmosphere. After the catalyst had been filtrated, the filtrate was dissolved in anhydrous THF (10 ml) and then gradually added to a solution cooled at 0° C., which was prepared by suspending lithium aluminum hydride (2.12 g) in anhydrous THF 20 ml, over 5 minutes, followed by stirring at 0° C. for 1 hour and then stirring at room temperature for 1.5 hours. After the addition of ethyl acetate and methanol, the solvent was distilled off and the residue was then purified through silica gel column chromatography (chloroform/methanol), thereby obtaining the subject compound (380.0 mg) as a white solid.

MS(FAB, Pos.): m/z=322[M+H]$^+$ $^1$H-NMR(500 MHz, DMSO-d$_6$+D$_2$O): δ=1.39(9H, s), 1.80–1.86(2H, m), 2.91–2.94(2H, m), 3.46–3.48(2H, m), 4.20(2H, s), 7.31(1H, dd, J=1.3 Hz,8.4 Hz), 7.56(1H, s), 7.79(1H, d, J=8.3 Hz).

Example 120-5

Synthesis of [2-(3-dipropylamino-propyl)-benzo[b]thiophen-5-ylmethyl]-carbamic acid t-butyl ester The compound (356.0 mg) obtained in Example 120-4 was dissolved in anhydrous dichloromethane (10 ml) and added with Dess-Martin periodinane (manufactured by Aldrich Corporation) (563.7 mg), followed by stirring at room temperature for 40 minutes. Then, the solution was added with water and extracted with chloroform. The organic layer was washed with saturated saline solution and dried with anhydrous sodium sulfate. The solvent was distilled off and the residue was then purified through silica gel column chromatography (hexane/ethyl acetate). The purified product was dissolved in methanol (10 ml) and then added with di-n-propylamine (0.19 ml), trimethyl orthoformate (0.15 ml), and sodium cyanoborohydride (87.6 mg), followed by stirring at room temperature for 30 hours. The solution was added with water and then extracted with chloroform. The organic layer was washed with saturated saline solution and then dried with anhydrous sodium sulfate. Subsequently, the solvent was distilled off and the residue was purified through silica gel column chromatography (hexane/ethyl acetate), thereby obtaining the subject compound (241.9 mg) as a pale-yellow solid.

MS(FAB, Pos.): m/z=405[M+H]$^+$ $^1$H-NMR(500 MHz, DMSO-d$_6$+D$_2$O): δ=0.84(6H, t, J=7.3 Hz), 1.39(9H, s), 1.77–1.80(2H, m), 2.30–2.33(4H, m), 2.40–2.43(2H, m), 2.88–2.91(2H, m), 4.20(2H, s), 7.12 (1H, s), 7.17(1H, dd, J=1.5 Hz,8.2 Hz), 7.56(1H, s), 7.89 (1H, d, J=8.2 Hz).

Example 120-6

Synthesis of [3-(5-{[(1H-imidazol-2-ylmethyl)-amino]-methyl}-benzo[b]thiophen-2-yl)-propyl]-dipropyl-amine The compound (237.7 mg) obtained in Example 120-5 was added to a 4 mol/l hydrogen chloride/dioxane solution (4.74 ml) and the whole was stirred for 17 hours. Then, the solvent was distilled off, and the residue was dried. The dried product was dissolved in methanol and then neutralized with an anion-exchange resin (Amberlite IRA-410). Subsequently, the solvent was distilled off and the residue was then dried under reduced pressure. After the dried product had been dissolved in methanol (8 ml), 2-imidazole carboxaldehyde (84.6 mg) and trimethyl orthoformate (0.19 ml) were added to the solution, and then the whole was stirred at room temperature for 20 hours. Subsequently, sodium borohydride (66.6 mg) was added to the solution, and then the whole was stirred at room temperature for 16 hours. After completion of the reaction, the solution was added with water and subjected to chloroform extraction. The resulting organic layer was washed with saturated saline solution, followed by drying with anhydrous sodium sulfate. The solvent was distilled off and the residue was then purified through silica gel column chromatography (chloroform/methanol), thereby obtaining the subject compound (197.9 mg) as a white yellow solid.

MS(FAB, Pos.): m/z=385[M+H]$^+$ $^1$H-NMR(500 MHz, DMSO-d$_6$+D$_2$O): δ=0.84(6H, t, J=7.3 Hz), 1.35–1.39(4H, m), 1.77–1.80(2H, m), 2.30–2.33 (4H, m), 2.41–2.44(2H, m), 2.88–2.91(2H, m), 3.69(2H, s), 3.74(2H, s), 6.83(1H, brs), 7.04(1H, brs), 7.11(1H, s), 7.26 (1H, dd, J=1.7, 8.4 Hz), 7.67(1H, s), 7.79(1H, d, J=8.2 Hz).

Example 120-7

Synthesis of [3-(5-{[(1H-imidazol-2-ylmethyl)-(1-methyl-1H-imidazol-2-ylmethyl)-amino]-methyl}-benzo[b]-thiophen-2-yl)-propyl]-dipropyl-amine [Compound No. 121]

The compound (197.9 mg) obtained in Example 120-6 was dissolved in methanol (10 ml) and then added with 1-methyl-2-imidazole carboxaldehyde (68.0 mg) and sodium cyanoborohydride (64.7 mg). After that, the solution was adjusted to pH 5 with acetic acid, followed by stirring overnight at room temperature. After the solvent had been distilled off, the residue was purified through silica gel column chromatography (chloroform/methanol) and treated with hydrochloric acid, thereby obtaining hydrochloride (228.7 mg) of the subject compound as a white solid.

MS(FAB, Pos.): m/z=479[M+H]$^+$ $^1$H-NMR(500 MHz, DMSO-d$_6$+D$_2$O): δ=0.90(6H, t, J=7.2 Hz), 1.16–1.19(2H, m), 1.62–1.67(4H, m), 1.99(3H, s), 2.01–2.10(4H, m), 2.95–3.03(6H, m), 3.09–3.12(2H, m), 3.70(2H, s), 3.80(2H, s), 4.01–4.08(4H, m), 4.15(2H, s), 7.20(1H, s), 7.31(1H, dd, J=1.4 Hz,8.3 Hz), 7.48(1H, s), 7.61(1H, s), 7.76(1H, s), 7.80(1H, d, J=8.4 Hz).

Production Example 121

Synthesis of 2-{[(1H-imidazol-2-ylmethyl)-(1-methyl-1H-imidazol-2-ylmethyl)-amino]-methyl}-6-(3-dipropylaminopropyl)-naphtalene [Compound No. 122]

Example 121-1

Synthesis of 2,6-dihydroxymethylnaphthalene 2,6-naphthalene dicarboxylic acid dimethyl (5.00 g) was dissolved in anhydrous THF (150 ml) and added with lithium aluminum hydride (1.55 g) under ice-cooling, followed by stirring at room temperature for 2 hours under a nitrogen atmosphere. After completion of the reaction, methanol and an aqueous potassium sodium tartrate solution were added to the solution in this order and the whole was stirred overnight. The solution was subjected to extraction with chloroform and ethyl acetate and the extract was then washed with saturated saline solution. Subsequently, the organic layer was dried with anhydrous sodium sulfate and the solvent was distilled off, thereby obtaining the subject compound (3.90 g) as a white solid.

$^1$H-NMR(500 MHz, CDCl$_3$): δ=4.87(4H, d, J=6.4 Hz), 7.50(2H, dd, J=1.5, 7.3 Hz), 7.83(2H, d, J=8.3 Hz), 7.84(2H, d, J=8.3 Hz).

Example 121-2

Synthesis of 2-t-butyldimethylsilyloxymethyl-6-hydroxymethylnaphthalene

The compound (3.41 g) obtained in Example 121-1 was dissolved in anhydrous DMF (200 ml). Then, t-butyldimethylsilyl chloride (2.73 g) dissolved in imidazole (1.48 g) and anhydrous DMF (50 ml) was dropped in this solution, and the whole was stirred overnight at room temperature. After completion of the reaction, the solution was added with a saturated aqueous ammonium chloride solution and stirred. The solution was extracted with chloroform and the extract was then washed with a saturated aqueous sodium bicarbonate solution, a saturated aqueous ammonium chloride solution, and saturated saline solution. Then, the organic layer was dried with anhydrous sodium sulfate. Subsequently, the solvent was distilled off and the residue was then purified through silica gel column chromatography (chloroform), thereby obtaining the subject compound (2.68 g) as a white solid.

$^1$H-NMR(500 MHz, CDCl$_3$): δ=0.13(6H, s), 0.97(9H, s), 1.74(1H, t, J=5.9 Hz), 4.86(2H, d, J=5.9 Hz), 4.90(2H, s), 7.44(1H, dd, J=1.5, 8.3 Hz), 7.48(1H, dd, J=2.0, 8.8 Hz), 7.77(1H, s), 7.80(2H, d, J=8.3 Hz), 7.83(1H, d, J=8.8 Hz).

Example 121-3

Synthesis of 2-t-butyldimethylsilyloxylmethyl-naphthalene-6-carboxaldehyde

The compound (255 mg) obtained in Example 121-2 was dissolved in chloroform (5.0 ml) and then added with manganese dioxide (chemically processed product) (366 mg), followed by stirring overnight at room temperature. After completion of the reaction, the solution was filtrated through Celite and the solvent was then distilled off, thereby obtaining the subject compound (245 mg) as a white solid.

Example 121-4

Synthesis of 3-(2-t-butyldimethylsilyloxylmethyl-naphthalen-6-yl)acrylic acid methyl ester The compound (245 mg) obtained in Example 121-3 was dissolved in anhydrous THF (5.0 ml), added with methyl triphenylphophoranylideneacetate (300 mg), and stirred at room temperature for 5 days under a nitrogen atmosphere. After completion of the reaction, the solvent was distilled off and the residue was then purified through silica gel column chromatography (hexane/ethyl acetate), thereby obtaining the subject compound (223 mg) as a white solid.

MS(FAB, Pos.): m/z=357[M+H]$^+$ $^1$H-NMR(500 MHz, CDCl$_3$): δ=0.14(6H, s), 0.97(9H, s), 3.83(3H, s), 4.90(2H, s), 6.55(1H, d, J=16.1 Hz), 7.46(1H, dd, J=1.7, 8.5 Hz), 7.66(1H, dd, J=1.7, 8.5 Hz), 7.77(1H, s), 7.82(2H, dd, J=3.4, 8.5 Hz), 7.85(1H, d, J=16.1 Hz), 7.91 (1H, s).

Example 121-5

Synthesis of 3-(6-t-butyldimethylsilyloxymethyl-naphthalen-2-yl)propionic acid methyl ester The compound (2.54 g) obtained in Example 121-4 was dissolved in anhydrous benzene (80 ml) and added with palladium black, followed by stirring at room temperature for 1 hour under a nitrogen atmosphere. After completion of the reaction, the solution was filtrated through Celite. Then, the solvent was distilled off, thereby obtaining the subject compound (2.62 g) as a white solid.

$^1$H-NMR(500 MHz, CDCl$_3$): δ=0.12(6H, s), 0.96(9H, s), 2.72(2H, t, J=7.6 Hz), 3.11(2H, t, J=7.6 Hz), 3.68(3H, s), 4.88(2H, s), 7.32(1H, dd, J=2.0, 8.5 Hz), 7.41(1H, dd, J=1.7, 8.5 Hz), 7.62(1H, s), 7.73(1H, s), 7.76(2H, d, J=8.1 Hz).

Example 121-6

Synthesis of 3-(6-t-butyldimethylsilyloxymethyl-naphthalen-2-yl)propan-1-ol

The compound (2.62 g) obtained in Example 121-5 was dissolved in anhydrous THF (100 ml) and added with lithium aluminum hydride (555 mg) under ice-cooling, followed by stirring for 30 minutes under a nitrogen atmosphere. After completion of the reaction, the solution was added with methanol and then added with an aqueous potassium sodium tartrate solution, followed by stirring overnight. The solution was extracted with chloroform and the extract was washed with saturate saline solution. Then, the organic layer was dried with anhydrous sodium sulfate. The solvent was distilled off, thereby obtaining the subject compound (2.64 g) as a white solid.

$^1$H-NMR(500 MHz, CDCl$_3$): δ=0.13(6H, s), 0.97(9H, s), 1.96–2.02(2H, m), 2.87(2H, t, J=7.3 Hz), 3.71(2H, q, J=6.3 Hz), 4.89(2H, s), 7.34(1H, dd, J=1.7, 8.3 Hz), 7.41(1H, dd, J=1.7, 8.3 Hz), 7.62(1H, s), 7.74(2H, d, J=8.3 Hz), 7.76(1H, d, J=8.3 Hz).

Example 121-7

Synthesis of 3-(6-t-butyldimethylsilyloxymethyl-naphthalen-2-yl)propionaldehyde

The compound (1.18 g) obtained in Example 121-6 was dissolved in anhydrous dichloromethane (25 ml) and added with Dess-Martin periodinane (1.82 g), followed by stirring at room temperature for 2 hours. After completion of the reaction, a sodium thiosulfate aqueous solution and a saturated aqueous sodium bicarbonate solution were added to the solution, and the whole was stirred. Then, the solution was extracted with chloroform and the extract was then washed with an aqueous mixture solution of a sodium thiosulfate aqueous solution and a saturated sodium bicarbonate aqueous solution. Then, the organic layer was dried with anhydrous sodium sulfate and the solvent was distilled off. The residue was purified through silica gel column chromatography (hexane/ethyl acetate), thereby obtaining the subject compound (981 mg) as a white solid.

$^1$H-NMR(500 MHz, CDCl$_3$): δ=0.13(6H, s), 0.96(9H, s), 2.88(2H, dt, J=1.7, 7.6 Hz), 3.12(2H, t, J=7.6 Hz), 4.88(2H, s), 7.32(1H, dd, J=2.0, 8.3 Hz), 7.41(1H, dd, J=1.7, 8.8 Hz), 7.61(1H, s), 7.73(1H, s), 7.74(1H, d, J=7.8 Hz), 7.76(1H, d, J=8.3 Hz), 9.87(1H, s).

Example 121-8

Synthesis of [3-(6-t-butyldimethylsilyloxymethyl-naphthalen-2-yl)propyl]dipropylamine Dipropylamine (363 mg) was dissolved in anhydrous methanol (20 ml) and then added with sodium cyanoborohydride (281 mg), trimethyl orthoformate (0.490 ml), and the compound (981 mg) obtained in Example 121-7, followed by stirring overnight at room temperature under a nitrogen atmosphere. After completion of the reaction, the solvent was distilled off. Then, the residue was dissolved in chloroform and added with a saturated aqueous sodium bicarbonate solution, followed by stirring. The solution was extracted with chloroform and the extract was then washed with a saturated aqueous sodium bicarbonate solution and saturated saline solution. After that, the organic layer was dried with anhydrous sodium sulfate. Subsequently, the solvent was distilled off and the residue was then purified through silica gel column chromatography (chloroform/ethyl acetate), thereby obtaining the subject compound (1.28 g) as a brown liquid.

MS(FAB, Pos.): m/z=414[M+H]$^+$ $^1$H-NMR(500 MHz, CDCl$_3$): δ=0.16(6H, s), 0.87(6H, t, J=7.3 Hz), 0.96(9H, s), 1.45(4H, sext., J=7.6 Hz), 1.86(2H, quint., J=7.8 Hz), 2.38(4H, t, J=7.6 Hz), 2.49(2H, t, J=7.8 Hz), 2.77(2H, t, J=7.8 Hz), 4.88(2H, s), 7.33(1H, dd, J=1.7, 8.4 Hz), 7.40(1H, dd, J=1.7, 8.1 Hz), 7.60(1H, s), 7.73(1H, s), 7.73(1H, d, J=8.4 Hz), 7.74(1H, d, J=8.5 Hz).

Example 121-9

Synthesis of 2-hydroxymethyl-6-(3-dipropylaminopropyl)naphthalene

The compound (1.28 g) obtained in Example 121-8 was added with a 1 mol/l TBAF/THF solution (6.20 ml) and stirred overnight at room temperature. After completion of the reaction, the solvent was distilled off. Then, the residue was dissolved in chloroform and added with distilled water, followed by stirring. The solution was extracted with chloroform and the extract was then washed with saturated saline solution. The resulting organic layer was dried with anhydrous sodium sulfate. Subsequently, the solvent was distilled off and the residue was then purified through silica gel column chromatography (chloroform/ethyl acetate), thereby obtaining the subject compound (472 mg) as a brown liquid.

MS(FAB, Pos.): m/z=300[M+H]$^+$ $^1$H-NMR(500 MHz, CDCl$_3$): δ=0.87(6H, t, J=7.6 Hz), 1.44(4H, sext., J=7.6 Hz), 1.86(2H, quint., J=7.1 Hz), 2.38 (4H, t, J=7.6 Hz), 2.49(2H, t, J=7.1 Hz), 2.78(2H, t, J=7.8 Hz), 4.85(2H, s), 7.35(1H, dd, J=2.0, 8.5 Hz), 7.46(1H, dd, J=1.7, 8.5 Hz), 7.62(1H, s), 7.76(1H, d, J=9.3 Hz), 7.78(1H, s), 7.78(1H, d, J=9.3 Hz).

Example 121-10

Synthesis of 2-phthalimidomethyl-6-(3-dipropylaminopropyl)naphthalene

The compound (453 mg) obtained in Example 121-9 was added with triphenylphosphine (516 mg) and phthalimide (245 mg), and then dissolved in anhydrous THF (10 ml). The solution was added with a 40% diethylazodicarboxylate/toluene solution (0.892 ml) in an ice bath and stirred at room temperature for 2 hours under a nitrogen atmosphere. After completion of the reaction, the solvent was distilled off and the residue was then purified through silica gel column chromatography (hexane/ethyl acetate), thereby obtaining the subject compound (439 mg) as a white solid.

MS(FAB, Pos.): m/z=429[M+H]$^+$ $^1$H-NMR(500 MHz, CDCl$_3$): δ=0.86(6H, t, J=7.6 Hz), 1.42(4H, sext., J=7.6 Hz), 1.82(2H, quint., J=7.6 Hz), 2.35 (4H, t, J=7.6 Hz), 2.45(2H, t, J=7.6 Hz), 2.75(2H, t, J=7.6 Hz), 4.99(2H, s), 7.32(1H, dd, J=1.7, 8.5 Hz), 7.52(1H, dd, J=2.0, 8.5 Hz), 7.57(1H, s), 7.70–7.74(4H, m), 7.84–7.87 (3H, m).

Example 121-11

Synthesis of 2-aminomethyl-6-(3-dipropylaminopropyl)naphthalene

The compound (439 mg) obtained in Example 121-10 was dissolved in a 40% methylamine/methanol solution (45 ml) and stirred at room temperature for 3 days. After completion of the reaction, the solvent was distilled off. Then, a 1 mol/l sodium hydroxide aqueous solution was added to the residue, and the whole was stirred. The solution was extracted with chloroform and the extract was washed with saturated saline solution. After that, the organic layer was dried with anhydrous sodium sulfate. Then, the solvent was distilled off, thereby obtaining the subject compound (283 mg) as a colorless oily substance.

MS(FAB, Pos.): m/z=299[M+H]$^+$ $^1$H-NMR(500 MHz, CDCl$_3$): δ=0.87(6H, t, J=7.3 Hz), 1.44(4H, sext., J=7.6 Hz), 1.85(2H, quint., J=7.8 Hz), 2.37 (4H, t, J=7.6 Hz), 2.48(2H, t, J=7.8 Hz), 2.77(2H, t, J=7.8 Hz), 4.02(2H, s), 7.34(1H, dd, J=1.7, 8.3 Hz), 7.41(1H, dd, J=2.0, 8.5 Hz), 7.60(1H, s), 7.71(1H, s), 7.74(1H, d, J=8.3 Hz), 7.75(1H, d, J=8.1 Hz).

Example 121-12

Synthesis of 2-{[(1H-imidazol-2-ylmethyl)-(1-methyl-1H-imidazol-2-ylmethyl)-amino]-methyl}-6-(3-dipropylaminopropyl)-naphtalene [Compound No. 122]

The compound (280 mg) obtained in Example 121-11 was dissolved in anhydrous methanol (5.0 ml) and added with trimethyl orthoformate (0.154 ml) and 2-imidazole carboxaldehyde (90.1 mg), followed by stirring at room temperature for 2 hours under a nitrogen atmosphere. Subsequently, the solution was added with sodium borohydride (53.3 mg) in an ice bath and stirred at room temperature for 30 minutes. After completion of the reaction, a saturated aqueous ammonium chloride solution was added to the solution, and the whole was stirred. The solution was subjected to extraction with chloroform. The extract was washed with a saturated aqueous sodium bicarbonate solution and saturated saline solution. Then, the organic layer was dried with anhydrous sodium sulfate. The residue obtained was dissolved in anhydrous methanol (10 ml) and added with sodium cyanoborohydride (93.6 mg), acetic acid (3.00 ml), and 1-methyl-2-imidazole carboxaldehyde (120 mg), followed by stirring at room temperature for 2 days under a nitrogen atmosphere. After completion of the reaction, the solvent was distilled off and the residue was then dissolved in chloroform. The solution was added with a saturated aqueous sodium bicarbonate solution and stirred. The solution was subjected to extraction with chloroform and the extract was then washed with a saturated aqueous sodium bicarbonate solution and saturated saline solution. The organic layer was dried with anhydrous sodium sulfate and then the solvent was distilled off. Subsequently, the residue was purified through silica gel column chromatography (chloroform/ethyl acetate) and treated with hydrochloric acid, thereby obtaining hydrochloride (318 mg) of the subject compound as a white solid.

MS(FAB, Pos.): m/z=473[M+H]$^+$ $^1$H-NMR(500 MHz, DMSO-d$_6$+D$_2$O): δ=0.89(6H, t, J=7.3 Hz), 1.62(4H, sext., J=7.3 Hz), 2.03(2H, quint. 7.9 Hz), 2.79(2H, t, J=7.8 Hz), 2.99–3.02(4H, m), 3.09(2H, t, J=8.1 Hz), 3.85(2H, s), 4.10(2H, s), 4.18(2H, s), 7.43(1H, d, J=1.8 Hz), 7.44(1H, s), 7.45(1H, d, J=1.8 Hz), 7.50(1H, d, J=8.4 Hz), 7.59(2H, d, J=1.4 Hz), 7.71(1H, s), 7.77(1H, d, J=8.5 Hz), 7.83(1H, s), 7.83(1H, d, J=8.4 Hz).

Production Example 122

Synthesis of N-(4-di-n-propylaminomethyl-phenyl)-4-{[(1-methyl-imidazol-2-ylmethyl)-(1H-[1,2,4]-triazol-3-ylmethyl)-amino]-methyl}-benzamide [Compound No. 123]

Example 122-1

Synthesis of 4-(t-butoxycarbonylaminomethyl)-benzoic acid

Commercially available 4-aminomethylbenzoic acid/hydrochloride (20.9 g) was dissolved in dioxane (200 ml), water (100 ml), and a 1 mol/l sodium hydroxide aqueous solution (137.9 ml). Then, under ice-cooling, di-t-butyl dicarbonate (30.7 g) was added to the solution. The reaction solution was stirred at room temperature for 17 hours and then concentrated under reduced pressure. The residue was added with a 1 mol/l sodium hydroxide aqueous solution and water, and then added with 1 mol/l hydrochloric acid to adjust the solution to pH 4. The precipitated solid was separated through filtration and heated and dried under reduced pressure, thereby obtaining the subject compound (31.3 g) as a white solid.

Example 122-2

Synthesis of [4-(4-dipropylaminomethyl-phenylcarbamoyl)-benzyl]-carbamic acid t-butyl ester The compound (1.95 g) obtained in Example 122-1 was dissolved in chloroform (20 ml) and DMF (8 ml) and then added with WSCI hydrochloride (1.50 g) and HOBt (1.08 g), followed by stirring at room temperature for 1 hour. The compound (1.23 g) obtained in Example 19-2 and chloroform (10 ml) were added to the solution, and the whole was stirred at room temperature for 15 hours. The reaction solution was concentrated under reduced pressure and the residue was then purified through silica gel column chromatography (chloroform/methanol), thereby obtaining the subject compound (2.86 g) as a yellow oily substance.

Example 122-3

Synthesis of 4-aminomethyl-N-(4-dipropylaminomethyl-phenyl)-benzamide

The compound (1.38 g) obtained in Example 122-2 was dissolved in methanol (10 ml), added with a 4 mol/l hydrogen chloride/dioxane solution (15 ml), and stirred at room temperature for 30 minutes. The reaction solution was concentrated under reduced pressure and neutralized with an anion-exchange resin (Amberlite IRA-410). The solvent was concentrated under reduced pressure and the residue was dried under vacuum, thereby obtaining the subject compound (0.79 g) as a yellow solid.

Example 122-4

Synthesis of N-(4-dipropylaminomethyl-phenyl)-4-{[(1-methyl-1H-imidazol-2-ylmethyl)-amino]methyl}benzamide The compound (290.2 mg) obtained in Example 122-3 was dissolved in methanol (8.71 ml) and added with 1-methyl-2-imidazole carboxaldehyde (141.2 mg) and trimethyl orthoformate (272.2 mg), followed by stirring for 22 hours. The reaction solution was cooled with ice and then added with sodium borohydride (97.0 mg), followed by stirring at room temperature for 0.5 hour. The reaction solution was concentrated under reduced pressure and the residue was then added with water, followed by separation/extraction with chloroform. The organic layer was washed with saturate saline solution and dried with anhydrous sodium sulfate, followed by concentration under reduced pressure. The residue was purified through silica gel column chromatography (chloroform/methanol), thereby obtaining the subject compound (256.8 mg) as a yellow oily substance.

Example 122-5

Synthesis of N-(4-di-n-propylaminomethyl-phenyl)-4-{[(1-methyl-imidazol-2-ylmethyl)-(1H-[1,2,4]-triazol-3-ylmethyl)-amino]-methyl}-benzamide [Compound No. 123]

The compound (256.8 mg) obtained in Example 122-4 was dissolved in methanol (7.7 ml) and added with 1H-[1,2,4]-triazol-3-carboxaldehyde (115.0 mg) and sodium cyanoborohydride (74.4 mg). Then, the solution was adjusted to pH 5 with acetic acid and stirred at room temperature for 14 hours. The reaction solution was concentrated under reduced pressure. Subsequently, the residue was purified through silica gel column chromatography (chloroform/methanol) and treated with hydrochloric acid, thereby obtaining hydrochloride (337.9 mg) of the subject compound as a white solid.

$^1$H-NMR(500 Mz, DMSO-$d_6$+$D_2$O): δ=0.88(6H, t, J=7.3 Hz), 1.62–1.76(4H, m), 2.92–2.98(4H, m), 3.77(3H, s), 3.81(2H, s), 3.92(2H, s), 4.11(2H, s), 4.28(2H, s), 7.47–7.52 (3H, m), 7.56(2H, d, J=8.5 Hz), 7.88(2H, d, J=8.5 Hz), 7.92(2H, d, J=8.3 Hz), 8.66(1H, brs).

Production Example 123

Synthesis of [5-(6-{[(1H-imidazol-2-ylmethyl)-(1-methyl-1H-imidazol-2-ylmethyl)-amino]-methyl}-quinolin-2-yl)-pentyl]-dipropylamine [Compound No. 124]

Example 123-1

Synthesis of (3-cyano-propyl)-triphenyl-phosphonium bromide

Triphenylphosphine (1.4789 g) was dissolved in anhydrous toluene (44.4 ml) and then added with 4-bromobutyronitrile (manufactured by Tokyo Kasei Kogyo Co., Ltd.) (834.7 mg), followed by thermal reflux for 22 hours. After the reaction, a precipitated product was filtrated. The precipitate obtained through filtration was washed with toluene and thermally dried under reduced pressure, thereby obtaining the subject compound (1.1697 g) as a white solid.

$^1$H-NMR(500 MHz, DMSO-$d_6$): δ=1.87(2H, dt, J=7.3, 11.7 Hz), 2.72(2H, t, J=7.3 Hz), 3.63–3.70(2H, m), 7.76–7.84(12H, m), 7.90–7.94(3H, m).

Example 123-2

Synthesis of 5-[6-(1,3-dioxo-1,3-dihydro-isoindol-2-ylmethyl)-quinolin-2-yl]-penta-4-ennitrile The compound (675.0 mg) obtained in Example 123-1 was suspended in anhydrous THF (30 ml) and cooled with ice. Then, the suspension was added with a 2 mol/l lithium diisopropylamide/heptane solution (0.825 ml), followed by stirring at room temperature for 1 hour. Then, the solution was gradually added with a solution prepared by suspending the compound (327.9 mg) obtained in Example 119-7 in anhydrous THF (20 ml), followed by stirring at room temperature for 3 hours. After completion of the reaction, the solvent was distilled off and the residue was then purified through silica gel column chromatography (chloroform/ ethyl acetate), thereby obtaining the subject compound (268.0 mg) as a yellow solid.

MS(FAB, Pos.): m/z=368[M+H]$^+$ $^1$H-NMR(500 MHz, CDCl$_3$): δ=2.66(2H, t, J=7.3 Hz), 3.19(2H, dq, J=1.5, 7.3 Hz), 5.03(2H, s), 6.03–6.08(1H, m), 6.69(1H, dt, J=1.5, 10.0 Hz), 7.29(1H, d, J=8.5 Hz), 7.71–7.75(2H, m), 7.77(1H, dd, J=2.0, 8.8 Hz), 7.83(1H, d, J=1.7 Hz), 7.86–7.89(2H, m), 7.98(1H, d, J=8.5 Hz), 8.08 (1H, d, J=8.3 Hz).

Example 123-3

Synthesis of [2-(4-cyano-butyl)-quinolin-6-ylmethyl]-carbamic acid t-butyl ester The compound (265.1 mg) obtained in Example 123-2 was dissolved in a 40% methylamine/methanol solution (8.0 ml) and then stirred at room temperature for 15 hours. After the reaction, the solvent was distilled off under reduced pressure. The residue was dissolved in chloroform and then washed with a 1 mol/l sodium hydroxide aqueous solution. The resultant was dried with magnesium sulfate and the solvent was then distilled off under reduced pressure.

The residue was dissolved in chloroform (5.1 ml) and added with di-t-butyl dicarbonate (235.7 mg) and triethylamine (0.151 ml), followed by stirring at room temperature for 5 hours. After the reaction, the solvent was distilled off under reduced pressure.

The residue was dissolved in ethanol (12 ml) and then added with 20% palladium hydroxide-carbon (242.9 mg), followed by stirring at room temperature for 1.5 hours under a hydrogen atmosphere. After the reaction, the solution was filtrated through Celite and the solvent was then distilled off. The residue was purified through silica gel column chromatography (hexane/ethyl acetate), thereby obtaining the subject compound (82.0 mg) as a yellow solid.

MS(FAB, Pos.): m/z=340[M+H]$^+$ $^1$H-NMR(500 MHz, CDCl$_3$): δ=1.48(9H, s), 1.78(1H, quint., J=7.3 Hz), 1.98–2.05(2H, m), 2.41(2H, t, J=7.3 Hz), 3.02(2H, t, J=7.6 Hz), 4.50(2H, d, J=5.9 Hz), 4.97(1H, br), 7.29(1H, d, J=8.3 Hz), 7.62(1H, d, J=8.8 Hz), 7.67(1H, s), 7.99(1H, d, J=8.5 Hz), 8.05(1H, d, J=8.3 Hz).

Example 123-4

Synthesis of [2-(5-dipropylamino-pentyl)-quinolin-6-ylmethyl]-carbamic acid t-butyl ester The compound (75.8 mg) obtained in Example 123-3 was dissolved in anhydrous THF (2.2 ml). Then, the solution was added with lithium aluminum hydride (33.4 mg) and stirred at room temperature for 1 hour. An aqueous potassium sodium tartrate solution was added in this solution, and the whole was stirred, followed by extraction with chloroform. The organic layer was dried with magnesium sulfate and the solvent was then dried off. The residue was dissolved in anhydrous methanol (2.3 ml) and added with propionaldehyde (0.048 ml), trimethyl orthoformate (0.072 ml), and sodium cyanoborohydride (55.3 mg), followed by stirring at room temperature for 19 hours. The solvent was distilled off. Subsequently, the solvent was purified through silica gel column chromatography (hexane/ethyl acetate), thereby obtaining the subject compound (56.6 mg) as a yellow solid.

MS(FAB, Pos.): m/z=428[M+H]$^+$ $^1$H-NMR(500 MHz, CDCl$_3$): δ=0.85(6H, t, J=7.3 Hz), 1.38–1.51(8H, m), 1.48(9H, s), 1.82(2H, quint., J=7.8 Hz), 2.34–2.37(4H, m), 2.40(2H, t, J=7.3 Hz), 2.96(2H, t, J=7.8 Hz), 4.49(2H, d, J=5.9 Hz), 4.95–4.98(1H, br), 7.29(1H, d, J=8.3 Hz), 7.61(1H, d, J=8.3 Hz), 7.66(1H, s), 8.00(1H, d, J=8.5 Hz), 8.03(1H, d, J=8.3 Hz).

Example 123-5

Synthesis of [5-(6-{[(1H-imidazol-2-ylmethyl)-(1-methyl-1H-imidazol-2-ylmethyl)-amino)-methyl}-quinolin-2-yl)-pentyl]-dipropylamine [Compound No. 124]

The compound (52.6 mg) obtained in Example 123-4 was dissolved in methanol (1.6 ml) and added with a 4 mol/l hydrogen chloride/dioxane solution (1.6 ml), followed by stirring at room temperature for 1.5 hours. After the reaction, the solvent was distilled off under reduced pressure. The residue was neutralized with an anion-exchange resin (Amberlite IRA-410) and the solvent was then distilled off. The residue was dissolved in anhydrous methanol (1.0 ml) and added with 2-imidazole carboxaldehyde (17.3 mg). The mixture was stirred at room temperature for 2 hours and then added with sodium borohydride (13.6 mg), followed by stirring at room temperature for 4 hours. After completion of the reaction, the solvent was distilled off and the residue was then dissolved in chloroform, followed by washing with water. The organic layer was dried with magnesium sulfate and the solvent was then distilled off. The residue was dissolved in anhydrous methanol (1.0 ml) and added with 1-methyl-2-imidazole carboxaldehyde (19.8 mg) and sodium cyanoborohydride (22.6 mg). The resulting solution was adjusted to pH 5 with acetic acid and then stirred at room temperature for 14 hours. After completion of the reaction, chloroform was added to the solution, followed by washing with a 1 mol/l sodium hydroxide aqueous solution. The organic layer was dried with magnesium sulfate and the solvent was then distilled off under reduced pressure. The residue was purified through silica gel column chromatography (chloroform/methanol) and treated with hydrochloric acid. Consequently, hydrochloride (45.4 mg) of the subject compound was obtained as a white solid.

MS(FAB, Pos.): m/z=502[M+H]$^+$ $^1$H-NMR(500 MHz, DMSO-d$_6$+D$_2$O): δ=0.91(6H, t, J=7.3 Hz), 1.39(2H, t, J=7.8 Hz), 1.60–1.73(6H, m), 1.82–1.88(2H, m), 2.97–3.09(6H, m), 3.16(2H, t, J=8.1 Hz), 3.73(3H, s), 3.97(2H, s), 4.13(2H, s), 4.20(2H, s), 7.46(2H, dd, J=2.0, 4.9 Hz), 7.59(2H, s), 7.85(1H, d, J=8.5 Hz), 8.01(1H, d, J=9.0 Hz), 8.13(1H, d, J=8.5 Hz), 8.18(1H, s), 8.78(1H, d, J=7.3 Hz).

Production Example 124

Synthesis of 2-{[(1H-imidazol-2-ylmethyl)-(1-methyl-1H-imidazol-2-ylmethyl)-amino]-methyl}-6-(4-dipropylaminobutyl)-naphtalene [Compound No. 125]

Example 124-1

Synthesis of t-butyl-[6-4-methoxy-3-butenyl)-naphthalen-2-yloxy]-dimethyl-silane Methoxymethyltrifluorophosphonium chloride (425 mg) was dissolved in anhydrous THF (10 ml). Then, the solution obtained was added with a 2 mol/l lithium diisopropylamide/ THF solution (0.619 ml) under ice-cooling, followed by stirring at room temperature for 1 hour. A solution of the compound (296 mg) obtained in Example 121-7 in anhydrous THF was added in this solution, and the whole was stirred overnight at room temperature. After completion of the reaction, distilled water was added to the solution, and the whole was stirred. The solution was extracted with chloroform and the extract was washed with saturated saline solution. The organic layer was dried with anhydrous sodium sulfate. The solvent was distilled off and the residue was then purified through silica gel column chromatography (hexane/ethyl acetate), thereby obtaining the subject compound (264 mg) (geometrical-isomer mixture) as a yellow oily substance.

(E Isomer)

$^1$H-NMR(500 MHz, CDCl$_3$): δ=0.12(6H, s), 0.96(9H, s), 2.33(2H, q, J=6.6 Hz), 2.79–2.83(2H, m), 3.48(3H, s), 4.78(1H, q, J=6.3 Hz), 4.88(2H, s), 6.32(1H, d, J=6.3 Hz), 7.29–7.36(1H, m), 7.38–7.41(1H, m), 7.59(1H, s), 7.73–7.74(3H, m).

(Z Isomer)

$^1$H-NMR(500 MHz, CDCl$_3$): δ=0.12(6H, s), 0.96(9H, s), 2.48(2H, q, J=6.6 Hz), 2.79–2.83(2H, m), 3.56(3H, s), 4.39(1H, q, J=12.5 Hz), 4.88(2H, s), 5.88(1H, d, J=12.5 Hz), 7.29–7.36(1H, m), 7.38–7.41(1H, m), 7.62(1H, s), 7.73–7.74(3H, m).

Example 124-2

Synthesis of 2-hydroxymethyl-6-(4-dipropylaminobutyl)naphthalene

The compound (263 mg) obtained in Example 124-1 was dissolved in THF (2.0 ml) and then added with distilled water (2.0 ml) and acetic acid (2.0 ml), followed by stirring overnight at room temperature. After completion of the reaction, the solvent was distilled off and the residue was obtained. Dipropylamine (253 mg) was dissolved in anhydrous methanol (5.0 ml). Then sodium cyanoborohydride (69.5 mg), acetic acid (3.0 ml), and the residue described above dissolved in anhydrous methanol were added to the solution, followed by stirring at room temperature for 3 days under a nitrogen atmosphere. After completion of the reaction, the solvent was distilled off. The residue was dissolved in chloroform and added with a saturated aqueous sodium bicarbonate solution, followed by stirring. Then, the solution was subjected to extraction with chloroform. The extract was washed with a saturated aqueous sodium bicarbonate solution and saturated saline solution. The organic layer was dried with anhydrous sodium sulfate. The solvent was distilled off and the residue was then purified through silica gel column chromatography (hexane/ethyl acetate), thereby obtaining the subject compound (70.0 mg) as a yellow oily substance.

MS(FAB, Pos.): m/z=314[M+H]$^+$

Example 124-3

Synthesis of 2-phthalimidomethyl-6-(4-dipropylaminobutyl)naphthalene

The compound (70.0 mg) obtained in Example 124-2 was added with triphenylphosphine (76.1 mg) and phthalimide (36.1 mg), and then dissolved in anhydrous THF (1.0 ml). Subsequently, the solution was added with a 40% diethyl azodicarboxylate/toluene solution (0.132 ml) in an ice bath and stirred at room temperature for 3 hours under a nitrogen atmosphere. After completion of the reaction, the solvent was distilled off and the residue was then purified through silica gel column chromatography (hexane/ethyl acetate), thereby obtaining the subject compound (75.0 mg) as a white solid.

MS(FAB, Pos.): m/z=443[M+H]$^+$

Example 124-4

Synthesis of 2-aminomethyl-6-(4-dipropylaminobutyl)naphthalene

The compound (75.0 mg) obtained in Example 124-3 was dissolved in a 40% methylamine/methanol solution (2.0 ml) and stirred overnight at room temperature. After completion of the reaction, the solvent was distilled off and then the residue was added with a 1 mol/l sodium hydroxide aqueous solution and stirred. The solution was subjected to extraction with chloroform and the extract was then washed with saturated saline solution. Subsequently, the organic layer was dried with anhydrous sodium sulfate and the solvent was then distilled off, thereby obtaining the subject compound (67.5 mg) as a colorless oily substance.

MS(FAB, Pos.): m/z=313[M+H]$^+$

Example 124-5

Synthesis of 2-{[(1H-imidazol-2-ylmethyl)amino] methyl}-6-(4-dipropylaminobutyl)naphthalene The compound (67.5 mg) obtained in Example 124-4 was dissolved in anhydrous methanol (2.0 ml) and added with trimethyl orthoformate (0.0354 ml) and 2-imidazole carboxaldehyde (20.8 mg), followed by stirring at room temperature for 2 hours under a nitrogen atmosphere. Subsequently, the solution was added with sodium borohydride (12.3 mg) in an ice bath and then stirred at room temperature for 1 hour. After completion of the reaction, a saturated aqueous ammonium chloride solution was added to the solution, and the whole was stirred. The solution was subjected to extraction with chloroform and the extract was then washed with a saturated aqueous sodium bicarbonate solution and saturated saline solution. The organic layer was dried with anhydrous sodium sulfate. The solvent was distilled off and the residue was then purified through silica gel column chromatography (chloroform/ethyl acetate), thereby obtaining the subject compound (39.0 mg) as a yellow oily substance.

MS(FAB, Pos.): m/z=393[M+H]$^+$

Example 124-6

Synthesis of 2-{[(1H-imidazol-2-ylmethyl)-(1-methyl-1H-imidazol-2-ylmethyl)-amino]-methyl}-6-(4-dipropylaminobutyl)-naphthalene [Compound No. 125]

The compound (39.0 mg) obtained in Example 124-5 was dissolved in anhydrous methanol (1.0 ml) and then added with sodium cyanoborohydride (9.40 mg), acetic acid (1.00 ml), and 1-methyl-2-imidazole carboxaldehyde (12.0 mg), followed by stirring at room temperature for 2 days under a nitrogen atmosphere. After completion of the reaction, the solvent was distilled off and the residue was then dissolved in chloroform. The solution was added with a saturated aqueous sodium bicarbonate solution and stirred. The solution was subjected to extraction with chloroform and the extract was then washed with a saturated aqueous sodium bicarbonate solution and saturated saline solution. The organic layer was dried with anhydrous sodium sulfate and the solvent was then distilled off. The residue was purified through silica gel column chromatography (chloroform/ ethyl acetate) and treated with hydrochloric acid, thereby obtaining hydrochloride (16.7 mg) of the subject compound as a white solid.

MS(FAB, Pos.): m/z=487[M+H]$^+$
$^1$H-NMR(500 MHz, DMSO-d$_6$): δ=0.88(6H, t, J=7.3 Hz), 1.60–1.75(8H, m), 2.77(2H, t, J=6.8 Hz), 2.90–2.98(4H, m), 3.05(2H, t, J=5.4 Hz), 3.68(3H, s), 3.82(2H, s), 4.11(2H, s), 4.18(2H, s), 7.39(1H, d, J=8.5 Hz), 7.50(2H, d, J=4.4 Hz), 7.56(1H, d, J=8.5 Hz), 7.64(2H, s), 7.67(1H, s), 7.74(1H, d, J=8.5 Hz), 7.81(1H, d, J=8.5 Hz), 7.90(1H, s).

Production Example 125

Synthesis of [4-(6-{[bis(1H-imidazol-2-ylmethyl)-amino]-methyl}-1-propyl-1H-benzimidazol-2-yl)-butyl]-dipropylamine [Compound No. 126]

Example 125-1

Synthesis of 4-amino-3-propylaminobenzoic acid methyl ester

In DMF (40 ml), methyl 3,4-diaminobenzoate (2.01 g) was dissolved and then the solution was added with potassium carbonate (2.00 g) and 1-iodopropane (1.4 ml), followed by stirring at room temperature for 22 hours. After completion of the reaction, the solvent was distilled off under reduced pressure. The residue was dissolved in ethyl acetate and washed with water, followed by extraction with ethyl acetate. The organic layer was washed with saturated saline solution and dried with anhydrous sodium sulfate. After filtration, the solvent was distilled off under reduced pressure and the residue was then purified through silica gel column chromatography (hexane/ethyl acetate), thereby obtaining the subject compound (1.06 g).

MS(FAB, Pos.): m/z=209[M+H]$^+$
$^1$H-NMR(500 MHz, CDCl$_3$): δ=1.05(3H, t, J=7.3 Hz), 1.71(2H, sext., J=7.3 Hz), 3.12(2H, t, J=7.1 Hz), 3.86(3H, s), 6.69(1H, d, J=8.1 Hz), 7.35(1H, s), 7.45(1H, d, J=8.1 Hz).

Example 125-2

Synthesis of 4-(5-t-butoxycarbonylamino pentanoylamino)-3-propylaminobenzoic acid methyl ester In chloroform (10 ml), 5-t-butoxycarbonylaminovaleric acid (574 mg), WSCI hydrochloride (690 mg), and HOBt (487 mg) were dissolved. Then, the resulting solution was stirred at room temperature for 30 minutes. The solution was added with 4-amino-3-propylaminobenzoic acid methyl (503 mg) and stirred overnight at room temperature. After completion of the reaction, the solvent was distilled off under reduced pressure and the residue was then dissolved in chloroform. After having been washed with a saturated aqueous sodium bicarbonate solution, a saturated aqueous ammonium chloride solution, and saturated saline solution, the solution was dried with anhydrous sodium sulfate. After filtration, the solvent was distilled off under reduced pressure and the residue was then purified through silica gel column chromatography (chloroform/ethyl acetate), thereby obtaining the subject compound (540 mg) as a colorless viscous substance.

MS(FAB, Pos.): m/z=408[M+H]$^+$
$^1$H-NMR(500 MHz, CDCl$_3$): δ=0.97(3H, t, J=7.3 Hz), 1.37(9H, s), 1.37–1.46(2H, m), 1.51-1.66(4H, m), 2.37(2H, t, J=7.3 Hz), 2.93(2H, q, J=6.6 Hz), 3.04(2H, q, J=7.1 Hz), 3.81(3H, s), 5.14(1H, br), 6.83(1H, br), 7.16(1H, s), 7.20 (1H, d, J=8.1 Hz), 7.45(1H, d, J=8.1 Hz), 9.24(1H, s).

Example 125-3

Synthesis of 2-(4-dipropylaminobutyl)-3-propyl-3H-benzimidazole-5-carboxylic acid methyl ester The compound (540 mg) obtained in Example 125-2 was dissolved in methanol (10 ml) and added with a 4 mol/l hydrogen chloride/dioxane solution (5 ml), followed by stirring at room temperature for 1.5 hours. After completion of the reaction, the solvent was distilled off under reduced pressure and the residue was then dissolved in methanol, followed by neutralization with the addition of an anion-exchange resin (Amberlite IRA-410). The solvent was distilled off and the residue was then dissolved in methanol (12 ml). Subsequently, the solution was added with acetic acid (0.425 ml) and sodium cyanoborohydride (135 mg), followed by cooling to 0° C. The solution was added with propionaldehyde (0.114 ml) and stirred at room temperature for 1 hour, followed by cooling to 0° C. again. The solution was added with sodium cyanoborohydride (132 mg) and propionaldehyde (0.115 ml) and then stirred overnight at room temperature. After completion of the reaction, the solvent was distilled off under reduced pressure and then the residue was dissolved in chloroform. The solution was washed with a 1 mol/l sodium hydroxide aqueous solution and then subjected to extraction with chloroform. The organic layer was washed with saturated saline solution and dried with anhydrous sodium sulfate. After filtration, the solvent was distilled off under reduced pressure and the residue was then purified through silica gel column chromatography (chloroform/methanol), thereby obtaining the subject compound (361 mg) as a colorless viscous substance.

MS(FAB, Pos.): m/z=374[M+H]$^+$
$^1$H-NMR(500 MHz, CDCl$_3$): δ=0.88(6H, t, J=7.3 Hz), 1.00(3H, t, J=7.3 Hz), 1.49(4H, q, J=7.5 Hz), 1.74–1.82(4H, m), 1.87(2H, sext., J=7.6 Hz), 1.91–2.09(4H, m), 2.93–3.01 (4H, m), 3.00(2H, t, J=7.1 Hz), 3.09(2H, t, J=7.6 Hz), 3.96(3H, s), 4.15(2H, t, J=7.6 Hz), 7.66(1H, d, J=8.5 Hz), 7.96(1H, d, J=8.5 Hz), 8.08(1H, s).

Example 125-4

Synthesis of [2-(4-dipropylaminobutyl)-3-propyl-3H-benzimidazol-5-yl]methanol

Lithium aluminum hydride (138 mg) was suspended in THF (7 ml) and then cooled to 0° C. After that, a solution of the compound (361 mg) obtained in Example 125-3 in THF (7 ml) was dropped in the suspension, followed by stirring at 0° C. for 1 hour. After completion of the reaction, sodium sulfate decahydrate was continuously added to the solution until bubbling was stopped, and a 1 mol/l sodium hydroxide aqueous solution was then added to the mixture until a white precipitate was generated. Solid matter was separated through filtration and the solvent was then distilled off from the filtrate under reduced pressure. The residue was dried under vacuum, thereby obtaining the subject compound (302 mg) as a pale-yellow viscous substance.

MS(FAB, Pos.): m/z=346[M+H]$^+$ $^1$H-NMR(500 MHz, DMSO-d$_6$): δ=0.82(6H, t, J=7.3 Hz), 0.89(3H, t, J=7.3 Hz), 1.37(4H, sext., J=7.3 Hz), 1.50(2H, quint., J=7.3 Hz), 1.70–1.81(4H, m), 2.29(4H, t, J=7.3 Hz), 2.39(2H, t, J=7.1 Hz), 2.84(2H, t, J=7.6 Hz), 4.11(2H, t, J=7.3 Hz), 4.59(2H, d, J=5.2 Hz), 5.16(1H, t, J=5.5 Hz), 7.09(1H, d, J=8.2 Hz), 7.42(1H, s), 7.45(1H, d, J=8.2 Hz).

Example 125-5

Synthesis of 2-[2-(4-dipropylaminobutyl)-3-propyl-3H-benzimidazol-5-ylmethyl]isoindole-1,3-dione The compound (302 mg) obtained in Example 125-4 was dissolved in toluene (6.0 ml) and added with triphenylphosphine (275 mg) and phthalimide (193 mg), followed by cooling to 0° C. In this solution, a 40% diethyl azodicarboxylate/toluene solution (452 mg) was dropped. After that, the solution was stirred overnight at room temperature. After completion of the reaction, the solvent was distilled off under reduced pressure. The residue was dissolved in chloroform and washed with water. Then, the solution was subjected to extraction with chloroform and the extract was then washed with saturated saline solution. The organic layer was dried with anhydrous sodium sulfate. After filtration, the solvent was distilled off under reduced pressure and the residue was then purified through silica gel column chromatography (chloroform/methanol), thereby obtaining the subject compound (174 mg) as a pale-yellow solid.

MS(FAB, Pos.): m/z=475[M+H]$^+$ $^1$H-NMR(500 MHz, DMSO-d$_6$): δ=0.79–0.83(6H, m), 0.86(3H, t, J=7.3 Hz), 1.31–1.40(4H, m), 1.46–1.51(2H, m), 1.63–1.80(4H, m), 2.29(4H, br), 2.39(2H, br), 2.83(2H, t, J=7.6 Hz), 4.12(2H, t, J=7.3 Hz), 4.87(2H, s), 7.08(1H, d, J=8.3 Hz), 7.46–7.48(2H, m), 7.83–7.89(2H, m), 7.90–7.93 (2H, m).

Example 125-6

Synthesis of [4-(6-aminomethyl-1-propyl-1H-benzimidazol-2-yl)butyl]dipropylamine The compound (173 mg) obtained in Example 125-5 was dissolved in a 40% methylamine/methanol solution (1.8 ml) and stirred at room temperature for 17 hours. After completion of the reaction, the solvent was distilled off under reduced pressure and the residue was then purified through silica gel column chromatography (chloroform/ethyl acetate), thereby obtaining the subject compound (130 mg) as a pale-yellow viscous substance.

MS(FAB, Pos.): m/z=345[M+H]$^+$

Example 125-7

Synthesis of [4-(6-{[bis(1H-imidazol-2-ylmethyl) amino]methyl}-1-propyl-1H-benzimidazol-2-yl) butyl]dipropylamine The compound (130 mg) obtained in Example 125-6 was dissolved in methanol (3.0 ml) and added with trimethyl orthoformate (0.130 ml) and 2-imidazole carboxaldehyde (37.3 mg), followed by stirring for 1 hour. Then, the solution was cooled to 0° C. The solution was added with sodium borohydride (21.5 mg) and stirred at room temperature for 3 hours. After completion of the reaction, the solvent was distilled off under reduced pressure and the residue was then dissolved in chloroform. The solution was washed with a 1 mol/l sodium hydroxide aqueous solution and then subjected to extraction with chloroform. The organic layer was washed with saturated saline solution and then dried with anhydrous sodium sulfate. After filtration, the solvent was distilled off under reduced pressure. Then, the residue was purified through silica gel column chromatography (chloroform/ methanol) and treated with hydrochloric acid, thereby obtaining hydrochloride (16.4 mg) of the subject compound as a white solid.

MS(FAB, Pos.): m/z=505[M+H]$^+$ $^1$H-NMR(500 MHz, DMSO-d$_6$): δ=0.91(6H, t, J=7.3 Hz), 0.99(3H, t, J=7.3 Hz), 1.66–1.71(4H, m), 1.78–1.82(4H, m), 1.83–1.96(2H, m), 2.97–3.00(4H, m), 3.08–3.16(2H, m), 3.25(2H, t, J=7.2 Hz), 3.87(2H, s), 4.16(4H, s), 4.54(2H, t, J=7.7 Hz), 7.52–7.55(1H, m), 7.61(3H, s), 7.64–7.70(1H, m), 8.43(1H, s), 10.31(1H, br)

Production Example 126

Synthesis of [4-(6-{[(1H-imidazol-2-ylmethyl)-(1-methyl-1H-imidazol-2-ylmethyl)-amino]-methyl}-1-propyl-1H-benzimidazol-2-yl)-butyl]-dipropylamine [Compound No. 127]

Example 126-1

Synthesis of [4-(6-{[(1H-imidazol-2-ylmethyl) amino]methyl}-1-propyl-1H-benzimidazol-2-yl) butyl]dipropylamine The compound (130 mg) obtained in Example 125-6 was dissolved in methanol (3.0 ml) and added with trimethyl orthoformate (0.130 ml) and 2-imidazole carboxaldehyde (37.3 mg), followed by stirring for 1 hour. Then, the solution was cooled to 0° C. The solution was added with sodium borohydride (21.5 mg) and stirred at room temperature for 3 hours. After completion of the reaction, the solvent was distilled off under reduced pressure and the residue was then dissolved in chloroform. The solution was washed with a 1 mol/l sodium hydroxide aqueous solution and then subjected to extraction with chloroform. The organic layer was washed with saturated saline solution and then dried with anhydrous sodium sulfate. After filtration, the solvent was distilled off under reduced pressure. Then, the residue was purified through silica gel column chromatography (chloroform/ methanol), thereby obtaining the subject compound (64.0 mg) as a pale-yellow viscous substance.

Example 126-2

Synthesis of [4-(6-{[bis(1H-imidazol-2-ylmethyl)-amino]-methyl}-1-propyl-1H-benzimidazol-2-yl)-butyl]-dipropylamine [Compound No. 126]

The compound (64.0 mg) obtained in Example 126-1 was dissolved in methanol (1.3 ml) and added with acetic acid (0.065 ml) and 1-methyl-2-imidazole carboxaldehyde (16.6 mg), followed by cooling to 0° C. Then, the solution was added with sodium cyanoborohydride (14.2 mg) and stirred at room temperature for 2 days. After completion of the reaction, the solvent was distilled off under reduced pressure and the residue was then dissolved in chloroform. After washing with a 1 mol/l sodium hydroxide aqueous solution, the solution was subjected to extraction with chloroform. The organic layer was washed with saturated saline solution and dried with anhydrous sodium sulfate. After filtration, the solvent was distilled off under reduced pressure. Subsequently, the residue was purified through silica gel column chromatography (chloroform/methanol) and treated with hydrochloric acid, thereby obtaining hydrochloride (30.0 mg) of the subject compound as a white solid.

MS(FAB, Pos.): m/z=519[M+H]$^+$ $^1$H-NMR(500 MHz, DMSO-d$_6$): δ=0.91(6H, t, J=7.3 Hz), 0.99(3H, t, J=7.3 Hz), 1.66–1.74(4H, m), 1.78–1.84(4H, m), 1.93(2H, t, J=7.3 Hz), 2.94–3.00(4H, m), 3.13(2H, br), 3.26(2H, t, J=7.3 Hz), 3.73(3H, s), 3.90(2H, s), 4.13(2H, s), 4.21(2H, s), 4.53(2H, t, J=7.6 Hz), 7.53–7.55(3H, m), 7.63 (2H, s), 7.70(1H, d, J=8.2 Hz), 8.41(1H, s), 10.48(1H, br).

Production Example 127

Synthesis of [4-(5-{[(imidazol-2-ylmethyl)-(1-methylimidazol-2-ylmethyl)-amino]-methyl}-1-methoxy-indan-2-yl)-butyl]-dipropylamine [Compound No. 128]

Example 127-1

Synthesis of 4-(t-butyldiphenylsilyloxyl)-butan-1-ol

Commercially available 1,4-butanediol (400 g) was dissolved in DMF (120 ml), added with imidazole (3.02 g) and t-butyldiphenylchlorosilane (12.2 g), and stirred at room temperature for 15 hours. The reaction solution was concentrated under reduced pressure and then added with a saturated aqueous ammonium chloride solution, followed by separation/extraction with chloroform. The organic layer was washed with saturated saline solution and dried with anhydrous sodium sulfate, followed by concentration under reduced pressure. The residue was purified through silica gel column chromatography (hexane/ethyl acetate), thereby obtaining the subject compound (6.56 g) as a transparent and colorless oily substance.

$^1$H-NMR(500 Mz, CDCl$_3$): δ=1.05(9H, s), 1.63–1.71(4H, m), 2.05(1H, t, J=5.1 Hz), 3.66(2H, dt, J=5.1, 5.9 Hz), 3.70(2H, t, J=5.9 Hz), 7.37–7.45(6H, m), 7.67(4H, d, J=8.5 Hz).

Example 127-2

Synthesis of 4-(t-butyldiphenylsilyloxy)butylaldehyde

The compound (6.56 g) obtained in Example 127-1 was dissolved in dichloromethane (262 ml) and then added with Molecular Sieves 4A (32.8 g), N-methylmorpholin-N-oxide (7.02 g), and tetrapropylammonium perruthenate (702 mg), followed by stirring at room temperature for 2 hours. The reaction solution was filtrated through Celite and the filtrate was then concentrated under reduced pressure. The residue was purified through silica gel column chromatography (hexane/ethyl acetate) and the subject compound (3.86 g) was then obtained as a colorless oily substance.

Example 127-3

Synthesis of 5-bromo-2-[4-(t-butyldiphenylsilyloxy) butyliden]indan-1-one

Commercially available 5-bromoindanone (2.50 g) was dissolved in THF (75.0 ml). The solution was added with a 1 mol/l lithium bistrimethylsilyl amide/hexane solution (11.8 ml) while being stirred at −78° C., followed by stirring for 30 minutes. Subsequently, a solution of the compound (3.86 g) obtained in Example 127-2 in THF (15.0 ml) was gradually added to the solution, and further the whole was stirred for 3 hours. The reaction solution was added with a saturated aqueous ammonium chloride solution and then subjected to separation/extraction with chloroform. The organic layer was dried with anhydrous sodium sulfate and concentrated under reduced pressure. The residue was dissolved in DMF (75.0 ml) and then added with methanesulfonyl chloride (2.71 g) and triethylamine (2.63 g) while being stirred under ice-cooling, followed by stirring at room temperature for 1 hour. Subsequently, the solution was added with 1,8-diazo-bicyclo[5,4,0]undec-7-en (3.97 g) and stirred at 70° C. for 1 hour. The reaction solution was concentrated under reduced pressure and the residue was then added with a saturated aqueous ammonium chloride solution, followed by separation/extraction with chloroform. The organic layer was dried with anhydrous sodium sulfate and concentrated under reduced pressure. The residue was purified through silica gel column chromatography (hexane/ diethyl ether), thereby obtaining the subject compound (4.56 g) as a brown oily substance.

$^1$H-NMR(500 Mz, CDCl$_3$): δ=1.06(9H, s), 1.77(2H, quint., J=6.1 Hz), 2.42(2H, dt, J=6.1, 7.6 Hz), 3.62(2H, s), 3.71(2H, t, J=7.1 Hz), 6.88(1H, t, J=7.6 Hz), 7.34–7.44(7H, m), 7.54(1H, d, J=8.3 Hz), 7.64(4H, d, J=8.1 Hz), 7.71(1H, d, J=8.3 Hz).

Example 127-4

Synthesis of 5-bromo-2-[4-(t-butyldiphenylsilyloxy) butyl]indan-1-one

The compound (4.56 g) obtained in Example 127-3 was dissolved in THF (136.8 ml). Then, the solution was added with a 1 mol/l K-Selectride® (manufactured by Aldrich Corporation)-THF solution (8.76 ml) while being stirred at −78° C., followed by stirring at the same temperature for 1 hour. The reaction solution was added with a saturated aqueous ammonium chloride solution and then subjected to separation/extraction with chloroform. The organic layer was washed with saturated saline solution and dried with anhydrous sodium sulfate, followed by concentration under reduced pressure. The residue was purified through silica gel column chromatography (hexane/diethyl ether), thereby obtaining the subject compound (2.03 g) as a yellow oily substance.

Example 127-5

Synthesis of 5-bromo-2-[4-(t-butyldiphenylsilyloxy) butyl]indan-1-ol

The compound (2.03 g) obtained in Example 127-4 was dissolved in methanol (60.9 ml) and THF (30.5 ml) and, under ice-cooling, added with sodium borohydride (0.442 g), followed by stirring at room temperature for 2 hours. The reaction solution was added with a saturated aqueous ammonium chloride solution and then subjected to separation/ extraction with chloroform. The organic layer was dried with anhydrous sodium sulfate and concentrated under reduced pressure. The residue was purified through silica gel column chromatography (hexane/ethyl acetate), thereby obtaining the subject compound (1.54 g) as a yellow oily substance.

Example 127-6

Synthesis of [4-(5-bromo-1-methoxymethoxy-1-indan-2-yl)-butoxy]-t-butyldiphenylsilane The compound (1.54 g) obtained in Example 127-5 was dissolved in DMF (46.2 ml) and, while being stirred under ice-cooling, added with 60% sodium hydride (235 mg) and chloromethylmethylether (592 mg), followed by stirring at room temperature for 24 hours. The reaction solution was added with water and subjected to separation/extraction with chloroform. After having been washed with saturated saline solution, the organic layer was dried with anhydrous sodium sulfate, concentrated under reduced pressure, and dried under vacuum. The residue was purified through silica gel column chromatography (hexane/ethyl acetate), thereby obtaining the subject compound (1.64 g) as a yellow oily substance.

Example 127-7

Synthesis of 3-(5-bromo-1-methoxymethoxy-indan-2-yl)butylaldehyde

The compound (1.64 g) obtained in Example 127-6 was dissolved in THF (49.2 ml), added with a 1 mol/l TBAF/THF solution (4.69 ml), and stirred at room temperature for 3 hours. The reaction solution was concentrated under reduced pressure and added with water, followed by separation/extraction with chloroform. After having been washed with saturated saline solution, the organic layer was dried with anhydrous sodium sulfate, concentrated under reduced pressure, and dried under vacuum. The residue was dissolved in dichloromethane (41.2 ml) again. Then, the solution was added with Molecular Sieves 4A (5.15 g), N-methylmorpholine-N-oxide (1.10 g), tetrapropylammonium perruthenate (109 mg), followed by stirring at room temperature for 1 hour. The reaction solution was filtrated through Celite and the filtrate was then concentrated under reduced pressure. The residue was purified through silica gel column chromatography (hexane/ethyl acetate), thereby obtaining the subject compound (0.574 g) as a pale-yellow oily substance.

Example 127-8

Synthesis of 5-bromo-2-(3-dipropylaminobutyl)-1-methoxy]methoxy-indane

The compound (574.0 mg) obtained in Example 127-7 was dissolved in 1,2-dichloroethane (28.7 ml), while being stirred at room temperature, added with di-n-propylamine (266.3 mg) and sodium triacetoxy borohydride (743.6 mg), followed by stirring for 20 hours. The reaction solution was added with a 1 mol/l sodium hydroxide aqueous solution and subjected to separation/extraction with chloroform. Then, the organic solvent was washed with saturated saline solution and dried with anhydrous sodium sulfate, followed by concentration under reduced pressure. The residue was purified through silica gel column chromatography (chloroform/methanol), thereby obtaining the subject compound (552.4 mg) as a yellow oily substance.

Example 127-9

Synthesis of 5-cyano-2-(3-dipropylaminobutyl)-1-methoxymethoxy-indane

The compound (552.4 mg) obtained in Example 127-8 was dissolved in DMF (1.67 ml) and added with zinc cyanide (94.3 mg) and tetrakistriphenyl phosphine palladium (61.8 mg), followed by stirring at 80° C. for 48 hours. The reaction solution was added with chloroform and washed with a 7% aqueous ammonium solution and saturated saline solution. The solution was dried with anhydrous sodium sulfate and concentrated under reduced pressure. The residue was purified through silica gel column chromatography (chloroform/methanol), thereby obtaining the subject compound (436.8 mg) as a yellow oily substance.

Example 127-10

Synthesis of 5-aminomethyl-2-(3-dipropylaminobutyl)-1-methoxymethoxy-indane

The compound (436.8 mg) obtained in Example 127-9 was dissolved in THF (21.8 ml) and added with lithium aluminum hydride (138.7 mg), followed by stirring at room temperature for 24 hours. The reaction solution was added with ethyl acetate, methanol, and a 10% aqueous potassium sodium tartrate solution, and stirred for 1 hour, followed by separation/extraction with chloroform. The extract was washed with saturated saline solution and dried with anhydrous sodium sulfate, followed by concentration under reduced pressure. The residue was purified through silica gel column chromatography (chloroform/ethyl acetate), thereby obtaining the subject compound (189.7 mg) as a yellow oily substance.

Example 127-11

Synthesis of 2-[2-(4-dipropylaminobutyl)-1-methoxymethoxy-indan-5-ylmethyl]-isoindole-1,3-dione The compound (189.7 mg) obtained in Example 127-10 was dissolved in DMF (5.69 ml) and added with potassium carbonate (108.5 mg) and carbethoxyphthalimide (172.0 mg), followed by stirring at room temperature for 3 hours. The reaction solution was added with water. Then, the solution was subjected to separation/extraction with chloroform, dried with anhydrous sodium sulfate, and concentrated under reduced pressure. The residue was purified through silica gel column chromatography (chloroform/methanol), thereby obtaining the subject compound (253.9 mg) as a yellow oily substance.
MS(FAB, Pos.): m/z=493[M+H]$^+$

Example 127-12

Synthesis of 2-[2-(4-dipropylamino-butyl)-1-methoxy-indan-5-ylmethyl]-isoindole-1,3-dione The compound (253.9 mg) obtained in Example 127-11 was dissolved in methanol (10.2 ml), added with a 10% hydrogen chloride/methanol solution (5.08 ml), and stirred for 16 hours at room temperature. Then, the reaction solution was concentrated under reduced pressure and dried under vacuum. The residue was purified through silica gel column chromatography (hexane/ethyl acetate), thereby obtaining the subject compound (95.7 mg) as a yellow oily substance.
MS(FAB, Pos.): m/z=463[M+H]$^+$

Example 127-13

Synthesis of [4-(5-aminomethyl-1-methoxyindan-2-yl)-butyl]-dipropylamine

The compound (95.7 mg) obtained in Example 127-12 was dissolved in methanol (4.79 ml) and added with hydrazine monohydrate (0.0957 ml), followed by thermal reflux for 1 hour. The reaction solution was concentrated under reduced pressure. Then, the residue was added with water and subjected to separation/extraction with chloroform, dried with anhydrous sodium sulfate, and concentrated under reduced pressure. The residue was purified through silica gel column chromatography (chloroform/ethyl acetate), thereby obtaining the subject compound (45.0 mg) as a yellow oily substance.

MS(FAB, Pos.): m/z=333[M+H]$^+$

Example 127-14

Synthesis of [4-(5-{[(imidazol-2-ylmethyl)-amino]-methyl}-1-methoxyindan-2-yl)-butyl]-dipropylamine The compound (45.0 mg) obtained in Example 127-13 was dissolved in methanol (2.25 ml) and added with 2-imidazole carboxaldehyde (19.5 mg) and trimethyl orthoformate (43.1 mg), followed by stirring at room temperature for 1 hour. Under ice-cooling, sodium borohydride (15.4 mg) was added to the solution, and the whole was stirred at room temperature for 30 minutes. The reaction solution was added with water and then subjected to separation/extraction with chloroform. The extract was washed with saturated saline solution, dried with anhydrous sodium sulfate, and concentrated under vacuum. The residue was purified through silica gel column chromatography (chloroform/methanol), thereby obtaining the subject compound (54.8 mg) as a yellow oily substance.

MS(FAB, Pos.): m/z=412[M+H]$^+$

Example 127-15

Synthesis of [4-(5-{[(imidazol-2-ylmethyl)-(1-methylimidazol-2-ylmethyl)-amino]-methyl}-1-methoxyindan-2-yl)-butyl]-dipropylamine [Compound No. 128]

The compound (54.8 mg) obtained in Example 127-14 was dissolved in methanol (2.74 ml) and added with 1-methyl-2-imidazole carboxaldehyde (21.9 mg) and sodium cyanoborohydride (16.7 mg). Then, the solution was adjusted to pH 4 with acetic acid and stirred at room temperature for 3 hours. The reaction solution was concentrated under reduced pressure and added with saturated saline solution. The solution was subjected to separation/extraction with chloroform. The extract was dried with anhydrous sodium sulfate, and concentrated under reduced pressure. The residue was purified through silica gel column chromatography (chloroform/methanol) and treated with hydrochloric acid, thereby obtaining hydrochloride (35.9 mg) of the subject compound as a white solid.

MS(FAB, Pos.): m/z=507[M+H]$^+$

Production Example 128

Synthesis of [4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropylamine [Compound No. 129]

Example 128-1

Synthesis of 3-nitro-4-propylamino benzonitrile

In DMF (15 ml), 3-nitro-4-aminobenzonitrile (500 mg) was dissolved, and the solution was added with sodium hydride (135 mg), followed by stirring at room temperature for 9 hours. The solution was added with 1-iodopropane (328 ml) and stirred overnight at room temperature. After completion of the reaction, the solvent was distilled off under reduced pressure and the residue was then dissolved in chloroform. The solution was washed with water and then subjected to extraction with chloroform. The organic layer was washed with saturated saline solution and dried with anhydrous sodium sulfate. After filtration, the solvent was distilled off under reduced pressure and the residue was then purified through silica gel column chromatography (chloroform), thereby obtaining the subject compound (362 mg) as a white solid.

MS(FAB, Pos.): m/z=206[M+H]$^+$
$^1$H-NMR(500 MHz, CDCl$_3$): δ=1.08(3H, t, J=7.6 Hz), 1.79(2H, sext., J=7.3 Hz), 3.33(2H, q, J=7.1 Hz), 6.91(1H, d, J=9.0 Hz), 7.60(1H, d, J=9.0 Hz), 8.43(1H, br), 8.52(1H, s).

Example 128-2

Synthesis of 3-amino-4-propylaminobenzonitrile

In ethanol (10 ml) and THF (1.0 ml), 3-amino-4-propylaminobenzonitrile (360 mg) and tin(II) chloride dihydrate (4.01 g) were dissolved. Then, the solution was heated to 60° C. and a solution (3.0 ml) of sodium borohydride (50.3 mg) in ethanol was then dropped therein, followed by stirring at 60° C. for 1 hour. After completion of the reaction, water was added to the solution, and the whole was neutralized with a 1 mol/l sodium hydroxide aqueous solution. Then, ethanol and THF were distilled off under reduced pressure. The residue was subjected to extraction with ether. The extract was washed with saturated saline solution and dried with anhydrous sodium sulfate. After filtration, the solvent was distilled off under reduced pressure. The residue was purified through silica gel column chromatography (chloroform/methanol), thereby obtaining the subject compound (284 mg) as a white solid.

MS(FAB, Pos.): m/z=176[M+H]$^+$
$^1$H-NMR(500 MHz, CDCl$_3$): δ=1.04(3H, t, J=7.6 Hz), 1.70(2H, sext., J=7.3 Hz), 3.13(2H, q, J=7.1 Hz), 6.58(1H, d, J=8.1 Hz), 6.94(1H, s), 7.17(1H, d, J=8.1 Hz).

Example 128-3

Synthesis of t-butyl[4-(5-cyano-2-propylaminophenylcarbamoyl)butyl]carbamate

In chloroform (5.0 ml), 5-t-butoxycarbonylaminovaleric acid (387 mg), WSCI hydrochloride (466 mg), and HOBt (328.3 mg) were dissolved. Then, the solution was stirred at room temperature for 1 hour. A solution (3.0 ml) of 3-amino-4-propylaminobenzonitrile (283 mg) in chloroform was dropped in this solution. Then, the solution was stirred overnight at room temperature. After completion of the reaction, the solvent was distilled off under reduced pressure. The residue was dissolved in chloroform and then washed with a saturated aqueous sodium bicarbonate solution, a saturated aqueous ammonium chloride solution, and saturated saline solution, followed by drying with anhydrous sodium sulfate. After filtration, the solvent was distilled off under reduced pressure and the residue was then purified through silica gel column chromatography (chloroform/ethyl acetate), thereby obtaining the subject compound as a colorless viscous substance.

MS(FAB, Pos.): m/z=375[M+H]$^+$ $^1$H-NMR(500 MHz, DMSO-d$_6$): δ=0.93(3H, t, J=7.3 Hz), 1.34–1.46(2H, m), 1.38(9H, s), 1.57(2H, sext., J=7.3 Hz), 2.34(2H, t, J=7.3 Hz), 2.93(2H, q, J=6.6 Hz), 3.10(2H, q, J=7.3 Hz), 5.86(1H, t, J=5.2 Hz), 6.69(1H, d, J=8.5 Hz), 6.83(1H, t, J=5.6 Hz), 7.41(1H, d, J=8.5 Hz). 7.51(1H, s), 9.13(1H, s).

Example 128-4

Synthesis of 2-(dipropylaminobutyl)-1-propyl-1H-benzimidazole-5-carbonitrile

The compound obtained in Example 128-3 was dissolved in methanol (3.0 ml) and added with a 4 mol/l hydrogen chloride/dioxane solution (3.0 ml), followed by stirring at room temperature for 14 hours. After completion of the reaction, the solvent was distilled off under reduced pressure and the residue was dried under vacuum. The dried product was dissolved in methanol and neutralized with an anion-exchange resin (Amberlite IRA-410), followed by distilling the solvent off. The residue was dissolved in methanol (8.0 ml) again. Then, the solution was added with acetic acid (0.268 ml) and propionaldehyde (0.225 ml), followed by cooling to 0° C. The solution was added with sodium cyanoborohydride (209.0 mg) and stirred overnight at room temperature. After completion of the reaction, the solvent was distilled off under reduced pressure. The residue was dissolved in chloroform and washed with a 1 mol/l sodium hydroxide aqueous solution, followed by extraction with chloroform. The organic layer was washed with saturated saline solution and then dried with anhydrous sodium sulfate. After filtration, the solvent was distilled off under reduced pressure and the residue was then purified through silica gel column chromatography (chloroform/methanol), thereby obtaining the subject compound (97.1 mg) as a colorless viscous substance.

MS(FAB, Pos.): m/z=341[M+H]$^+$

Example 128-5

Synthesis of [4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropylamine [Compound No. 129]

Lithium aluminum hydride (40.6 mg) was suspended in THF (3.0 ml) and cooled to 0° C. A solution (2.0 ml) of the compound (97.1 mg) obtained in Example 128-4 in THF was dropped in this suspension. Then, the suspension was stirred at 0° C. for 1 hour. Furthermore, lithium aluminum hydride (41.0 mg) was added to the suspension, and the whole was stirred for 2 days. After completion of the reaction, sodium sulfate decahydrate was added to the suspension until bubbling was stopped. Subsequently, a 1 mol/l sodium hydroxide aqueous solution was added to the suspension until a white precipitate was generated. Solid matter was separated through filtration and the solvent was then distilled off from the filtrate under reduced pressure. The residue was dried under vacuum, dissolved in methanol (2.0 ml), and added with trimethyl orthoformate (0.11 ml) and 2-imidazole carboxaldehyde (31.0 mg). Then, the solution was stirred for 1 hour and then cooled to 0° C. The solution was added with sodium borohydride (19.7 mg) and stirred at room temperature for 1 hour. After completion of the reaction, the solvent was distilled off under reduced pressure and the residue was then dissolved in 1 mol/l hydrochloric acid and the aqueous layer was then washed with chloroform. The resultant was added with a 1 mol/l sodium hydroxide aqueous solution and then extracted with chloroform. The organic layer was washed with saturated saline solution and dried with anhydrous sodium sulfate, followed by distilling the solvent off. The residue was dissolved in methanol (2.0 ml) and added with acetic acid (0.10 ml) and 1-methyl-2-imidazole carboxaldehyde (35.1 mg), followed by cooling to 0° C. The solution was added with sodium cyanoborohydride (31.7 mg) and stirred at room temperature for 14 hours. After completion of the reaction, the solvent was distilled off under reduced pressure. The residue was dissolved in chloroform and washed with a 1 mol/l sodium hydroxide aqueous solution, followed by extraction with chloroform. The organic layer was washed with saturate saline solution and dried with anhydrous sodium sulfate. After filtration, the solvent was distilled off under reduced pressure. Then, the residue was purified through silica gel column chromatography (chloroform/methanol) and treated with hydrochloric acid, thereby obtaining hydrochloride (89.4 mg) of the subject compound as a white solid.

MS(FAB, Pos.): m/z=519[M+H]$^+$ $^1$H-NMR(500 MHz, DMSO-d$_6$): δ=0.89–0.95(9H, m), 1.67–1.94(10H, m), 2.96–3.00(4H, m), 3.12–3.13(2H, m), 3.26(2H, t, J=7.3 Hz), 3.72(3H, s), 3.91(2H, s), 4.13(2H, s), 4.21(2H, s), 4.41(2H, t, J=7.3 Hz), 7.49(1H, s), 7.52(1H, s), 7.64(2H, s), 7.72(1H, d, J=8.5 Hz), 7.82(1H, s), 7.90(1H, d, J=8.5 Hz), 10.61 (1H, s).

Production Example 129

Synthesis of 2-(4-di-n-propylamino-butyl)-5-{[(1H-imidazol-2-ylmethyl)-(1-methyl-1H-imidazol-2-ylmethyl)-amino]-methyl}-isoindole-1,3-dione [Compound No. 130]

Example 129-1

Synthesis of 4-methylphthalic acid dimethyl ester

In methanol (60 ml), 4-methylphthalic acid (3.00 g) was dissolved. Then, WSCI hydrochloride (9.62 g) and 4-dimethylaminopyridine (3.07 g) were added to the solution, and the whole was stirred at room temperature for 3.5 hours. The reaction solution was added with water and then subjected to extraction with chloroform. The organic layer was washed with water, 1 mol/l hydrochloric acid, and saturated saline solution, and then dried with anhydrous sodium sulfate. The solvent was distilled off and the residue was purified through silica gel column chromatography (hexane/ethyl acetate), thereby obtaining the subject compound (2.54 g) as a colorless oily substance.

MS(FAB, Pos.): m/z=209[M+H]$^+$

¹H-NMR(500 MHz, CDCl₃): δ=2.42(3H, s), 3.89(3H, s), 3.91(3H, s), 7.33(1H, dd, J=1.7, 8.6 Hz), 7.47(1H, d, J=1.2 Hz), 7.68(1H, d, J=7.8 Hz).

Example 129-2

Synthesis of 4-(1,3-dioxo-1,3-dihydro-isoindol-2-ylmethyl)-phthalic acid dimethyl ester The compound (202 mg) obtained in Example 129-1 was dissolved in carbon tetrachloride (7.1 ml) and added with N-bromosuccinimide (205 mg) and azobisisobutyronitrile (15.8 mg), followed by thermal reflux for 20 hours. The solution was further added with carbon tetrachloride (7.0 ml) and N-bromosuccinimide (51.3 mg), followed by thermal reflux for 4 hours. After having been stood to cool, the solution was added with water and then subjected to extraction with chloroform. The organic layer was washed with water and saturated saline solution and then dried with anhydrous sodium sulfate. The solvent was distilled off and the residue was then dissolved in DMF (5.8 ml). The solution was added with potassium phthalimide (359 mg) and stirred at room temperature for 16 hours. The residue obtained by distilling the solvent off was purified through silica gel column chromatography (hexane/ethyl acetate), thereby obtaining the subject compound (226 mg) as a white solid.

MS(FAB, Pos.): m/z=354[M+H]⁺

¹H-NMR(500 MHz, CDCl₃): δ=3.88(3H, s), 3.90(3H, s), 4.89(2H, s), 7.60(1H, dd, J=1.8, 8.1 Hz), 7.71(1H, d, J=7.9 Hz), 7.74(2H, dd, J=2.9, 5.5 Hz), 7.75(1H, m), 7.87(2H, dd, J=2.9, 5.5 Hz).

Example 129-3

Synthesis of 4-(t-butoxycarbonylamino-methyl)-phthalic acid dimethyl ester

The compound (909 mg) obtained in Example 129-2 was suspended in methanol (22 ml). Hydrazine monohydrate (0.13 ml) was dropped in this suspension. Then, the solution was subjected to thermal reflux for 4 hours. After completion of the reaction, the solvent was distilled off under reduced pressure and then the residue was subjected to extraction with chloroform. The organic layer was washed with water and then washed with saturated saline solution, followed by drying with anhydrous sodium sulfate. The residue obtained by distilling the solvent off was dissolved in DMF (15 ml) and added with triethylamine (0.54 ml) and di-t-butyl dicarbonate (851 mg), followed by stirring at room temperature for 15 hours. After the solvent had been distilled off, the residue was subjected to extraction with chloroform. The organic layer was washed with water and saturated saline solution and then dried with anhydrous sodium sulfate. The residue obtained by distilling the solvent off was purified through silica gel column chromatography (hexane/ethyl acetate), thereby obtaining the subject compound (779 mg) as a yellow oily substance.

MS(FAB, Pos.): m/z=324[M+H]⁺

¹H-NMR(500 MHz, CDCl₃): δ=1.47(9H, s), 3.90(3H, s), 3.91(3H, s), 4.38(2H, d, J=6.1 Hz), 4.94(1H, br), 7.46(1H, d, J=8.5 Hz), 7.61(1H, d, J=1.5 Hz), 7.72(1H, d, J=7.8 Hz).

Example 129-4

Synthesis of 4-(t-butoxycarbonylamino-methyl)-phthalic acid

The compound (76.4 mg) obtained in Example 129-3 was dissolved in methanol (4.5 ml). A 1 mol/l sodium hydroxide aqueous solution (2.3 ml) was dropped in this solution. Then, the solution was stirred at room temperature for 2 hours and then neutralized with the addition of 1 mol/l hydrochloric acid (2.3 ml). The residue obtained by distilling the solvent off was purified through silica gel column chromatography (chloroform/methanol), thereby obtaining the subject compound (65.3 mg) as a pale-yellow oily substance.

MS(FAB, Pos.): m/z=296[M+H]⁺

¹H-NMR(500 MHz, CDCl₃): δ=1.45(9H, s), 4.30(2H, s), 7.45(1H, d, J=7.6 Hz), 7.80(1H, s), 7.88(1H, d, J=8.1 Hz).

Example 129-5

Synthesis of [2-(4-di-N-propylamino-butyl)-1,3-dioxo-2,3-dihydro-1H-isoindol-5-ylmethyl]-carbamic acid t-butyl ester The compound (209.4 mg) obtained in Example 129-4 was dissolved in xylene (8.0 ml) and added with the compound (150 mg) obtained in Example 1-2, followed by thermal reflux for 24 hours. The solution was added with water and then extracted with chloroform. The organic layer was washed with water and saturated saline solution, followed by drying with anhydrous sodium sulfate. The solvent was distilled off and the residue was then purified through silica gel column chromatography (hexane/ethyl acetate), thereby obtaining the subject compound (92.3 mg) as a yellow solid.

MS(FAB, Pos.): m/z=432[M+H]⁺

¹H-NMR(500 MHz, CDCl₃): δ=0.85(6H, t, J=7.4 Hz), 1.40–1.50(6H, m), 1.47(9H, s), 1.64–1.70(2H, m), 2.34(4H, t, J=7.4 Hz), 2.42(2H, t, J=7.5 Hz), 3.69(2H, t, J=7.3Hz), 4.45(2H, d, J=6.1 Hz), 5.04(1H, br), 7.62(1H, d, J=7.5 Hz), 7.76(1H, d, J=0.8 Hz), 7.79(1H, d, J=7.6 Hz).

Example 129-6

Synthesis of 2-(4-di-N-propylamino-butyl)-5-{[(1H-imidazol-2-ylmethyl)-amino]-methyl}-isoindole-1,3-dione The compound (128 mg) obtained in Example 129-5 was dissolved in methanol (1.5 ml). A 4 mol/l hydrogen chloride/dioxane solution (1.5 ml) was dropped in this solution. Then, the solution was stirred at room temperature for 1 hour. The residue obtained by distilling the solvent off was dissolved in methanol and added with an anion-exchange resin (Amberlite IRA-410), followed by adjusting the solution to pH 7–8. The resin was separated through filtration and the solvent was distilled off from the filtrate. Subsequently, the residue was dissolved in methanol (3.0 ml) and added with trimethyl orthoformate (0.1 ml) and 2-imidazole carboxaldehyde (43.2 mg), followed by stirring at room temperature for 2 hours. The solution was added with sodium borohydride (17.0 mg) and stirred for 4 hours. Then, the solution was added with water and extracted with chloroform. The organic layer was washed with water and saturated saline solution and dried with anhydrous sodium sulfate. The residue obtained by distilling the solvent off was purified through silica gel column chromatography (chloroform/methanol), thereby obtaining the subject compound (25.8 mg) as a white solid.

MS(FAB, Pos.): m/z=412[M+H]$^+$ $^1$H-NMR(500 MHz, CDCl$_3$): δ=0.79(6H, t, J=7.4 Hz), 1.30–1.38(6H, m), 1.57–1.62(2H, m), 2.25(4H, t, J=7.2 Hz), 2.33(2H, t, J=6.9 Hz), 3.57(2H, t, J=6.9 Hz), 3.68(2H, s), 3.84(2H, s), 6.79(1H, s), 7.02(1H, s), 7.79(1H, d, J=7.1 Hz), 7.80(1H, d, J=7.4 Hz), 7.88(1H, s), 11.81(1H, br).

Example 129-7

Synthesis of 2-(4-di-n-propylamino-butyl)-5-{[(1H-imidazol-2-ylmethyl)-(1-methyl-1H-imidazol-2-ylmethyl)-amino]-methyl}-isoindole-1,3-dione [Compound No. 130]

The compound (24.9 mg) obtained in Example 129-6 was dissolved in methanol (2.0 ml) and added with 1-methyl-2-imidazole carboxaldehyde (7.9 mg) and sodium cyanoborohydride (7.5 mg). Then, the solution was adjusted to pH 4 with acetic acid and stirred at room temperature for 16 hours. The solution was further added with 1-methyl-2-imidazole carboxaldehyde (6.6 mg) and sodium cyanoborohydride (3.8 mg) and stirred for additional 20 hours. The solution was added with water and then added with sodium bicarbonate to adjust the solution to pH 8, followed by extraction with chloroform. The organic layer was washed with a saturated aqueous sodium bicarbonate solution and dried with anhydrous sodium sulfate. The residue obtained by distilling the solvent off was purified through silica gel column chromatography (chloroform/methanol) and treated with hydrochloric acid, thereby obtaining hydrochloride (30.7 mg) of the subject compound as a pale-yellow solid.

MS(FAB, Pos.): m/z=506[M+H]$^+$ $^1$H-NMR(500 MHz, CDCl$_3$): δ=0.89(6H, t, J=7.3 Hz), 1.60–1.70(8H, m), 2.92–2.96(4H, m), 3.00–3.05(2H, m), 3.59(2H, t, J=6.8 Hz), 3.70(3H, s), 3.92(2H, s), 4.12(2H, s), 4.20(2H, s), 7.51(1H, d, J=1.7 Hz), 7.53(1H, d, J=1.7 Hz), 7.64(2H, s), 7.75(1H, d, J=7.6 Hz), 7.83(1H, d, J=7.6 Hz), 7.86(1H, s), 10.24(1H, br).

Next, the structural formulas of the respective compounds produced in Production Examples described above are listed in Table 1.

TABLE 1

| No. | Structural Formula |
| --- | --- |
| 1 | |
| 2 | |
| 3 | |

TABLE 1-continued
| No. | Structural Formula |
|---|---|
| 4 | 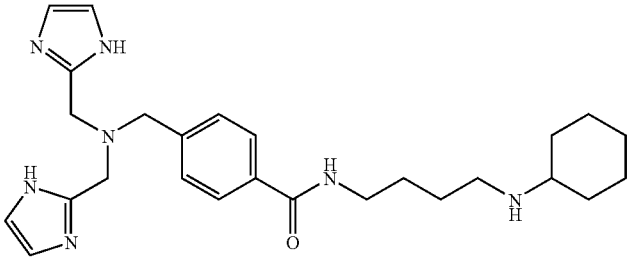 |
| 5 | 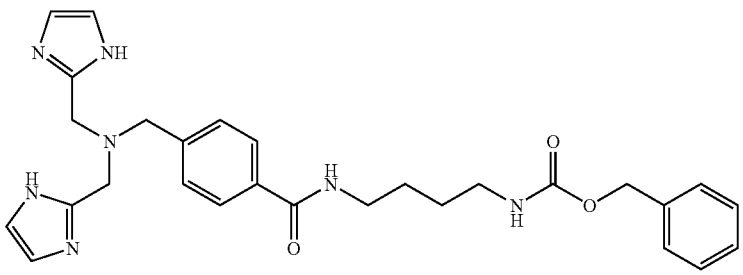 |
| 6 | 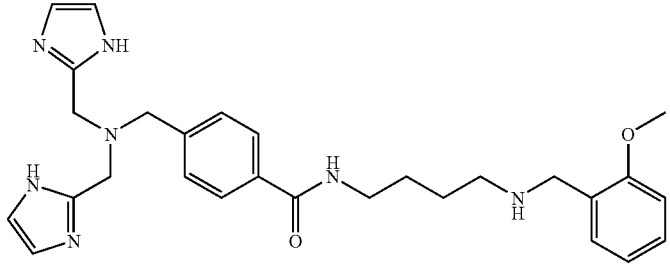 |
| 7 | 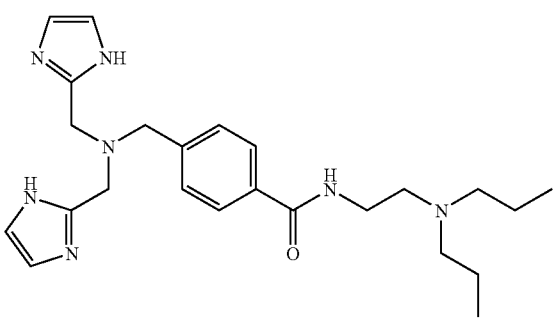 |
| 8 | 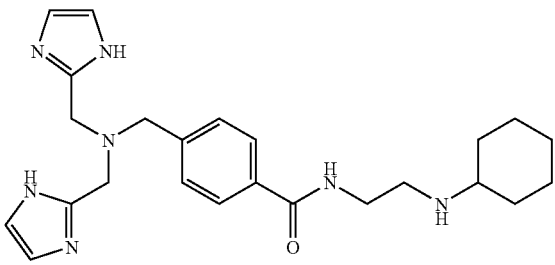 |

TABLE 1-continued

| No. | Structural Formula |
|---|---|
| 9 | |
| 10 | |
| 11 | |
| 12 | |
| 13 | |

TABLE 1-continued
| No. | Structural Formula |
|---|---|
| 14 | 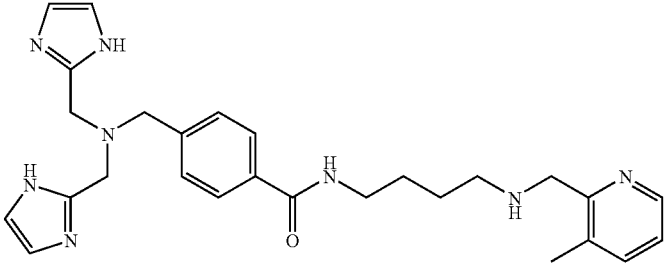 |
| 15 | 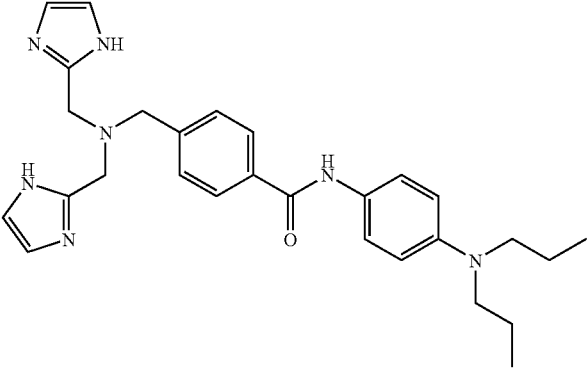 |
| 16 | 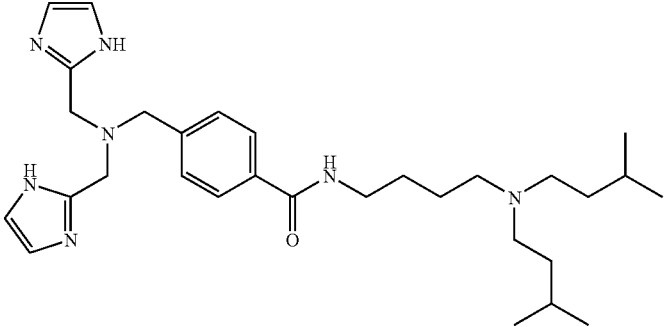 |
| 17 | 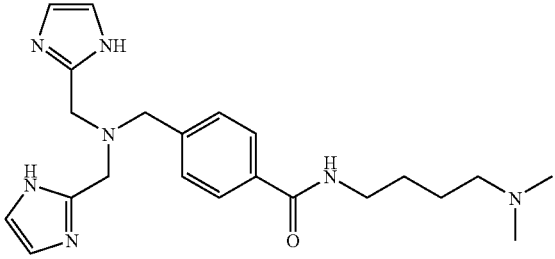 |
| 18 | 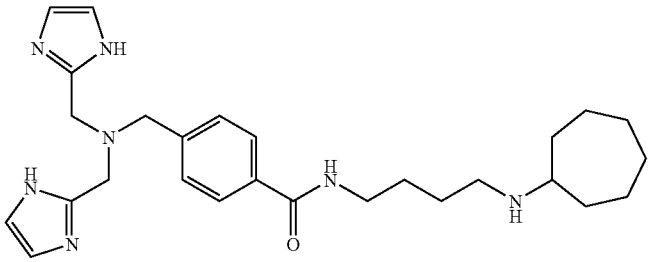 |

TABLE 1-continued
| No. | Structural Formula |
|---|---|
| 19 | 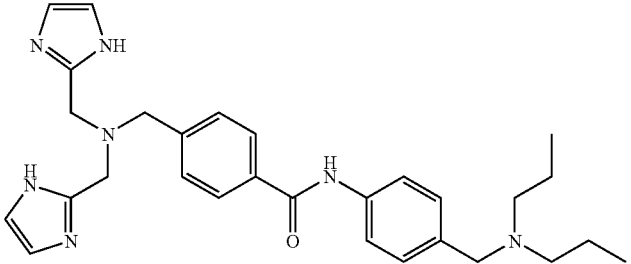 |
| 20 | |
| 21 | 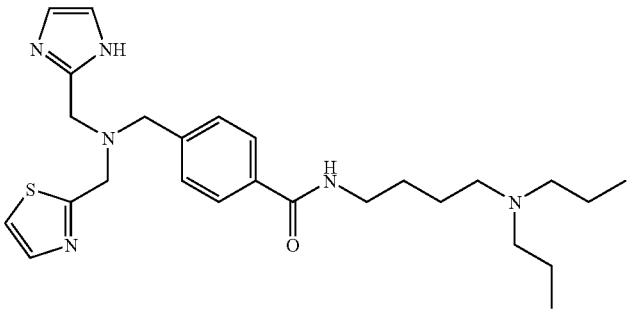 |
| 22 | 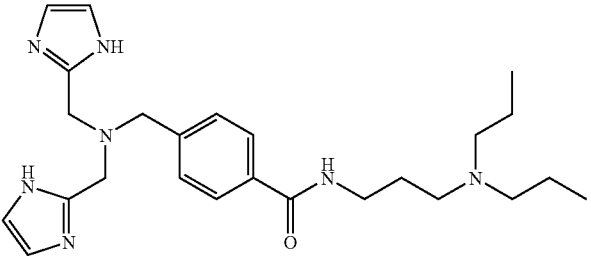 |
| 23 | 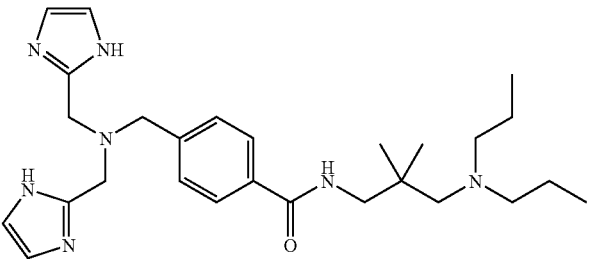 |
| 24 | 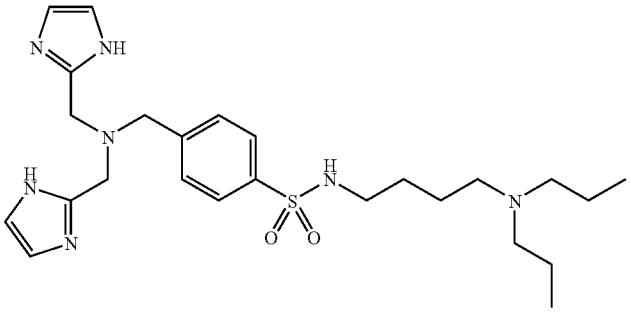 |

TABLE 1-continued
| No. | Structural Formula |
|---|---|
| 25 | 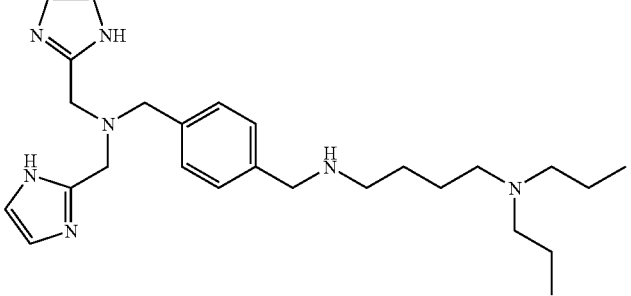 |
| 26 | 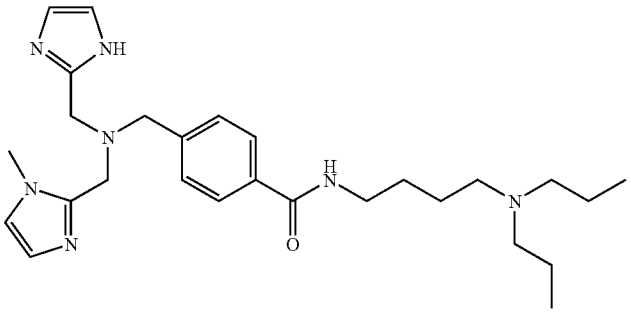 |
| 27 | 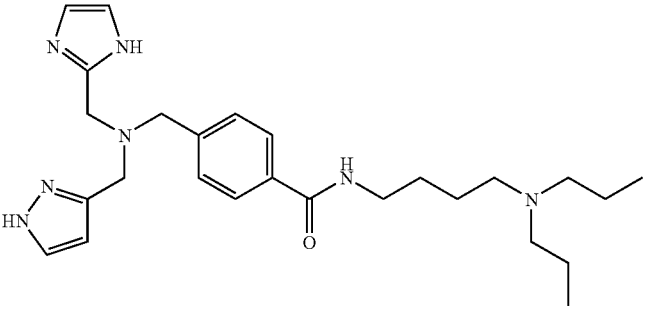 |
| 28 | 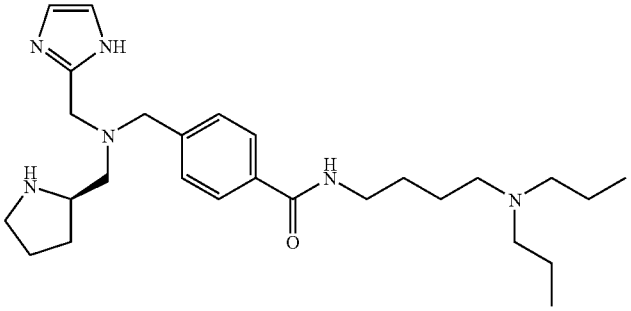 |
| 29 | 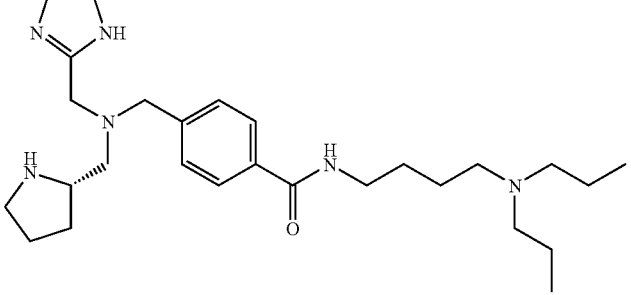 |

TABLE 1-continued
| No. | Structural Formula |
|---|---|
| 30 | 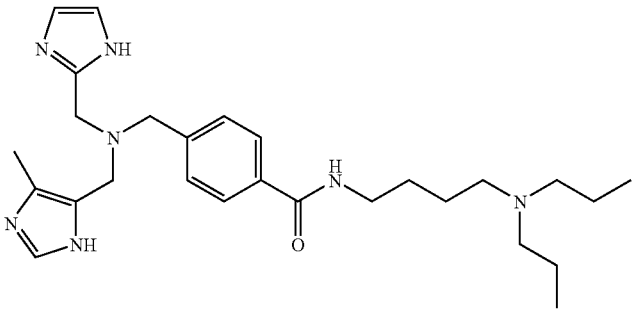 |
| 31 | 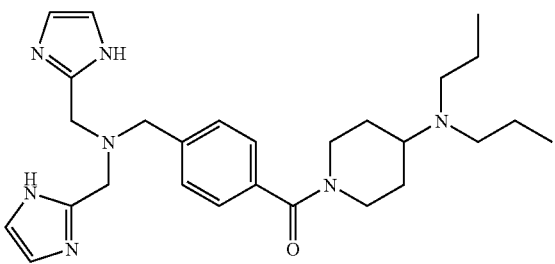 |
| 32 | 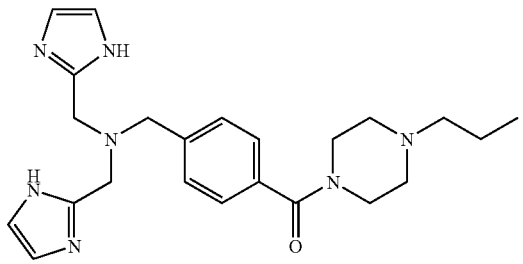 |
| 33 | 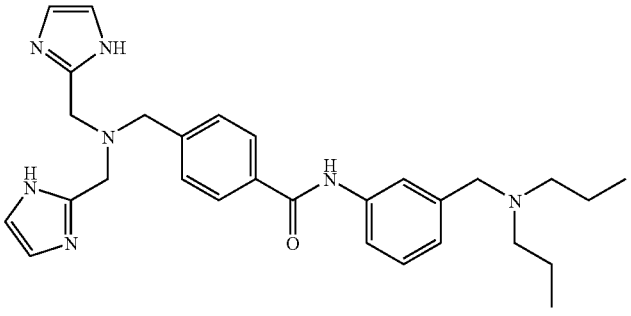 |
| 34 | 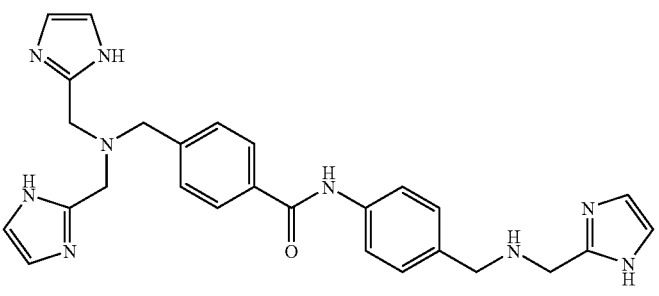 |

TABLE 1-continued

| No. | Structural Formula |
|-----|-------------------|
| 35  |  |
| 36  |  |
| 37  |  |
| 38  |  |
| 39  |  |

TABLE 1-continued
| No. | Structural Formula |
|---|---|
| 40 | 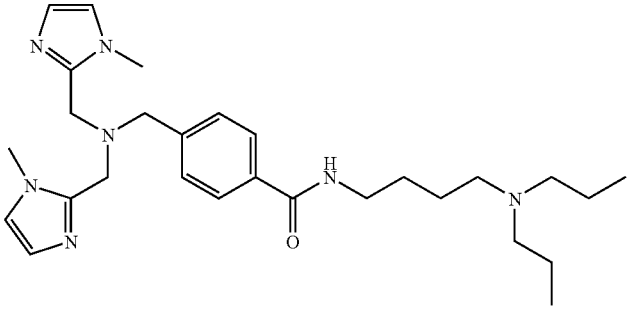 |
| 41 | 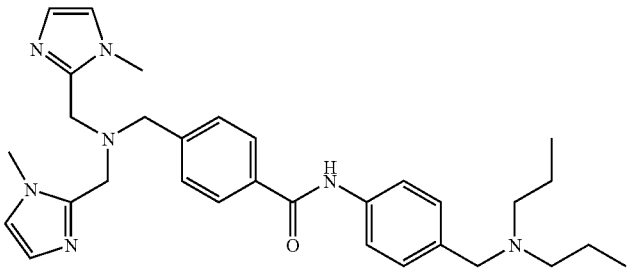 |
| 42 | 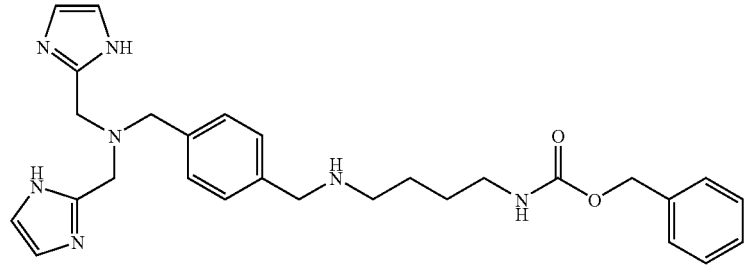 |
| 43 | 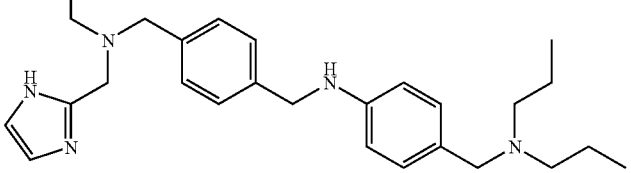 |
| 44 | 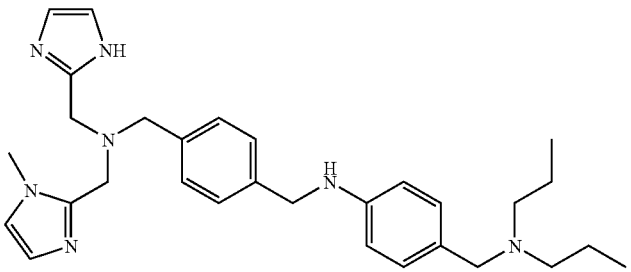 |

TABLE 1-continued

| No. | Structural Formula |
|---|---|
| 45 | |
| 46 | |
| 47 | |
| 48 | |
| 49 | |

TABLE 1-continued

| No. | Structural Formula |
|---|---|
| 50 | |
| 51 | |
| 52 | |
| 53 | |
| 54 | |

TABLE 1-continued

| No. | Structural Formula |
|---|---|
| 55 | |
| 56 | |
| 57 | |
| 58 | |
| 59 | |

TABLE 1-continued
| No. | Structural Formula |
|---|---|
| 60 | 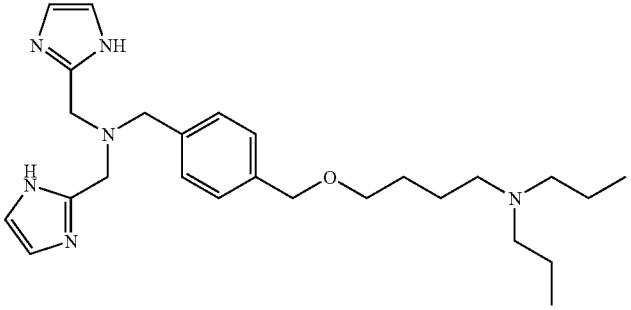 |
| 61 | 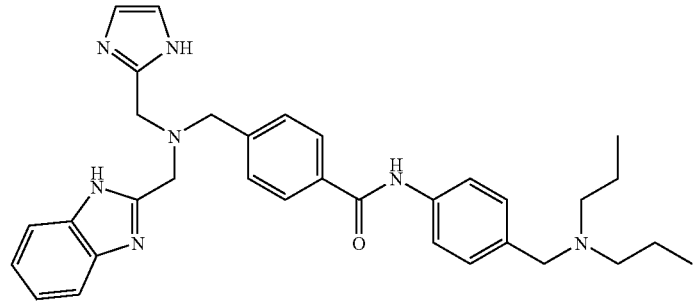 |
| 62 | 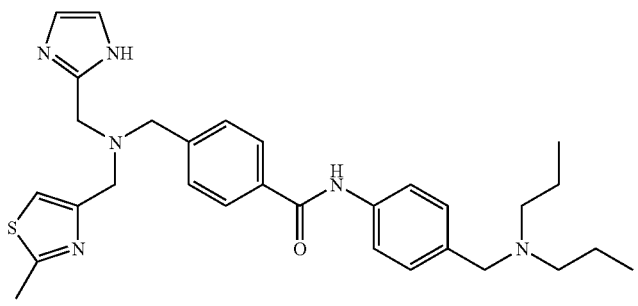 |
| 63 | 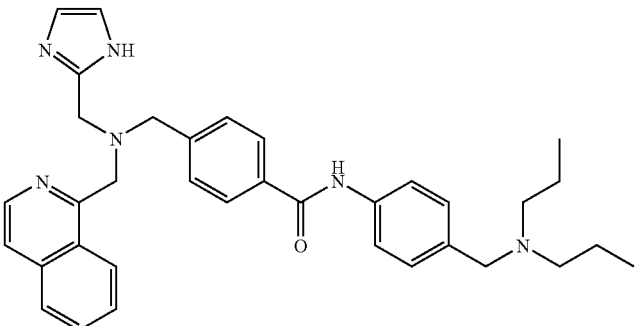 |

TABLE 1-continued
| No. | Structural Formula |
|---|---|
| 64 | 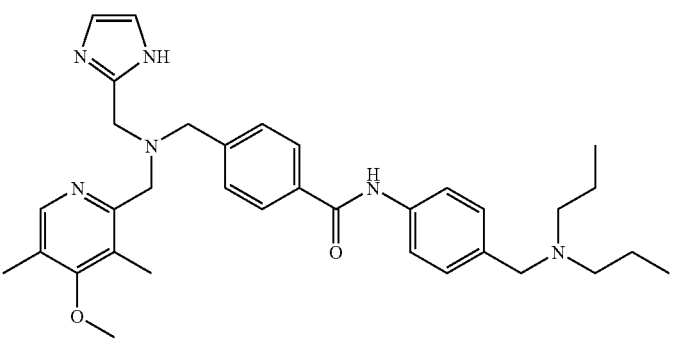 |
| 65 | 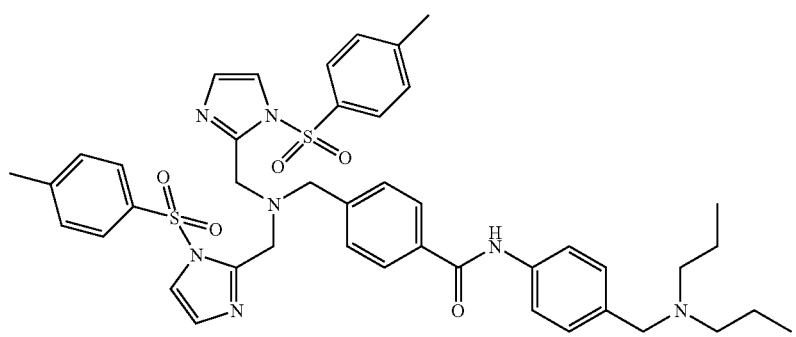 |
| 66 | 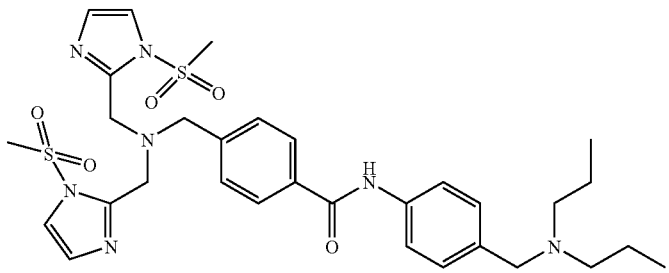 |
| 67 | 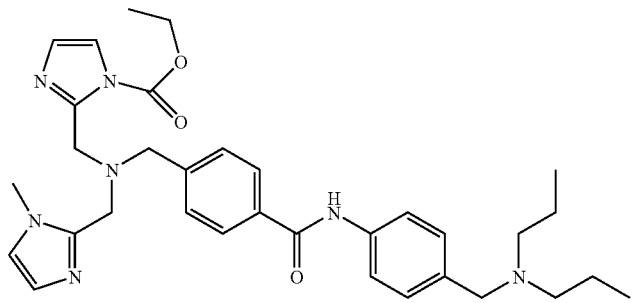 |
| 68 | 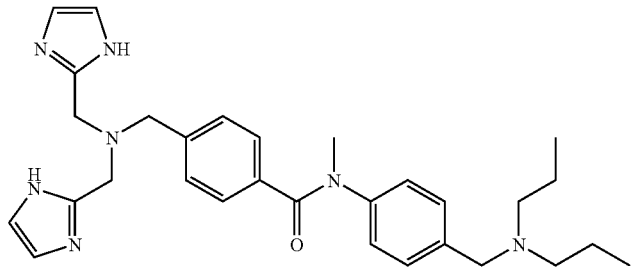 |

TABLE 1-continued

| No. | Structural Formula |
|-----|--------------------|
| 69 | |
| 70 | |
| 71 | |
| 72 | |
| 73 | |

TABLE 1-continued
| No. | Structural Formula |
|---|---|
| 74 | 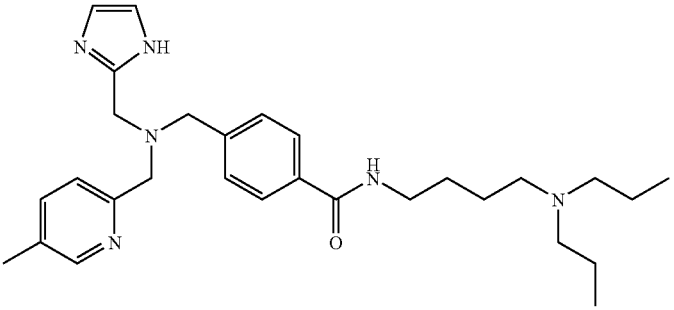 |
| 75 | 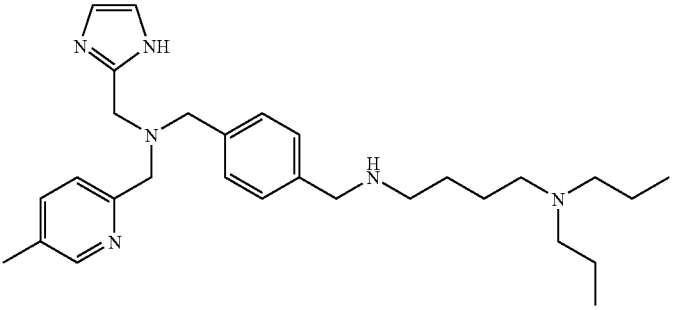 |
| 76 | 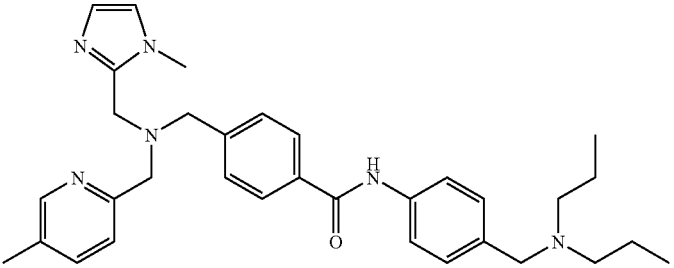 |
| 77 | 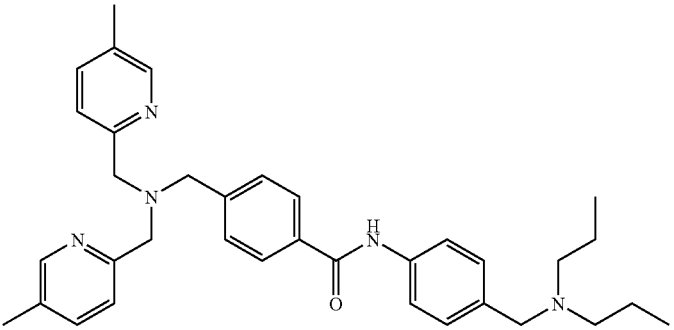 |
| 78 | 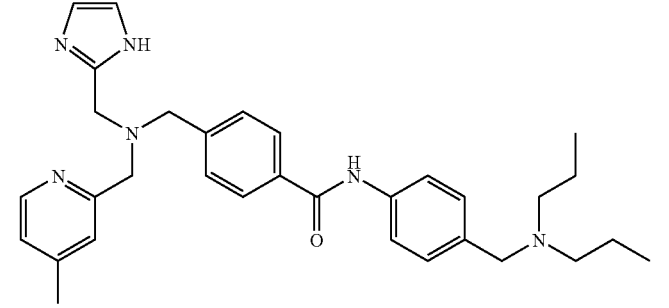 |

TABLE 1-continued

| No. | Structural Formula |
|---|---|
| 79 | |
| 80 | |
| 81 | |
| 82 | |
| 83 | |

TABLE 1-continued

| No. | Structural Formula |
|---|---|
| 84 | |
| 85 | |
| 86 | |
| 87 | |
| 88 | |

TABLE 1-continued

| No. | Structural Formula |
|---|---|
| 89 | |
| 90 | |
| 91 | |
| 92 | |
| 93 | |

TABLE 1-continued
| No. | Structural Formula |
|---|---|
| 94 | 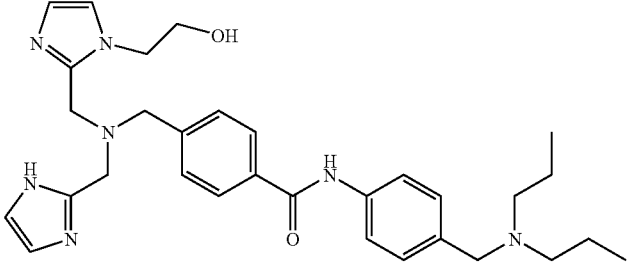 |
| 95 | 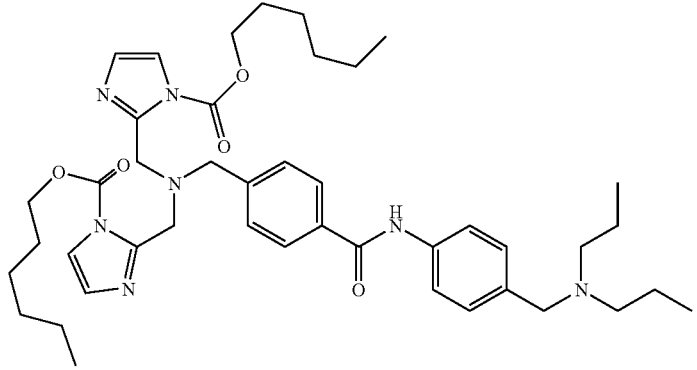 |
| 96 | 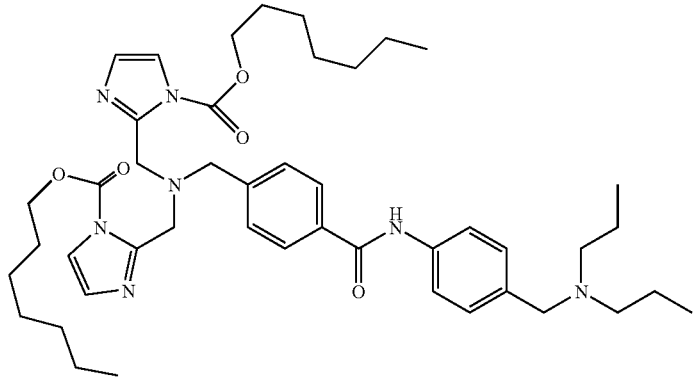 |
| 97 | 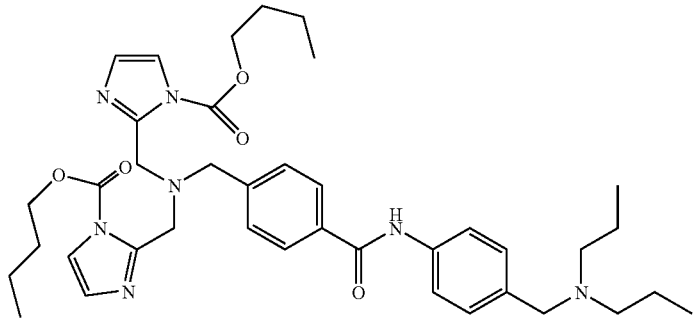 |

TABLE 1-continued
| No. | Structural Formula |
|---|---|
| 98 | 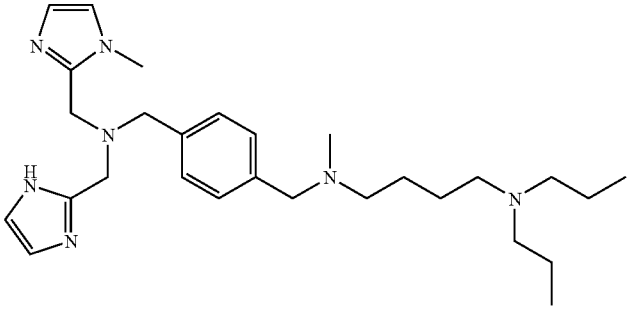 |
| 99 | 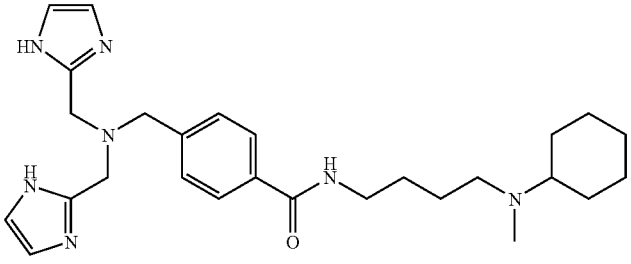 |
| 100 | 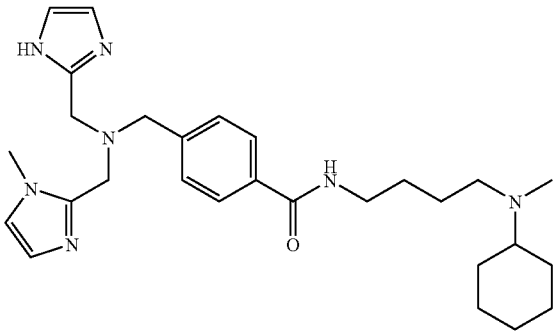 |
| 101 | 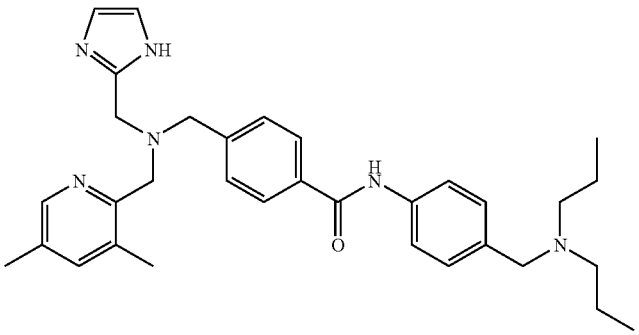 |

TABLE 1-continued
| No. | Structural Formula |
|---|---|
| 102 | 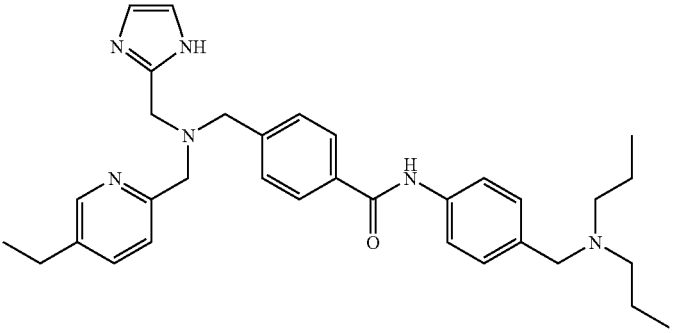 |
| 103 | 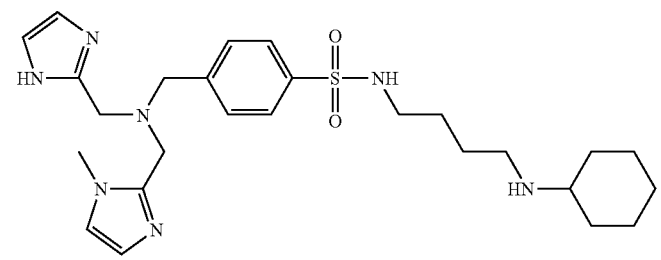 |
| 104 | 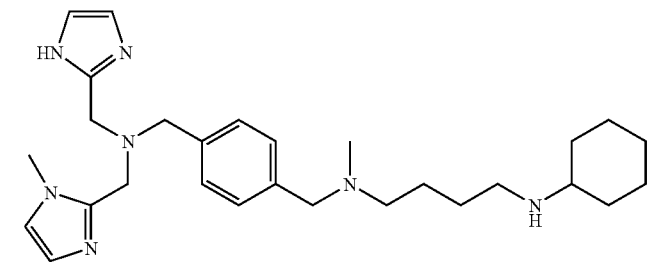 |
| 105 | 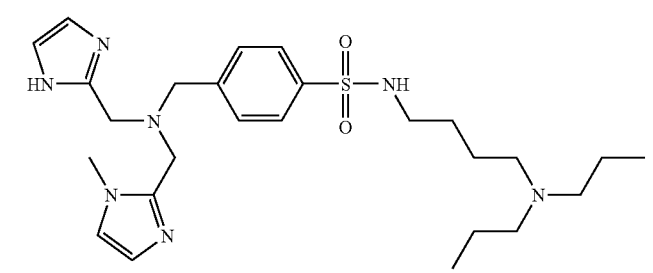 |
| 106 | 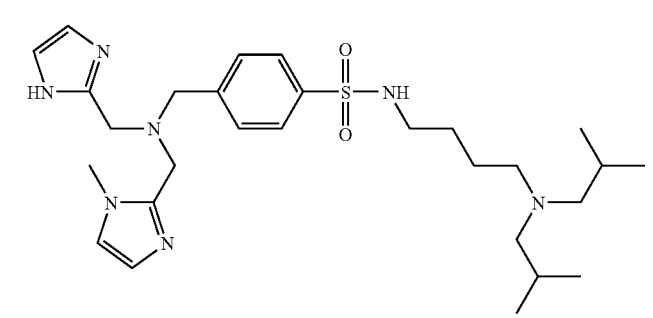 |

TABLE 1-continued

| No. | Structural Formula |
|-----|--------------------|
| 107 | |
| 108 | |
| 109 | |
| 110 | |
| 111 | |

TABLE 1-continued
| No. | Structural Formula |
|---|---|
| 112 | 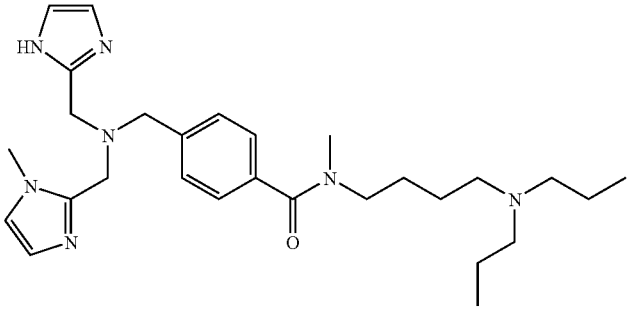 |
| 113 | 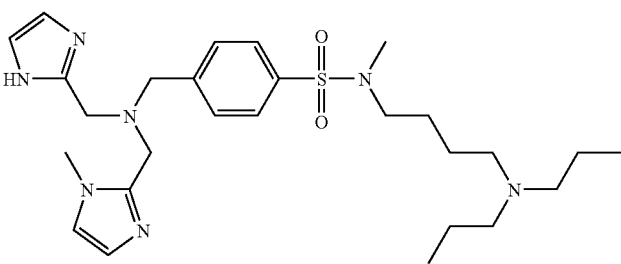 |
| 114 | 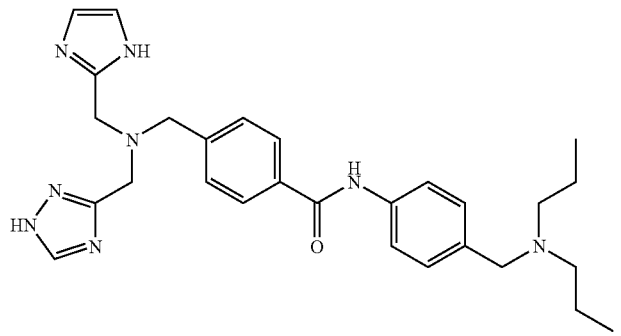 |
| 115 | 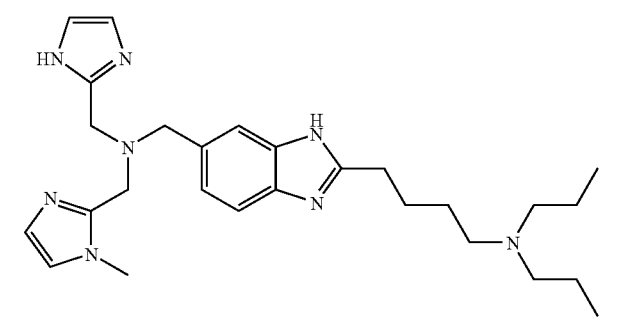 |
| 116 | 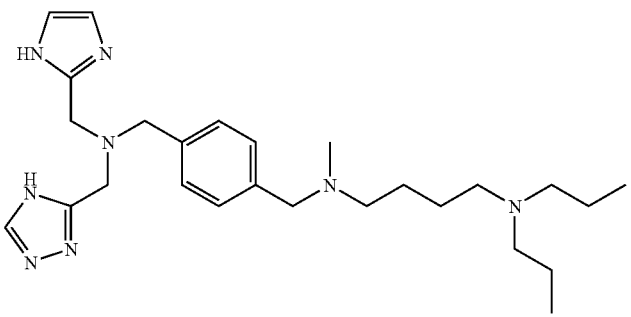 |

TABLE 1-continued
| No. | Structural Formula |
|---|---|
| 117 | 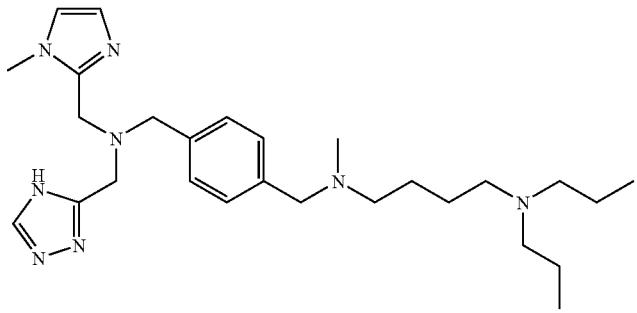 |
| 118 | 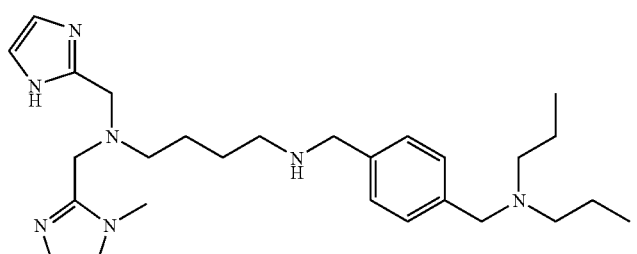 |
| 119 | 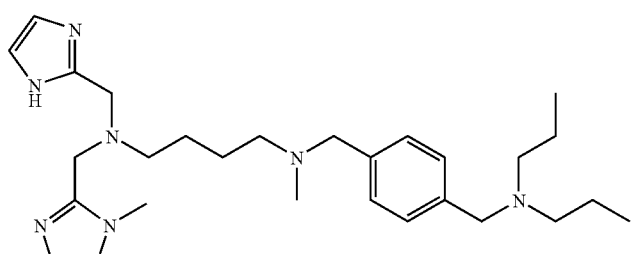 |
| 120 | 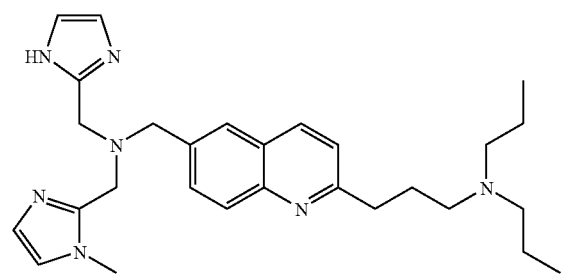 |
| 121 | 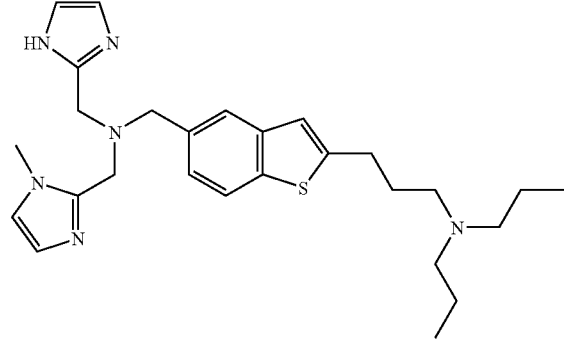 |

TABLE 1-continued
| No. | Structural Formula |
|---|---|
| 122 | 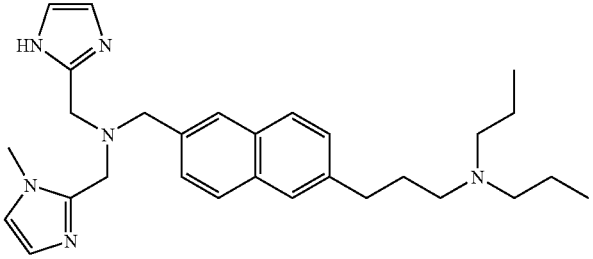 |
| 123 | 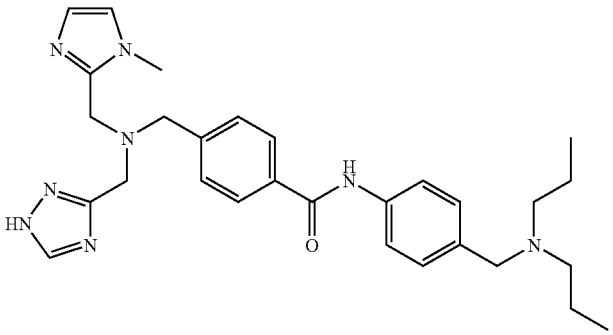 |
| 124 | 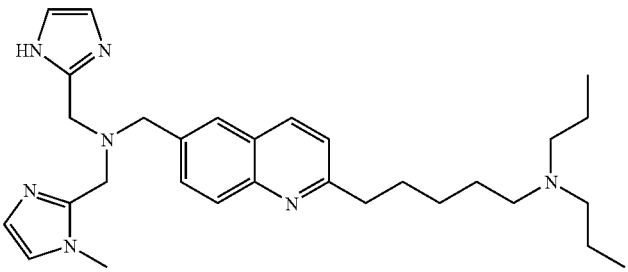 |
| 125 | 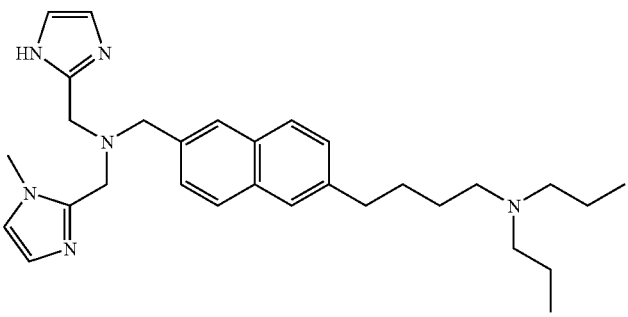 |
| 126 | 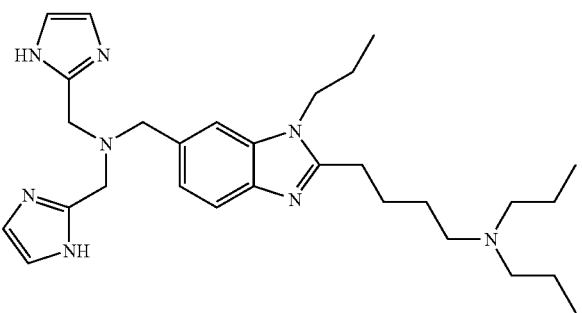 |

TABLE 1-continued
| No. | Structural Formula |
|---|---|
| 127 | 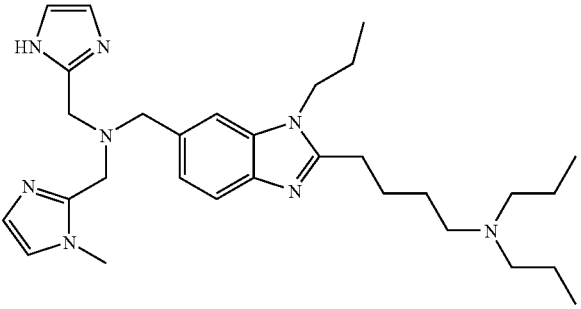 |
| 128 | 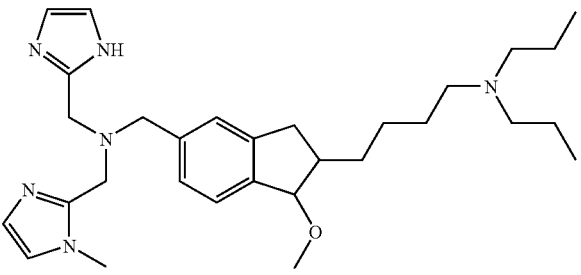 |
| 129 | 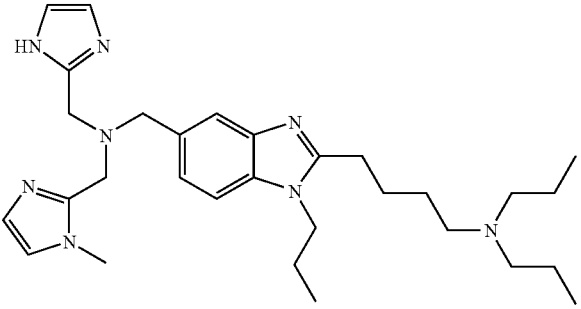 |
| 130 | 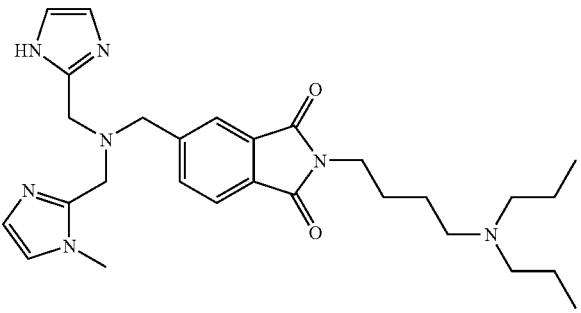 |
| 131 | 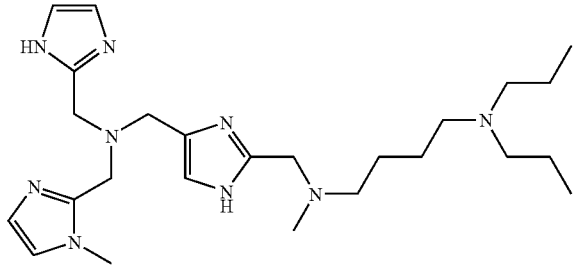 |

TABLE 1-continued
| No. | Structural Formula |
|-----|-------------------|
| 132 | 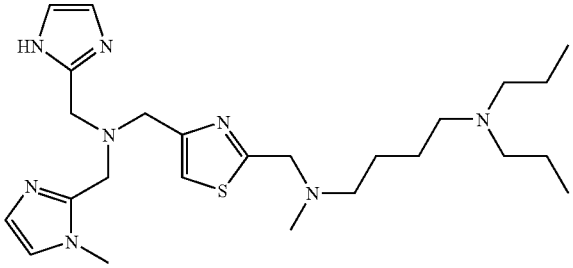 |
| 133 | 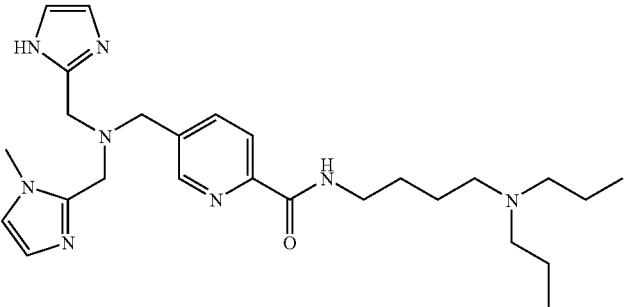 |
| 134 | 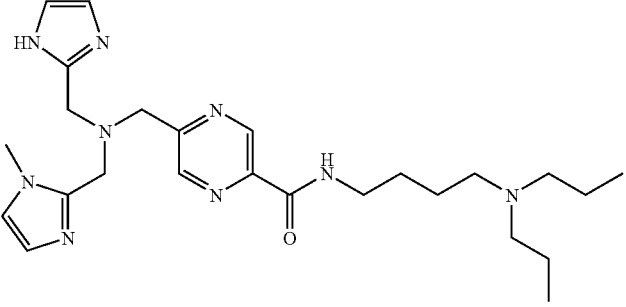 |
| 135 | 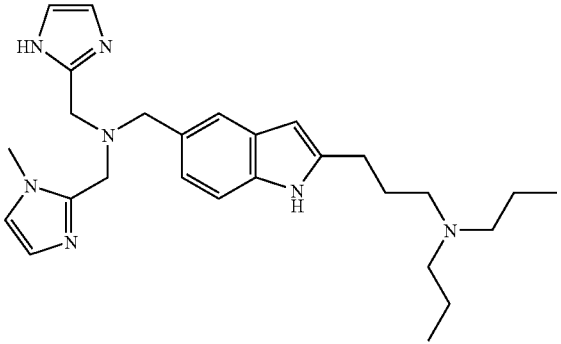 |
| 136 | 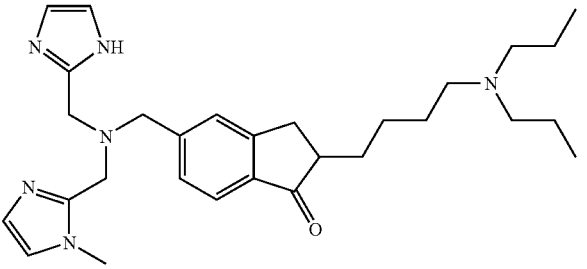 |

TABLE 1-continued
| No. | Structural Formula |
|---|---|
| 137 | 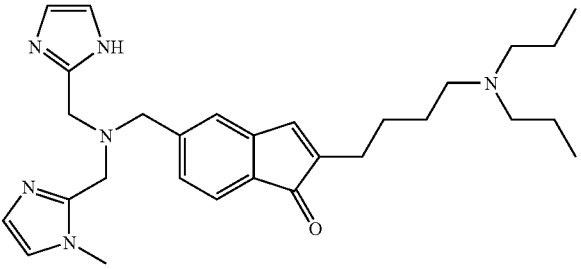 |
| 138 | 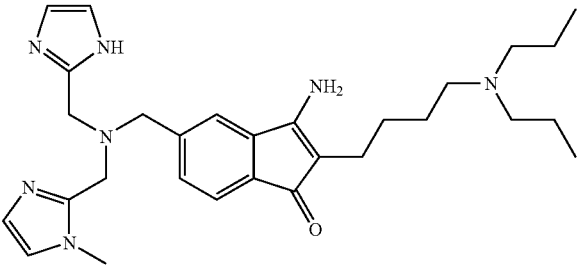 |
| 139 | 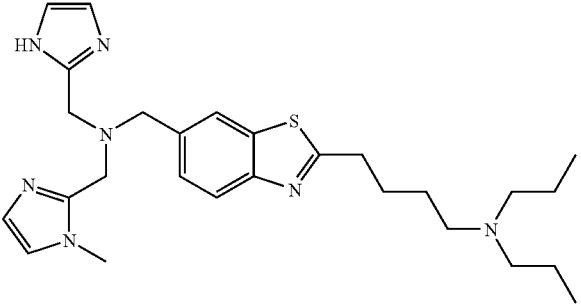 |
| 140 | 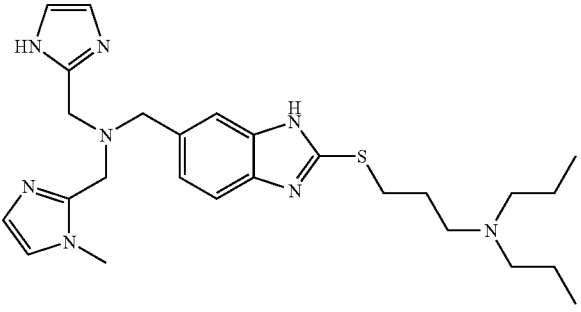 |
| 141 | 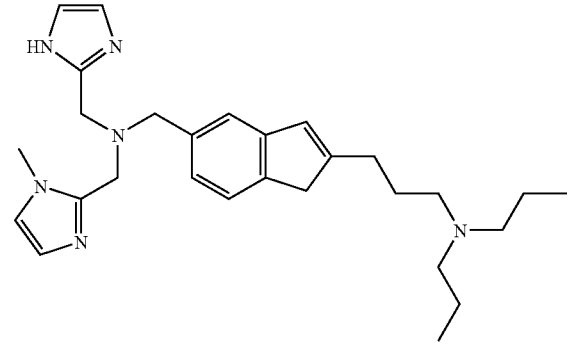 |

TABLE 1-continued
| No. | Structural Formula |
|---|---|
| 142 | 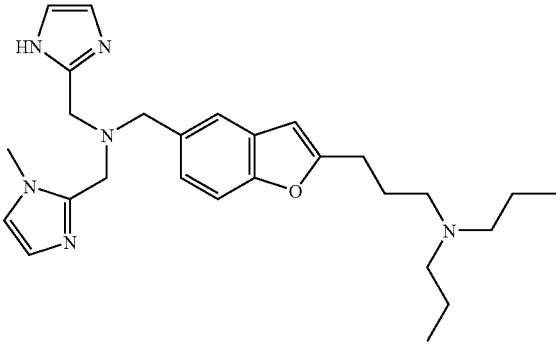 |
| 143 | 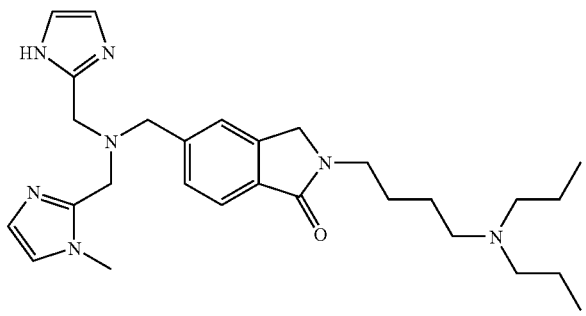 |
| 144 | 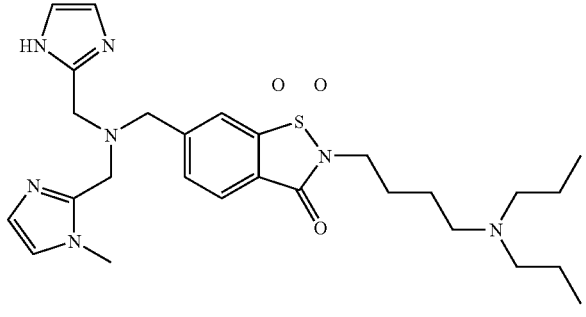 |
| 145 | 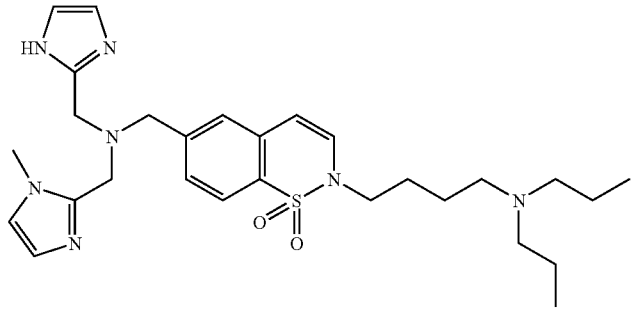 |

TABLE 1-continued

| No. | Structural Formula |
|-----|--------------------|
| 146 | |
| 147 | |
| 148 | |
| 149 | |
| 150 | |

TABLE 1-continued
| No. | Structural Formula |
|---|---|
| 151 | 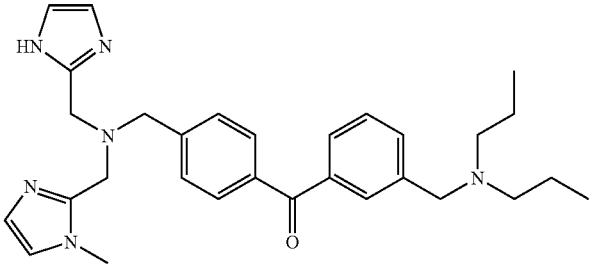 |
| 152 | 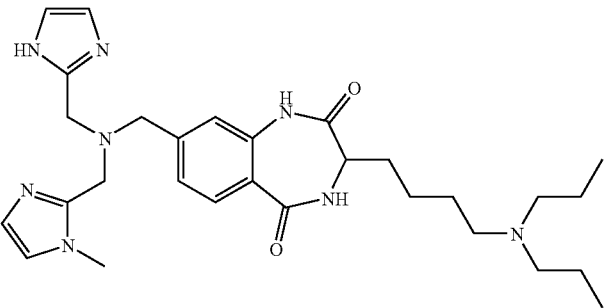 |
| 153 | 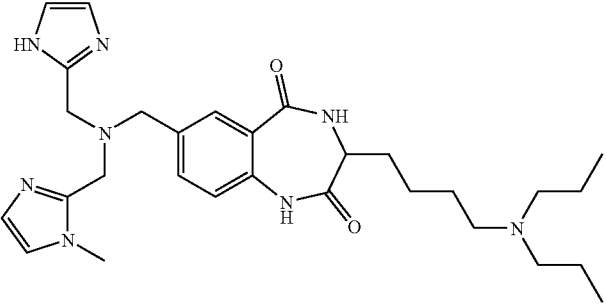 |
| 154 | 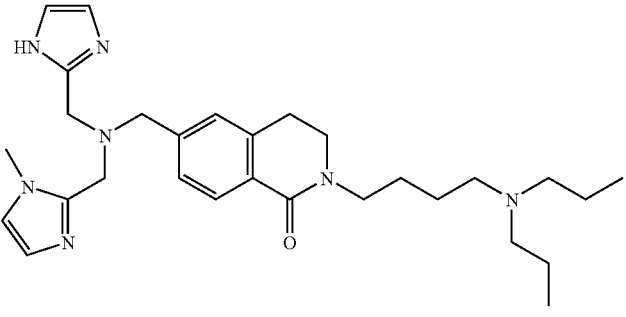 |
| 155 | 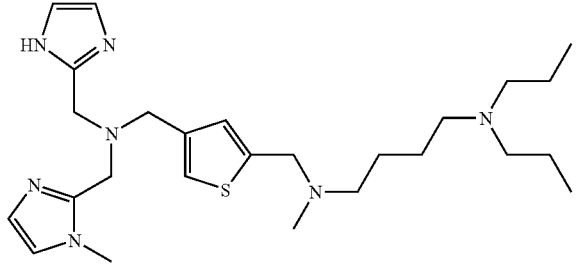 |

TABLE 1-continued

| No. | Structural Formula |
| --- | --- |
| 156 | |
| 157 | |
| 158 | |
| 159 | |
| 160 | |

TABLE 1-continued
| No. | Structural Formula |
|---|---|
| 161 | 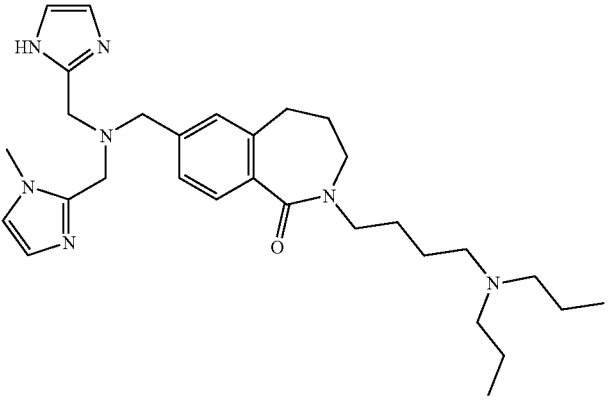 |
| 162 | 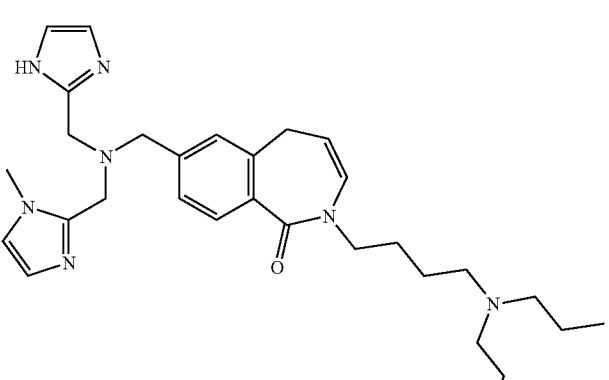 |
| 163 | 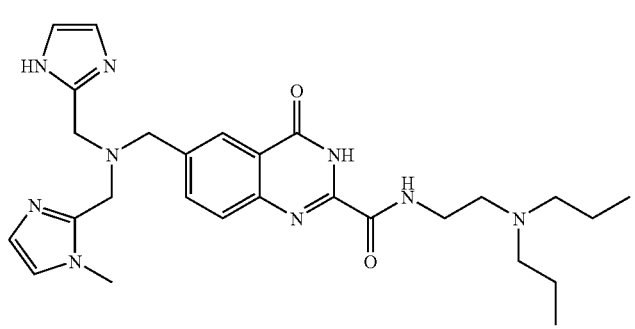 |
| 164 | 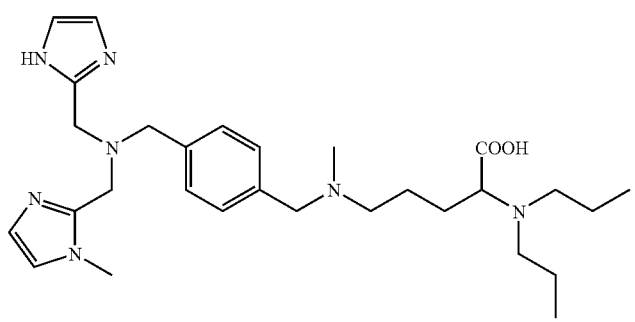 |

TABLE 1-continued
| No. | Structural Formula |
|---|---|
| 165 | 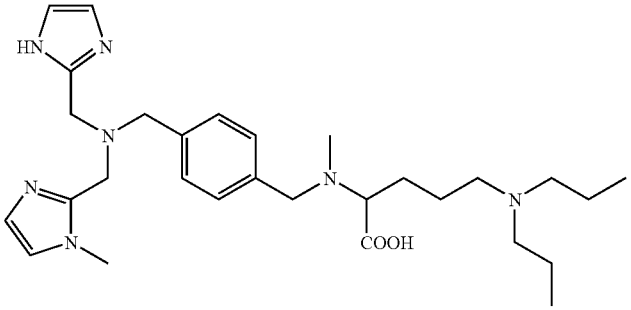 |
| 166 | 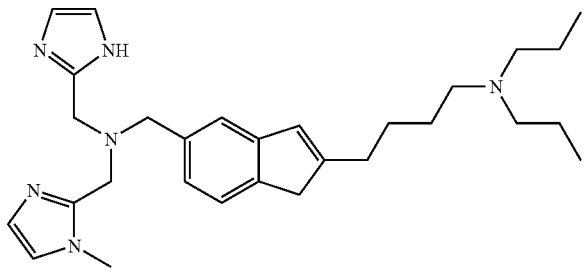 |
| 167 | 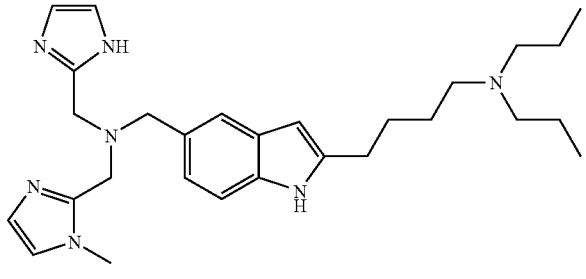 |
| 168 | 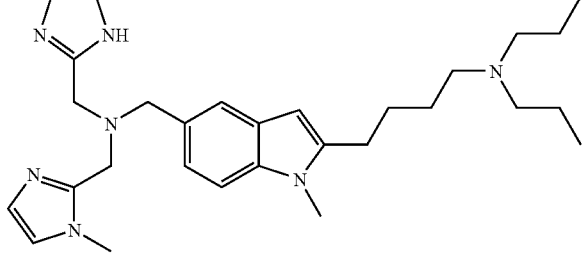 |
| 169 | 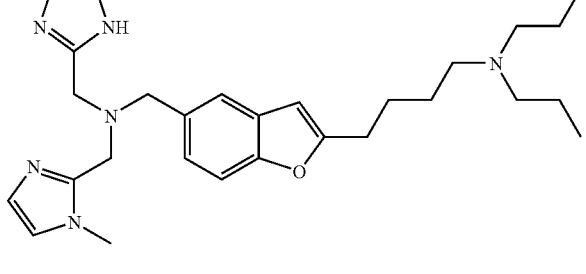 |

TABLE 1-continued

| No. | Structural Formula |
|---|---|
| 170 | 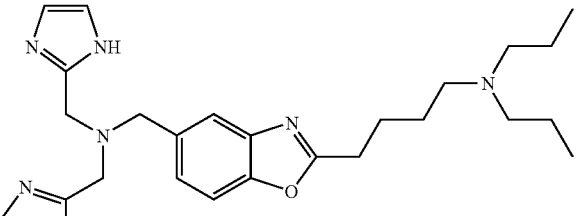 |
| 171 | 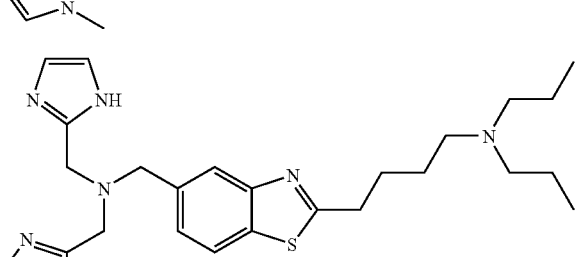 |

The results of the activity test and the like for the compound of the present invention will be shown below.

Test Example 1

Immediately after infection, HIV-1$_{IIIB}$ infected MT-4 cells (3.0×10$^4$/well, MOI (Multiplicity of infection): 0.01) were added to a 96-well microtiter plate together with the test compounds having different concentrations. The cells were cultured in a carbon dioxide incubator at 37° C. for 5 days, and the number of living cells was measured in accordance with the MTT (tetrazolium) method (Pawels, et al., Journal of Virology Method, 20, 309–321 (1998)). The antiviral activity is represented by the concentration required for inhibition of cell disorder due to HIV infection by 50% (EC$_{50}$: 50% Effective Concentration) (μM), and the results are shown in Table 2.

TABLE 2

| Compound No. | EC50[μM] |
|---|---|
| 1 | 0.004 |
| 2 | 0.003 |
| 3 | 0.003 |
| 11 | 0.023 |
| 12 | 0.049 |
| 19 | 0.002 |
| 25 | 0.002 |
| 49 | 0.002 |
| 61 | 0.002 |
| 75 | 0.002 |
| 98 | 0.003 |
| 109 | 0.002 |
| 116 | 0.002 |
| 127 | 0.003 |

Test Example 2

MT-4 cells (5×10$^6$/0.2 ml/well) were cultured on a 24-well microtiter plate. After the cells were incubated for 24 hours at 37° C. in a carbon dioxide gas incubator, a culture medium was replaced with a buffer solution (0.1% BSA-containing RPMI-1640). Together with a ligand $^{125}$I-SDF-1, (specific activity: 2,200 Ci/mmol; available from Daiichi Pure Chemicals Co., Ltd. (Tokyo)), test materials with various concentrations were subjected to a binding reaction for 2 hours under ice-cooling. Ligands that did not bind in cold PBS were washed out, and then the radioactivities of bound ligands were measured with a scintillation counter (available from Japan Packard (Tokyo)). Then, a rate of inhibition of the binding between radio-active ligands and receptors CXCR4 by a test material was calculated (a binding-inhibition % at 0.1 μM).

The results are shown in Table 3.

TABLE 3

| Compound No. | Inhibition rate (%) |
|---|---|
| 1 | 100.0 |
| 2 | 100.0 |
| 3 | 100.0 |
| 11 | 95.0 |
| 12 | 95.0 |
| 19 | 100.0 |
| 25 | 100.0 |
| 49 | 100.0 |
| 61 | 100.0 |
| 75 | 100.0 |
| 98 | 100.0 |
| 109 | 100.0 |
| 116 | 100.0 |
| 127 | 100.0 |

Test Example 3

The aforementioned compound was examined for acute toxicity. Specifically, 7-week-old ICR mice (male) were divided into several groups (4 or 5 mice in each group), and the mice were bred for 1 week for habituation. Subsequently, each of the compounds of Examples was dissolved in distilled water or physiological saline, and the solution was administered to the mice via tail vein (dose: 2.5 mg/kg) once. Then, dead mice were counted. The results are shown in Table 4.

As shown in Table 4, Test Example 3 confirmed that the administration of each compound did not cause any death and the compounds did not have acute toxicity.

TABLE 4

| Compound No. | Dead mice/ test mice |
|---|---|
| 1 | 0/5 |
| 2 | 0/5 |
| 3 | 0/5 |
| 11 | 0/5 |
| 12 | 0/5 |
| 19 | 0/5 |
| 25 | 0/5 |
| 49 | 0/5 |
| 61 | 0/5 |
| 75 | 0/5 |
| 98 | 0/5 |
| 109 | 0/5 |
| 116 | 0/5 |
| 127 | 0/5 |

Test Example 4

34.6% of the compound No. 86, 34.6% of lactose (Japanese Pharmacopoeia; hereinafter, referred to as "JP"), 17.3% of corn starch (JP), 7.3% of hydroxypropylcellulose (JP), and 6.2% of low-substitution hydroxypropylcellulose (JP) were sieved and mixed well in a plastic bag. Purified water (JP) in an amount equal to those compounds was added to the mixture, and then a wet cake was obtained by kneading the mixture for 20 minutes with a biaxial kneader. The wet cake was granulated using an extrusion granulating machine (diameter of cylindrical aperture: 1 mm), and then the granulated product was dried using a fluidized-bed dryer (40° C., 30 minutes). The dried granules were sieved. Subsequently, magnesium stearate was added to the sieved product in the proportion of 1% of magnesium stearate to 99% of sieved product and then the whole was mixed well, followed by making tablets having an average weight of 292 mg using a tableting machine.

In addition, an undercoat solution was prepared by dissolving 8% of hydroxypropylmethylcellulose (JP) and 1.6% of macrogol 6000 (JP) in purified water (JP) so as to be 100% in total. An under coat tablet was prepared by: spraying the undercoat solution using a hicoater in a ratio of 5% with respect to the weight of the tablet which was previously made; and subjecting the sprayed tablet to drying for 20 minutes.

Furthermore, an enteric coating solution was prepared by dissolving 10% of hydroxypropylcellulose acetate succinate (Pharmaceutical excipient standards), 3% of triethyl citrate (JP), 2% of titanium oxide (JP), and 0.05% of hydroxypropylcellulose (JP) in purified water (JP) so as to be 100% in total. The enteric coating solution was sprayed using a hicoater in a ratio of 10% with respect to the tablet weight. After the spraying, the tablet was dried for 30 minutes, thereby an enteric tablet was prepared. This enteric tablet had properties of not allowing a main component to be eluted within 2 hours in first liquid (JP), and allowing 80% or more of the main component to be eluted within 30 minutes in second liquids (JP).

INDUSTRIAL APPLICABILITY

The new amine compound according to the present invention, a pharmacologically acceptable salt thereof, or a prodrug thereof can provide a new CXCR4 antagonist. The new CXCR4 antagonist of the present invention has a CXCR4 antagonism, and shows, based on the CXCR4 antagonism, excellent effects as a therapeutic or preventive for a disease such as: a viral infectious disease such as HIV; rheumatism; or cancer metastasis.

The invention claimed is:

1. A compound represented by the following general formula (1), a pharmacologically acceptable salt thereof, or a prodrug thereof:

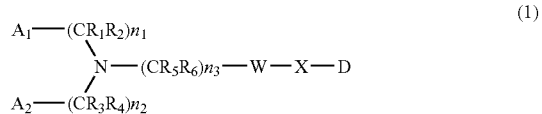

(1)

wherein
each of $n_1$, $n_2$, and $n_3$ is an integer of 1;
each of $R_1$, $R_2$, $R_3$, $R_4$, $R_5$, and $R_6$ is independently a hydrogen atom;
$A_1$ is imidazole;
$A_2$ is imidazole or imidazole substituted with an alkyl group;
W is a phenyl group or naphthyl group;
X is $CH_2$;
D is a group represented by -Q-Y—B, wherein:
Q is $NR_{12}$ and $R_{12}$ is a hydrogen atom or an alkyl group;
Y is $(CH_2)m_3$ and $m_3$ is an integer of 2 to 4; and
B is $N(R_{25}R_{26})$, wherein each of $R_{25}$ and $R_{26}$ are independently a hydrogen atom, a $C_1$–$C_6$ alkyl group or a $C_3$–$C_6$ cycloalkyl group.

2. A compound according to claim 1, wherein $A_2$ is imidazole.

3. A compound according to claim 1, wherein $A_2$ is imidazole substituted with an alkyl group.

4. A compound according to claim 1, wherein W is a phenyl group.

5. A compound according to claim 1, wherein $R_{12}$ is a methyl group.

6. A compound according to claim 1, wherein $R_{25}$ and $R_{26}$ are a $C_1$–$C_6$ alkyl group.

7. A pharmaceutical composition, comprising as an active ingredient a compound, a pharmacologically acceptable salt thereof, or a prodrug thereof according to claim 1.

8. A compound, a pharmacologically acceptable salt thereof, or a prodrug thereof selected from the group consisting of:
N-(4-{[bis(1H-imidazol-2-ylmethyl)-amino]-methyl}-benzyl)-N',N'-dipropylbutane-1,4-diamine,
N-(4-{[bis(1H-imidazol-2-ylmethyl)-amino]-methyl}-benzyl)-N-methyl-N',N'-dipropylbutane-1,4-diamine,
N-(4-{[(1H-imidazol-2-ylmethyl)-(1-methyl-1H-imidazol-2-ylmethyl)-amino]-methyl}-benzyl)-N',N'-dipropylbutane-1,4-diamine,
N-(4-{[(1H-imidazol-2-ylmethyl)-(1-methyl-1H-imidazol-2-ylmethyl)-amino]-methyl}-benzyl)-N-methyl-N',N'-dipropylbutane-1,4-diamine, and
N-cyclohexyl-N'-(4-{[(1H-imidazol-2-ylmethyl)-(1-methyl-1H-imidazol-2-ylmethyl)-amino]-methyl}-benzyl)-N'-methyl-butane-1,4-diamine.

9. A pharmaceutical composition, comprising as an active ingredient a compound, a pharmacologically acceptable salt thereof, or a prodrug thereof according to claim 8.

* * * * *